US011278572B2

(12) United States Patent
Gao et al.

(10) Patent No.: US 11,278,572 B2
(45) Date of Patent: Mar. 22, 2022

(54) REDUCING CXCR4 EXPRESSION AND/OR FUNCTION TO ENHANCE ENGRAFTMENT OF HEMATOPOIETIC STEM CELLS

(71) Applicant: THE UNITED STATES OF AMERICA, as represented by the Secretary, Department of Health and Human Services, Bethesda, MD (US)

(72) Inventors: Jiliang Gao, Potomac, MD (US); Philip M. Murphy, Rockville, MD (US); David H. McDermott, Olney, MD (US); Marie Siwicki, Washington, DC (US); Harry L. Malech, Bethesda, MD (US); Joy Liu, Boyds, MD (US); Paejonette Jacobs, Bronx, NY (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 0 days.

(21) Appl. No.: 15/324,219

(22) PCT Filed: Jul. 17, 2015

(86) PCT No.: PCT/US2015/040954
§ 371 (c)(1),
(2) Date: Jan. 5, 2017

(87) PCT Pub. No.: WO2016/011381
PCT Pub. Date: Jan. 21, 2016

(65) Prior Publication Data
US 2017/0196911 A1 Jul. 13, 2017

Related U.S. Application Data

(60) Provisional application No. 62/026,138, filed on Jul. 18, 2014.

(51) Int. Cl.
*A61K 35/28* (2015.01)
*C12N 5/0789* (2010.01)
*A61B 6/00* (2006.01)
*A61K 45/06* (2006.01)

(52) U.S. Cl.
CPC ............. *A61K 35/28* (2013.01); *A61B 6/54* (2013.01); *A61K 45/06* (2013.01); *C12N 5/0647* (2013.01)

(58) Field of Classification Search
CPC .......... A61K 35/28; A61K 45/06; A61B 6/54; C12N 5/0647
See application file for complete search history.

(56) References Cited

U.S. PATENT DOCUMENTS

| | | | |
|---|---|---|---|
| 5,716,827 A | 2/1998 | Tsukamoto et al. | |
| 9,822,370 B2 * | 11/2017 | Musunuru | C12N 15/907 |
| 2010/0291048 A1 * | 11/2010 | Holmes | C07K 14/70596 424/93.21 |
| 2011/0230422 A1 * | 9/2011 | Tudan | A61K 38/10 514/19.6 |
| 2012/0177616 A1 | 7/2012 | Serikov et al. | |
| 2014/0357530 A1 * | 12/2014 | Zhang | C12N 15/63 506/16 |
| 2018/0141992 A1 * | 5/2018 | Cowan | C07K 14/70539 |

FOREIGN PATENT DOCUMENTS

EP 2603227 A2 6/2013
WO WO 2008/136656 A1 11/2008

OTHER PUBLICATIONS

Frueahauf et al Transfusion Medicine and Hemotherapy, 246-250 (Year: 2013).*
Grzegorz et al Annals of Hematology, 90, 557-568 (Year: 2010).*
Accession No. BBG72374, Jul. , pp. 1-3 (Year: 2014).*
Spangers Kidney International 74, 14-21 (Year: 2008).*
Samstein et al Journal of American Society of Nephrology 12: 182-193 (Year: 2001).*
Fred Gage Nature 392: 18-24 (Year: 1998).*
Dow et al Trends in Molecular Medicine, 21, 609-621 (Year: 2015).*
Hauschild PNAS, 108( 29), 12013-12017 (Year: 2011).*
Li Nature, Jul. 14, 475, 7355, 217-221 (Year: 2011).*
Porteus Nature Biotechnology, vol. 23, No. 8, 967-973 (Year: 2005).*
Kosicki et al Nature Biotechnology, 1-8 (Year: 2018).*
Meyts et al Journal of Clinical Immunology, vol. 32, Supp. Suppl. 1, pp. S92 (Year: 2012).*
Fricker S Expert Opinion Invest. Drug, 17(11) 1749-1760 (Year: 2008).*
Bikash et al Theranostics, vol. 3, No. 1. 47-75 (Year: 2013).*
Kawai et al Blood, 109, 1, 78-84 (Year: 2007).*
Yang et al Curr. Protoc. Mol. Biol. 107:31.1.1-31.1.17. (Year: 2014).*
Hsu et al Nat Biotechnology. Sep.;31(9):827-32 (Year: 2013).*
Basak et al., "Hematopoietic stem cell mobilization with the reversible CXCR4 receptor inhibitor plerixafor (AMD3100)—Polish compassionate use experience," *Ann Hematol.* 90:557-568, 2011.
(Continued)

*Primary Examiner* — Anoop K Singh
(74) *Attorney, Agent, or Firm* — Klarquist Sparkman, LLP

(57) ABSTRACT

Provided herein are methods of enhancing engraftment of hematopoietic stem cells (HSC) in recipient subjects by reducing expression (or activity) of CXC chemokine receptor 4 (CXCR4). Such methods can be used in gene therapy protocols and in HSC transplantation, for example allowing this to occur without radiation or chemotherapy conditioning as is typically done in non-myeloablative HSC transplant. In some examples, gene editing methods are used to delete one copy of the CXCR4 gene before HSC or bone marrow transplantation, enhancing the efficiency and durability of donor cell repopulation.

9 Claims, 37 Drawing Sheets

Specification includes a Sequence Listing.

(56) References Cited

OTHER PUBLICATIONS

Bolan et al., "Prospective evaluation of cell kinetics, yields and donor experiences during a single large-volume apheresis versus two smaller volume consecutive day collections of allogeneic peripheral blood stem cells," *Br J Haematol.* 720:801-807, 2003.
Cashen, "Plerixafor Hydrochloride: A Novel Agent for the Mobilization of Peripheral Blood Stem Cells," *Drugs of Today* 45:497-505, 2009.
Flomenberg et al., "Plerixafor (Mozobil) alone to mobilize hematopoietic stem cells from multiple myeloma patients for autologous transplantation," *Biol Blood Marrow Transplant.* 16:695-700, 2010.
Foguenne et al., "Ex vivo expansion of hematopoietic progenitor cells is associated with downregulation of alpha4 integrin- and CXCR4-mediated engraftment in NOD/SCID beta2-microglobulin-null mice," *Haematologica* 94:185-194, 2009.
Foudi et al., "The Hematopoietic reconstitution defect of mice lacking CXCR4 is related to an altered retention of hematopoietic cells in the bone marrow," Blood 104:38A, 46th Annual Meeting of the American Society of Hematology, San Diego, CA, Dec. 2004. Accession No. PREV200510268093, Database Biosis [Online], Nov. 2004.
Fricker, "A Novel CXCR4 Antagonist for Hematopoietic Stem Cell Mobilization," *Expert Opinion on Investigational Drugs* 17:1749-1760, 2008.
Fricker, "Physiology and Pharmacology of Plerixafor," *Transfus Med Hemother.* 40:237-245, 2013.
Fruehauf, "Current Clinical Indications for Plerixafor," *Transfus Med Hemother.* 40:246-250, 2013.
Hsu et al., "Development and Applications of CRISPR-Cas9 for Genome Engineering," *Cell* 157:1262-1278, 2014.
Kawabata et al., "A cell-autonomous requirement for CXCR4 in long-term lymphoid and myeloid reconstitution," *Proc Natl Acad Sci U S A.* 96:5663-5667, 1999.
Kawai et al., "WHIM syndrome myelokathexis reproduced in the NOD/SCID mouse xenotransplant model engrafted with healthy human stem cells transduced with C-terminus- truncated CXCR4," *Blood* 109:78-84, 2007.
Kawai et al., "39: Enhanced Engraftment of Human Hematopoietic Stem Cells Infected with Integration Defective Lentivirus Vector Encoding Whim-Type Mutant CXCR4 in NOD/SCID Mouse Xenograft Model," *J Gene Med.* 11, p. 1167, 2009.
Lapidot et al., "How do Stem Cells Find Their Way Home?," *Blood* 106:1901-1910, 2005.
Ma et al., "The Chemokine Receptor CXCR4 Is Required for the Retention of B Lineage and Granulocytic Precursors within the Bone Marrow Microenvironment," *Immunity* 10:463-471, 1999.
McDermott et al., "Chromothriptic Cure of WHIM Syndrome," *Cell* 160:686-699, 2015.
Park et al., "Targeted inversion and reversion of the blood coagulation factor 8 gene in human iPS cells using TALENs," *Proc Natl Acad Sci U S A.* 111:9253-9258, 2014.
Rettig et al., "Mobilization of hematopoietic stem and progenitor cells using inhibitors of CXCR4 and VLA-4," *Leukemia* 26:34-53, 2012.
Shen, "CRISPR technology leaps from lab to industry," *Nature/News*, Dec. 3, 2013 (4 pages).
Tsai et al., "Dimeric CRISPR RNA-guided FokI nucleases for highly specific genome editing," *Nat Biotechnol.* 32:569-576, 2014.
Ye et al., "Seamless modification of wild-type induced pluripotent stem cells to the natural CCR5Δ32 mutation confers resistance to HIV infection," *Proc Natl Acad Sci U S A.* 111:9591-9596, 2014.
PCTUS2015040954 International Search Report and Written Opinion dated Oct. 28, 2015 (16 pages).

\* cited by examiner

FIG. 16A

Human CXCR4 sequence:

```
                    TALEN L1
5" AATGGATTGGTCATCATCCTGGTCATCTGGTTACCAGAAGAAACTGAGAAGCATGACGGACAAGTACAGGCTGCA 3"
3" TTACCTAACCAGTAGTAGGACCAGTAGACCAATGGTCTTCTTTGACTCTTCGTACTGCCTGTTCATGTCCGACGT 5"
                                                                  TALEN R2
```

FIG. 17E

REDUCING CXCR4 EXPRESSION AND/OR FUNCTION TO ENHANCE ENGRAFTMENT OF HEMATOPOIETIC STEM CELLS

CROSS-REFERENCE TO RELATED APPLICATION

This is the U.S. National Stage of International Application No. PCT/US2015/040954, filed Jul. 17, 2015, which was published in English under PCT Article 21(2), which in turn claims the benefit of U.S. Provisional Application No. 62/026,138, filed Jul. 18, 2014, herein incorporated by reference.

FIELD

This application relates to methods of enhancing engraftment of donor hematopoietic stem cells (HSCs), for example increasing the efficiency and durability of donor HSC repopulation, by reducing expression or activity of CXCR4 in HSCs. In some examples such methods are used in combination with gene therapy.

BACKGROUND

WHIM syndrome (warts, hypogammaglobulinemia, infections, and myelokathexis syndrome) is an autosomal dominant immunodeficiency that can be caused by multiple heterozygous mutations in the carboxy-terminus of the chemokine receptor, CXCR4. (Hernandez et al., 2003) These mutations disrupt negative regulatory elements and thus enhance function of the receptor (Haribabu et al., 1997; Signoret et al., 1998; Venkatesan et al., 2003). The syndrome name is an acronym for the four major clinical features that result from this: Warts, Hypogammaglobulinemia, Infections, and Myelokathexis (Wetzler et al., 1990). Warts are the manifestation of chronic human papillomavirus (HPV) infection of the skin or oral or genital mucosa and are a severe and chronic problem in these patients (Beaussant Cohen et al., 2012; Dotta et al., 2011; Kawai and Malech, 2009). Hypogammaglobulinemia (low immunoglobulin G) is typically mild but variable and can predispose to frequent sinopulmonary infections and poor vaccine responses. The patients also suffer from oral, skin/soft tissue and bone and joint infections that arise because of severe blood neutropenia. This occurs in conjunction with an excess of neutrophils and myeloid precursors in the bone marrow that has been termed 'myelokathexis', from the Greek for marrow (myelo) and retention (kathexis) (Krill et al., 1964; Zuelzer, 1964). In fact the excessive CXCR4 function actually causes a panleukopenia in the blood with particularly severe reductions of neutrophils and B cells, and moderate reductions of T cells and monocytes.

CXCR4 is a chemokine receptor expressed on the surface of most leukocytes whose human ligand is CXCL12 (also known as stromal cell derived factor-1 or SDF-1) (Bachelerie et al., 2014). CXCR4 was originally discovered as a fusion co-factor (with CD4) for HIV viral entry and is particularly important in late stage HIV disease (Berger et al., 1999; Feng et al., 1996); while CXCL12 is constitutively expressed in the bone marrow stroma and is known to play a vital role in hematopoietic stem cell (HSC) retention in the marrow (Bleul et al., 1996; Broxmeyer et al., 2005). A small molecule CXCR4 antagonist, plerixafor (formerly known as AMD3100), is FDA approved to facilitate the collection of HSC by apheresis for autologous bone marrow transplantation in certain malignancies. Plerixafor has also been successful at reversing the panleukopenia and treating WHIM syndrome in small studies (Dale et al., 2011; McDermott et al., 2011; McDermott et al., 2014).

Human hematopoiesis is a complex, hierarchical differentiation of a variety of progenitor cells that form all the terminally differentiated elements of the blood including red blood cells, platelets, lymphocytes, monocytes, and granulocytes (Seita and Weissman, 2010). All of these lineages can be traced back to a group of true pluripotent HSC that are capable of life-long self-renewal. These HSC undergo regulated differentiation to maintain homeostasis and markedly increased proliferation during injury or infection (emergency hematopoiesis) and have been identified by the expression of unique combinations of cell surface markers as well as in vitro and in vivo functional assays. In addition to playing an adhesive role for HSC in the bone marrow niche, CXCR4 signaling promotes HSC quiescence and homeostasis and can also play a role in HSC differentiation into committed myeloid progenitors such as the common myeloid progenitor (CMP) (Broxmeyer et al., 2003a; Broxmeyer et al., 2003b; Nie et al., 2008; Sugiyama et al., 2006).

Chromothripsis is derived from the Greek root for chromosome (chromo='color', soma='body') and shattering to pieces (thripsis) (Stephens et al., 2011). The phenomenon was recently discovered when new genetic techniques of whole genome sequencing, single nucleotide polymorphism microarray, and bioinformatics analysis were applied to malignant tumor DNA. It represents a new paradigm for oncogenesis where a sudden catastrophic event can create multiple clustered genetic rearrangements and deletions rather than the sequential genetic changes that result in most tumorigenesis (Stephens et al., 2011). It is currently estimated that approximately 2% of all cancers exhibit somatic mutations compatible with chromothripsis (Jones and Jallepalli, 2012) and the same process has been identified in a patient with a severe congenital cognitive syndrome (Kloosterman et al., 2011). A very strong predisposition to chromothripsis has been demonstrated in a specific subtype of medulolobastoma tumors that have defects in the TP53 gene which indicates that loss of this cell cycle checkpoint may allow cells with severe genetic damage resulting from chromothripsis to survive (Rausch et al., 2012). Criteria developed to allow the inference of chromothripsis include clustering of breakpoints in limited areas of one or several chromosomes with large intervening regions of normal sequence, copy number states that suddenly oscillate between areas of normal heterozygosity and loss of heterozygosity, rearrangements affecting a single haplotype and with multiple fragments rearranged in random orientation and order (Korbel and Campbell, 2013).

SUMMARY

Provided herein are methods enhancing engraftment of donor hematopoietic stem cells (HSCs), for example increasing the efficiency and durability of donor HSC repopulation in a recipient subject. In particular examples the methods include reducing expression or function of CXC chemokine receptor 4 (CXCR4) in a donor HSC, thereby generating a CXCR4 knockdown HSC. For example, expression and/or activity of CXCR4 can be reduced by at least 20%, at least 30%, at least 40%, at least 50% or at least 75% (but not 100%) in the CXCR4 knockdown HSC as compared to expression of CXCR4 in the donor HSC prior to reducing CXCR4 expression and/or activity. In some examples, this is done ex vivo, for example after obtaining HSCs from a donor. In some examples, donor HSCs are obtained from the recipient subject, while in other examples donor HSCs are obtained from a subject different from the recipient subject. Thus, the method can further include harvesting HSC from a donor subject. The disclosure is not limited to specific methods of editing gene expression or activity in a cell, but in some examples gene editing or RNA interference (RNAi) methods are used to manipulate a CXCR4 gene or other CXCR4 nucleic acid in the HSC. In other examples, the CXCR4 protein is targeted, for example with CXCR4 protein antagonists, such as small molecules, antibodies, or aptamers.

The resulting CXCR4 knockdown HSCs are then administered or transplanted into a recipient subject in therapeutically effective amounts, thereby increasing HSC engraftment in the recipient subject. In some examples at least $1\times10^6$, at least $1\times10^7$, or at least $1\times10^8$ CXCR4 knockdown HSCs are administered to the subject. Any method of administration can be used that allows proper function of the HSCs in vivo (for example allows the CXCR4 knockdown HSCs to reach the bone marrow), such as by injection of the CXCR4 knockdown HSCs into the subject, such as by intravenous administration. In some examples, the recipient subject has not received conditioning prior to administering the CXCR4 knockdown HSCs to the recipient subject, such as chemotherapy and/or total body irradiation.

In some examples, the methods further include manipulating one or more other genes (such as correcting a mutation and/or altering its expression) in the CXCR4 knockdown HSCs, which can then be used to treat a disease or disorder in the subject related to the gene that is manipulated. For example, manipulating one or more other genes in the donor HSC can include one or more of correcting a genetic defect in the HSC, wherein the genetic defect causes a disease in the recipient subject; reducing expression of a first target gene in the HSC, wherein reducing expression of the first target gene treats a disease caused by upregulation of the first target gene in the recipient subject or treats a disease that benefits from reducing expression of the first target gene in the recipient subject; and increasing expression of a second target gene in the HSC, wherein increasing expression of the second target gene treats a disease caused by downregulation of the second target gene in the recipient subject or treats a disease that benefits from increasing expression of the second target gene in the recipient subject.

In some examples, manipulation of CXCR4 expression in the HSC and manipulation of one or more other genes is performed at the same time, such as by using gene editing methods or RNAi methods. In other examples, the donor HSC is first manipulated to decrease CXCR4 expression/activity, and then the donor HSC is manipulated to correct a mutation and/or alter expression of one or more other genes (or vice versa). Thus, a CXCR4 knockdown HSC can include other genetic alterations.

In some examples, the method is a method of treating a disease or disorder in the subject. For example, CXCR4 knockdown HSCs, which may include other genetic manipulations, can be used to treat a hematologic malignancy (such as chronic myelogenous leukemia wherein a BCR-ABL fusion gene is silenced or removed from the donor HSC), HIV-1 (wherein expression of the viral coreceptor and CC chemokine receptor CCR5 is reduced in the donor HSC), anemia, and a genetic disease of the blood, such as any of sickle cell anemia, hemophilia A, hemophilia B, alpha-thalassemia, beta-thalassemia, delta-thalassemia, von Willebrand Disease, pernicious anemia, Fanconi anemia, thrombocytopenic purpura, thrombophilia, and all primary immunodeficiency diseases.

The foregoing and other objects and features of the disclosure will become more apparent from the following detailed description, which proceeds with reference to the accompanying figures.

BRIEF DESCRIPTION OF THE DRAWINGS

FIGS. 16A-16D. Complete TALEN system creates deletions in CXCR4 resulting in loss of CXCR4 expression. (A) Genomic DNA sequence of human CXCR4. TALEN sequences are underlined. (SEQ ID NO: 11 top, SEQ ID NO: 12 bottom) (B) FACS analysis of HeLa cells 2 days after transfection with maxGFP as a transfection control, CXCR4-copGFP-CXCR4 donor, incomplete TALEN (L1) with CXCR4-copGFP-CXCR4 donor, or complete TALEN (L1+R2) system with CXCR4-copGFP-CXCR4 donor; (C) HeLa cells that were transfected with the complete TALEN system were sorted by FACS (top), cultured for 7 days and analyzed by FACS analysis 7 days later (bottom); (D) Sequence analysis of the GFP negative cell population from (B). Sequences corresponding to L1 and R2 TALENs are highlighted in green. Red box highlights sequences (sequences from top SEQ ID NOS: 13, 15, 13, 13, 16, 13, 13, 17, 13, 13, 13, and 13) from cells that express low levels of CXCR4 (CXCR4 Lo) population. SEQ ID NOS: 13, 13, 13, 14, 13, 13, 15, 13, 13, 16, 13, 13, 17, 13, 13, 13 and 13 from top to bottom.

FIGS. 17A-17E. CRISPR-Cas9 system creates deletions in CXCR4 to generate cells with one copy of CXCR4. (A) Genomic DNA sequence of human CXCR4. CRISPR guide sequences are underlined, PAM motif is in italics; (SEQ ID NO: 18 top, SEQ ID NO: 19 bottom) (B) FACS analysis 6 days after HeLa cells were transfected with 2 µg maxGFP (transfection efficiency control), 2 µg CRISPR-cas9 D10A Nickase or 1 µg Nickase with 0.5 µg of each guide; (C) HeLa cells that were transfected with the complete Nickase system were sorted by FACS (top), after which surveyor assay was carried out to detect mutations in the sorted populations. CXCR4 Lo cells were cultured for 4 days and analyzed by FACS analysis (bottom); (D) Sequence analysis of populations of cells that expressed high (CXCR4 Hi; SEQ ID NOS: 20, 21, 20, 20, 20, 20, 20, 20, 20, 22, 20, 20, 20 and 20 from top to bottom), medium (CXCR4 Mid SEQ ID NOS: 20, 20, 23, 24, 20, 20, 20, 25, and 20 from top to bottom), and low (CXCR4 Lo SEQ ID NOS: 26, 20, 20, 27, 20, 20, 20, 28, 20, 20, 20, 20, 20, 20, 20, 29, 30, 31, 31, 31, 31, 20, 20, 20, 20, 20, 20, 32, 31, 31, 31, 31, and 31 from top to bottom) levels of CXCR4 and a consensus sequence is shown at the bottom (SEQ ID NO: 20); (E) Sequence analysis from 5 single cell clones. Each clone has at least 2 sequence reads. Sequences corresponding to guides are highlighted in green. SEQ ID NOS: 33, 33, 33, 34, 34, 34, 33, 34, 35, 34, 33, 33, and 33 from top to bottom.

SEQUENCE LISTING

Figure 1A:
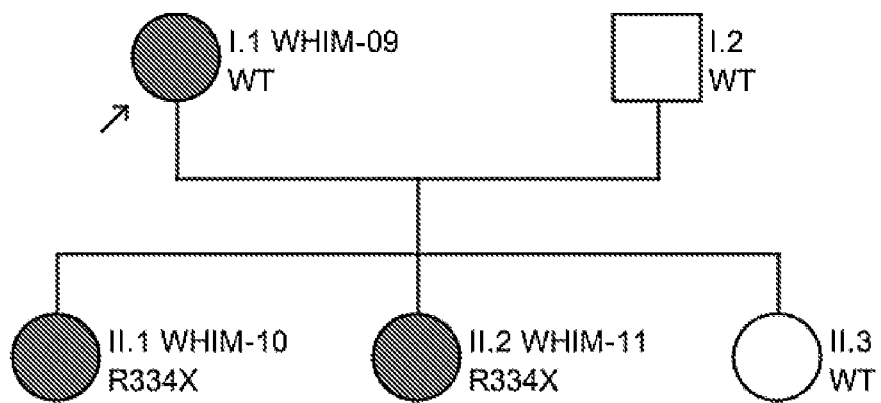
FIGS. 1A-1C. DNA sequencing of a family with WHIM syndrome revealed genetic mosaicism of the index patient. (A) Family Pedigree. males (squares); females (circles); shaded (history of or current evidence of clinical WHIM); arrow (index patient); WT (wild-type CXCR4 genotype); R334X ($CXCR4^{R334X}$ heterozygous genotype). (B) DNA sequencing of the family. Shown are representative Sanger sequencing results from blood DNA for the 3 patients of the family at the site of the $CXCR4^{R334X}$ mutation (nucleotide position 1000). (C) DNA sequencing from different tissues of the index patient at position 1000. Shown are the discrepant results from blood versus cheek versus skin fibroblast DNA.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file Sequence Listing, 32 KB, generated on Jan. 4, 2017, which is incorporated by reference herein.

SEQ ID NOS: 1-4 are PCR primers for amplification of CXCR4.

SEQ ID NOS: 5 and 6 are exemplary human CXCR4 coding and protein sequences. In the nucleic acid sequence, nt 1-2643 is the promoter, 2603-2607 TATA signal, 2632-6409 the gene, with nt 2721 . . . 2735 joined to 4844 . . . 5911 to form the coding sequence.

SEQ ID NOS: 7-8 are PCR primers for genomic DNA amplification of CXCR4 for indel analysis.

SEQ ID NOS: 9-10 are PCR primers for genomic DNA amplification of CXCR4 for single cell clonal analysis.

SEQ ID NOS: 11-12 are human CXCR4 genomic DNA sequence targeted by TALENs.

SEQ ID NOS: 13-17 are resulting mutated human CXCR4 genomic DNA sequences using the TALEN system. A consensus sequence is shown in SEQ ID NO: 13.

SEQ ID NOS: 18-19 are human CXCR4 genomic DNA sequence containing CRISPR guide sequences and PAM sequences.

SEQ ID NOS: 20-32 are resulting mutated human CXCR4 genomic DNA sequences using the nickase system. SEQ ID NOS: 20 and 22 are sequences from cells that expressed high (CXCR4 Hi) levels of CXCR4; SEQ ID NOS: 20, 23, 24 and 25 are sequences from cells that expressed medium (CXCR4 Mid) levels of CXCR4, and SEQ ID NOS: 20, 26, 27, 28, 29, 30, 31 and 32 are sequences from cells that expressed low (CXCR4 Lo) levels of CXCR4.

SEQ ID NOS: 33-35 are normal (SEQ ID NO: 33) and resulting mutated human CXCR4 genomic DNA sequences (SEQ ID NOS: 34-35) using the nickase system from 5 single cell clones.

SEQ ID NOS: 36-50 are exemplary sequences that can be used to knock-down CXCR4 expression using CRISPR or TALEN.

DETAILED DESCRIPTION

Unless otherwise noted, technical terms are used according to conventional usage. Definitions of common terms in molecular biology can be found in Benjamin Lewin, *Genes VII*, published by Oxford University Press, 1999; Kendrew et al. (eds.), *The Encyclopedia of Molecular Biology*, published by Blackwell Science Ltd., 1994; and Robert A. Meyers (ed.), *Molecular Biology and Biotechnology: a Comprehensive Desk Reference*, published by VCH Publishers, Inc., 1995; and other similar references.

As used herein, the singular forms "a," "an," and "the," refer to both the singular as well as plural, unless the context clearly indicates otherwise. As used herein, the term "comprises" means "includes." Thus, "comprising a nucleic acid molecule" means "including a nucleic acid molecule" without excluding other elements. It is further to be understood that any and all base sizes given for nucleic acids are approximate, and are provided for descriptive purposes, unless otherwise indicated. Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting. All references, including patent applications and patents, and sequences associated with the GenBank® Accession Numbers listed (as of Jul. 18, 2014) are herein incorporated by reference.

In order to facilitate review of the various embodiments of the disclosure, the following explanations of specific terms are provided:

Administration: To provide or give a subject an agent, such as a CXCR4 knock down HSC, by any effective route. Exemplary routes of administration include, but are not limited to, injection (such as subcutaneous, intramuscular, intradermal, intraperitoneal, and intravenous), transdermal, intranasal, and inhalation routes.

Antisense and Sense: Double-stranded DNA (dsDNA) has two strands, a 5'→3' strand, referred to as the plus strand, and a 3'→5' strand (the reverse complement), referred to as the minus strand. Because RNA polymerase adds nucleic acids in a 5' to 3' direction, the minus strand of the DNA serves as the template for the RNA during transcription. Thus, the RNA formed will have a sequence complementary to the minus strand and identical to the plus strand (except that U is substituted for T).

CD34: A cell surface antigen formerly known as hematopoietic progenitor cell antigen 1, and MY10, which is a marker of human hematopoietic stem cells. For example, CD34 is expressed selectively on human hematopoietic progenitor cells. CD34 is an adhesion molecule. The human CD34 gene, which maps to chromosome 1q32, spans 26 kb and has 8 exons. CD34 is a 67 kDa transmembrane glycoprotein.

CD34 sequences are publically available, for example from the GenBank® sequence database (e.g., Accession Nos. NP_001020280.1 (precursor) and AAB25223.1 provide exemplary human CD34 protein sequences; while Accession Nos. M81104.1 and BC039146.1 provide exemplary human CD34 nucleic acid sequences). One of ordinary skill in the art can identify additional CD34 nucleic acid and protein sequences, including CD34 variants (e.g., sequences having at least 80%, at least 85%, at least 90%, at least 95%, at least 97%, at least 98% or at least 99% sequence identity to the sequence of any Accession number listed).

Cell Culture: Cells grown under controlled conditions. A primary cell culture is a culture of cells, tissues or organs taken directly from an organism (such as a human or other mammal). Cells are expanded in culture when they are placed in a growth medium under conditions that facilitate cell growth and/or division, resulting in a larger population of the cells. When cells are expanded in culture, the rate of cell proliferation is typically measured by the amount of time required for the cells to double in number, otherwise known as the doubling time. In some examples, donor HSCs are grown in culture prior to introduction into a recipient. For example, HSCs grown in culture can be manipulated to downregulate CXCR4 expression or activity.

CXC chemokine receptor 4 (CXCR4): OMIM 162643. Also known as fusin, or CD184, is a gene that encodes for the CXCR4 protein, an alpha-chemokine receptor found on most leukocytes that is specific for stromal cell-derived-factor-1 (CXCL12), a molecule that has chemotactic activity for both lymphocytes and phagocytes. In humans, the CXCR4 gene is found on chromosome 2 (2q22.1), and in mice it is found on chromosome 1.

CXCR4 sequences are publically available, for example from the GenBank® sequence database (e.g., Accession Nos. NP_001008540 and CAA12166.1 provide exemplary human CXCR4 protein sequences; NP_034041.2 and AAH31665.1 provide exemplary mouse CXCR4 protein sequences, while Accession Nos. NG_011587.1 and AJ224869.1 provide exemplary human CXCR4 nucleic acid sequences and Accession Nos. NM_009911.3 and BC098322.1 provide exemplary mouse CXCR4 nucleic acid sequences). One of ordinary skill in the art can identify additional CXCR4 nucleic acid and protein sequences, including CXCR4 variants (e.g., sequences having at least 80%, at least 85%, at least 90%, at least 95%, at least 97%, at least 98% or at least 99% sequence identity to the sequence of any Accession number listed, or to SEQ ID NO: 5 or 6).

Downregulated or knocked down: When used in reference to the expression of a molecule, such as a (e.g., CXCR4) gene or a protein, refers to any process which results in a decrease in production of a gene product, but in some examples not complete elimination of the gene product or gene function. A gene product can be RNA (such as mRNA, rRNA, tRNA, and structural RNA) or protein. Therefore, downregulation or knock down includes processes that decrease transcription of a gene or translation of mRNA and thus decrease the presence of proteins or nucleic acids, such as a CXCR4 protein or nucleic acid molecule.

Examples of processes that decrease transcription include those that facilitate degradation of a transcription initiation complex, those that decrease transcription initiation rate, those that decrease transcription elongation rate, those that decrease processivity of transcription and those that increase transcriptional repression. Gene downregulation can include reduction of expression above an existing level. Examples of processes that decrease translation include those that decrease translational initiation, those that decrease translational elongation and those that decrease mRNA stability. In some examples, a gene editing method, inhibitory RNA, antibody, or other specific binding agent is used to decrease or knock down expression, such as expression or activity of CXCR4.

Downregulation or knock down includes any detectable decrease in the production of a gene product, such as a CXCR4 protein. In certain examples, detectable target protein or nucleic acid expression in a cell (such as a HSC cell) decreases by at least 20%, at least 30%, at least 40%, at least 50%, at least 60%, at least 70%, at least 75%, at least 80%, at least 90%, at least 95%, at least 96%, at least 97%, at least 98%, or at least 99% (such as a decrease of 40% to 90%, 40% to 80% or 50% to 95%) as compared to a control (such an amount of protein or nucleic acid expression detected in a corresponding normal cell or sample). In one example, a control is a relative amount of expression in a normal HSC (e.g., a non-recombinant HSC or an HSC from a healthy or normal subject).

In one example, downregulation or knock down does not result in complete elimination of detectable expression or activity (such as expression or activity of CXCR4).

Expression: The process by which the coded information of a nucleic acid molecule, such as a CXCR4 nucleic acid molecule (e.g., Cxcr4 gene) is converted into an operational, non-operational, or structural part of a cell, such as the synthesis of a protein (e.g., CXCR4 protein). Expression of a gene can be regulated anywhere in the pathway from DNA to RNA to protein. Regulation can include controls on transcription, translation, RNA transport and processing, degradation of intermediary molecules such as mRNA, or through activation, inactivation, compartmentalization or degradation of specific protein molecules after they are produced.

The expression of a nucleic acid molecule or protein (such as CXCR4) can be altered relative to a normal (wild type) nucleic acid molecule or protein (such as in a normal non-recombinant HSC). Alterations in gene expression, such as differential expression, include but are not limited to: (1) overexpression (e.g., upregulation); (2) underexpression (e.g., downregulation); or (3) suppression of expression. Alternations in the expression of a nucleic acid molecule can be associated with, and in fact cause, a change in expression of the corresponding protein.

Protein expression can also be altered in some manner to be different from the expression of the protein in a normal (wild type) situation. This includes but is not necessarily limited to: (1) a mutation in the protein such that one or more of the amino acid residues is different; (2) a short deletion or addition of one or a few (such as no more than 10-20) amino acid residues to the sequence of the protein; (3) a longer deletion or addition of amino acid residues (such as at least 20 residues), such that an entire protein domain or subdomain is removed or added; (4) expression of an increased amount of the protein compared to a control or standard amount (e.g., upregulation); (5) expression of a decreased amount of the protein compared to a control or standard amount (e.g., downregulation); (6) alteration of the subcellular localization or targeting of the protein; (7) alteration of the temporally regulated expression of the protein (such that the protein is expressed when it normally would not be, or alternatively is not expressed when it normally would be); (8) alteration in stability of a protein through increased longevity in the time that the protein remains localized in a cell; and (9) alteration of the localized (such as organ or tissue specific or subcellular localization) expression of the protein (such that the protein is not expressed where it would normally be expressed or is expressed where it normally would not be expressed), each compared to a control or standard.

Controls or standards for comparison to a sample, for the determination of differential expression, include samples believed to be normal (in that they are not altered for the desired characteristic, for example a HSC from a normal subject) as well as laboratory values, even though possibly arbitrarily set, keeping in mind that such values can vary from laboratory to laboratory. Laboratory standards and values may be set based on a known or determined population value and can be supplied in the format of a graph or table that permits comparison of measured, experimentally determined values.

FokI nuclease: A nonspecific DNA nuclease that occurs naturally in *Flavobacterium okeanokoites*. The term includes fragments of the FokI nuclease protein that retain nuclease activity that are, or may be, fused to a DNA-binding polypeptide. Also includes variants of a wild-type FokI sequence.

Functional deletion: A mutation, partial or complete deletion, insertion, or other variation made to a gene sequence that reduces or can even inhibit production of the gene product or renders the gene product non-functional. For example, a functional deletion of a single CXCR4 allele in a HSC results in a cell that cannot produce CXCR4 protein from that allele (but can produce CXCR4 from the other allele), which results in the HSC having an increased engraftment and repopulation abilities.

Genomic insertion site: A site of the genome that is targeted for, or has undergone, insertion of an exogenous polynucleotide.

Hematopoietic stem cell (HSC): The stem cells that give rise to all blood cells. Thus, HSCs have the ability to durably generate all blood lineages in vivo. They are present in the umbilical cord, blood, and bone marrow (BM). In some examples, HSCs express CD34. In some examples, HSCs express the following markers:

Mouse HSC: $CD34^{lo/-}$, $SCA-1^+$, $Flt-3^+$, $C-kit^+$, lin−
Human HSC: $CD34^+$, $CD59^+$, $Thy1/CD90^+$, $CD38^{lo/-}$, $C-kit/CD117^+$, lin−

CXCR4 knock down HSC is a recombinant HSC having reduced, but not eliminated, CXCR4 expression and activity, such as a reduction of at least 20%, at least 30%, at least 40%, at least 50%, at least 60%, at least 70%, at least 75%, at least 80%, at least 90%, at least 95%, at least 96%, at least 97%, at least 98%, or at least 99% (such as a decrease of 40% to 60%, 40% to 90%, 40% to 80%, 50% to 90%, or 50% to 95%) as compared to a control (such as a non-recombinant HSC with normal or wild-type CXCR4 expression).

Human Immunodeficiency Virus (HIV). A retrovirus that causes immunosuppression in humans and leads to a disease complex known as acquired immunodeficiency syndrome (AIDS). This immunosuppression results from a progressive depletion and functional impairment of T lymphocytes expressing the CD4 cell surface glycoprotein. The loss of CD4 helper/inducer T cell function may underlie the loss of cellular and humoral immunity leading to the opportunistic infections and malignancies seen in AIDS. HIV subtypes can be identified by particular number, such as HIV-1 and HIV-2.

Increase or Decrease: A statistically significant positive or negative change, respectively, in quantity from a control value. An increase is a positive change, such as an increase at least 50%, at least 100%, at least 200%, at least 300%, at least 400% or at least 500% as compared to the control value. A decrease is a negative change, such as a decrease of at least 20%, at least 25%, at least 50%, at least 75%, at least 80%, at least 90%, at least 95%, at least 98%, at least 99%, or at least 100% decrease as compared to a control value. In some examples the decrease is less than 100%, such as a decrease of no more than 90%, no more than 95% or no more than 99%.

Isolated: An "isolated" biological component (such as an HSC cell, nucleic acid or protein) has been substantially separated, produced apart from, or purified away from other biological components in the cell or tissue of the organism in which the component naturally occurs, such as other cells, chromosomal and extrachromosomal DNA and RNA, and proteins. Nucleic acids and proteins which have been "isolated" include nucleic acids and proteins purified by standard purification methods. The term also embraces nucleic acids and proteins prepared by recombinant expression in a host cell as well as chemically synthesized nucleic acids and proteins. Isolated HSCs in some examples are at least 50% pure, such as at least 75%, at least 80%, at least 90%, at least 95%, at least 98%, or at least 100% pure (that is free from other cell types in the blood or bone marrow).

Mammal: This term includes both human and non-human mammals. Similarly, the term "subject" includes both human and veterinary subjects.

Modulate: A change in the content of genomic DNA gene. Modulation can include, but is not limited to, gene activation (e.g., upregulation), gene repression (e.g., downregulation), gene deletion, polynucleotide insertion, and/or polynucleotide excision.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Pharmaceutically acceptable carriers: The pharmaceutically acceptable carriers useful in this invention are conventional. *Remington's Pharmaceutical Sciences*, by E. W. Martin, Mack Publishing Co., Easton, Pa., 15th Edition (1975), describes compositions and formulations suitable for pharmaceutical delivery of a CXCR4 knock down HSC.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Promoter: A promoter is an array of nucleic acid control sequences which direct transcription of a nucleic acid. A promoter includes necessary nucleic acid sequences near the start site of transcription. A promoter also optionally includes distal enhancer or repressor elements. A "constitutive promoter" is a promoter that is continuously active and is not subject to regulation by external signals or molecules. In contrast, the activity of an "inducible promoter" is regulated by an external signal or molecule (for example, a transcription factor). In one example, the promoter is a U6 promoter or a CMV promoter.

Recombinant or host cell: A cell that has been genetically altered, or is capable of being genetically altered by introduction of an exogenous polynucleotide, such as a recombinant plasmid or vector. Typically, a host cell is a cell in which a vector can be propagated and its DNA expressed. In one example the cell is an HSC. The term also includes any progeny of the subject host cell. It is understood that all progeny may not be identical to the parental cell since there may be mutations that occur during replication. However, such progeny are included when the term "host cell" is used.

RNA interference (RNAi): A post-transcriptional gene silencing mechanism mediated by RNA molecules. Introduction of short RNA molecules into cells (such as double stranded RNA), results in binding of the RNA molecules to other specific messenger RNA (mRNA) molecules and can either increase or decrease their activity, for example by preventing an mRNA from producing a protein. Examples of inhibitory RNA molecules include small interfering RNA (siRNA), micro RNA (miRNA), ribozymes (such as a hammerhead ribozyme, VS ribozyme, or hairpin ribozyme), and antisense molecules. In certain examples, an RNAi molecule is directed against a target gene, such as CXCR4 in an HSC, and is used to increase engraftment of the resulting recombinant CXCR4 knockdown HSC following introduction into a recipient. In some examples, an RNAi molecule is at least about 19 nucleotides (nt), such as at least 20, at least 21, at least 22, at least 23, at least 24, at least 25, at least 26, or at least 27 nt in length.

Selectable marker: A gene introduced into a cell, such as HSCs in culture, which confers a trait suitable for artificial selection from HSCs that do not possess the gene.

Sequence identity/similarity: The similarity between amino acid (or nucleotide) sequences is expressed in terms of the similarity between the sequences, otherwise referred to as sequence identity. Sequence identity is frequently measured in terms of percentage identity (or similarity or homology); the higher the percentage, the more similar the two sequences are.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of protein and nucleic acid sequences known in the art and disclosed herein are typically characterized by possession of at least about 80%, at least 90%, at least 95%, at least 96%, at least 97%, at least 98% or at least 99% sequence identity counted over the full length alignment with the amino acid sequence using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or at least 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Thus, a CXCR4 protein can have at least 80%, at least 85%, at least 90%, at least 91%, at least 92%, at least 95%, at least 96%, at least 97%, at least 98% or at least 99% sequence identity to any of GenBank® Accession Nos. NP_001008540, CAA12166.1, NP_034041.2 and AAH31665.1. Similarly, exemplary CXCR4 nucleic acid sequences in some examples have at least 70%, at least 80%, at least 85%, at least 90%, at least 92%, at least 95%, at least 98%, or at least 99% sequence identity to any of GenBank® Accession Nos. NG_011587.1, AJ224869.1, NM_009911.3 and BC098322.1.

Subject: Any subject that has a vascular system and has hematopoietic cells in the wild-type organism. In one embodiment, the subject is a non-human mammalian subject, such as a monkey or other primate, mouse, rat, rabbit, pig, goat, sheep, dog, cat, horse, or cow. In another embodiment, the subject is a human subject. In some examples, the subject has a genetic disease of the blood (e.g. sickle cell disease, primary immunodeficiency diseases), HIV (such as HIV-1), anemia, or a hematologic malignancy or cancer, such as one of those listed in Table 1.

Therapeutically effective amount: The amount of agent, such as CXCR4 knock down HSCs (which may include one or more other repaired genetic mutations as discussed herein), that is sufficient to prevent, treat, reduce and/or ameliorate the symptoms and/or underlying causes of a disorder or disease. For example, it can be an amount of CXCR4 knock down HSCs sufficient to reconstitute hematopoiesis in a subject receiving the CXCR4 knock down HSCs, such as a subject having genetic disease of the blood (e.g. sickle cell disease, primary immunodeficiency diseases), HW (such as HIV-1), or a hematologic malignancy or cancer, such as one of those listed in Table 1. An effective amount of CXCR4 knock down HSCs can be determined by various methods, including generating an empirical dose-response curve, predicting potency and efficacy by using modeling, and other methods used in the art. In one embodiment, a therapeutically effective amount of CXCR4 knock down HSCs is at least 10,000, at least 20,000, at least 30,000, at least 40,000, at least 50,000, at least 100,000, at least 500,000, at least 1,000,000, at least 2,000,000, at least 3,000,000, at least 4,000,000, at least 5,000,000, at least 10,000,000, at least 20,000,000, at least 25,000,000, or at least 50,000,000 CXCR4 knockdown HSCs. Specific assays for determining the therapeutically effective amount of CXCR4 knock down HSCs are provided herein. For example donor HSC engraftment (e.g., by measuring HSC repopulation) can be measured in the recipient subject.

In one embodiment, an "effective amount" of CXCR4 knockdown HSCs is an amount sufficient to reduce symptoms of a genetic disease of the blood, such as a primary immunodeficiency disease, for example by at least 10%, at least 20%, at least 50%, at least 70%, or at least 90% (as compared to no administration of the CXCR4 knockdown HSCs).

In one embodiment, an "effective amount" of CXCR4 knockdown HSCs is an amount sufficient to reduce symptoms of anemia for example by at least 10%, at least 20%, at least 50%, at least 70%, or at least 90% (as compared to no administration of the CXCR4 knockdown HSCs). In one embodiment, a therapeutically effective amount of CXCR4 knockdown HSCs is an amount of CXCR4 knockdown HSCs sufficient to increase the number of red blood cells in an anemic recipient, wherein such cells are generated from the CXCR4 knockdown HSCs. In some examples the anemia is Fanconi anemia, and the CXCR4 HSCs include a repaired Fanconi anemia gene(s).

In one embodiment, an "effective amount" of CXCR4 knockdown HSCs is an amount sufficient to increase the number of CD4+ T cells in an HIV-infected subject. In one example, an "effective amount" of CXCR4 knockdown HSCs is an amount sufficient to reduce symptoms of HW-1 infection, for example by at least 10%, at least 20%, at least 50%, at least 70%, or at least 90% (as compared to no administration of the CXCR4 knockdown HSCs).

In one embodiment, an "effective amount" of CXCR4 knockdown HSCs is an amount sufficient to reduce the number of abnormal white blood cells in a subject with a hematological malignancy, such as a leukemia. In one embodiment, an "effective amount" of CXCR4 knockdown HSCs is an amount sufficient to reduce the number of abnormal plasma cells in a subject with multiple myeloma. In one example, an "effective amount" of CXCR4 knockdown HSCs is an amount used to treat or reduce the undesirable effects of a lymphoma, such as reduce the size of the lymphoma, volume of the lymphoma, rate of growth of the lymphoma, and/or metastasis of the lymphoma. Such reduction can be at least 10%, at least 20%, at least 50%, at least 70%, or at least 90% (as compared to no administration of the CXCR4 knock down HSCs). In one example, an "effective amount" is an amount of CXCR4 knockdown HSCs sufficient to reduce symptoms of a hematological malignancy, for example by at least 10%, at least 20%, at least 50%, at least 70%, or at least 90% (as compared to no administration of the CXCR4 knockdown HSCs).

The therapeutically effective amount of cells can be dependent on the subject being treated (e.g., the species or size of the subject), the severity of the disease in the recipient subject. In one embodiment, a therapeutically effective amount of CXCR4 knockdown HSCs is an amount of CXCR4 knockdown HSCs sufficient to increase the number of B cells, T cells, monocytes and/or macrophages in the peripheral blood of a recipient, wherein such cells are generated from the CXCR4 knockdown HSCs.

Transduced, Transformed and Transfected: A virus or vector "transduces" a cell when it transfers nucleic acid molecules into a cell, such as an HSC. A cell is "transformed" or "transfected" by a nucleic acid transduced into the cell (such as an HSC) when the nucleic acid becomes stably replicated by the cell, either by incorporation of the nucleic acid into the cellular genome, or by episomal replication.

These terms encompasses all techniques by which a nucleic acid molecule can be introduced into such a cell, including transfection with viral vectors, transformation with plasmid vectors, and introduction of naked DNA by electroporation, lipofection, particle gun acceleration and other methods in the art. In some example the method is a chemical method (e.g., calcium-phosphate transfection), physical method (e.g., electroporation, microinjection, particle bombardment), fusion (e.g., liposomes), receptor-mediated endocytosis (e.g., DNA-protein complexes, viral envelope/capsid-DNA complexes) and biological infection by viruses such as recombinant viruses (Wolff, J. A., ed, *Gene Therapeutics*, Birkhauser, Boston, USA, 1994). In the case of infection by retroviruses, the infecting retrovirus particles are absorbed by the target cells, resulting in reverse transcription of the retroviral RNA genome and integration of the resulting provirus into the cellular DNA. Methods for the introduction of genes into cells are known (e.g., see U.S. Pat. No. 6,110,743). These methods can be used to transduce a HSC to manipulate its genome.

Genetic modification of the target cell is an indicium of successful transfection. "Genetically modified cells" refers to cells whose genotypes have been altered as a result of cellular uptakes of exogenous nucleotide sequence by transfection, transduction, or transformation. A reference to a transfected cell or a genetically modified cell includes both the particular cell into which a vector or polynucleotide is introduced and progeny of that cell.

Transgene: An exogenous gene.

Transplantation: The transfer of a tissue or an organ, or cells (such as HSCs), from one body or part of the body to another body or part of the body. An "allogeneic transplantation" or a "heterologous transplantation" is transplantation from one individual to another, wherein the individuals have genes at one or more loci that are not identical in sequence in the two individuals. An allogeneic transplantation can occur between two individuals of the same species, who differ genetically, or between individuals of two different species. An "autologous transplantation" is a transplantation of a tissue or cells from one location to another in the same individual, or transplantation of a tissue or cells from one individual to another, wherein the two individuals are genetically identical.

Treating, Treatment, and Therapy: Any success or indicia of success in the attenuation or amelioration of an injury, pathology or condition, including any objective or subjective parameter such as abatement, remission, diminishing of symptoms or making the condition more tolerable to the patient, slowing in the rate of degeneration or decline, making the final point of degeneration less debilitating, improving a subject's physical or mental well-being, or prolonging the length of survival. The treatment may be assessed by objective or subjective parameters; including the results of a physical examination, blood and other clinical tests, and the like.

Upregulated: When used in reference to the expression of a molecule, such as a gene or a protein, refers to any process which results in an increase in production of a gene product. A gene product can be RNA (such as mRNA, rRNA, tRNA, and structural RNA) or protein. Therefore, upregulation includes processes that increase transcription of a gene or translation of mRNA and thus increase the presence of proteins or nucleic acids.

Examples of processes that increase transcription include those that increase transcription initiation rate, those that increase transcription elongation rate, those that increase processivity of transcription and those that decrease transcriptional repression. Gene upregulation can include increasing expression above an existing level. Examples of processes that increase translation include those that increase translational initiation, those that increase translational elongation and those that increase mRNA stability. In some examples, a gene editing method, antibody, or other specific binding agent is used to increase expression.

Upregulation includes any detectable increase in the production of a gene product. In certain examples, detectable target protein or nucleic acid expression in a cell (such as a HSC cell) increases by at least 20%, at least 30%, at least 40%, at least 50%, at least 60%, at least 70%, at least 75%, at least 80%, at least 90%, at least 95%, at least 100%, at least 200%, at least 400%, or at least 500% as compared to a control (such an amount of protein or nucleic acid expression detected in a corresponding normal cell or sample). In one example, a control is a relative amount of expression in a normal HSC (e.g., a non-recombinant HSC or an HSC from a healthy or normal subject).

Under conditions sufficient for: A phrase that is used to describe any environment that permits a desired activity. In one example the desired activity is introduction of a nucleic acid molecule into an HSC, for example to reduce expression and activity of CXCR4 in the HSC.

Vector: A nucleic acid molecule into which a foreign nucleic acid molecule can be introduced without disrupting the ability of the vector to replicate and/or integrate in a host cell (such as an HSC). A vector can include nucleic acid sequences that permit it to replicate in a host cell, such as an origin of replication. A vector can also include one or more selectable marker genes and other genetic elements known in the art. An integrating vector is capable of integrating itself into a host nucleic acid. An expression vector is a vector that contains the necessary regulatory sequences to allow transcription and translation of inserted gene or genes. Vectors include plasmid vectors and viral vectors.

In one example the vector is a plasmid vector engineered to target CXCR4 by expressing single guide RNA (sgRNA) under the control of the U6 promoter and contain selection markers of puromycin resistance (e.g., from Genecopoeia, Rockville, Md.). The sgRNA sequences target the Cas9 nuclease enzyme or the D10A mutant of the Cas9 nuclease enzyme known as 'nickase' encoded on a second plasmid to the wild-type or WHIM CXCR4 gene to create a double strand break (DSB) or single strand break (SSB) in the gene, respectively. Donor sequence encoding markers to interrupt CXCR4 can also be incorporated such that a fluorescent molecule such as GFP is inserted into the CXCR4 gene inactivating it or sequences designed to result in the repair of the targeted gene such as the mutant $CXCR4^{WHIM}$ allele or other genes listed in Table 1 can be accomplished at the same time.

In one example a TALEN encoding vector includes the promoter EF-1alpha and the selection marker puromycin (e.g., made by Sidansai Biotechnology, Shanghai, China). Methods to transfect HSC with plasmid DNA are available (e.g., Lonza nucleofector technology, Walkersville, Md.). Other methods to transfect HSC include 3rd generation integration-deficient lentiviral vectors (for example Life Technologies, Gaithersburg, Md.) and Adeno-Associated viral (AAV) vectors (for example Clontech, Moutain View, Calif.).

Overview

Chromothripsis is a recently discovered phenomenon of multiple clustered genetic abnormalities occurring simultaneously. It is estimated to occur in at least 2% of all cancers and occurs with varying frequency in a wide variety of malignancies. This disclosure describes a patient who was born with a congenital immunodeficiency called WHIM syndrome due to a nonsense point mutation in the chemokine receptor CXCR4. As an adult she exhibits phenotypic and genetic evidence of reversion of her immunodeficiency syndrome and she is now a somatic mosaic within the hematopoietic system. Interestingly this appears to be due to a chromothriptic event in a hematopoietic stem cell involving only the chromosomal copy that carried her WHIM mutation allele. Her case demonstrates that chromothripsis may occasionally have beneficial effects and has implications for understanding hematopoietic stem cell development, bone marrow transplantation, and the immune system's control of human papillomavirus infection.

A patient with WHIM syndrome described herein was found to have all the above features of chromothripsis confined to a single copy of chromosome 2 (the location of CXCR4) and associated with loss of the disease allele (and 163 other genes on one copy of chromosome 2) and durable resolution of the clinical manifestations of her disease. The chromothriptic event most probably occurred in a single HSC that engrafted and acquired a selective advantage enabling it to repopulate her bone marrow with cells lacking the disease allele, thus affecting cure. To the inventors' knowledge this is the first chromothripsis event to be described that has a positive medical outcome.

In the course of studying gene(s) critical for the selective advantage in the patient, the inventors discovered that HSC engraftment can be durably enhanced by silencing one copy of CXCR4. In competitive repopulation experiments, deletion of one Cxcr4 allele was sufficient to confer a selective advantage on donor cells when transplanted into a mouse model of WHIM syndrome, phenocopying the patient. Further, Cxcr4 haploinsufficiency also enhanced engraftment of HSCs in wild-type mice.

It is shown herein that the patient in which one copy of CXCR4 had been deleted in a somatic mutation of an HSC, resulted in clonal repopulation of this cell in the bone marrow. In a bone marrow transplantation model in mice, donor cells with a single copy of the Cxcr4 gene repopulate recipient mice much faster and last much longer than donor cells having two copies of the Cxcr4 gene. Based on these observations, provided herein are methods to enhance HSC engraftment, for example in gene therapy protocols and in HSC transplantation. In some examples, this is done in non-conditioned recipients (e.g., subject does not receive radiation or chemotherapy conditioning prior to receiving HSCs as is typically done in a HSC transplant). Methods can be used to reduce CXCR4 expression and activity, for example by using gene editing to specifically delete one copy of the CXCR4 gene in the donor HSCs before HSC transplantation into a recipient (e.g., prior to bone marrow transplantation), enhancing the efficiency and durability of donor HSC repopulation. This concept may also overcome a major hurdle limiting all gene therapy applications, namely that the corrected cell numbers wane with time.

One problem in gene therapy is the short-lived nature of gene-corrected cells. The discovery that hematopoietic stem cells with one copy of the CXCR4 gene have a durable selective advantage in bone marrow repopulation can solve this problem. For example, gene editing methods can be used to delete one copy of CXCR4 gene in gene-corrected cells (though other methods can be used to decrease CXCR4 expression, such as RNAi methods and use of agents that target CXCR4 proteins, such as antibodies or aptamers). As a result, these CXCR4 knocked down HSCs will out-grow the existing recipient cells bearing a disease-causing mutation, which have two copies of the CXCR4 gene putting them at a relative disadvantage.

The disclosed methods in some examples include (1) reducing expression or activity of CXCR4 in a donor HSC, for example by inactivating one copy of CXCR4 in the donor HSC, and (2) introducing (e.g., infusing, administering, transplanting) the CXCR4 knockdown HSCs into a recipient subject (e.g., if the HSC was manipulated ex vivo). Such methods can be used to treat diseases which benefit from improved HSC engraftment. For example, the disclosed methods can be used to improve bone marrow transplants (BMTs). In some examples, subjects need not undergo conditioning traditionally used in BMTs, but engraftment still occurs, thus reducing major side effects. In addition, these methods can be used in combination with manipulating one or more other genes in the donor HSC, for example using genome editing techniques, for controlling HIV and in treating diseases that benefit from gene therapy.

Methods of Enhancing HSC Engraftment

Provided herein are methods enhancing engraftment of donor hematopoietic stem cells (HSCs), for example increasing the efficiency and durability of donor HSC repopulation in a recipient subject. Subjects that can be treated with the disclosed methods include those with a hematopoietic system, such as a mammal, for example a non-human primate (such as an ape or monkey), veterinary subject (such as a cat, dog, mouse, rat, horse, cow, goat, sheep or pig), and humans.

In some examples, engraftment is increased by at least 50%, at least 60%, at least 70%, at least 75%, at least 80%, at least 90%, at least 95%, at least 100%, at least 2-fold, at least 3-fold, at least 4-fold, at least 5-fold, at least 10-fold, at least 20-fold, or at least 30-fold, for example at 30 days, 60 days, 90 days, 120 days, 1 year or 2 years following the HSC transplant. In some examples, enhanced engraftment is indicated by an increase in donor HSC repopulation in the recipient faster than donor HSC with normal CXCR4 expression or activity. For example, the donor HSCs can repopulate at least 50%, at least 60%, at least 70%, at least 75%, at least 80%, at least 90%, at least 95%, at least 100%, at least 2-fold, at least 3-fold, at least 4-fold, at least 5-fold, at least 10-fold, at least 20-fold, or at least 30-fold, faster than donor HSCs with normal CXCR4 expression or activity (e.g., a wild-type HSC), for example at 30 days, 60 days, 90 days, 120 days, 1 year or 2 years following the HSC transplant. In some examples, enhanced engraftment is indicated by donor HSC lasting longer in the recipient than donor HSC with normal CXCR4 expression or activity. For example, the donor HSCs can survive at least 20%, at least 30%, at least 40%, at least 50%, at least 60%, at least 70%, at least 75%, at least 80%, at least 90%, at least 95%, at least 100%, at least 2-fold, at least 3-fold, at least 4-fold, at least 5-fold, at least 10-fold, at least 20-fold, or at least 30-fold longer than donor HSCs with normal CXCR4 expression or activity (e.g., a wild-type HSC), for example at 30 days, 60 days, 90 days, 120 days, 1 year or 2 years following the HSC transplant. In mouse models donor cells can be tracked by virtue of CD45.1 and CD45.2 variants. In humans that receive an allogeneic transplant, the donor chimerism can be tracked using specific common polymorphic genetic variations. In humans that receive an autologous transplant, correction of the genetic defect that is targeted can be determined (e.g., loss of the $CXCR4^{WHIM}$ allele as occurred naturally in the patient).

In particular examples the methods include reducing expression of (e.g., downregulating) CXC chemokine receptor 4 (CXCR4) in a donor HSC, thereby generating a CXCR4 knockdown HSC. For example, expression and/or activity (e.g., function) of CXCR4 can be reduced in the donor HSC by at least 20%, at least 30%, at least 40%, at least 50%, at least 75%, at least 80%, at least 90%, at least 95% or at least 98% (but not 100%, such a reduction of 20% to 50%, 40% to 50%, 20 to 75%, 40% to 60%, or 20% to 90%) in the HSC as compared to expression of CXCR4 in the donor HSC prior to reducing CXCR4 expression and/or activity. In some examples, reducing expression of CXCR4 includes functionally deleting one copy of a CXCR4 allele in the donor HSC. HSCs having reduced CXCR4 activity are referred to herein as CXCR4 knockdown HSCs. In some examples, this downregulation of CXCR4 is done ex vivo, for example after obtaining HSCs from a donor. In other examples, this is done in vivo. The method can further include harvesting or obtaining HSC from a donor subject. For example, HSCs can be obtained from peripheral blood, bone marrow, and umbilical cord blood.

In some examples, donor HSCs are obtained from the recipient subject, and then re-introduced into the recipient subject after they are manipulated (e.g., to downregulate CXCR4), while in other examples donor HSCs are obtained from a subject different from the recipient subject. The disclosure is not limited to specific methods of editing gene expression or activity in a cell, but in some examples gene editing or RNA interference (RNAi) methods are used to manipulate a CXCR4 gene or other CXCR4 nucleic acid in the HSC. In other examples, the CXCR4 protein is targeted, for example with CXCR4 protein antagonists, such as small molecules, antibodies, or aptamers.

The resulting CXCR4 knockdown HSCs are administered or transplanted into a recipient subject in therapeutically effective amounts, thereby increasing HSC engraftment in the recipient subject. In some examples at least $1 \times 10^6$, at least $1 \times 10^7$, or at least $1 \times 10^8$ CXCR4 knockdown HSCs are administered to the subject. Any method of administration can be used that allows proper function of the HSCs in vivo (for example, allows the CXCR4 knockdown HSCs to reach the bone marrow), such as by injection of the CXCR4 knockdown HSCs into the subject, such as by intravenous administration. In some examples, the recipient subject has not received conditioning prior to administering the CXCR4 knockdown HSCs to the recipient subject, such as chemotherapy and/or total body irradiation which is typically used prior to bone marrow transplantation.

In some examples, the methods further include manipulating one or more other genes (such as correcting a mutation and/or altering its expression) in the CXCR4 knockdown HSCs, wherein the resulting HSCs are used to treat a disease or disorder in the subject related to the gene that is manipulated. For example, manipulating one or more other genes in the donor HSC can include one or more of correcting a genetic defect in the HSC, wherein the genetic defect causes a disease in the recipient subject; reducing expression of a first target gene in the HSC, wherein reducing expression of the first target gene treats a disease caused by upregulation of the first target gene in the recipient subject or treats a disease that benefits from reducing expression of the first target gene in the recipient subject; and increasing expression of a second target gene in the HSC, wherein increasing expression of the second target gene treats a disease caused by downregulation of the second target gene in the recipient subject or treats a disease that benefits from increasing expression of the second target gene in the recipient subject. Examples of genetic defects that can be fixed or corrected in the HSC include one or more of nucleotide point mutations, nucleotide deletions, nucleotide insertions, gene rearrangements, gene deletions, and gene insertions.

In some examples, manipulation of CXCR4 expression in the HSC and manipulation of one or more other genes is performed at the same time, such as by using gene editing methods or RNAi methods. In other examples, the donor HSC is first manipulated to decrease CXCR4 expression/activity, and then the donor HSC is manipulated to correct a mutation and/or alter expression of one or more other genes (or vice versa). Thus, a CXCR4 knockdown HSC can include other genetic alterations.

In some examples, the method is a method of treating a disease or disorder in the subject. In one example, CXCR4 knockdown HSCs (such as allogeneic HSCs) are administered to a subject to treat a hematologic malignancy, such as a leukemia, lymphoma, or myeloma (including those listed in Table 1). In some examples, administration of CXCR4 knockdown HSCs not only enhances HSC engraftment, but results in a graft vs. tumor effect, thereby treating the hematologic malignancy.

In some examples, CXCR4 knockdown HSCs (such as autologous HSCs) include other genetic manipulations, which can be used to treat a disorder associated with a genetic mutation or a disorder that would benefit from upregulation a target gene or from downregulation of a target gene. The use of autologous HSCs can reduce or eliminate a graft vs. host disease effect.

For example, CXCR4 knockdown HSCs (such as autologous HSCs) that include other genetic manipulations can be used to treat a hematologic malignancy, such as one that results from a genetic mutation (e.g., chronic myelogenous leukemia wherein a BCR-ABL fusion gene is repaired or silenced in the donor HSC), HIV-1 (wherein expression of CCR5 is reduced in the donor HSC), anemia, and a genetic disease of the blood, such as any of sickle cell anemia, hemophilia A, hemophilia B, alpha-thalassemia, beta-thalassemia, delta-thalassemia, von Willebrand Disease, pernicious anemia, Fanconi anemia, thrombocytopenic purpura, thrombophilia, or a primary immunodeficiency disease. For example, if the subject has sickle cell anemia, the genetic defect that is repaired in the donor HSC is a Glu to Val mutation in amino acid 6 of a β-globin chain of hemoglobin. For example, if the subject has hemophilia A, the genetic defect that is repaired in the donor HSC can be a mutation in clotting factor VIII. For example, if the subject has hemophilia B, the genetic defect that is repaired in the donor HSC can be a mutation in clotting factor IX. For example, if the subject has thrombocytopenic purpura, the genetic defect that is repaired in the donor HSC can be a mutation in ADAMTS13. For example, if the subject has thrombophilia, the genetic defect that is repaired in the donor HSC can be a mutation in factor V Leiden or prothrombin. Other exemplary diseases and mutations are provided in Table 1 below. However, the disclosure is not limited to particular diseases or mutations, as one skilled in the art will appreciate that based on the teaching provided herein, any genetic disease of the blood or any primary immunodeficiency disease that is due to a particular genetic mutation, can be treated with the disclosed methods.

I. Obtaining HSCs

HSCs can be harvested from the umbilical cord, blood, and/or bone marrow. In some examples, the HSCs are obtained from the same subject to be treated (autologous, the donor and recipient are the same person). In other examples, the HSCs are obtained from a subject different from the one to be treated (allogeneic, the donor and recipient are different individuals, or syngeneic, the donor and recipient are identical twins). Generally, hematopoietic progenitors present at a frequency of 0.05-0.2% among peripheral blood mononuclear cells (PBMCs), 0.1-0.5% among cord blood mononuclear cells (MNCs) or 0.5-3% among bone marrow MNCs.

The resulting HSCs are used to generate CXCR4 knock down HSCs (which can include further genetic manipulations to treat a disease). The population of HSCs used to generate the CXCR4 knock down HSCs, and the CXCR4 knock down HSCs administered to a subject, do not need to be 100% pure; lower amounts of purity are acceptable. For example, a population of cells that contains at least 50%, at least 60%, at least 70%, at least 80%, at least 90%, at least 95%, or at least 99% HSCs or CXCR4 knock down HSCs can be used. In some examples, unpurified HSCs are used, such as by using the bone marrow (or PBMCs) directly from the donor, without isolating the HSCs from the bone marrow (or PBMCs).

A. Bone Marrow

For example, HSC can be obtained from the bone marrow (BM) of the pelvis or femur using a needle and syringe. In addition to HSCs, BM contains other cells including stromal cells, stromal stem cells, blood progenitor cells, and mature and maturing white and red blood cells. The resulting BM sample can then be used to isolate HSCs.

B. Peripheral Blood

To obtain stem cells from the circulating peripheral blood, donor subjects are injected with a cytokine, such as granulocyte colony-stimulating factor (G-CSF), to induce cells to leave the bone marrow and circulate in the blood vessels. For example, the donor can be injected with G-CSF alone or in combination with a CXCR4 inhibitor (e.g., plerixafor) before the cell harvest. In one example, G-CSF (e.g., 10 µg/kg) is administered subcutaneously to donor subjects daily for four days and on the fifth day in addition to G-CSF, a CXCR4 inhibitor (e.g., plerixafor) (e.g., 240 µg/kg) is administered subcutaneously. A mobilized peripheral blood stem cell (PBSC) concentrate can then be collected by leukapheresis on day 5 twelve hours after the administration of plerixafor and 2 hours after the last dose of G-CSF. In another example, G-CSF (e.g., 10 µg/kg) is administered subcutaneously to donor subjects daily for five days and a mobilized PBSC concentrate can then be collected by leukapheresis on day 5. The PBSCs express CD34 and/or CD133. In one example, the method of Bloan et al. is used to obtain PBMCs (Br. J. Haematol. 120:801-7, 2003).

The resulting PBSC sample is used to isolate HSCs.

1. PBSCs Collected by Apheresis without CD34 Selection

Donor stem cell mobilization with G-CSF can be performed as follows. After medical evaluation and clearance for suitability as an autologous or allogeneic donor, donors undergo mobilization with G-CSF (e.g., filgrastim, Neupogen, Amgen). The G-CSF can be administered in a dose of approximately 10-12 ug/kg/day for 5-6 days, subcutaneously. The doses for days 1-4 may be given at any time of day, but the doses for day 5 and if necessary, day 6 is given early in the morning, at least one hour and preferably two hours prior to starting apheresis. Side effects of G-CSF, including headache, bone pain, and myalgia, can be treated with acetaminophen or ibuprofen. G-CSF can be administered according to a vial-based algorithm to reduce wastage and increase the G-CSF dose given to lighter weight donors to improve CD34 yields as shown below:

| Donor Wt | Total GCSF Dose (range) |
| --- | --- |
| 38-60 kg | 600 mcg (10.0 to 15.8 mcg/kg) |
| 61-78 kg | 780 mcg (10.0 to 12.8 mcg/kg) |
| 79-90 kg | 900 mcg (10.0 to 11.4 mcg/kg) |
| 91-96 kg | 960 mcg (10.0 to 10.5 mcg/kg) |
| 97-108 kg | 1080 mcg (10.0 to 11.0 mcg/kg) |
| >109 kg | 1200 mcg (<11.0 mcg/kg) |

Peripheral blood stem cell (PBSC) collection is then performed. An optimum $CD34^+$ HSC dose to be collected by apheresis is $>5\times10^6$/kg. The minimum $CD34^+$ HSC dose that is recovered in order to proceed with further therapy is $\sim3\times10^6$/kg. Donors can receive prophylactic continuous intravenous calcium chloride infusions to prevent citrate toxicity during apheresis. The volume processed per apheresis procedure can be determined by medical staff on the day of apheresis, based on peak $CD34^+$ HSC cell mobilization response to G-CSF, optimum and minimum $CD34^+$ HSC cell dose needed, and kilogram weight of recipient. Volume of blood processed can range from 12 to 30 liters per procedure for 1 to 2 consecutive daily procedures, not to exceed a total of 60 liters over 2 days. In pediatric subjects, defined as less than 40 kg, a maximum of 8 blood volumes will be processed per procedure, for up to 2 consecutive daily procedures.

In children less than 18 kg undergoing autologous leukapheresis procedures, three additional considerations apply. A central venous double-lumen catheter can be used for apheresis. It may be necessary to "prime" the apheresis instrument with a unit of allogeneic red cells, due to the fact that the volume of blood in the device during apheresis will exceed the safe extracorporeal volume (SEV) allowed for the patient. The SEV is generally about 15% of circulating blood volume or 10.5 mL/kg. In extremely small children (less than 16 kg), it may not be possible to use citrate anticoagulant without risk of severe citrate toxicity, thus, systemic heparinization can be used during apheresis.

2. PBSCs Collected by Apheresis with CD34 Selection

GCSF is administered as described above, except at the following dosage:

| Donor Wt | Total GCSF Dose (range) |
| --- | --- |
| 38-48 kg | 600 mcg (12.5 to 15.8 mcg/kg) |
| 49-56 kg | 780 mcg (13.9 to 15.9 mcg/kg) |
| 57-60 kg | 900 mcg (15.0 to 15.8 mcg/kg) |
| 61-67 kg | 960 mcg (14.3 to 15.7 mcg/kg) |
| 68-108 kg | 1080 mcg (10.0 to 15.9 mcg/kg) |
| ≥109 kg | 1200 mcg (≤11.0 mcg/kg) |

PBMC donors can receive prophylactic continuous intravenous calcium chloride infusions. The target (or "optimum") $CD34^+$ HSC dose recovered after CD34 selection of the apheresis component is $>5\times10^6$/kg. The minimum post-selection $CD34^+$ HSC dose recovered in order to proceed with further therapy is $\sim3\times10^6$/kg. Since approximately 60% of the $CD34^+$ HSC cells in the apheresis product are recovered following $CD34^+$ HSC cell selection, the targeted $CD34^+$ HSC dose to be collected by apheresis is $5/0.6=8\times10^6$/kg. The volume processed per apheresis procedure will be determined by medical staff on the day of apheresis, based on peak $CD34^+$ HSC cell mobilization response to G-CSF, optimum and minimum $CD34^+$ HSC cell dose needed, and kilogram weight of recipient. Volume processed will range can 12 to 30 liters per procedure for 1 to 2 consecutive daily procedures, not to exceed a total of 60 liters over 2 days. In pediatric subjects (less than 40 kg), a maximum of 8 blood volumes will be processed per procedure, for up to 2 consecutive daily procedures. The same pediatric considerations discussed above apply.

3. Pediatric Apheresis in Subjects≤20 kg: Unstimulated Mononuclear Cell (MNC) and Stimulated Peripheral Blood Stem Cell (PBSC) Collection on the COBE® Spectra Safe extracorporeal volume is defined as less than or equal to 15% of intravascular volume. Intravascular volume is defined as: 80 mL/kg for children who weigh≤20 kg and 75 mL/kg for children who weigh>20 to ≤40 kg. Extracorporeal volume in the COBE® Spectra Apheresis System is 285 mL. This can vary further depending on the number of leukocytes targeted for collection and the subject's hemoglobin and WBC count. In general, safe extracorporeal volume is exceeded with use of Spectra when the weight is less than 20 kg. Since it is not acceptable to administer a red blood cell prime for research purposes, the NIH Department of Transfusion Medicine (DTM) does not collect cells for research use in children less than 20 kg.

Citrate is the routine anticoagulant used in apheresis procedures. This method uses continuous intravenous calcium and magnesium replacement in all subjects less than 40 kg undergoing more than 2 blood volumes processed. No adverse events related to divalent cation replacement have occurred with use of the Alaris Guardrail Continuous IV Monitoring System. Citrate may safely be used as the sole anticoagulant in subjects as small as 18-20 kg; below this, the citrate mg/kg infusion rate exceeds a safe level. The acceptable range of citrate infusion rates in DTM is 1.2-3.5 mg/kg/min. Heparin is generally required in subjects less than 18-20 kg. For such patients, full systemic heparinization is used, in addition to a reduced amount of citrate. Since heparin causes systemic anticoagulation and carries additional risk, DTM does not collect cells for research in children less than 20 kg.

The inlet whole blood flow rate (WBFR) for Spectra is defined as the: AC Pump Rate (mL/min)×(Inlet:AC Ratio). In this calculation, for subjects≤20 kg, the default citrate infusion rate (CIR) is 2.5 mg/kg/min. The CIR may be increased up to 3.5 mg/kg/min. For subjects≤20 kg, the default Inlet:AC ratio is 25:1. The Inlet:AC ratio may be set at 20:1, 25:1, or 30:1.

Threshold CBC values are the same in children and in adults, and are based on worst case scenarios, such as machine malfunction with inability to return the blood in the machine to the donor. Minimum hematocrit is 28%, minimum platelet count 10,000/uL (50,000 for research procedures), and minimum WBC count 2000/uL.

When MNC is selected on the COBE® Spectra Apheresis System, the program will set up with a specific separation factor that is a measure of the centrifugal force to which the blood is exposed. Gambro BCT recommends a MNC separation factor of 500 g-minutes for MNC collection. This is the product of the centrifugal force and the length of time a blood element entering the channels is subjected to this force.

| WBC Disposable Tubing Set Fluid Volumes | |
|---|---|
| Disposable tubing set volume | 285 mL |
| Total equivalent whole blood volume | 285 mL |
| Total RBC volume | 114 mL |
| Residual RBC volume | 24 mL |
| Rinseback (total) | 413 mL Normal Saline |
| Rinseback (net return to patient) | 263 mL Normal saline |
| Prime Divert | 150 mL Normal Saline |

Preparation of the COBE® Spectra Apheresis System

1. Power the machine on.
2. Ensure that single-stage filler is in the centrifuge. Tube the Spectra following manufacturer's guidelines. See the COBE®Spectra Apheresis System Operator's Manual (Terumo BCT).
3. When the Set Selection screen appears on the operator interface screen, select 3=WBC. The WBC procedure section screen will then appear, select 1=MNC.
4. If performing blood prime, follow steps in Appendix (below), from this point.

If not performing blood prime, proceed with below procedural steps.

5. Prime the Spectra with 0.9% normal Saline following manufacturer's guidelines.
6. Perform the alarm tests following manufacturer's guidelines.
7. Enter the patient/procedure data as prompted on the operator screen (gender, height, weight, patient's hematocrit).
8. Press YES to accept the target end results or NO to change the target end results (Inlet Volume, Inlet pump flow rate, Run time or Collect volume) as ordered by the physician and continue with "Connecting the Patient". See the COBE®Spectra Apheresis System Operator's Manual (Terumo BCT).to change patient/procedure data.
9. After prime, the procedure is started within 4 hours or the disposable kit is discarded.

Preparing the Patient/Donor for Procedure

1. Identify the patient/donor.
2. Check the patient/donor BP, pulse and temperature to ensure they are within the patient's normal limits.
3. Establish venous access.
4. Draw pre-lab samples if ordered by the DTM or primary care physician.

Labeling the Product Bag(s)

At the time of collection of blood (or components) and at the time of preparation of components, a label will be placed on each container.

To obtain the amount of AC in the collection bag for recording on transfusable product labels: press the MENU button on the operator interface screen; select 1=Data Entry; select 4=AC Data; and record the number of mL in the Collect field on the product label.

Starting the Procedure

1. Anticoagulation with ACD-A

The inlet flow rate for Spectra is=AC Pump Rate (mL/min)×(Inlet:AC Ratio). For subjects≤20 kg, the default Inlet:AC Ratio is set at 25:1. On Spectra, the true whole blood flow rate is the inlet flow rate minus the ACDA infusion rate The citrate infusion rate (CIR) in subjects>20 kg may range from 2.5 to 3.5 mg/kg/min, per MD order. The maximum allowable CIR will determine the AC pump rate. For subjects≤20 kg, the default citrate infusion rate is 2.5 mg/kg/min 2. Anticoagulation with Heparin Loading Dose: Heparin (50 U/kg) bolus IV push into return line, administer ordered dose immediately before attaching patient to the machine. If a red cell prime is used, the heparin should be given prior to the infusion of the red cell prime. Maintenance dose: Heparin (20 U/kg) IV push into draw/access line; administer ordered dose every 60 minutes, starting exactly one hour after administration of the loading dose.

3. If calcium chloride and magnesium sulfate intravenous replacement solutions are ordered, follow DTM SOP: 2401 Prophylactic Calcium Infusion and DTM SOP: 2402 Prophylactic Magnesium Sulfate Infusion for set up and dosing.
4. Return line: Attach a 4-way stop-cock to end of return line of Spectra tubing. Connect the calcium IV line to a port of the 4-way stop-cock and prime. Connect the magnesium IV line to the remaining port of the 4-way stop-cock and prime. Attach a Braun Extension Set to the proximal port of the 4-way stopcock and prime.
5. Draw line: Attach a 3-way stop-cock to the end of the draw line. Attach a Braun Extension Set to the proximal port of the 3-way stopcock and prime.
6. Follow the guidelines for "Connecting the Patient" in the COBE®Spectra Apheresis System Operator's Manual (Terumo BCT).
7. When prompted by Spectra, press Continue at the prompt for Diverting prime saline. (150 mL of NS will be diverted to the waste bag). The prime may be given at the direction of the DTM physician.
8. Spectra will prompt: Close return line saline. Press Clear.
9. Initiate calcium and magnesium infusions at the end of divert prime as the blood begins to return to the patient.
10. Monitor the patient/donor's temperature, BP and pulse at the beginning and end of the procedure and as needed.
11. Monitor and record fluid volumes for the Spectra's operators screen with each change or approximately every 15-30 minutes.

Quick Start

Quick Start is an automated method to establish the interface in WBC procedures. The Plasma pump will automatically change to position the interface. An accurate patient/donor hematocrit is required to properly establish the interface. To exit Quick Start, change the plasma pump flow rate or press the Manual button twice. After Quick Start is complete, the collect valve moves to the open position. Quick Start is completed after the system processes 200 mL of RBC.

Interface Control

To maintain interface once it is established or to refine positioning at the end of Quick Start:

Monitor the collect line hematocrit as it exits the centrifuge using the Colorgram™

View the WBC collect tube (WBC out) through the port in the centrifuge door. If the WBC collect tube fills with RBC, the collection is too deep into the RBC or WBC layer→decrease the plasma pump flow rate in larger increments (1.0-3.0 mL/min) If the WBC collect tube is clear without RBC present, the collection is not deep enough into the RBC layer→increase the plasma pump flow rate in larger increments (1.0-3.0 mL/min)

Make small incremental changes in the plasma pump flow rate (0.5-1.0 mL/min)

Allow 3-5 minutes between changes in the plasma pump flow rate

Interface is correct when the RBC layer is halfway up the channel, streaks of RBC are visible in the collect line, and the collect line exiting the centrifuge is at the desired hematocrit based on the Colorgram.

Colorgram™

The WBC Colorgram™ assists in determining the hematocrit of the product in the collect line. Insert the Colorgram™ under the smallest clear collect line where it exits the centrifuge. Compare the colored rectangles on the Colorgram™ to the color of the collect line. The hematocrit in the collect line, when compared against the Colorgram™ chart, should be maintained at 1-4% (such as 2-4%) for an MNC collection. Collecting light (1-2%) results in more platelets in the product. Collecting dark (4-5%) results in more granulocytes and RBC in the product. Adjust the plasma pump flow rate to adjust the hematocrit. See section 7.7 in the COBE®Spectra Apheresis System Operator's Manual (Terumo BCT).for additional information.

Collect Pump Flow Rate

For MNC procedures, the Collect Flow Rate (CFR) defaults to 1.0 mL/min. The CFR generally varies between 0.8 and 1.5 mL/min which is the CFR recommended by the manufacturer to minimize cross cellular contamination. The CFR will be adjusted depending on the WBC count. The CFR cannot be changed during Quick Start (See above for information on Quick Start). CBC results may be obtained from Cell Processing Laboratory on the pre-apheresis tube.

| WBC | CFR | Colorgram ™ HCT Unstimulated Donor | Colorgram ™ HCT Stimulated Donor |
| --- | --- | --- | --- |
| 1000-10,000 | 0.8-1.0 | 1-2% | 3-4% |
| 10,000-25,000 | 1.0-1.3 | 1-2% | 3-4% |
| >25,000 | 1.3-2 | 1-2% | 3-4% |

Configuration of MNC Inlet:AC Ratio

The manufacturer's default Inlet:AC ratio for MNC procedures is 12:1. The default AC infusion rate is 0.8 mL/min/L of TBV. The AC infusion rate may be increased to 1.2 mL/min/L of TBV without operator override. Change the Inlet:AC to 25:1 if systemic heparinization is used. It is at physician discretion to order ratio's of 20:1, 25:1, or 30:1. See the COBE® Spectra Apheresis System Operator's Manual (Terumo BCT).for guidance though the operator interface screen. See SOP 2401 *Prophylactic Calcium Infusion* for calcium infusion guidelines.

The presence of cloudy, clumped light colored cells in the collect line and in the line entering the product bag may indicate platelet clumping and the need to decrease the AC ratio. The intermittent loss of a stable optimal interface during the procedure may indicate platelet clumping and that a clump has pushed through the collect line. This may require a decrease in the AC ratio.

Adding ACD-A to the Product

Using aseptic technique, add 15 ml of ACD-A to the collection bag after the first 150 mL of product has been collected. This is done to prevent clumping.

Plasma Collection during WBC Procedures

Plasma may be collected during a WBC procedure in the automatic mode. Plasma collection will not begin until Quick Start has completed. To enter the desired amount of plasma to be collected, use the Target Plasma key to enter the volume. The plasma will be collected at the rate the Plasma pump has been set to minimize disruption of the interface, however, the manufacturer recommends collecting the plasma at the end of the procedure as plasma collection may cause temporary interface instability. The Plasma valve will automatically close when the desired amount has been collected. The plasma collection may be started at any time during the procedure. If no plasma is to be collected, close the plasma line of the WBC set before starting prime.

Configuration of MNC End Point

The manufacturer's default end point for MNC procedures is 2.0×TBV. The endpoint maybe configured to: Specific run time, Specific volume of blood (inlet volume) to process, multiple of the donor/patient total blood volume. See COBE® Spectra Apheresis System Operator's Manual (TerumoBCT) for guidance in setting these endpoints though the operator interface screen.

Pausing and Restarting the Procedure

If the procedure is paused, the centrifuge may not spin longer than 10 minutes. Allow the centrifuge to automatically stop after 10 minutes. While in Pause, if the centrifuge is allowed to continue to spin, there is potential for hemolysis to the cells. The centrifuge can remain off for a maximum of 60 minutes. If the centrifuge is restarted, drainage of the tubing is required as described below. Opening the normal saline from the draw and return lines drains only approximately 3 inches of non-anticoagulated tubing between the apheresis kit and the donor connection. Complete drainage of the tubing is also required because there are no filters on the tubing below the return filter therefore, the pumps must be running to move blood sitting below the return filter out of the system. There is 1 mL of blood in every 6 inches of apheresis kit tubing. The operator will determine the amount of drainage required based on possible visible clots seen and whole blood flow rate speed while draining the tubing.

If the centrifuge is off less than 60 minutes and the procedure is able to be restarted, drain the draw and return line tubing as described below.

1. Clamp the donor's IV access.
2. Disconnect donor's draw line and open access NS roller-clamp.
3. Allow fluid to run into MPW bag until no visible clots are seen.
4. Close access NS roller-clamp.
5. Reconnect access tubing to donor's IV access, keeping the draw line clamped.
6. Clamp the return line.
7. Disconnect return line and open return NS roller-clamp.

8. Allow fluid to run into MPW bag until no visible clots are seen.
9. Close return NS roller-clamp.
10. Open draw line NS roller-clamp
11. Keeping return line over MPW box, restart procedure and allow fluid to drain until no visible clots are seen. (Rationale: The NS will serve as donor access fluid. The movement of the machine pumps will push the fluid below the return filter line out of the system for drainage. This will ensure that all possible clots are removed from the system.)
12. Close access NS roller-clamp.
13. Reconnect the donor return tubing and unclamp.
14. Unclamp donor's draw line.
15. Continue procedure. (Note: NS that was used as the donor access fluid during flushing may dilute the apheresis circuit. It may take a few more minutes to set the interface.)

If the centrifuge is off for greater than 60 minutes, drain the draw and return line tubing as described in Section above and then proceed below.

1. Begin Rinseback following manufacturer's guidelines.
2. Remove the product from the apheresis set and add anticoagulant if indicated.
3. When Rinseback is complete, disconnect the donor from the apheresis kit.
4. If the procedure is to be restarted, keep venous access open with normal saline and set up and prime a new apheresis kit.

Ending the Procedure

The Run mode continues until the target end results are reached. To end the Run, press 1=Rinseback and follow the prompts on the operator interface screen. If a red cell prime is used, DO NOT infuse the rinseback. To continue the Run, press 2=Continue run and increase the flashing target limits as directed on the operator interface screen. When a Functionally Closed WBC disposable set is in use and the inlet flow is >50 mL\min, change the inlet flow to 50 mL\min to avoid ACCESS PRESSURE LOW alarms during Rinseback. Change the flow rate before starting Rinseback.

Disconnect the patient line from the patients' access using Nursing SOP/PRO: Venous Access Devices, Care and Maintenance of Central or remove the antecubital IVs, apply direct pressure until bleeding has stopped then apply a pressure dressing. Repeat and document vital signs, including temperature, blood pressure and pulse in procedures where 5 L or greater of volume is processed or as indicated. Record Final values from the operator interface screen on the Apheresis Procedure Record. Complete the product label if the collection will be used for transfusion. Remove the procedural kit in the reverse order used to set it up. Dispose of all blood contaminated waste in the MPW container. Clean any spills.

Calculation of Net Fluid Balance

Subtract the fluid removed from the fluid infused.

Fluids IN: Rinseback+Prime (optional)+Calcium infusion (optional)+Magnesium infusion (optional)+Fluid Bolus+AC Fluids OUT: Product Removed (cells+plasma)+pre-apheresis tube samples Appendix 1. Using the 600 mL transfer bag, sterile connect the needle adapter (from the Plasma transfer set with spike) to replace the spike adapter attached to the transfer bag
2. Verify that the patient's Typenex bracelet is in place. Verify that the patient's inpatient ID bracelet is in place or that patient has a outpatient ID card
3. Obtain patient's pre-procedure vital signs.
4. Pre-medicate if ordered by physician.
5. Establish IV access
6. Draw pre-lab samples if ordered.
7. Prime IV NS lines with 4-way stop-cock and extension tubing and attach to IV Access and Return lines
8. Administer NS at KVO infusion rate via Alaris pump to both lumens of CVAD or peripheral access
9. Prime the Spectra with 0.9% Normal Saline following manufacturer's guidelines.
10. Attach a 3-way stop-cock to end of return and access line of Spectra tubing and prime.
11. Perform the alarm tests following manufacturer's guidelines.
12. Enter the patient/procedure data as prompted on the operator screen (gender, height, weight, and patient's hematocrit)
13. Press YES to accept the target end results or NO to change the target end results (Inlet Volume, Inlet pump flow rate, Run time or Collect volume) as ordered by the DTM physician and continue with "Connecting the Patient". See the COBE® *Spectra Apheresis System Cell Therapy Guide* to change patient/procedure data.
14. Obtain PRBC unit from Transfusion Services Laboratory (TSL)
15. Perform blood administration clerical checks on all units to be infused per NIH CC SOP: Blood Product Administration. In addition, visually compare the Typenex Barcode number on blood component tag with the number embossed on the Typenex barcode band; visually compare ABO compatibility on unit; visually inspect expiration date has not exceeded on unit; visually inspect the interpretation of crossmatch is performed on unit; visually inspect appearance of unit to ensure they appear normal; and after the clerical checks are complete, the unit must be secured and may not leave the bedside.
16. Prime Blood Product IV Administration Set with Saline
17. When prompted by Spectra to Connect Access and Return Lines, Connect Blood Product IV Administration Set to Spectra Access Line via 3-way stop-cock
18. Attach Spectra return line to empty transfer bag via 3-way stopcock
19. Close roller clamps on Spectra access and return saline lines.
20. Open pinch clamps on the Spectra access and return lines.
21. Open roller clamp on the Blood Product IV Administration Set. Spectra Saline drip not necessary during blood prime as patient is not connected at this time.
22. Launch CareFusion Verification Application (Not Rapid Infusion)
23. Log in using valid User ID and Password
24. Scan patient ID and request patient to state first/last name and DOB to confirm identity. Scan product's donation ID number (upper left corner of the product's labeling system). Scan product Code (lower left corner of the product's labeling system).
25. Select the type of administration set to be used (gravity, infusion pump, apheresis)
26. Record vital signs (temperature, pulse, respirations, blood pressure)
27. Enter desired initial infusion rate. Per WBFR guidance on Pediatric Large-Volume Leukapheresis Worksheet, use the following calculation to enter Carefusion documentation of ml/hr. WBFR=0; Note: Start of collection rate=0 as transfusion is not yet running.
28. Complete the pre-transfusion checklist 29. Utilizing the unused spike, spike Blood Product IV Administration Set with PRBC 30. Press continue on Spectra machine. The Spectra draws blood from the PRBC unit into the extracorporeal circuit. The following information will display on the Spectra screen: Diverting Prime Saline.

a. To decrease processing time for the PRBC unit, increase AC ratio to 50:1. This will increase your inlet flow rate.

31. Post Spectra Saline Prime Divert and Valve Position Check, Spectra display screen will advise to close return saline and press clear.

32. Continue to process the PRBC Unit. If PRBC undiluted, process entire unit. If PRBC diluted, process 300 mL to 500 mL. As volume processed increases, effects of dilution decreases 33. Continue performing the blood prime (in the run mode) until the leukoreduced PRBC unit begin entering the transfer pack from the return line and the inlet and return lines are approximately the same color.

34. When PRBC unit processed, Press pause on Spectra machine

35. Close pinch clamps to access and return lines

36. Using aseptic technique, disconnect PRBC Unit, transfer bag and 3-way stop-cocks from Spectra access and return lines. Cap the access and return lines with female leur adapter for safety and aseptic environment maintenance.

37. Record all values from the Spectra machine

38. Add inlet processed during blood prime to the target inlet volume

39. If the AC ratio was increased, change it back to desired AC ratio

40. In Data Entry, Change HCT back to patients HCT

41. Administer Heparin Loading Dose per order via bolus IV push into return line.

42. Flush with approximately 10 mL NS from KVO-NS bag

43. Connect Spectra access and return lines to patient

44. Open pinch clamps on Spectra access and return lines

45. Press CONTINUE on Spectra machine

46. Begin the transfusion as soon as you receive a "Match confirmation" message

47. Select close

48. If calcium chloride and magnesium sulfate intravenous replacement solutions are ordered, attach medications to available 4-way stopcocks to return line and follow DTM SOP: 2401 Prophylactic Calcium Infusion and DTM SOP: 2402 Prophylactic Magnesium Sulfate Infusion for set up and dosing and per Pediatric Large-Volume Leukapheresis Worksheet orders.

49. (If applicable) After initial 15 minutes: Launch CareFusion Transfusion Verification application 50. Log in using valid User ID and Password 51. Scan patient ID 52. Click on the individual order of the transfusing product (showing blue) to show the transfusion activities hyperlink 53. Click transfusion activities 54. Select vitals menu and add, and enter vital signs as prompted 55. Enter new infusion rate: WBFR×60=mL/hr 56. Select close 57. When the Inlet Volume processed has doubled from the prime volume processed, COMPLETE the transfusion via Carefusion.

58. Launch TV application and login using valid User ID and Password

59. Scan patient ID

60. Select transfusing blood component (showing blue) to show transfusion activities 61. Click transfusion activities 62. Click on Complete button 63. Record vital signs as prompted 64. Enter ending infusion rate as ("0")

65. Enter total volume PRBC infused

66. Select close

67. Exit Carefusion system

68. Continue processing MNC procedure

Upon attempt to transfuse a red cell unit, the Carefusion system will issue an alert if the red cell units are not started within 30 minutes of issue. Select override reason, "Other/DTM Physician Authorized" and proceed. Upon attempt to complete a red cell unit, the Carefusion system will issue an alert if the red cell unit is not completed within 4 hours of issue. If this time has been exceeded, you must stop the transfusion and seek DTM Physician approval to continue the transfusion. If approval via DTM Physician given, select override reason, "Other/DTM Physician Authorized" and proceed.

Carefusion: Stopping/Re-starting a Transfusion

For interruption of transfusion

1. Launch TV application and login as usual
2. Scan patient ID
3. Select transfusing blood component (showing blue)
4. Select STOP and document rationale
5. Select close
6. If and when ready to restart, launch TV as usual
7. Scan product donation ID number and Product code
8. Enter vital signs
9. Enter infusion rate
10. Select close 4. Mononuclear Cell (MNC) and Peripheral Blood Stem Cell (PBSC) Collection on the COBE® Spectra When MNC is selected on the COBE® Spectra Apheresis System, the program will set up with a specific separation factor that is a measure of the centrifugal force to which the blood is exposed. Terumo BCT recommends a MNC separation factor of 500 g-minutes for MNC collection. This is the product of the centrifugal force and the length of time a blood element entering the channels is subjected to this force.

WBC Disposable Tubing Set Fluid Volumes are as in the section above.

Preparation of the COBE® Spectra Apheresis System.

1. Power the machine on.
2. Ensure that single-stage filler is in the centrifuge.
3. Tube the Spectra following manufacturer's guidelines (See the COBE® Spectra Apheresis Cell Therapy Guide).
4. When the Set Selection screen appears on the operator interface screen, select 3=WBC. The WBC procedure section screen will then appear, select 1=MNC.
5. Prime the Spectra with 0.9% Saline following manufacturer's guidelines.
6. Optional: Attach a 4-way stop-cock to end of draw line of Spectra tubing and prime. This step is at the nurses discretion for lab draws and line flushes, as needed.
7. Perform the alarm tests following manufacturer's guidelines.
8. Enter the patient/procedure data as prompted on the operator screen (gender, height, weight, patient's hematocrit).
9. Press "YES" to accept the target end results or "NO" to change the target end results (Inlet Volume, Inlet pump flow rate, Run time or Collect volume) as ordered by the physician and continue with "Connecting the Patient". See the COBE® Spectra Apheresis System Cell Therapy Guide to change patient/procedure data.

10. After prime, the procedure is started within 4 hours or the disposable kit is discarded.

Connecting the Patient/Donor

1. Identify the patient/donor following Clinical Center (CC) guidelines (name and date of birth).

2. Check the patient/donor BP, pulse and temperature to ensure they are within the patient's normal limits.

3. Establish venous access per BSS SOP-2400 Dowling Apheresis Clinic Policies and Procedures 4. Draw specific pre-apheresis lab samples as ordered by the DTM or primary care physician 5. Draw standard pre-apheresis lab samples for transfusable products, per BSS SOP-2400 Dowling Apheresis Policies and Procedures.

6. Follow the guidelines for "Connecting the Patient" in the COBE® Spectra Cell Therapy Guide.

Starting the Procedure

1. When prompted by Spectra, press Continue at the prompt for Diverting prime saline. (150 mL of NS be diverted to the waste bag). The prime may be given at the direction of the DTM physician.

2. If calcium replacement is ordered, follow DTM SOP: 2401 Prophylactic Calcium Infusion for set up and dosing of calcium. Attach a 4-way stop-cock to end of return line of Spectra tubing. Attach a Braun Extension Set to the proximal port of the 4-way stopcock (on return line) and prime. Connect the calcium IV line to the medial port of the 4-way stop-cock. Initiate calcium infusion after prime has been diverted.

3. Spectra will prompt: Close return line saline. Press Clear.

4. Monitor and record fluid volumes for the Spectra's operators screen with each change or approximately every 15-30 minutes.

Quick Start

Quick Start is as in the section above

Interface Control

Interface control is as in the section above.

Colorgram™

The WBC Colorgram™ is as in the section above.

Collect Pump Flow Rate

The Collect Flow Rate (CFR) is as in the section above, with this modification.

| WBC | CFR | Colorgram™ HCT Unstimulated Donor Lymphocytes | Colorgram™ HCT Unstimulated Donor Monocytes | Colorgram™ HCT Stimulated Donor |
|---|---|---|---|---|
| 1,000-10,000 | 0.8-1.0 | 2-3% | 3-4% | 3-4% |
| 10,000-25,000 | 1.0-1.3 | 2-3% | 3-4% | 3-4% |
| >25,000 | 1.3-2 | 2-3% | 3-4% | 3-4% |

Configuration of MNC Inlet:AC Ratio

The device defaults to an Inlet:AC ratio of 12:1. If the pre-apheresis platelet count is greater than or equal to 250,000/uL, the initial Inlet:AC Ratio should be set at the device default of 12:1, but should be changed to 13:1 after the first 2-3 liters are processed. If the pre-apheresis platelet count is less than 250,000, the Inlet:AC ratio should be set at 13:1 at the start of the procedure.

| Pre- Platelet Count/uL | AC Ratio |
|---|---|
| ≥250,000 | 1:12 initially, then change to 1:13 after 2-3 liters of whole blood are processed. (A substantial number of platelets are removed during the first 2-3 liters of blood processing.) |
| <250,000 | 1:13 |

The default AC infusion rate is 0.8 mL/min/L of TBV. The AC infusion rate may be increased to 1.1 mL/min/L of TBV without operator override. Increases in the AC infusion rate exceeding these manufacturer's recommendations must have physician approval and prophylactic calcium infusions ordered. See the COBE® Spectra Cell Therapy Guide for guidance though the operator interface screen. See SOP 2401 Prophylactic Calcium Infusion for calcium infusion guidelines.

The presence of cloudy, clumped light colored cells in the collect line and in the line entering the product bag may indicate platelet clumping and the need to decrease the AC ratio. The intermittent loss of a stable interface during the procedure may indicate platelet clumping and that a clump has pushed through the collect line. This may require a decrease in the AC ratio.

Adding ACD-A to the Product

Post procedure using aseptic technique; add 15 ml of ACDA for every final product collected that contains 150 ml or greater. This is done to prevent clumping. If less than 150 ml product is collected, no ACDA is added to the product.

Plasma Collection during WBC Procedures

Plasma may be collected during a WBC procedure in the automatic mode. Plasma collection will not begin until Quick Start has completed. To enter the desired amount of plasma to be collected, use the Target Plasma key to enter the volume. The plasma will be collected at the rate the Plasma pump has been set to minimize disruption of the interface, however, the manufacturer recommends collecting the plasma at the end of the procedure as plasma collection may cause temporary interface instability. The Plasma valve will automatically close when the desired amount has been collected. The plasma collection may be started at any time during the procedure.

Configuration of MNC End Point

The default end point for MNC procedures is 2.0×TBV. The endpoint maybe configured to: specific run time, specific volume of blood (inlet volume) to process, multiple of the donor/patient total blood volume. See the COBE® Spectra Cell Therapy Guide for guidance in setting these endpoints though the operator interface screen.

Pausing and Restarting the Procedure, Ending the Procedure, and Calculation of Net Fluid Balance A blood prime may be done if ordered by the physician or if the system's extracorporeal blood volume exceeds 10-15% of the patient's TBV. See "Maintaining Hemodynamic Stability in Pediatric Apheresis Patients" in the COBE® *Spectra Apheresis System Essentials Guide* and see BSS SOP 2425 *Pediatric Apheresis in Subjects less than* 20 *kg: MNC/PBSC on Spectra*

5. Prophylactic Calcium Infusion during Large-Volume Apheresis

To avoid serious citrate toxicity while maintaining efficient whole blood processing rates, patients/donors who are scheduled for large volume leukapheresis procedures involving citrate infusion rates of greater than 1.2 mg/kg/min should receive prophylactic calcium infusions. Prophylactic infusion refers to administration of calcium at the beginning of apheresis, to prevent subsequent development of symptoms during the procedure. Prophylactic calcium infusions may also be administered during red blood cell exchanges and therapeutic plasma exchanges.

In general, donors/patients at risk for citrate toxicity include: donors/patients who have had a recent prior apheresis procedure as progressive depletion of calcium and albumin stores may occur; donors/patients with lighter body mass who are exposed to higher citrate infusion rates per kg of body weight; donors/patients who experience early onset of mild symptoms as mild symptoms are strongly predictive of the subsequent occurrence of more serious symptoms; donors/patients who are unable to promptly and clearly describe the onset, nature and severity of their symptoms to the apheresis operator (poor communication occurs when donors are not fluent in the language of the apheresis operator or do not communicate their symptoms due to personal or cultural reluctance); and women, due to lower body calcium stores, lower body weight, and smaller blood volumes than men.

Calcium infusions should not be administered to patients with known renal impairment unless they become symptomatic. Ceftriaxone and calcium solutions must not be administered simultaneously due to risk of ceftriaxone-calcium precipitation. Ceftriaxone should not be administered during an apheresis procedure.

Calcium Infusion Rate Calculation

The rate of calcium administration is based on the rate of ACD-A administration or replacement fluid administration (red cell or plasma exchange). The ACD-A rate is, in turn, related to the WBFR and the type of procedure being performed. Therefore, calcium infusions maybe be adjusted according to either the ACD-A flow rate or the WBFR.

IV calcium infusion rates are dosed to administer 0.6 calcium ion per 1 mL ACD-A. The initial dose of calcium may be increased by 10 to 15% in donors at high risk for citrate toxicity, and in all donors undergoing apheresis procedures at citrate infusion rates greater than 2.0 mg/kg/min. The maximum dose of calcium administration is set by the Alaris system, and will vary according to the weight of the donor. Changes in WBFR during the procedure are accompanied by changes in the calcium infusion rate.

Fenwal Amicus: The formula below starts with a WBFR that is measured in mL/min, and converts it to a calcium solution infusion rate that is measured in mL/hr.

$$[WBFR/(AC\ Ratio+1)\times 18]=\text{Calcium solution flow rate}$$

For example, if the AC ratio is 12, then (AC ratio+1)=13, and the WBFR is multiplied by 18/13=1.38. So, for a WBFR of 70, and AC ratio of 12, the CaCl solution would be set for 70/13×18 (or 70×1.38)=97 mL/hour.

COBE Spectra™: The Spectra is configured such that the ACD-A flow rate can be read directly from instrument's digital display panel. In addition to LVL, the Spectra may be used to perform plasma exchange and red cell exchange. The formulas below start with an ACD-A infusion rate that is measured in mL/min, and converts it to a calcium infusion rate that is measured in mL/hr.

Leukapheresis using the COBE Spectra™: For LVL collection with a 12:1 WB:AC ratio, to achieve a calcium infusion rate of 0.6 mg $Ca^{++}$/mL of ACD-A, the rate of Calcium 2 mg/mL solution is 18 times the ACD-A infusion rate.

$$(18)\times(\text{ACD-A flow rate in mL/min})=\text{calcium IV rate (in mL/hr)}$$

Plasma or Red Cell Exchange using the COBE Spectra™: These procedures may cause citrate-related symptoms due to infusion of replacement fluids containing citrate (plasma and red cells) or decreased levels of calcium (albumin). The dose of calcium replacement is further modified because a large part of the administered ACD-A is removed with the waste product. The rate of citrate administered to the patient depends on the rate of replacement fluid administration. Therefore, calcium replacement is based on the WBFR (as for the Amicus). Thawed Plasma: (1.7)×(whole blood flow rate in mL/min)=calcium solution IV rate (in mL/hr). Albumin/Saline replacement: (1.4)×(whole blood flow rate in mL/min)=calcium solution IV rate (in mL/hr). Red cell exchange: (1.1)×(whole blood flow rate in mL/min)=calcium solution IV rate (in mL/hr). In general, maximum allowable administration of calcium solution will not exceed:1.8 times the WBFR on the Amicus or 25 times the AC infusion rate on Spectra.

Alaris Medley II Infusion Pump Set-Up

Obtain the correct medication for the correct patient from the refrigerator in Dowling designated for the storage of medications. Verify the expiration date. Verify the patient/donor ID following CC policies. Verify the medication against the physician order. Using aseptic technique, spike the IV calcium infusion bag with Alaris Medley/Gemini Infusion Set. Prime the tubing with IV fluid. Place the primed tubing in Pump Module following manufacturer's guidelines.

Alaris Medley II Infusion Pump Programming

Turn the Alaris Programming Module on by pressing Systems On. First Screen: Is this a new patient? Enter: Yes. Second Screen: Dept of Transfusion Med? Press: Yes. Third Screen: Select: Channel Select on Pump Module A or B Fourth Screen: Select: Guardrails Drug Library. Fifth Screen: Select: DTM calcium ion CL (544 mg/270 mL) or DTM calcium ion GLUC (588 mg/280 mL). Sixth Screen: Confirm by pressing: Yes. Seventh Screen: Enter the patient weight in kilograms. Press Next. Eighth Screen: Enter the Rate of calcium infusion in mL/hr (calculated from the WBFR or ACD-A infusion rate). Calcium infusion rates must be rounded to the nearest whole number (round up when the decimal is 0.5 or greater). Do not use decimal places. Enter the VTBI (volume to be infused). The Dose will be calculated and displayed on the LCD read-out on the front of the pump module. Press Start. Do not enter more than 280 mL. Do not hang more than one bag of calcium solution at a time. For further details regarding Alaris pump operation, see manufacturer's manual.

Connecting the Infusion Set to the Apheresis Tubing Kit

Strict aseptic technique must be used in connecting the IV pump tubing to the apheresis tubing kit.

Fenwal Amicus: Attach a 4 way stopcock to the end of the return line of the apheresis Attach the calcium solution IV tubing to the medial port of a 4 way stopcock. Divert the prime saline into the a waste bag (volume≈150 mL). Start the calcium solution IV drip at the end of the diversion of the saline prime (as the blood begins to return to the patient).

COBE Spectra™: Attach a 4 way stopcock to the end of the return line of the apheresis kit. Attach the calcium solution IV tubing to the medial port of a 4 way stopcock. The Spectra automatically diverts the prime to a waste bag unless the operator changes the default setting. Start the calcium solution IV drip at the end of the diversion of the saline prime (as the blood begins to return to the patient).

Calcium Infusion

Calcium infusions of 2 mg/mL are used. Calcium infusions are given via an Alaris Medley II IV pump. Calcium infusions are monitored continuously during the apheresis procedure. Rates of calcium infusion are recorded on the Apheresis Procedure Record (BSS form 2400) at 30 minute intervals or at the time of adjustments in WBFR or IV solution flow rate. At any cessation of blood flow, including PAUSE immediately PAUSE the calcium infusion. Failure to do so may cause clotting in the return line.

Discontinuation of Calcium Infusion

For the COBE Spectra™ discontinue the calcium infusion just before initiating Rinseback For the Fenwal Amicus, discontinue the calcium infusion at the end of the procedure prior to Rinseback.

Hypocalcemia, Citrate Induced, during Calcium Infusion

Both the duration of the apheresis procedure and the citrate infusion rate contribute to the risk of citrate toxicity. Mild symptoms, such as circumoral tingling, may occur even at relatively low citrate infusion rates of 1.2 mg/kg/min. These can be treated by methods known in the art.

C. Umbilical Cord

Blood is retrieved from the umbilical cord following birth. HSCs can be isolated from this blood sample, for example using CD34 and/or CD133 antibodies as described herein.

D. Isolation Methods

Once cells are obtained from the BM, blood or umbilical cord, the HSCs in the sample can be optionally isolated or purified. Any methods of separating or isolating the HSCs from such samples can be used. Negative and positive selection methods can be used. Negative selection methods take advantage of cell surface markers which are not expressed on HSCs. Positive selection methods take advantage of cell surface markers, such as CD34 and CD133, which are expressed on HSCs.

In one example, methods are used that deplete non-HSCs from the sample, thereby permitting enrichment of the HSCs (that is, negative selection). For example, methods that substantially reduce the number of B cells, T cells, Natural Killer cells, dendritic cells, monocytes, granulocytes, and/or red blood cells can be used. In one example, labeled antibodies specific for the undesired cells can be incubated with the sample, allowing the labeled antibodies to bind to the undesired cells. Separation methods can then be used to remove those cells from the sample. For example, if the antibody label (such as biotin) is mixed with ferromagnetic particles coated with streptavidin, then passing the mixture through columns in the presence of a magnetic field can be used to remove the undesired cells. Thus, after incubation with the labeled antibodies, the sample is applied to the column, such that undesired cells bind to the column, while the HSCs pass through the column and can be collected. In some examples, the label is a fluorophore and flow cytometry can be used to remove the cells.

In addition, commercially available kits can be used to deplete non-HSCs from the sample, such as those from Miltenyi Biotec (San Diego, Calif.) and StemCell Technologies (Vancouver, Canada). For example, if mouse samples are used, the mouse lineage depletion kit (Miltenyi Biotec catalog number 130-090-858) or the EasyStep Mouse Hematopoietic Cell Isolation Kit (StemCell Technologies catalog #19856) can be used. The kit eliminates most B/T/monocytes/Neutrophils/red cells using a cocktail of biotinylated antibodies followed by magnetic bead selection. The BM cells are magnetically labeled with a cocktail of biotinylated antibodies against a panel of lineage antigens (CD5, CD45R (B220), CD11b, Gr-1 (Ly-6G/C), 7-4, and Ter-119) and Anti-Biotin MicroBeads. The labeling procedure leaves lineage-negative cells (e.g., HSCs) untouched, allowing further magnetic separation of lineage-negative cells according to expression of markers such as CD117 or Sca-1. For example, if human BM is used, the human lineage depletion kit (Miltenyi Biotec catalog number 130-092-211) can be used. Cells are labeled with a cocktail of biotin-conjugated antibodies against lineage-specific antigens (CD2, CD3, CD11b, CD14, CD15, CD16, CD19, CD56, CD123, and CD235a (Glycophorin A)). These cells are subsequently magnetically labeled with anti-biotin beads. Lineage-negative stem and progenitor cells are obtained by depletion of the magnetically labeled cells.

In one example, methods are used that recover HSCs from the sample, thereby permitting enrichment of the HSCs (positive selection). In one example, labeled antibodies specific for HSCs can be incubated with the sample, allowing the labeled antibodies to bind to the HSCs, and subsequent recovery of the labeled HSCs. In one example, the sample is exposed or incubated with labeled CD34 or CD133 antibodies, thereby labeling the HSCs. The labeled HSCs can then be recovered, for example using flow cytometry (e.g., if the label is a fluorophore) or by use of a column (e.g., if the label is a magnetic label, such as magnetic beads containing CD34 and/or CD133). In some examples, CD133+ cells can be isolated from the sample by positive selection with anti-CD133 and magnetic microparticles. In some examples, CD34+ cells can be isolated from the sample by positive selection with anti-CD34 and magnetic microparticles. In some examples, the antibodies are labeled with biotin, and the HSCs subsequently magnetically labeled with anti-biotin beads, thereby allowing selection of the magnetically labeled HSCs. Commercially available kits can be used to recover HSCs from the sample, such as those from Miltenyi Biotec (San Diego, Calif.). In some examples, the CD34 MicroBead Kit is used (e.g., Miltenyi Biotec catalog numbers 130-100-453 or 130-046-702) is used. In some examples, the human CD133 MicroBead Kit is used (e.g., Miltenyi Biotec catalog number 130-050-801) is used.

The resulting HSCs can be used immediately to generate CXCR4 knock down HSCs, or frozen for future use (for example frozen in growth media containing DMSO).

E. Culturing HSCs

Isolated HSCs can be cultured ex vivo, for example to expand the HSC population prior to knocking down CXCR4 expression (and in some examples additional genetic manipulations). In some examples the HSCs are grown in Iscove's modified Dulbecco's Medium (IMDM), or RPMI-1640, plus animal or human serum, or in serum free media designed for HSC culture such as mTesSR 1 medium (Stem Cell Technologies, catalog number 05850), DMEM:F12 (Lonza catalog number 12-719F, Walkersville, Md.) supplemented with 20% serum replacement (Invitrogen, catalog number 10828-028) and in some examples also with cytokines, amino acids, and other growth supplements.

In some examples the grown medium includes one or more of stem cell factor (SCF), thrombopoietin (TPO), and FMS-like tyrosine kinase 3 ligand (Flt-3L). In one example the HSCs are grown in HPGM hematopoietic progenitor growth medium from Lonza (Walkersville, Md. catalog PT-3926), Stemline® II Hematopoietic Stem Cell Expansion Medium (Sigma-Aldrich, catalog #S0192, St. Louis, Mo.) for mouse cells or Stemline® Hematopoietic Stem Cell Expansion Medium (Sigma-Aldrich, catalog #S0189) for human cells.

II. Decreasing CXCR4 Expression and/or Activity in HSC and other Genetic Manipulation Any method that reduces CXCR4 signaling can be used to confer a selective advantage to donor HSCs relative to wild type recipient HSCs for engraftment in bone marrow. HSCs obtained from a donor can be manipulated to downregulate CXCR4. In some examples, such manipulation is done at the nucleic acid level, for example by mutating the genome (e.g., genetically inactivating one of the two CXCR4 alleles in the HSC), by mutating CXCR4 mRNA or cDNA (e.g., by using an RNAi molecule), or by interfering with the function of a produced CXCR4 protein (e.g., by using a CXCR4 protein specific-binding agent). Thus, exemplary CXCR4 editing methods target the CXCR4 sequences shown in GenBank Accession No. NG_011587.1, AJ224869.1, NM_009911.3 or BC098322.1 (sequence available on Jul. 18, 2014). In some examples, manipulating CXCR4 at the nucleic acid level in an HSC allows the HSC progeny to retain the manipulated (e.g., downregulated) CXCR4. Thus, in certain examples the disclosed methods include introducing an appropriate nucleic acid molecule (such as a marker designed to disrupt the gene) into an HSC that downregulates CXCR4 expression and/or activity.

In some examples, in addition to decreasing CXCR4 expression or activity in the HSCs, one or more other genes are manipulated, such as correction of a genetic mutation that results in disease, or increasing or decreasing expression of a target gene to treat a disease. The methods described herein for CXCR4 can be similarly used to manipulate any gene of interest, for example to upregulate the target, downregulate the target, or fix genetic mutations (e.g., point mutations, gene rearrangements, and the like). In some examples, manipulations to CXCR4 are made at the same time as a manipulation is made to another target gene (e.g., those in Table 1). In other examples, manipulations to CXCR4 are made before or after making a manipulation to another target gene (e.g., those in Table 1). Thus, in certain examples the disclosed methods include introducing an appropriate nucleic acid molecule (such as a vector encoding a transcription factor) into an HSC that upregulates or downregulates expression and/or activity of a target gene, or that corrects a genetic defect in a target gene associated with disease.

Although not necessary, detectable markers or selection markers can be introduced into the genome, to help permit the identification of cells with the desired target mutation. For example, such markers can be introduced into an allele of the target gene to be downregulated (e.g., CXCR4), such that the gene will be interrupted and nonfunctional and the markers help permit the identification of cells with the desired target mutation. In some examples introduced selection markers can be removed later (e.g., see Ye et al., *Proc Natl Acad Sci USA.* 111(26):9591-6, 2014).

A. Gene/Genome Editing

Gene editing methods can be used to manipulate expression of CXCR4, for example in combination with altering a gene associated with disease, in HSCs. For example, gene editing can be used to reduce or silence gene expression, enhance gene expression or change specific genes, for example by correcting a gene carrying a harmful mutation (e.g., see those in Table 1). Such methods enable a specific area of a genome to be modified, thereby increasing the precision of the correction or insertion. Genome editing is based on the use of engineered nucleases composed of sequence-specific DNA-binding domains fused to a non-specific DNA cleavage module. These chimeric nucleases enable efficient and precise genetic modifications by inducing targeted DNA double-strand breaks (DSBs) that stimulate the cellular DNA repair mechanisms, including error-prone non-homologous end joining (NHEJ) and homology-directed repair (HDR). NHEJ is an error-prone process that is often accompanied by insertion or deletion of nucleotides (indels) at the targeted site, resulting in a genetic knockout of the targeted region of the genome due to frameshift mutations or the insertion of a premature stop codon. HDR relies on template DNA containing sequences homologous to the targeted site to repair the double stranded break.

Examples of such methods include multiplex automated genomic engineering (MAGE), zinc finger nuclease based engineering, transcription activator-like effector nucleases (TALENs), and clustered regularly interspaced short palindromic repeat (CRISPR). Prior to the discovery of CRISPR RNA-guided nucleases, most methods for genome editing involved protein engineering of zinc finger nucleases (ZFNs), transcription activator-like effector nucleases (TALENs), or homing meganucleases. CRISPR RNA-guided nucleases rely on simple Watson-Crick base pairing rules that abrogate the need for protein engineering.

(i) Zinc Finger Nucleases (ZFNs) and TALENs

Zinc-finger nucleases (ZFNs) and transcription activator-like effector nucleases (TALENs) are chimeric nucleases composed of programmable, sequence-specific DNA-binding modules linked to a nonspecific DNA cleavage domain (such as FokI nuclease). ZFNs and TALENs enable a broad range of genetic modifications by inducing DNA double-strand breaks that stimulate error-prone nonhomologous end joining or homology-directed repair at specific genomic locations (for review see Gaj et al., *Trends Biotechnol.* 31:397-405, 2013, herein incorporated by reference). Zinc-finger proteins and TALEs can be fused to enzymatic domains, such as site-specific nucleases, recombinases and transposases, that catalyze DNA integration, excision, and inversion. Because these enzymes can perform DNA cleavage and re-ligation autonomously, potentially toxic DNA double-strand breaks should not accumulate in the genome. Additionally, for applications that require targeted gene addition, recombinase and transposase activity is marked by the insertion of donor DNA into the genome, thereby enabling off-target effects to be monitored directly. Thus, zinc finger nuclease based engineering methods can edit a target sequence (such as CXCR4) by using zinc-finger nucleases to edit a target gene. Similarly, the TALEN method can be used to edit a target sequence (such as CXCR4) by using transcription activator-like effector nucleases to edit a target gene.

In some examples, a wild-type FokI cleavage domain is used, but FokI cleavage domain variants with mutations designed to improve cleavage specificity and/or cleavage activity can also be used (e.g., see Bitinaite et al. (1998) *Proc. Natl. Acad. Sci. USA* 95:10570-5 and U.S. Published Patent Application No. 20110027235).

In zinc finger nuclease based engineering, a ZFN is used to cut genomic DNA at a desired location. Two ZFNs are used, with each containing two functional domains. The first is a DNA-binding domain comprised of a chain of at least two (such as 2, 3, 4, 5 or 6) zinc finger modules, each recognizing a unique hexamer (6 bp) sequence of DNA (such as a 6 bp sequence of CXCR4). Two-finger modules are stitched together to form a Zinc Finger Protein, each with specificity of ≥24 bp. The second is a DNA-cleaving domain that includes a FokI endonuclease (such as the catalytic domain). When the DNA-binding and DNA-cleaving domains are fused together, a highly-specific pair of 'genomic scissors' are created. This permits editing of the HSC genome, for example downregulation of CXCR4. For example, following introduction of the two ZFNs into an HSC (e.g., using transfection, electroporation, or viral delivery), the ZFN pair recognizes and heterodimerizes around the target site (e.g., a CXCR4 allele). The ZFN pair makes a double strand break and then dissociates from the target DNA. If a corresponding repair template is co-transfected with the ZFN pair, this will result in repair of the target gene (e.g., repair a deletion, insertion, substitution, or other genetic alteration) by homologous recombination. Thus, the repair template can be designed to repair a mutated gene or upregulate gene expression or activity. If no corresponding repair template is co-transfected with the ZFN pair, this will result in disruption of the target gene (e.g., downregulation due to mutations introduced by nonhomolgus end joining). Thus, such a method can be use to disrupt CXCR4.

Several approaches can be used to design specific zinc finger nucleases for the target sequence(s), such as CXCR4 or a gene listed in Table 1 (or other gene associated with the disorders provided herein). The most widespread involves combining zinc-finger units with known specificities (modular assembly). Various selection techniques, using bacteria, yeast or mammal cells have been developed to identify the combinations that offer the best specificity and the best cell tolerance. A zinc finger DNA binding domain is a protein domain that binds DNA in a sequence-specific manner through one or more zinc fingers, which are regions of amino acid sequence within the binding domain whose structure is stabilized through coordination of a zinc ion. Zinc finger binding domains, for example the recognition helix of a zinc finger, can be "engineered" to bind to a predetermined nucleotide sequence (e.g., engineer it to bind to CXCR4 or other target). Rational criteria for design of zinc finger binding domains include application of substitution rules and computerized algorithms for processing information in a database storing information of existing ZFN pair designs and binding data, see for example U.S. Pat. Nos. 5,789,538; 5,925,523; 6,007,988; 6,013,453; 6,140, 081; 6,200,759; 6,453,242; and 6,534,261; and PCT Publication Nos. WO 95/19431; WO 96/06166; WO 98/53057; WO 98/53058; WO 98/53059; WO 98/53060; WO 98/54311; WO 00/27878; WO 01/60970; WO 01/88197; WO 02/016536; WO 02/099084 and WO 03/016496.

In addition, commercially available kits can be used to design and develop vectors that include ZFNs specific for a target (e.g., CompoZR® targeted integration kits from Sigma-Aldrich).

In some examples, two different sets (pairs) of ZFNs are used, such that one set is specific for downregulating CXCR4, while the other set is specific for another genetic mutation that is to be corrected in the HSC (such as one listed in Table 1). One skilled in the art will appreciate that more than two different sets of ZFNs can be used (e.g., at least 2, at least 3, at least 4, or at least 5 different sets, such as 2, 3, 4, 5, 6, 7, 8, 9, or 10 different sets), such that one set is specific for downregulating CXCR4, while another set is specific for a different genetic mutation that is to be corrected in the HSC. Such ZFN sets can be introduced into the HSC simultaneously, or at different times.

Methods for designing TALENs (e.g., see Bogdanove and Voytas, *Science*. 333(6051):1843-6, 2011; Cermak et al., *Nucleic Acids Res*. 39:e82, 2011; Sander et al., *Nat Biotechnol*. 29(8):697-8, 2011) and performing TALEN-mediated gene targeting in human embryonic stem cells (hESCs) and iPSCs (e.g., see Hockenmeyer et al., *Nat Biotechnol* 29: 731-734) are known and can be applied to the present disclosure. Genomic editing with TALENs and ZFNs capitalizes on the cell's ability to undergo homology directed repair (HDR), following an induced and targeted double-stranded DNA break (DSB). During this time a donor DNA template can be provided to the cell to insert new transgene or delete DNA sequences at the site of DSB (e.g., see Cheng et al., *Genes Cells*. 17(6):431-8, 2012). In addition, commercially available kits can be used to design and develop vectors that include TALENs specific for a target (e.g., Golden Gate TALEN and TAL Effector Kit from Addgene (Cambridge, Mass.), catalog #1000000024 and Joung Lab REAL Assembly TALEN kit, from Addgene, catalog #1000000017).

In the TALEN method, the TALE DNA binding domains, which can be designed to bind any desired DNA sequence (such as CXCR4 or those genes in Table 1), come from TAL effectors, DNA-binding proteins excreted by certain bacteria that infect plants (*Xanthomonas*). These are combined with a DNA cleavage domain. The DNA binding domain contains a repeated highly conserved 33-35 amino acid sequence with the exception of the 12th and 13th amino acids. These two locations are highly variable (Repeat Variable Diresidue, RVD) and have specific nucleotide recognition. This relationship between amino acid sequence and DNA recognition has allowed for the engineering of specific DNA binding domains by selecting a combination of repeat segments containing the appropriate RVDs. The non-specific DNA cleavage domain, for example from the end of a FokI endonuclease, can be used to construct hybrid nucleases. The FokI domain functions as a dimer, so that using two constructs with unique DNA binding domains for sites in the target genome with proper orientation and spacing allows excellent specificity. Both the number of amino acid residues between the TALE DNA binding domain and the FokI cleavage domain and the number of bases between the two individual TALEN binding sites can be varied.

TALENs are used in a similar way to design zinc finger nucleases. TALE specificity is determined by two hyper-variable amino acids known as the repeat-variable diresidues (RVDs). Like zinc-fingers, modular TALE repeats are linked together to recognize contiguous DNA sequences. However in contrast to zinc finger proteins, there is no re-engineering of the linkage between repeats necessary to construct long arrays of TALEs with the ability to address single sites in the genome. In one example, TALENs are used to downregulate expression and/or activity of CXCR4 in a donor HSC. In some examples, in addition to downregulating CXCR4 expression in the donor HSC, other genetic defects are corrected using TALENs. For example, Park et al. (PNAS 111:9253-8, 2014, herein incorporated by reference) describe the use of the TALEN method to correct a defect in a mutated coagulation factor VIII (which can be used to treat hemophilia A). Similar methods can be used to correct other genetic defects (such as those listed in Table 1).

Once the TALEN genes have been assembled they can be inserted into plasmids or other vectors; which are used to transfect the donor HSC where the gene products are expressed and enter the nucleus to access the genome. In one example, TALENs are delivered to the donor HSC as mRNA, which removes the possibility of genomic integration of the TALEN protein-encoding DNA. It can also increase the level of homology directed repair (HDR) and the success of integration during gene editing.

In some examples, two different sets (pairs) of TALENs are used, such that one set is specific for downregulating CXCR4, while the other set is specific for another genetic mutation that is to be corrected in the HSC (such as one listed in Table 1). One skilled in the art will appreciate that more than two different sets of TALENs can be used (e.g., at least 2, at least 3, at least 4, or at least 5 different sets, such as 2, 3, 4, 5, 6, 7, 8, 9, or 10 different sets), such that one set is specific for downregulating CXCR4, while each other set is specific for a different genetic mutation that is to be corrected in the HSC. Such TALENs sets can be introduced into the HSC simultaneously, or at different times.

(ii) Clustered Regularly Interspaced Short Palindromic Repeat (CRISPR)

Clustered regularly interspaced short palindromic repeat (CRISPR) RNA-guided adaptive immune systems that protect bacteria and archaea from infection by viruses have been repurposed for genome engineering in a wide variety of cell types and multicellular organisms. CRISPRs are DNA loci containing short repetitions of base sequences. Each repetition is followed by short segments of spacer DNA from previous exposures to a virus. CRISPRs are often associated with Cas genes. By introducing plasmids containing a Cas gene and specifically constructed CRISPRs into eukaryotic cells, the eukaryotic genome can be cut at any desired position. The Cas9 nuclease for targeted genome editing can include fused nuclear localization signals (NLSs) to a codon-optimized version of the Cas9 gene. This Cas9 sequence can be co-expressed with plasmids expressing the tracrRNA and a crRNA-guide, or a single chimeric guide RNA (gRNA).

The CRISPR/Cas system can be used for gene editing in mammalian cells, for example of donor HSCs (see for example Le Cong et al., *Science.* 339:819-23, 2013; Mali et al., *Science.* 339:823-6, 2013; Wilkinson and Wiedenfeft F1000*Prime Reports* 6:3, 2014; Hsu et al., *Cell* 157:1262-78, 2014, all herein incorporated by reference). In addition, commercially available kits can be used to design and develop vectors that include CRISPR/Cas9 genome editing materials for manipulating a specific target (e.g., those from Origene, Rockville, Md., from Addgene, Cambridge, Mass., such as the Church Lab CRISPR Plasmids, and from Life Technologies, Gaithersburg, Md., such as the GeneArt® CRISPR Nuclease Vector Kit). In addition commercial services to engineer specific CRISPR/Cas9 genome editing materials are available from companies such as Genecopoeia, Rockville, Md.

The CRISPR/Cas system includes two components: (1) Cas9 protein (such as a wt or modified Cas9 gene, such as one that is codon optimized and/or mutated for specific nuclease activity), whose expression can be driven by a promoter, such as CMV and (2) single guide RNA (sgRNA) which is operably linked downstream of a target sequence (e.g., CXCR4) and upstream of a promoter (such as the U6 promoter). When introduced into cells (for example as part of a single vector or plasmid or divided into multiple vectors or plasmids), the gRNA guides the Cas9 nuclease to the locus and Cas9 will cut the target site. Cas9 unwinds the DNA duplex and cleaves one or both strands upon recognition of a target sequence by the gRNA, but only if the correct protospacer-adjacent motif (PAM) is present at the 3' end. Non-homologous end joining (NHEJ) repair of this cut will result in small insertions and deletions (indels), so the technique can be used to knockout genes. If short, homologous DNA is also included in the transfection, the technique can also be used to insert this DNA into the cut site through HDR. Using this system, DNA sequences within the endogenous genome and their functional outputs are easily edited or modulated, for example in a donor HSC. The sgRNA and Cas9 protein can also be delivered to the target cell in fixed amounts using encapsulation techniques such as gesicles (Clontech).

In some examples, a native or wild-type Cas9 sequence is used. In such examples, double strand (ds) breaks are introduced at sequences homologous to co-expressed gRNA. In another example, a mutated Cas9 sequence is used. In one example, the Cas9 sequence is codon optimized for mammalian or human cells. In one example a mutated "nickase" version of Cas9 is used, which generates a single-strand DNA break, instead of a ds break (for example to knock down CXCR4 expression). In one example a catalytically inactive Cas9 (dCas9) is used to knockdown gene expression by interfering with transcription (for—example to knock down CXCR4 expression). The dCas9 can be fused to an additional repressor peptide if desired, A catalytically inactive Cas9 (dCas9) fused to an activator peptide can activate or increase gene expression (for example to treat a genetic disorder in which upregulation of a target gene is desired).

In some examples, instead of using a Cas9 nuclease, CRISPR RNA-guided FokI nucleases are used (e.g., for downregulation of CXCR4 and in some examples editing of one or more other target genes) (e.g., see Tsai et al., *Nature Biotechnol.* 32:569-76, 2014). Dimeric RNA-guided FokI nucleases (RFNs) can recognize extended sequences and edit endogenous genes with high efficiencies in human cells. RFN cleavage activity depends on the binding of two guide RNAs (gRNAs) to DNA with a defined spacing and orientation. Such a method can be used to express multiple gRNAs bearing any 5' end nucleotide.

In one example, CRISPR is used to downregulate expression of CXCR4 in a donor HSC. In one example, multiple plasmids are used for the gene editing. The Cas9 or modified Cas9 (e.g., nickase) enzyme (or the FokI nuclease) is provided, for example on one vector or plasmid, and the guide RNA (gRNA) on another plasmid. One or more other plasmids or vectors can supply a sequence for (1) downregulating CXCR4, (2) correction of a mutation using homologous recombination or an oligonucleotide template can be used, (3) downregulation of a target gene, or (4) upregulation of a target gene. Multiple plasmids can be mixed and transfected into HSCs at the same time, for example using Lonza nucleofector technology for the simultaneous transfection of multiple plasmids at this time. But one skilled in the art will appreciate that other methods can be used to introduce these sequences, such as viral transduction using lentiviral, adeno-associated virus (AAV), retrovirus, adenovirus, or alphavirus technology, or by using vesicles preloaded with sgRNA and Cas9 protein. Another method that can be used is to generate induced pluripotent stem cells and then edit them and test them using DNA sequencing to find correctly edited cell clones. Then these cells can be differentiated in vitro into HSC and infused into a recipient subject (e.g., see Suzuki, et al., *Mol. Therapy* 21(7):1424-31, 2013).

In other examples, instead of using a plurality of plasmids or vectors, a single vector is used to both supply the Cas9 or modified Cas9 (e.g., nickase) enzyme (or the FokI nuclease) and the guide RNA (gRNA) with the target sequence. In some examples a plurality of different gRNAs, one for each target, are present on a single plasmid. In one example for plasmid delivery to an HSC, the pCas-Guide vector from Origene can be used. In one example, for example for viral delivery to an HSC, the pLenti-Cas Guide vector from Origene (Rockville, Md.) can be used. Thus, the method can include introducing an appropriate sequence. The CRISPR Nuclease OFP Reporter vector from Life Technologies can be similarly used. In some examples, in addition to downregulating CXCR4 expression in the donor HSC, other genes are manipulated, for example using the pCas-Guide vector or the pLenti-Cas Guide vector from Origene but with an appropriate target sequence specific for the target gene and the modification desired.

B Inhibitory RNA (RNAi) Methods

RNAi methods can be used to downregulate expression of CXCR4, for example in combination with altering a gene associated with disease, in HSC cells. For example, RNAi can be used to reduce or silence gene expression of an undesired gene, for example where upregulation of the gene causes or results in disease, or is undesirable (e.g., decreasing expression of CCR5 in a subject with HIV).

An RNAi molecule includes antisense molecules, siRNAs, miRNAs, and ribozymes specific for a target gene whose expression is to be downregulated (such as CXCR4 or CCR5), which reduce or prevent expression of the target, for example by at least 50%, at least 60%, at least 75%, or at least 90%. In some examples, RNAi molecules are at least 12 nt in length, at least 15 nt, or at least 19 nt in length, such as about 19 to 30 or 15 to 200 nucleotides in length, such as at least 21 nucleotides, for example at least 23 nucleotides (for example 19, 20, 21, 22, 23, 24, 25, 26, 27, 28, 29, or 30 nucleotides). Once expressed in a cell, such as an HSC, the RNAi molecule interacts with the target nucleic acid and generates an RNAi response.

Targeted gene knockdown by RNA interference (RNAi) can be used to decrease expression of a target gene, such as CXCR4, in a donor HSC. For example, a single CXCR4 can be mutated by RNAi methods to decrease expression of CXCR4, which thus will decrease CXCR4 activity. In some examples, such methods decrease CXCR4 expression at least 20%, at least 30%, at least 40%, at least 50%, at least 60%, at least 70%, at least 75%, at least 80%, at least 90%, at least 95%, at least 96%, at least 97%, at least 98%, or at least 99% (such as a decrease of 40% to 90%, 40% to 80% or 50% to 95%) as compared to a control (such as a non-recombinant HSC with normal or wild-type CXCR4 expression). Exemplary CXCR4 RNAi molecules target a CXCR4 sequence shown in GenBank Accession No. NG_011587.1, AJ224869.1, NM_009911.3 or BC098322.1. Examples of RNAis that can be used to interrupt or alter translation of a target nucleic acid molecule (such as CXCR4) include, but are not limited to, antisense RNA, miRNA, ribozymes, antisense molecules, or an siRNA, that bind specifically to the target nucleic acid molecule (such as CXCR4).

Methods of generating RNAi molecules, and introducing them into a cell, are known in the art. For example, nucleic acid molecules (such as a vector containing the RNAi molecule) can be introduced into HSCs by a variety of methods known to those of skill in the art, such as by transfection or transformation (e.g., by encapsulation in liposomes, by iontophoresis, by incorporation into viruses or vectors which are introduced into the cell, or by incorporation into other delivery vehicles, such as hydrogels, cyclodextrins, biodegradable nanocapsules, and bioadhesive microspheres.). In some examples, RNAi molecules are expressed within an HSC from a eukaryotic promoter. In some examples, the RNAi molecules are administered directly to a subject, for example by injection (i.v., i.p., i.m.), topical administration, oral administration, by inhalation; or other routes.

In certain examples, expression vectors are used to express the RNAi molecule in an HSC. For example, an expression vector can include a nucleic acid sequence encoding at least one RNAi molecule that recognizes a target nucleic acid molecule (such as CXCR4 or CCR5). In a particular example, the vector contains a sequence encoding both strands of an RNAi molecule comprising a duplex. In another example, the vector also contains a sequence encoding a single nucleic acid molecule that is self-complementary and thus forms an RNAi molecule. Non-limiting examples of such expression vectors are described in Paul et al., Nature Biotech. 19:505, 2002; Miyagishi and Taira, Nature Biotech. 19:497, 2002.

In other examples, RNAi molecules can be expressed from transcription units (see for example, Couture et al., 1996, TIG 12:510) inserted into DNA or RNA vectors. The recombinant vectors can be DNA plasmids or viral vectors. RNAi expressing viral vectors can be constructed based on, for example, but not limited to, adeno-associated virus, retrovirus, adenovirus, lentivirus or alphavirus. In another example, pol III based constructs are used to express RNAi molecules (see for example, U.S. Pat. Nos. 5,902,880 and 6,146,886).

The recombinant vectors capable of expressing the RNAi molecules can be delivered as described above, and persist in target cells. Alternatively, viral vectors can be used that provide for transient expression of RNAi molecules.

In one example, an RNAi molecule is an siRNA. siRNAs are double-stranded RNAs that can induce sequence-specific post-transcriptional gene silencing, thereby decreasing or in some examples inhibiting gene expression. In one example, siRNA triggers the specific degradation of homologous RNA molecules, such as mRNAs, within the region of sequence identity between both the siRNA and the target RNA. In some examples, siRNA molecules are about 19-27 nucleotides (nt) in length, such as 20-25 nt, or 20 to 27 nt, for example 19, 20, 21, 22, 23, 24, 25, 26 or 27 nt in length.

One of ordinary skill in the art can readily generate siRNAs which specifically bind to a target nucleic acid sequence, such as CXCR4 or any gene whose expression needs to be decreased (such as CCR5 in an HIV-infected patient). Commercially available kits, such as siRNA synthesizing kits from Qiagen, Origene (Rockville, Md.), Life Technologies (Grand Island, N.Y.), and SuperArray Bioscience Corporation (Hamburg, Germany) can be used to synthesize siRNA molecules. In addition, siRNAs can be obtained from commercial sources, such as from Life Technologies (Grand Island, N.Y.) and GE Dharmacon (Lafayette, Colo.). Exemplary CXCR4 siRNA molecules target the CXCR4 sequences shown in GenBank Accession No. NG_011587.1, AJ224869.1, NM_009911.3 or BC098322.1 (sequence available on Jul. 18, 2014).

In one example, an RNAi molecule is an antisense oligonucleotide. Antisense RNA prevents protein translation of a target mRNA by binding to it. Thus, an antisense molecule can hybridize to a portion of a target (such as CXCR4 or CCR5). In some examples, antisense oligonucleotides are at least 19 nucleotides (nt) in length, such as at least 20, at least 30, at least 40, at least 50, at least 75, at least 100, or at least 200 nt in length. The antisense oligonucleotide can be modified at the base moiety, sugar moiety, or phosphate backbone, and can include other appending groups such as peptides, or agents facilitating transport across a cell membrane (e.g., see Letsinger et al., Proc. Natl Acad. Sci. USA 1989, 86:6553-6; Lemaifre et al., Proc. Natl. Acad. Sci. USA 1987, 84:648-52; WO 88/09810), hybridization triggered cleavage agents (Krol et al., BioTechniques 1988, 6:958-76) or intercalating agents (Zon, Pharm. Res. 5:539-49, 1988). Antisense molecules can be synthesized by standard methods, for example by use of an automated DNA synthesizer. In a specific example, an antisense oligonucleotide includes catalytic RNA, or a ribozyme (see WO 90/11364, Sarver et al., Science 247:1222-5, 1990).

The antisense oligonucleotides can include a sequence complementary to at least a portion of an RNA transcript of target gene, such as CXCR4 or CCR5. However, absolute complementarity is not required. Exemplary CXCR4 antisense oligonucleotides target the CXCR4 sequences shown in GenBank Accession No. NG_011587.1, AJ224869.1, NM_009911.3 or BC098322.1 (sequence available on Jul. 18, 2014).

In one example, an RNAi molecule is a ribozyme. Ribozymes are enzymatic RNA molecules capable of catalyzing the specific cleavage of RNA. Ribozymes can be synthesized and administered to the subject, or can be encoded on an expression vector, from which the ribozyme is synthesized in the targeted cell (e.g., see WO 9523225, and Beigelman et al., *Nucl. Acids Res.* 1995, 23:4434-42). Methods of using ribozymes to decrease or inhibit RNA expression are known in the art. For example, specific ribozyme cleavage sites within an RNA target can be identified by scanning the target molecule for ribozyme cleavage sites that include the following sequence: GUA, GUU and GUC. Once identified, short RNA sequences of about 15 ribonucleotides (such as 15 to 30 or 15 to 25 ribonucleotides) corresponding to the region of the target gene containing the cleavage site may be evaluated for predicted structural features, such as secondary structure, that may render the oligonucleotide sequence unsuitable. The suitability of candidate targets can also be evaluated by testing their accessibility to hybridization with complementary oligonucleotides, using ribonuclease protection assays. An overview of ribozymes and methods of their use is provided in Kashani-Sabet (*J. Imvestig. Dermatol Symp. Proc,* 7:76-78, 2002). Methods describing endogenous and exogenous delivery are known (e.g., see Marschall et al., *Cell Mol. Neurobiol* 14:523-38, 1994). For example, a plasmid that contains a ribozyme directed against CXCR4, placed behind a promoter, can be transfected into donor HSCs. Expression of this plasmid in the HSC will decrease CXCR4 expression. Exemplary CXCR4 ribozymes target the CXCR4 sequences shown in GenBank Accession No. NG_011587.1, AJ224869.1, NM_009911.3 or BC098322.1 (sequence available on Jul. 18, 2014), and thus can include one or more sequences complementary to a CXCR4 mRNA and can include the well-known catalytic sequence responsible for mRNA cleavage (see U.S. Pat. No. 5,093,246).

C. Introduction of Nucleic Acids into the Donor HSC

Nucleic acids encoding the necessary elements for the gene editing methods and RNAi methods can be introduced into a donor HSC using routine methods. In one example, such nucleic acids are cloned into a vector or plasmid, which is then used to transfect or transform a cell. In other examples, naked nucleic acid molecules are used.

Following isolation, donor HSCs can be incubated in a culturing medium in a culture apparatus for a period of time or until the cells reach confluency before passing the cells to another culture apparatus. The culturing apparatus can be of any culture apparatus commonly used for culturing cells in vitro. In one example, the level of confluency of the cells is greater than 70% before passing the cells to another culture apparatus. More preferably, the level of confluency of the cells is greater than 90%. A period of time can be any time suitable for the culture of cells in vitro. The culturing medium may be replaced during the culture of the HSCs. HSCs are then harvested from the culture apparatus. The HSCs can be used immediately or they can be cryopreserved and stored for use at a later time. For example the NANEX system (Arteriocyte Inc., Cleveland, Ohio) can be used to culture and expand HSC from blood and bone marrow.

The HSCs to be transformed or transfected can be grown in culture. Standard culture media typically contains a variety of essential components required for cell viability, including inorganic salts, carbohydrates, hormones, essential amino acids, vitamins, and the like. In some embodiments, DMEM or F-12 is used as a culture medium. Additional additives can be used, such as glutamine, heparin, sodium bicarbonate and/or N2 supplement (Life Technologies, Gaithersburg, Md.). The pH of the culture medium is typically between 6-8, such as about 7, for example about 7.4. Cells are typically cultured at a temperature between 30-40° C., such as between 35-38° C., such as between 35-37° C., for example at 37° C.

Methods for introducing DNA into HSCs in culture include chemical and physical methods. Chemical methods include liposome-based gene transfer or lipofection, calcium phosphate-mediated gene transfer, DEAE-dextran transfection techniques, and polyethyleneimine (PEI)-mediated delivery. Physical methods include ballistic gene transfer (introduces particles coated with DNA into cells), microinjection, and nucleofection (e.g., from Lonzasuch as the Amaxa biosystem). In some embodiments, nucleofection can be used to introduce the nucleic acids disclosed herein into HSCs. In specific non-limiting examples, the nucleofection involves the use of a Nucleofector 4d apparatus.

D. CXCR4 Inhibitors

In one example, methods of decreasing CXCR4 activity occur at the protein level. That is, CXCR4 produced in an HSC can be contacted with agents that decrease its activity, such as a decrease of at least 20%, at least 30%, at least 40%, at least 50%, at least 60%, at least 70%, at least 75%, at least 80%, at least 90%, at least 95%, at least 96%, at least 97%, at least 98%, or at least 99% (such as a decrease of 40% to 90%, 40% to 80% or 50% to 95%) as compared to a control (such as a non-recombinant HSC with normal or wild-type CXCR4 expression). Examples of such agents include small molecules and specific binding agents. Such agents can reduce CXCL12 binding to CXCR4.

In one example the agent that reduces CXCR4 protein activity is a CXCR4 antagonist, such as a small molecule (e.g., AMD3100 (plerixafor), AMD3465, T22 ([Tyr$^{5,12}$, Lys$^7$]-polyphemusin II), T134 (des-[Cys$^{8,13}$, Tyr$^{9,12}$]-[d-Lys$^{10}$, Pro$^{11}$, 1-citrulline$^{16}$]-T22 without C-terminal amide), T140 {[1-3-(2-naphthyl)alanine3]-T134}, and AMD070 (for review see Debnath et al., *Theranostics,* 2013; 3(1):47-75, herein incorporated by reference).

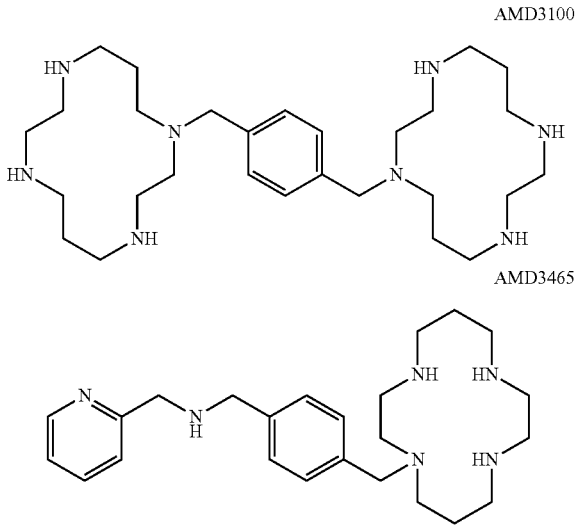

A specific binding agent is an agent that binds substantially only to a defined target, such as a CXCR4 protein. For example, a CXCR4 protein-specific binding agent binds substantially only to a CXCR4 protein (such as a protein provided in any of GenBank® Accession Nos. NP_001008540, CAA12166.1, NP_034041.2 and AAH31665.1). Specific binding agents include CXCR4 antibodies (including polyclonal or monoclonal antibodies and functional fragments thereof, as well as humanized and chimeric antibodies), CXCR4 aptamers, and other agents that bind substantially only to the CXCR4 protein.

CXCR4 antibodies can be produced using standard procedures such as those described in Harlow and Lane (*Using Antibodies: A Laboratory Manual*, Cold Spring Harbor Laboratory Press: Cold Spring Harbor, 1998). Antibodies can be polyclonal or monoclonal antibodies, humanized antibodies, Fab fragments, F(ab')2 fragments, single chain antibodies, or chimeric antibodies. In addition, CXCR4 antibodies are commercially available such as those from Abcam, Cambridge, Mass. (e.g., ab2074, ab58176, or ab1617) and Novus Biologicals, Littleton, Colo. (e.g., NB100-74396 or NB100-77835). In one example a CXCR4 antibody is a neutralizing antibody (such as one from a non-Hodgkin's lymphoma patient, or an antibody derived from such).

The determination that a particular agent binds substantially only to the target protein readily can be made by using or adapting routine procedures. For example, Western blotting can be used to determine that a given protein binding agent, such as a CXCR4 antibody or aptamer, binds substantially only to the CXCR4 protein. Other assays include, but are not limited to, competitive and non-competitive homogenous and heterogeneous enzyme-linked immunosorbent assays (ELISA) as symmetrical or asymmetrical direct or indirect detection formats; "sandwich" immunoassays; immunodiffusion assays; in situ immunoassays (for example, using colloidal gold, enzyme or radioisotope labels); agglutination assays; complement fixing assays; immunoelectrophoretic assays; enzyme-linked immunospot assays (ELISPOT); radioallergosorbent tests (RAST); fluorescent tests, such as used in fluorescent microscopy and flow cytometry; Western, grid, dot or tissue blots; dip-stick assays; halogen assays; or antibody arrays for example, see O'Meara and Tovey, *Clin. Rev. Allergy Immunol.*, 18:341-95, 2000; Sambrook et al., 2001, Appendix 9; Simonnet and Guilloteau, in: *Methods of Immunological Analysis*, Masseyeff et al. (Eds.), VCH, New York, 1993, pp. 270-388).

Thus, in some examples, an HSC is contacted in vivo or ex vivo (or both) with a therapeutically effective amount of one or more agents that decrease CXCR4 activity, such as one or more of the agents listed above.

III. Introduction of CXCR4-Knockdown HSCs into a Subject

CXCR4 knockdown HSCs, which may include one or more other repaired genetic mutations as discussed herein, can be introduced, that is administered or transplanted, into a subject. Such subjects are referred to as recipient subjects. The CXCR4 knockdown HSCs can be generated from the recipient subject (autologous), or a different subject (allogeneic). In some examples, the subject has a hematologic malignancy and the CXCR4 knockdown HSCs used are allogeneic, for example to have graft vs. tumor effect. In some examples, the subject has a genetic hematologic disease and the CXCR4 knockdown HSCs used are autologous to reduce or eliminate risk of graft vs. host disease after transplant. Such methods can be used to enhance engraftment of HSCs. Thus, transplantation of the disclosed CXCR4 knockdown HSCs can be used to treat patients with hematological cancers and other disorders of the blood and immune systems.

In some examples, the CXCR4 knockdown HSCs include other undesirable mutations, such as those shown in Table 1. In such examples, one or more other undesirable mutations can be repaired, for example to treat a disease. Furthermore, if the donor HSCs include any gene that is undesirably up- or down-regulated, that too can be repaired in the HSC as described herein.

In some examples therapeutically effective amounts of CXCR4 knockdown HSCs, which may include one or more other repaired genetic mutations as discussed herein, include at least $1 \times 10^6$, at least $2 \times 10^6$, at least $3 \times 10^6$, at least $4 \times 10^6$, at least $5 \times 10^6$, at least $6 \times 10^6$, at least $7 \times 10^6$, at least $8 \times 10^6$, at least $9 \times 10^6$, at least $1 \times 10^7$, at least $2.5 \times 10^7$, at least $5 \times 10^7$, at least $1 \times 10^8$, at least $2.5 \times 10^8$, or at least $5 \times 10^8$ CXCR4 knockdown HSCs. Such amounts can be introduced into the recipient subject, for example by injection, such as intravenously.

In some examples, administration of the CXCR4 knockdown HSCs, which may include one or more other repaired genetic mutations as discussed herein, increases engraftment of the CXCR4 knockdown HSCs by at least 20%, at least 30%, at least 40%, at least 50%, at least 60%, at least 70%, at least 75%, at least 80%, at least 90%, at least 95%, at least 100%, at least 2-fold, at least 3-fold, at least 4-fold, at least 5-fold, at least 10-fold, at least 20-fold, or at least 30-fold, for example at 30 days, 60 days, 90 days, 120 days, 1 year or 2 years following the HSC transplant, for example as compared to engraftment observed with HSCs without downregulated CXCR4. In some examples, enhanced engraftment is indicated by an increase in donor HSC repopulation in the recipient faster than donor HSC with normal CXCR4 expression. For example, the CXCR4 knockdown HSCs can repopulate at least 20%, at least 30%, at least 40%, at least 50%, at least 60%, at least 70%, at least 75%, at least 80%, at least 90%, at least 95%, at least 100%, at least 2-fold, at least 3-fold, at least 4-fold, at least 5-fold, at least 10-fold, at least 20-fold, or at least 30-fold, faster than donor HSCs with normal CXCR4 expression (e.g., a wild-type HSC), for example at 30 days, 60 days, 90 days, 120 days, 1 year or 2 years following the HSC transplant. In some examples, enhanced engraftment is indicated by CXCR4 knockdown HSCs lasting longer in the recipient than donor HSC with normal CXCR4 expression. For example, the donor HSCs can survive at least 20%, at least 30%, at least 40%, at least 50%, at least 60%, at least 70%, at least 75%, at least 80%, at least 90%, at least 95%, at least 100%, at least 2-fold, at least 3-fold, at least 4-fold, at least 5-fold, at least 10-fold, at least 20-fold, or at least 30-fold, longer than donor HSCs with normal CXCR4 expression (e.g., a wild-type HSC), for example at 30 days, 60 days, 90 days, 120 days, 1 year or 2 years following the HSC transplant.

A. Subjects

In some examples, the subject receiving the CXCR4 knockdown HSCs (which may include one or more other repaired genetic mutations as discussed herein) does not receive a conditioning regimen prior to administration of the CXCR4 knockdown HSCs. For example, the subject does not receive chemotherapy or irradiation (such as total body irradiation) that is typically used to suppress the immune system and/or destroy the bone marrow. Thus, in some examples the subject to receive the CXCR4 knockdown HSCs does not previously receive a myeloablative regimen, such as chemotherapy agents given at maximally tolerated doses expected to eradicate the hematopoietic cells in the bone marrow and resulting in profound pancytopenia within one to three weeks from the time of administration. In some examples, the subject does not previously receive a non-myeloablative regimen, such as reduced doses of chemotherapy or whole body irradiation expected to partially ablate but not eliminate the recipient bone marrow. In some examples the recipient subject does not receive a therapy that will deplete or ablate the recipient's immune system, such as T cells, prior to receiving the CXCR4 knockdown HSCs.

Examples of chemotherapeutic agents that have been used in conditioning regimens for HSC transplantation include but are not limited to: carmustine, busulfan, carboplatin, cyclophosphamide, cytoxan, etoposide, fludarabine, melphalan, methotrexate, thiotepa, topotecan, or combinations thereof. Thus, in some examples the recipient subject to receive the CXCR4 knockdown HSCs provided herein does not receive any of these chemotherapies prior to administration of the CXCR4 knockdown HSCs. In some examples the recipient subject does not receive an induction chemotherapy regimen which includes a therapeutically effective amount of etoposide, doxorubicin, vincristine, cyclophosphamide, and prednisone (EPOCH) or cytarabine with daunorubicin or idarubicin (7+3 regimen) prior to administration of the CXCR4 knockdown HSCs. In another example, the recipient subject does not receive fludarabine prior to administration of the CXCR4 knockdown HSCs.

Thus, in some examples the subject to be treated with the methods provided herein does not receive irradiation, such as does not receive 1200 to 1300 centigray over three to four days, for example prior to receiving the CXCR4 knockdown HSCs.

B. Disorders

Diseases that can be treated with the disclosed methods include any genetic disease of the blood (e.g. sickle cell disease, primary immunodeficiency diseases), HIV (such as HIV-1), and hematologic malignancies or cancers, as well as WHIM syndome. Thus, in some examples, the subject who receives the CXCR4 knockdown HSCs has one of these diseases.

Primary immunodeficiency diseases weaken the immune system, allowing repeated infections and other health problems to occur more easily. Examples of primary immunodeficiency diseases and their corresponding mutations include those listed in Al-Herz et al., *Frontiers in Immunology*, volume 5, article 162, Apr. 22, 2014, herein incorporated by reference. Specific examples are provided in Table 1.

Hematologic malignancies or cancers are those tumors that affect blood, bone marrow, and lymph nodes. Examples include leukemia (e.g., acute lymphoblastic leukemia, acute myelogenous leukemia, chronic lymphocytic leukemia, chronic myelogenous leukemia, acute monocytic leukemia), lymphoma (e.g., Hodgkin's lymphoma and non-Hodgkin's lymphoma), and myeloma. In some examples, a subject with a hematologic malignancy benefits from receiving CXCR4 knockdown HSCs (such as allogeneic HSCs) without the need for repair of other genetic mutations (e.g., the cancer is not caused by a genetic mutation). For example, receiving the CXCR4 knockdown HSCs can be used to induce a graft versus tumor effect in the subject with the hematologic malignancy. In other examples, a subject with a hematologic malignancy benefits from receiving CXCR4 knockdown HSCs (such as autologous HSCs) which further have a genetic mutation that causes the malignancy, which has been repaired prior to introduction of the donor HSCs into the recipient. For example, receiving the repaired CXCR4 knockdown HSCs can be used to treat CML caused by a BCR-ABL fusion (which is repaired in the CXCR4 knockdown HSCs prior to administration to the recipient).

TABLE 1

Exemplary disorders and corresponding mutations

| Disease | Gene | Mutation |
| --- | --- | --- |
| Blood cell disorder | | |
| sickle cell anemia | β-globin chain of hemoglobin | SNP (A to T) that gives rise to point mutation (Glu->Val at 6$^{th}$ aa) |
| hemophilia | any of clotting factors I through XIII | |
| hemophilia A | clotting factor VIII | large deletions, insertions, inversions, and point mutations |
| hemophilia B | clotting factor IX | |
| Alpha-Thalassemia | HBA1 or HBA2 | Mutation or a deletion in chromosome 16 p |
| Beta-Thalassemia | HBB | Mutations in chromosome 11 |
| Delta-Thalassemia | HBD | mutation |
| von Willebrand Disease | von Willebrand factor | mutations or deletion |
| pernicious anemia | MTHFR | |
| Fanconi anemia | FANCA, FANCC, FANCD2, FANCG, FANCJ | FANCA: c.3788_3790del (p.Phe1263del); c.1115_1118delTTGG (p.Val372fs); Exon 12-17del; Exon 12-31del; c.295C>T (p.Gln99X) FANCC: c.711+4A>T (originally reported as IVS4+4A>T); c.67delG (originally reported as 322delG) FANCD2: c.1948-16T>G |

TABLE 1-continued

Exemplary disorders and corresponding mutations

| Disease | Gene | Mutation |
|---|---|---|
| | | FANCG; c.313G>T (p.Glu105X); c.1077−2A>G; c.1480+1G>C; c.307+1G>C; c.1794__1803del (p.Trp599fs); c.637__643del (p.Tyr213fs) FANCJ: c.2392C>T (p.Arg798X) |
| Thrombocytopenic purpura | ADAMTS13 | Missense and nonsense mutations |
| thrombophilia | Factor V Leiden Prothrombin | Mutation in the F5 gene at position 1691 Prothrombin G20210A |
| Primary Immunodeficiency Diseases | | |
| T-B+ SCID | IL-2RG, JAK3, defect in gamma chain of receptors for IL-2, -4, -7, -9, -15 and -21 | |
| T-B− SCID | RAG1, RAG2 | |
| WHIM syndrome | CXCR4 | heterozygous mutations (e.g., in the carboxy-terminus); carboxy-terminus truncation (e.g., 10-19 residues) |
| Other disorders | | |
| HIV | C-C chemokine receptor type 5 (CCR5) | Deletion of 32 bp in CCR5 |
| CML | BCR-ABL | fusion |
| AML | Chromosome 11q23 or t(9; 11) | translocation |

Administration of the CXCR4 knockdown HSCs can be used to treat any of these disorders. Treatment does not require 100% removal of all characteristics of the disorder, but can be a reduction in such. Although specific examples are provided below, based on this teaching one will understand that symptoms of other disorders can be similarly affected.

For example, administration of CXCR4 knockdown HSCs can be used to treat or reduce the undesirable effects of a genetic disease of the blood, such as a primary immunodeficiency disease.

For example, administration of CXCR4 knockdown HSCs (which can also include genetic alterations to correct a mutation in the β-globin chain of hemoglobin) can be used to treat or reduce the undesirable effects of sickle cell disease. In one example, the donor HSC includes a genetic modification to correct a mutation in the β-globin chain of hemoglobin that results in the sickle-cell disease. In one example the disclosed methods reduce the symptoms of sickle-cell disease in the recipient subject (such as one or more of, presence of sickle cells in the blood, pain, ischemia, necrosis, anemia, vaso-occlusive crisis, aplastic crisis, splenic sequestration crisis, and haemolytic crisis) for example a reduction of at least 10%, at least 20%, at least 50%, at least 70%, or at least 90% (as compared to no administration of the CXCR4 knock down HSCs). In one example the disclosed methods decrease the number of sickle cells in the recipient subject, for example a decrease of at least 10%, at least 20%, at least 50%, at least 70%, at least 90%, or at least 95% (as compared to no administration of the CXCR4 knock down HSCs).

For example, administration of CXCR4 knockdown HSCs (which can also include genetic alterations to correct a mutation in the factor V Leiden or prothrombin gene) can be used to treat or reduce the undesirable effects of thrombophilia. In one example, the donor HSC includes a genetic modification to correct a mutation in the factor V Leiden or prothrombin gene that results in the thrombophilia. In one example the disclosed methods reduce the symptoms of thrombophilia in the recipient subject (such as one or more of, thrombosis, such as deep vein thrombosis, pulmonary embolism, venous thromboembolism, swelling, chest pain, palpitations) for example a reduction of at least 10%, at least 20%, at least 50%, at least 70%, or at least 90% (as compared to no administration of the CXCR4 knock down HSCs). In one example the disclosed methods decrease the activity of coagulation factors in the recipient subject, for example a decrease of at least 10%, at least 20%, at least 50%, at least 70%, at least 90%, or at least 95% (as compared to no administration of the CXCR4 knock down HSCs).

For example, administration of CXCR4 knockdown HSCs (which can also include genetic alterations to correct a mutation in the CD40 ligand gene) can be used to treat or reduce the undesirable effects of CD40 ligand deficiency. In one example, the donor HSC includes a genetic modification to correct a mutation in the CD40 ligand gene that results in the CD40 ligand deficiency. In one example the disclosed methods reduce the symptoms of CD40 ligand deficiency in the recipient subject (such as one or more of, elevate serum IgM, low serum levels of other immunoglobulins, opportunistic infections, autoimmunity and malignancies) for example a reduction of at least 10%, at least 20%, at least 50%, at least 70%, or at least 90% (as compared to no administration of the CXCR4 knock down HSCs). In one example the disclosed methods increase the amount or activity of CD40 ligand deficiency in the recipient subject, for example an increase of at least 10%, at least 20%, at least 50%, at least 70%, at least 90%, at least 100%, at least 200% or at least 500% (as compared to no administration of the CXCR4 knock down HSCs).

For example, administration of CXCR4 knockdown HSCs (which can also include genetic alterations to decrease CCR5 activity) can be used to treat or reduce the undesirable effects of HIV-1 infection. In one example, the donor HSC includes a genetic modification to decrease CCR5 activity in the HSC, such as a decrease of at least 20%, at least 50%, at least 70% or at least 90%. In one example, the CCR5 is modified to include a 32-bp deletion (CCR5Δ32, as described in Ye et al., PNAS, 111:9591-6, 2014, herein incorporated by reference). In one example the disclosed methods reduce the symptoms of HIV-1 infection in the recipient subject (such as one or more of, fever, large tender lymph nodes, throat inflammation, a rash, headache, sores of the mouth, nausea, vomiting, diarrhea, peripheral neuropathy, Guillain-Barre syndrome, weight loss, viral load, decreased levels of CD4+ T cells, pneumocystis pneumonia, cachexia in the form of HIV wasting syndrome and esophageal candidiasis) for example a reduction of at least 10%, at least 20%, at least 50%, at least 70%, or at least 90% (as compared to no administration of the CXCR4 knock down HSCs). In one example the disclosed methods increase levels of CD4+ T cells in the HIV-infected recipient subject, for example an increase of CD4+ T cells of at least 10%, at least 20%, at least 50%, at least 70%, at least 90%, at least 100%, at least 200%, at least 500% or at least 1000% (as compared to no administration of the CXCR4 knock down HSCs).

For example, administration of CXCR4 knockdown HSCs can be used to treat or reduce the undesirable effects of a hematological malignancy in the recipient subject. In one example the disclosed methods reduce the number of abnormal white blood cells (such as B cells) in the recipient subject (such as a subject with leukemia), for example a reduction of at least 10%, at least 20%, at least 50%, at least 70%, or at least 90% (as compared to no administration of the CXCR4 knock down HSCs). In one example, administration of CXCR4 knockdown HSCs can be used to treat or reduce the undesirable effects of a lymphoma, such as reduce the size of the lymphoma, volume of the lymphoma, rate of growth of the lymphoma, metastasis of the lymphoma, for example a reduction of at least 10%, at least 20%, at least 50%, at least 70%, or at least 90% (as compared to no administration of the CXCR4 knock down HSCs). In one example, administration of CXCR4 knockdown HSCs can be used to treat or reduce the undesirable effects of multiple myeloma, such as reduce the number of abnormal plasma cells in the recipient subject, for example a reduction of at least 10%, at least 20%, at least 50%, at least 70%, or at least 90% (as compared to no administration of the CXCR4 knock down HSCs).

For example, administration of CXCR4 knockdown HSCs can be used to treat or reduce the undesirable effects of WHIM syndrome. In one example, the donor HSC includes a genetic modification to reduce expression of CXCRx, such as by disrupting one functional allele of CXCR4. In one example the disclosed methods reduce the symptoms of WHIM syndrome in the recipient subject (such as one or more of, warts, bacterial infection, viral infection, reduction of lymphocytes, neutropenia, hypogammaglobulinemia, myelokathexis, cervical and vulval premalignant dysplasia, and human papillomavirus (HPV) infection) for example a reduction of at least 10%, at least 20%, at least 50%, at least 70%, or at least 90% (as compared to no administration of the CXCR4 knock down HSCs). In one example the disclosed methods decrease the number of warts in the recipient subject, for example a decrease of at least 10%, at least 20%, at least 50%, at least 70%, at least 90%, or at least 95% (as compared to no administration of the CXCR4 knock down HSCs). In one example the disclosed methods decrease the frequency of bacterial and/or viral infections in the recipient subject, for example a decrease of at least 10%, at least 20%, at least 50%, at least 70%, at least 90%, or at least 95% (as compared to no administration of the CXCR4 knock down HSCs). In one example the disclosed methods increase white blood cell counts in the recipient subject, for example an increase of at least 10%, at least 20%, at least 50%, at least 70%, at least 90%, at least 100%, at least 200%, or at least 500% (as compared to no administration of the CXCR4 knock down HSCs).

Example 1

Materials and Methods

This example describes the methods used to obtain the results described in Examples 2-10.

Patients

All patients and unaffected relatives signed informed consent consistent with the Declaration of Helsinki under clinical protocols approved by the Institutional Review Board of the National Institute of Allergy and Infectious Disease (NIAID) before taking part in research at the National Institutes of Health Clinical Center.

Animal Experiments

Cxcr4 targeted (Floxed mice=Strain 008767) and EIIa promoter driven Cre recombinase transgenic mice (Strain 003724) mice were obtained from The Jackson Laboratory (Bar Harbor, Me.) and bred together to generate Cxcr4 heterozygote knock out mice (Cxcr4$^{+/-}$). Creation of WHIM knockin mice bearing a heterozygous CXCR4$^{+/S338X}$ mutation have been previously described and sperm from these mice were used for in vitro fertilization at NIH to impregnate female C57BL/6 mice from Taconic Farms (Hudson, N.Y.) (Balabanian et al., 2012). These mice were bred to backgrounds that expressed either CD45.1 or CD45.2 or both for purposes of tracking bone marrow engraftment in mixed bone marrow reconstitution assays where 5 million bone marrow cells were transferred intravenously into the recipient mouse via tail vein injection. In some experiments, recipient mice underwent lethal irradiation (900 rads) 6 to 8 hours prior to transplant.

Flow Cytometry, Cell Purification, and Culture

Patient cells were isolated from heparinized blood or bone marrow aspirate and purified by Ficoll-Hypaque centrifugation and stained as previously described (McDermott et al., 2014). Cell purification was performed either using magnetic bead selection (Miltenyi Biotec, Cambridge, Mass.) following manufacturer recommendations for blood samples or using a sorting cytometer (FACS Aria II, BD Biosciences, San Jose, Calif.) for bone marrow samples. Flow cytometric data was analyzed with FlowJo v10 (TreeStar Inc, Ashland, Oreg.). Peripheral blood mononuclear cells (PBMC) and purified bone marrow cells were cultured to expand CD34$^+$ hematopoietic progenitors (HPC) and PBMC were used to create lymphoblastoid cell lines (LCL) from Epstein-Barr virus (EBV) transformed B cells (detailed methods below).

100 µl of mouse blood was collected from the mandibular vein into EDTA anticoagulant tubes (Becton Dickinson, Franklin Lakes, N.J.) then 2 µl Fc block (BioLegend, San Diego, Calif.) was added and incubated for 10 min prior to the addition of specific antibodies incubated on ice for 30 min. Red blood cells were then lysed with 1 ml of ACK lysis buffer (Quality Biologicals Inc., Gaithersburg, Md.) for 1 min at room temperature before centrifugation and washing with flow cytometry buffer twice. Cells were then fixed with 1% paraformaldehyde, stored on ice, and run on a FACS LSRII instrument (BD Biosciences). A similar procedure was followed for staining bone marrow cells isolated from sacrificed animals from the femurs.

Flow Cytometric Sorting and HSC Selection and Culture

A Fluorescence activated cell sorter (FACS Aria II (SORP)) made by Becton-Dickinson Biosciences (San Jose, Calif.) and equipped with 405 nm, 488 nm, 561 nm, and 633 nm lasers was used to sort cells. For sorting of bone marrow hematopoietic progenitors, Enrich mode (Purity mask=0; Yield mask=8) to select CD34+ cells was performed first followed by Purity mode sorting for HSC, CLP, CMP, and GMP populations. Purified monoclonal anti-human antibodies labeled with fluorochromes were obtained from BD Biosciences and for blood sorting included: CD14-Fluorescein Isothiocyanate, CD19-Phycoerythrin, CD4-Allophycocyanin, and CD8-Pacific Blue; while for bone marrow sorting included: CD14-Fluorescein Isothiocyanate, CD19-Phycoerythrin, CD34-Allophycocyanin, and CD3-Alexa Fluor 700. In other experiments, blood and bone marrow derived CD34+ cells were positively selected with Miltenyi Biotec (San Diego, Calif.) microbeads then cultured using the Arteriocyte (Cleveland, Ohio) NANEX HSC expansion system following manufacturer's directions. In some experiments, the CD34+ cells were cultured in HSC expansion serum free media (Stem Cell Technologies, Vancouver, Canada) supplemented with the cytokine cocktail (hSCF, hTPO, hflt3-L) obtained from Peprotech (Rocky Hill, N.J.) and human LDL from Athens Research and Technology (Athens, Ga.).

Mutation Detection and Sanger DNA Sequencing

Polymerase chain reaction—restriction fragment length polymorphism (PCR-RFLP) analysis was performed as previously described (Hernandez et al., 2003) using genomic DNA isolated from purified cell populations or whole blood. Amplification utilized the following primers: 5'-ATCCTC-TATGCTTTCCTTGGAGCC-3' (SEQ ID NO: 1) and 5'-GTGGAAACAGATGAATGTCCACCGC-3' (SEQ ID NO: 2). The CXCR4$^{R334X}$ mutation (1000C→T) destroys a naturally present BstUI restriction enzyme site such that the mutant allele is uncut (126 bp amplicon versus 104 and 22 bp digested pieces). In addition the same DNA was subjected to traditional Sanger method DNA sequencing at a Clinical Laboratory Improvement Amendment of 1988 (CLIA-88) certified core facility.

A PCR assay was designed to detect the derivative chromosome by spanning one of the novel junctions created by the chromothripsis event such that the normal chromosome should not amplify. This assay used the following primers: 5'-GGAATCTCACATCCAGAATCATGC-3' (SEQ ID NO: 3) and 5'-TTGTTCTCACCTTTGGCCAGTGG-3' (SEQ ID NO: 4) and generates a 242 bp amplicon spanning the junction of pieces 16 and 13 in the derivative chromosome. Amplicons for 3 other junctions yielded similar results.

Cytogenetics

Cytogenetics was performed on bone marrow aspirate samples, purified CD19+ B cells, and LCL cell lines by a clinical laboratory using standard techniques (Quest Diagnostics, Chantilly, Va.).

Microarray and Analysis

An Affymetrix Cytoscan HD array (Affymetrix, Santa Clara, Calif.) was used to identify chromosomal breakpoints using DNA from the same cells used in cytogenetic analysis, purified neutrophils and skin fibroblasts following the manufacturer recommended procedures. The Chromosome Analysis software suite (Affymetrix) was used to identify the approximate location of these breakpoints via loss of heterozygosity (LOH) determination using single nucleotide polymorphism (SNP), insertion/deletion (indel), and copy number variant (CNV) analysis.

Molecular Pathology Testing and Cytokine Analysis

A formalin fixed paraffin embedded (FFPE) block was obtained from the patient's splenectomy in 1963. This was examined histologically and DNA was extracted using the methods described below. This DNA was then used in the PCR-RFLP analysis. A variety of short tandem repeat (STR) loci were compared between the patient's neutrophil and buccal DNA using an STR chimerism assay developed for the tracking of bone marrow transplant engraftment at the Hematology Service, Division of Laboratory Medicine, NIH Clinical Center. This assay is capable of detecting 5-95% donor chimerism and has a standard deviation of ±5%. Purified CD3+ and CD19+ DNA was checked for T and B cell clonality using previously published methods. (Lawnicki et al., 2003; Ramasamy et al., 1992; van Dongen et al., 2003) Finally, a specific mutation (V617F) in the JAK2 oncogene and presence of the BCR-ABL gene fusion were excluded using DNA sequencing and a specific real time PCR assay respectively (see below). Serum samples from the index patient, 5 WHIM patients and 5 healthy blood donors were obtained and immediately frozen at ≤-80° C. until time of assay. Samples were then thawed and run at the same time. Assays for serum cytokine, interleukin, and chemokine concentrations were performed by RayBiotech, Inc. (Norcross, Ga.) using a multiplex quantitative enzyme-linked immunosorbent assay (ELISA) method with appropriate controls to insure signal linearity of signal to concentration in the reported measurement range.

Whole Genome Sequencing and Analysis

DNA from fibroblasts obtained from a skin biopsy and blood neutrophils were used to prepare paired-end libraries using the TruSeq DNA protocol following the manufacturer's instructions (Illumina Inc., San Diego, Calif.). For each DNA sample, two different size libraries were generated, one of 200 to 400 bp and one of 300 to 500 bp. Each library was sequenced on 2 lanes of a HiSeq 2000 next generation sequencer (Illumina) and generated ~380 million reads per library of 2×100 bp paired-end. Reads were trimmed for adaptor and poor quality sequence and mapped to build hg19 of the human genome using publically available Tophat2 software from the McKusick-Nathans Institute of Genetic Medicine (Kim et al., 2013) using the fusion search option. The output from this software (fusion.out file) was used to identify candidate fusion junctions that were present in the neutrophil but not the fibroblast samples. All fusion junctions were verified by visual inspection using publically available software from the Broad Institute: Integrative Genomics Viewer (IGV version 2.3). (Robinson et al., 2011) Rearrangements were visualized using publically available software from the Canadian Michael Smith Genome Centre: Circos. (Krzywinski et al., 2009)

T Cell Clonality Testing

DNA was extracted from peripheral blood cells using an automated DNA extraction system and tested for quality prior to PCR amplification for detection of T cell receptor (TRG locus) gene rearrangements. A single multiplexed PCR reaction was performed as described by Lawnicki et al. using primers that interrogate TRG rearrangements involving all of the known Vg family members, and the Jg1/2, JP1/2 and JP joining segments. (Lawnicki et al., 2003) To allow for fluorescence detection, each joining region primer was covalently linked to a unique fluorescent dye. The products were analyzed by capillary electrophoresis on an ABI 3130x1 Genetic Analyzer, and electropherograms were analyzed using GeneMapper software version 4.) (Applied Biosystems, Life Technologies, Grand Island, N.Y.). A polyclonal rearrangement pattern was detected and there was no evidence of a clonal T-cell process, within the detection limits of the assay. TRG PCR is capable of detecting a clonal population comprising a minimum of 2-5% of the total T-cell population, and as performed at the NIH-CC, can identify>90-95% of all TRG gene rearrangements occurring in clonal T-cell proliferations.

B Cell Clonality Testing

DNA from peripheral blood cells isolated as above was PCR amplified for detection of immunoglobulin (IGH and IGk loci) gene rearrangements. For the IGH locus, two separate reactions were performed, one using consensus primers to framework region III and the joining region of the immunoglobulin heavy chain gene (FRIII-IGH PCR) and a second using primers directed to the framework region II and the joining region of the immunoglobulin heavy chain gene (FRII-IGH PCR) as described by Ramasamy et al. (Ramasamy et al., 1992) Primers directed to the joining region were linked to the fluorescent marker FAM (carboxyfluorescein). Two additional reactions were performed for the IGk locus using the Biomed II primer set described by van Dongen et al and supplied by InVivoScribe Technologies (San Diego, Calif.) using the IGK Gene clonality assay and ABI Fluorescence Detection). (van Dongen et al., 2003) These reactions interrogate rearrangements involving the Vk loci and Jk, the Vk locus and the kDE locus, and the k intron RSS locus and the kDE locus. Products were run on an ABI 3130x1 Genetic Analyzer and electropherograms were analyzed using GeneMapper software version 4 (ABI). Polyclonal rearrangement patterns were detected in all reactions and there was no evidence of clonal B cell proliferation within the limits of the assay. These assays performed at the NIH-CC are capable of detecting a clonal population comprising 2-10% of the total B cell population and can identify about 85-90% of all clonal B cell proliferations.

JAK2 and BCR-ABL Mutation Analysis

The JAK2 V617F mutation was not detected on CLIA-88 approved testing developed by Ipsogen (Qiagen, Germantown, Md.). A quantitative PCR assay was used to determine the relative levels of BCR-ABL and ABL using cDNA obtained by reverse transcribing RNA extracted from peripheral blood leukocytes. The levels of BCR-ABL and ABL were quantitated by comparison to plasmid reference standards using real time PCR. The ratio (BCR-ABL/ABL) was found in WHIM-09 to be 0.12%. In patients with newly diagnosed or relapsed chronic myeloid leukemia this typically varies between 50-150%. The coefficient of variation for replicate assays at the NIH-CC is 40-50%.

Example 2

Index Patient is a Genetic Mosaic for the CXCR4$^{R334X}$ Mutation

Figure 1B:
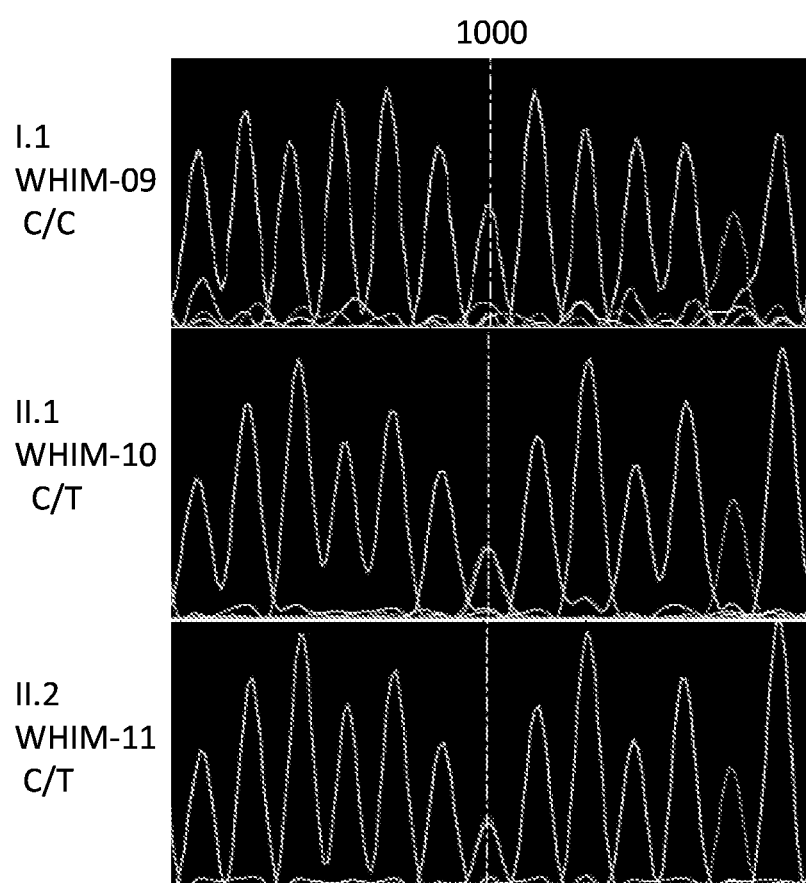

The index patient and 2 of her 3 daughters self referred themselves to NIH for evaluation of their immunodeficiency. The index patient was the initial patient diagnosed with myelokathexis and had undergone bone marrow biopsy, splenectomy and extensive investigation of her congenital neutropenia at age 9 (Krill et al., 1964; Zuelzer, 1964). Her family's immunodeficiency syndrome was compatible with autosomal dominant transmission of WHIM syndrome and at least one of the daughters had previously been clinically diagnosed with this (FIG. 1A). However, to our knowledge genetic testing for a CXCR4 mutation had not been previously performed in this family. Since mutations in this gene account for more than 95% of the known WHIM cases, most individuals would be expected to have one of the eight currently described carboxy terminal mutations. Therefore, the index patient, her husband, and all 3 daughters were genotyped. Two of the three daughters (WHIM-10 and WHIM-11) who had neutropenia and severe human papillomavirus disease (warts) tested positive for the most common truncation mutation causing WHIM, CXCR4$^{R334X}$, while the husband and third daughter without these symptoms tested negative (FIG. 1B). However, unexpectedly a blood sample from the index patient (WHIM-09), tested negative for the same mutation and her immunophenotype was markedly different from her 2 daughters (Table 2) and other WHIM patients studied.

Figure 1C:
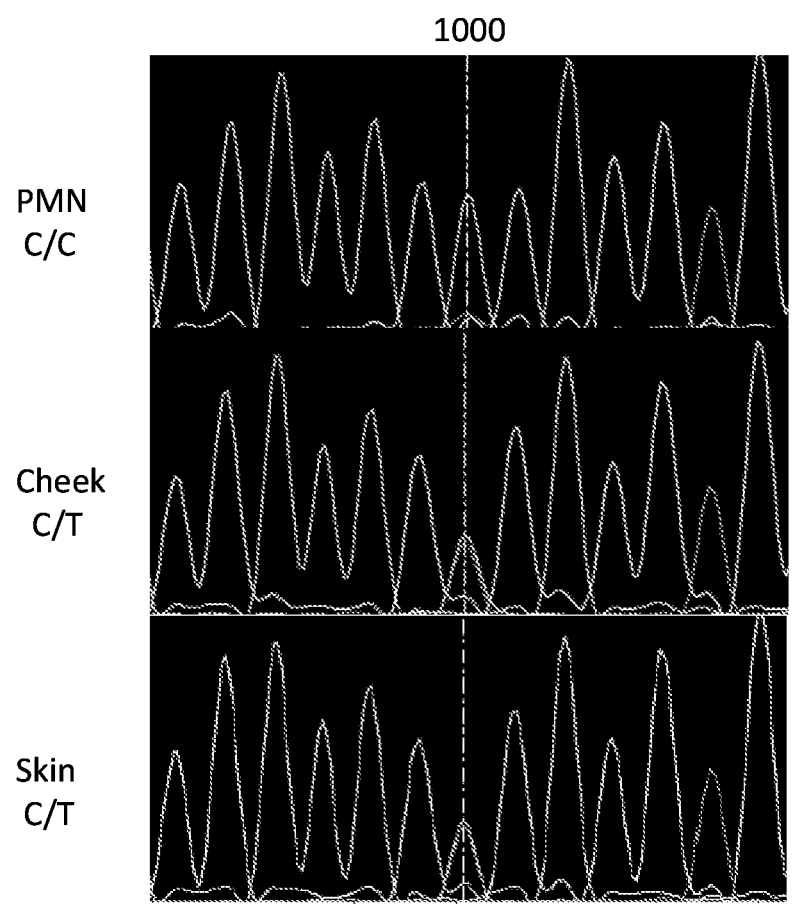

This prompted a repeat blood sample to be tested and it confirmed the initial negative result followed by a cheek swab and skin biopsy both of which demonstrated that the patient was in fact heterozygous for the CXCR4$^{R334X}$ mutation in non-hematologic tissues (FIG. 1C). A WHIM pedigree with germ-line/somatic genetic mosaicism where the mother of 2 affected children was hematologically normal had been previously described (Hernandez et al., 2003) but this was deemed unlikely in this case because the index patient had been markedly symptomatic with severe neutropenia as a child. (Krill et al., 1964; Zuelzer, 1964) Therefore, it was suspected that a genetic reversion had occurred and whether this was the case and when this had happened was determined.

TABLE 2

Immunophenotype of 3 WHIM patients

| Cell subsets (cells/μL) | WHIM-09 | WHIM-10 | WHIM-11 | Reference range for adults, cells/μL of blood, mean† |
|---|---|---|---|---|
| CD3$^+$ T cell | 1736 | 382 | 218 | 714-2266 |
| CD4$^+$ T cell | 1389 | 317 | 155 | 359-1565 |
| CD4$^+$ CD45RA$^+$ naïve T cell | 211 | 44 | 12 | 454-733 |
| CD4$^+$ CD45RO$^+$ memory T cell | 1178 | 273 | 143 | 219-1048 |
| CD8$^+$ T cell | 222 | 41 | 45 | 178-853 |
| CD8$^+$ CD45RA$^+$ naïve T cell | 44 | 22 | 14 | 231-371 |
| CD8$^+$ CD45RO$^+$ memory T cell | 178 | 19 | 31 | 57-130 |
| CD3$^-$ CD56$^+$ NK cell | 1270 | 32 | 51 | 126-729 |
| CD19$^+$ B cell | 18 | 5 | 10 | 61-329 |
| CD19$^+$ CD27$^+$ memory B cell | 2 | 1 | 1 | 12-68 |
| CD19$^+$ CD27$^-$ B cell | 16 | 4 | 9 | 90-176 |
| CD19$^+$ CD27$^-$ IgD$^+$ IgM$^+$ transitional/naïve B cell | 12 | 3 | 4 | 42-85 |

TABLE 2-continued

Immunophenotype of 3 WHIM patients

| Cell subsets (cells/µl) | WHIM-09 | WHIM-10 | WHIM-11 | Reference range for adults, cells/µL of blood, mean† |
|---|---|---|---|---|
| CD19+ CD27− IgD− IgM+ immature B cell | 4 | 1 | 1 | 2-10 |
| CD14+ CD16− Classical Monocyte | 1344 | 35 | 117 | 371-539 |
| CD14+ CD16+ Inflammatory Monocyte | 235 | 5 | 23 | 14-30 |

Low patient values are underlined and high patient values are in bold font.
ND, not defined.
†Based on the values of 11-40 healthy blood donors seen at the NIH Clinical Center.

Example 3

Index Patient Exhibits a Genetic Myeloid/Lymphoid Dichotomy

Testing of multiple purified leukocyte lineages from blood revealed that the $CXCR4^{R334X}$ mutation was present in lymphocytic lineages (CD56+ NK, CD19+ B and CD3+ T cells) but was absent from myeloid lineages (CD14+ monocytes and neutrophils) and CD34+ hematopoietic stem cells. These results were initially demonstrated using PCR-RFLP (FIG. 2A) and confirmed by Sanger DNA sequencing. A pathological specimen was obtained from the splenectomy performed at age 9 and DNA extracted for testing and this revealed the presence of the $CXCR4^{R334X}$ mutation.

In order to test whether the myeloid components expressing the $CXCR4^{R334X}$ mutation might be differentially retained in bone marrow and thus absent from the blood, a bone marrow biopsy and aspirate were performed. An identical myeloid/lymphoid dichotomous result was obtained from cells purified by flow cytometric sorting from the bone marrow aspirate (FIG. 2B) and in CD34+ hematopoietic stem cells obtained both by flow cytometric sorting and ex vivo culture from blood and bone marrow. Thus the combined evidence suggested that an early myeloid progenitor or HSC had undergone genetic reversion of the $CXCR4^{R334X}$ mutation.

Example 4

Neutropenia and Other Symptoms of WHIM Resolved at About Age 30

Figure 3:
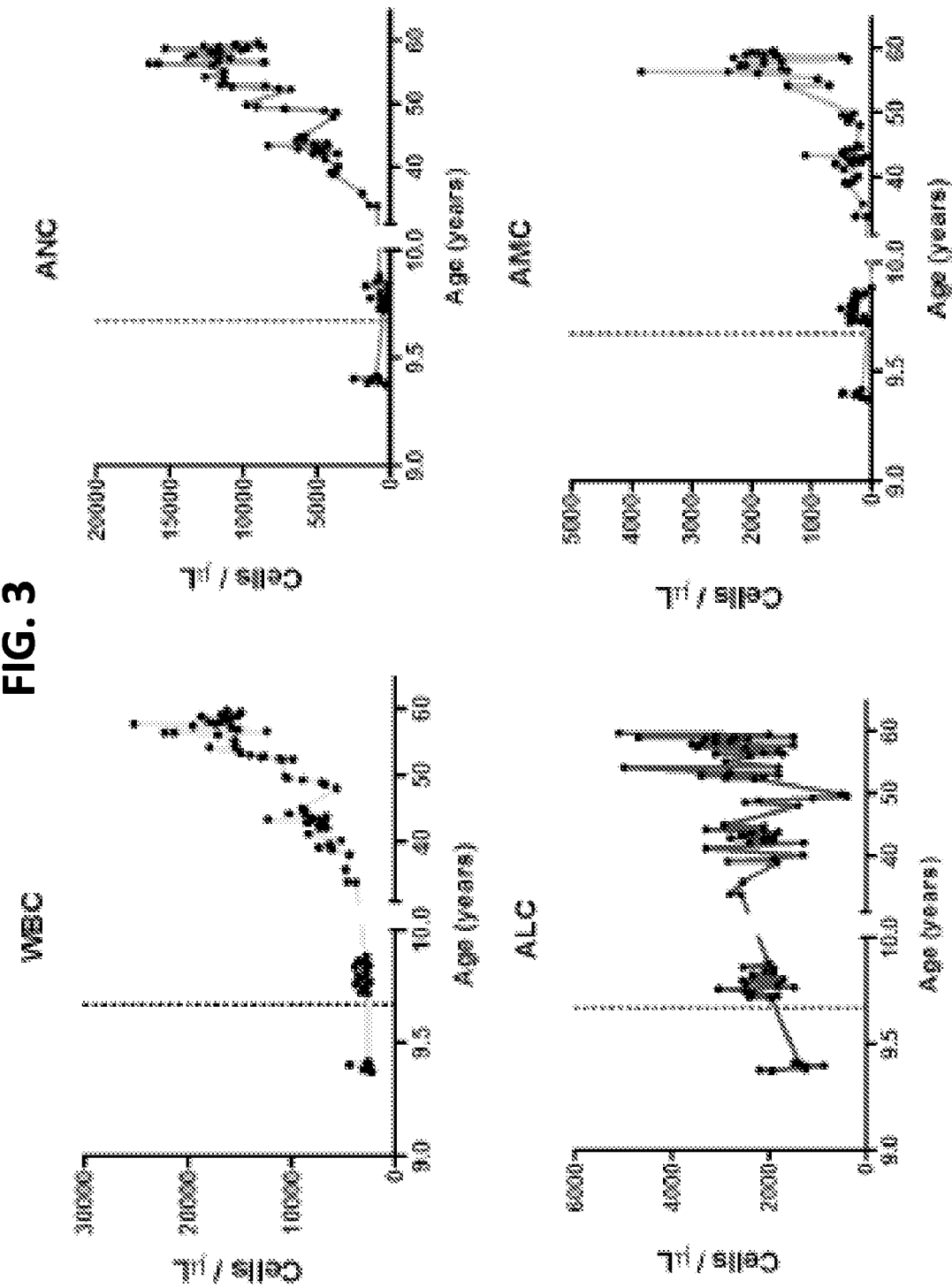
FIG. 3. Blood counts by age in the index patient. WBC, white blood count; ANC, absolute neutrophil count; AMC, absolute monocyte count; ALC, absolute lymphocyte count. Arrow indicates age at splenectomy, horizontal lines indicate normal range of values. Note x axis is discontinuous to show pre/post splenectomy results more clearly.

A careful analysis of blood cell counts and symptoms of the index patient with time revealed that the patient's neutropenia had resolved around the age of 30 years (FIG. 3). This was accompanied by increased monocytes with similar kinetics. In addition, the patient reported that her last serious infection requiring hospitalization occurred at about this age and for the past 30 years she had been largely infection free except for some recurrent episodes of sinusitis and bronchitis treated as an outpatient. WHIM-09 also noted that while she had previously had many confluent warts on her left hand, these had resolved at about the same time without surgery, cytotoxic treatment, or residual scars. Since the patient reported she had undergone several surgeries and blood transfusions at about the same time as her neutrophil counts normalized, we tested her blood for any evidence of allogeneic chimerism and found none. Taken together this evidence indicated that the patient had undergone a clinical and genetic reversion of the $CXCR4^{R334X}$ mutation at about age 30. Surprisingly this reversion had apparently occurred in a hematopoietic stem cell that then developed a proliferative advantage and fully repopulated the HSC niche in the absence of chemotherapy or radiation therapy as is commonly performed in bone marrow transplantation. The mechanism of this phenomenon was explored.

Example 5

Bone Marrow Pathology, Cytogenetics, Microarray

Figure 4C:
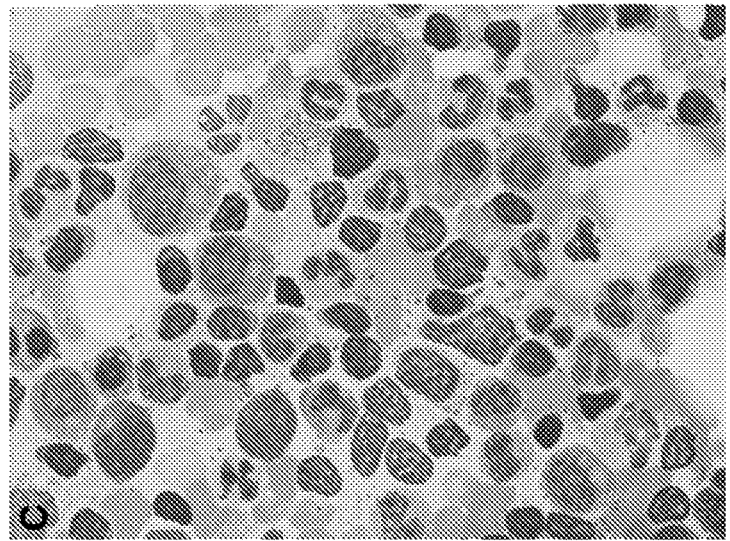
FIGS. 4A-4C. Bone marrow pathology. A representative hematoxylin and eosin stain of the bone marrow is shown for an unrelated adult female WHIM patient (WHIM-03, A) and the index patient (WHIM-09) at age 9 (B, taken from Zuelzer, 1964) and at age 59 (C). Bone marrow characteristics of myelokathexis seen in WHIM-03 at age 30 and in WHIM-09 at age 9 such as an increased myeloid to erythroid ratio, increased late myeloid precursors, and hypersegmented, pyknotic appearing mature neutrophils with dense nuclear lobes connected by long, thin intranuclear strands and intracytoplasmic vacuolization are no longer present in WHIM-09 at age 59.
Figure 4B:
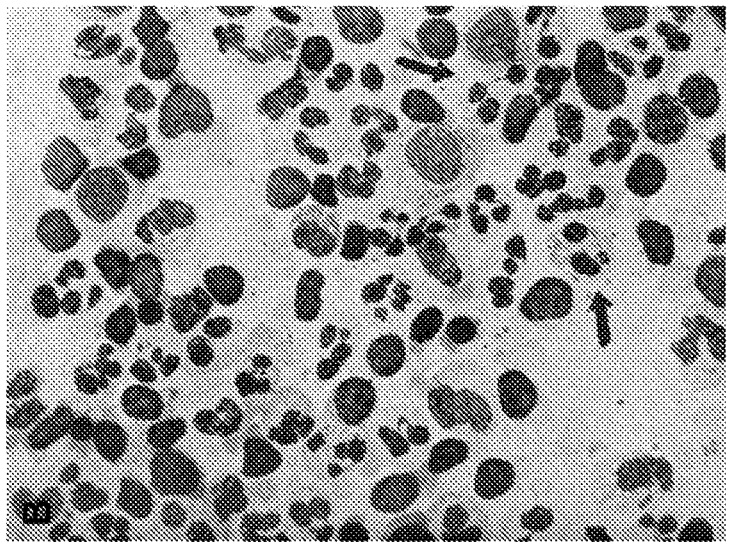
Figure 4A:
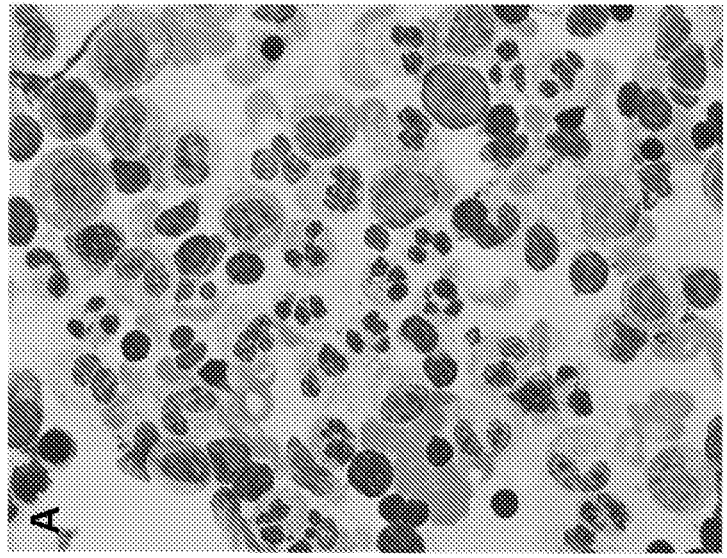
Figure 5A:
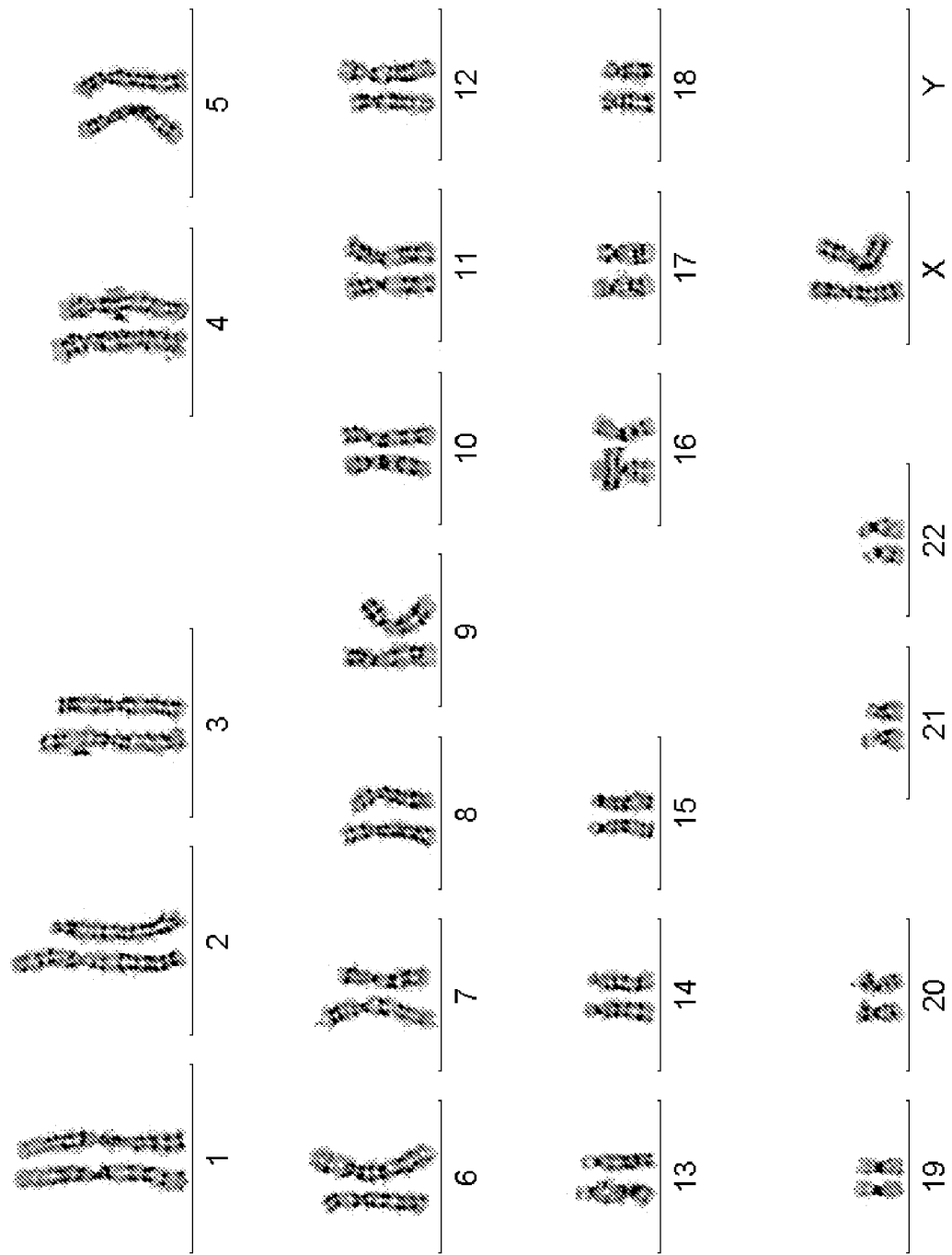
FIGS. 5A-5C. Cytogenetics and Hybridization. Bone marrow aspirate was cultured and metaphase cells were lysed and stained with Giemsa. An analysis of the chromosomal banding pattern revealed that some of the patient cells were lacking part of one copy of chromosome 2 and that there was evidence of partial translocation of the centromere (A) while other chromosomes were normal. Fluorescence in situ hybridization (FISH) was performed on these cells for ALK (B), multicolor stain revealed translocation from 2p to 2q arm) and for MYCN (green) and the centromere (red) (C). The latter revealed a deletion of MYCN with a partial centromeric translocation. When this FISH test was applied to cells with polymorphic nuclei nearly all were positive, but roughly 40% of the cells with round nuclei were negative (data not shown).
Figure 5B:
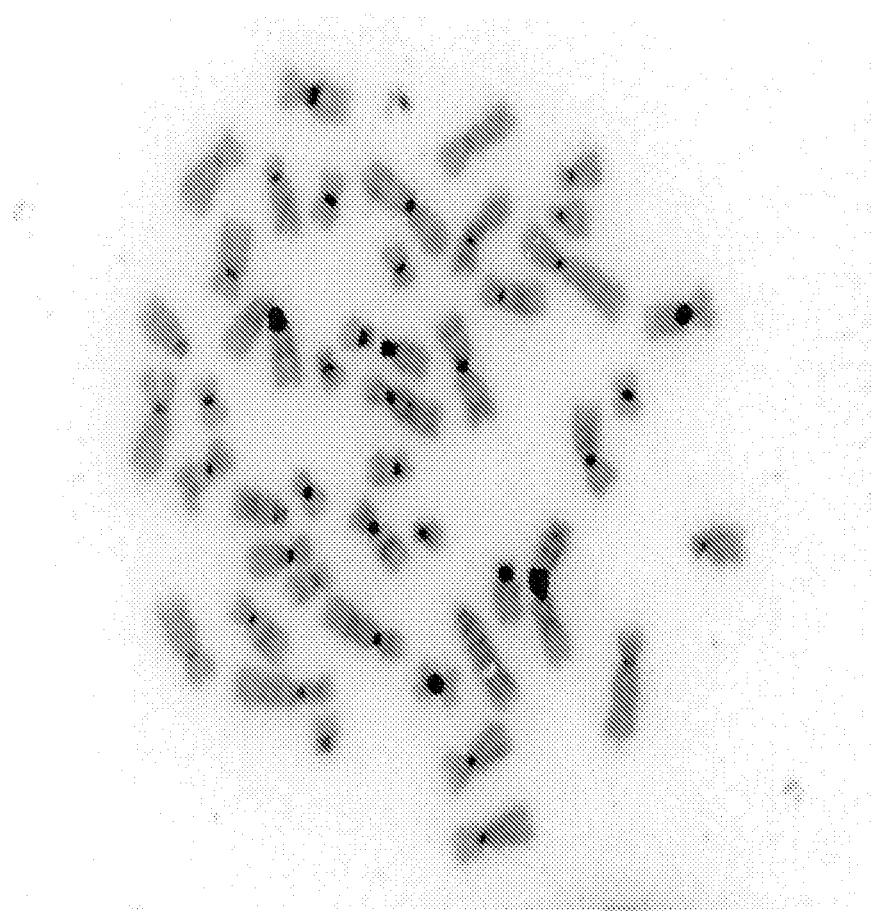
Figure 5C:
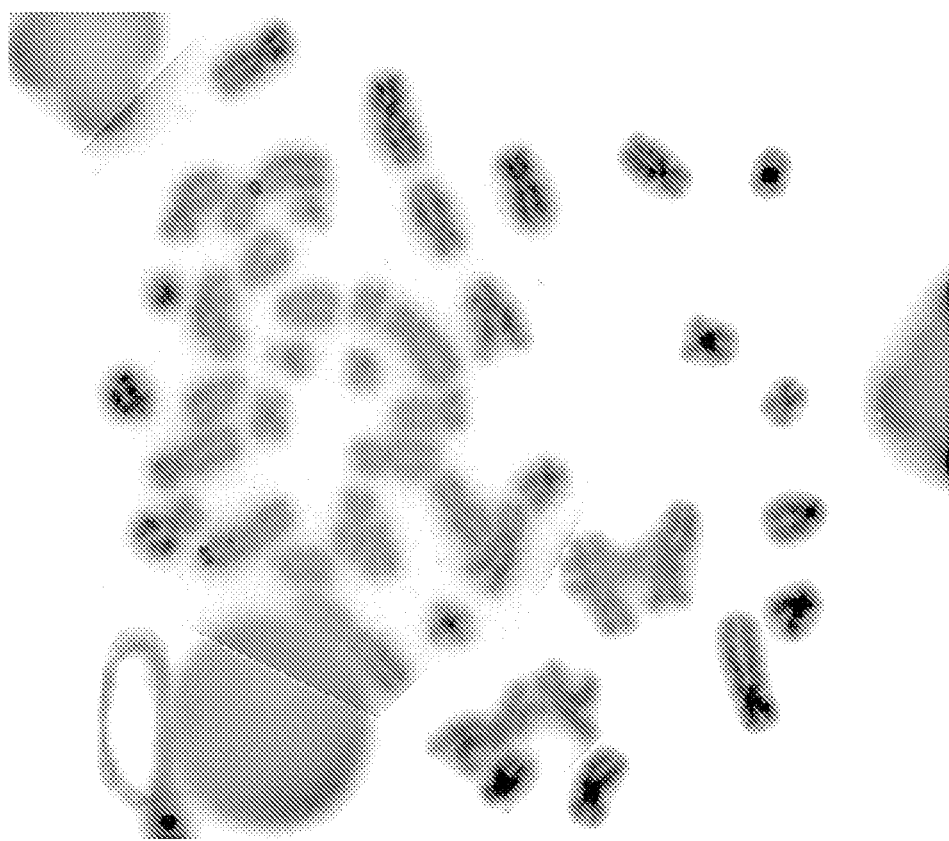
Figure 14:
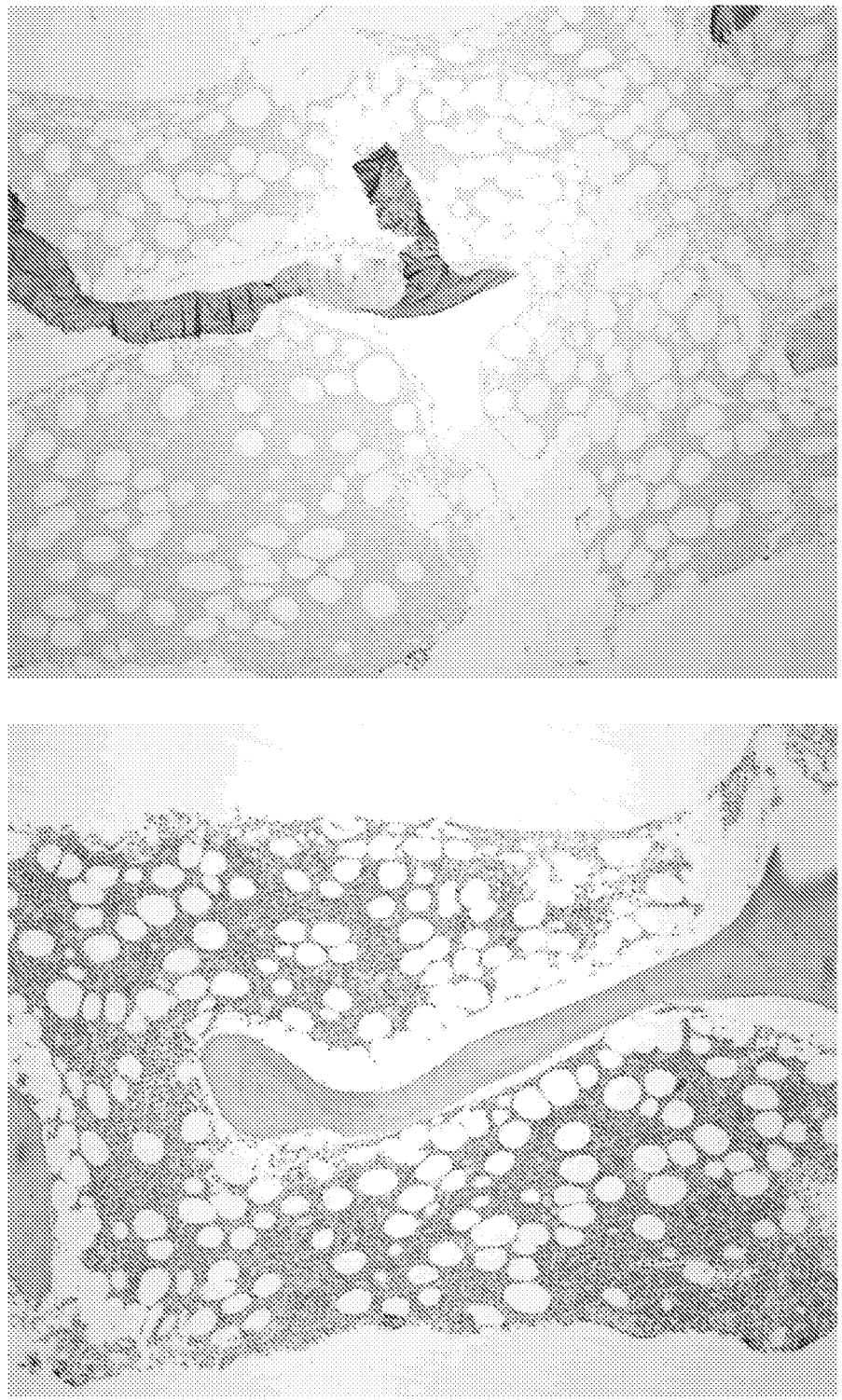
FIG. 14. Bone marrow Testing for ALK activity. Two representative photomicrographs from a WHIM-09 bone marrow biopsy are shown. On the left is a typical hematoxylin and eosin stain and on the right is an immunohistochemical stain for anaplastic lymphoma receptor tyrosine kinase (ALK) activity. Lack of brown color indicates that although the ALK gene is translocated there is no detectable increased enzymatic activity.

Bone marrow histology at time of examination did not reveal the characteristic findings of myelokathexis expected in WHIM syndrome (FIG. 4) in contrast to her previously reported bone marrow results and as noted above the patient's blood immunophenotype was abnormal and markedly different from her daughters (Table 2). Despite the patient's neutrophilia, monocytosis, CD4+ T cell lymphocytosis, and thrombocytosis, there was no evidence for CML, CMML, or myelodysplastic syndrome in the bone marrow pathology and specific testing for BCR-ABL and JAK mutations were negative. Cytogenetics was performed on the bone marrow aspirate and revealed that one copy of chromosome 2 was markedly abnormal but the other chromosomes exhibited a normal banding pattern (FIG. 5A). Fluorescent in situ hybridization (FISH) testing was performed and revealed that the anaplastic lymphoma receptor tyrosine kinase (ALK) gene and parts of the centromere were translocated in the abnormal chromosomal copy and the N-myc gene (MYCN) was absent on the abnormal chromosome (FIGS. 5B and 5C). Almost all of the bone marrow cells with polymorphic nuclei had the abnormal chromosome, while the cells with round nuclei had a lower percentage of the abnormal chromosome. An immunohistochemical stain of ALK activity on a bone marrow core biopsy section did not reveal abnormal activation of the enzyme despite the translocation (FIG. 14).

Figure 6A:
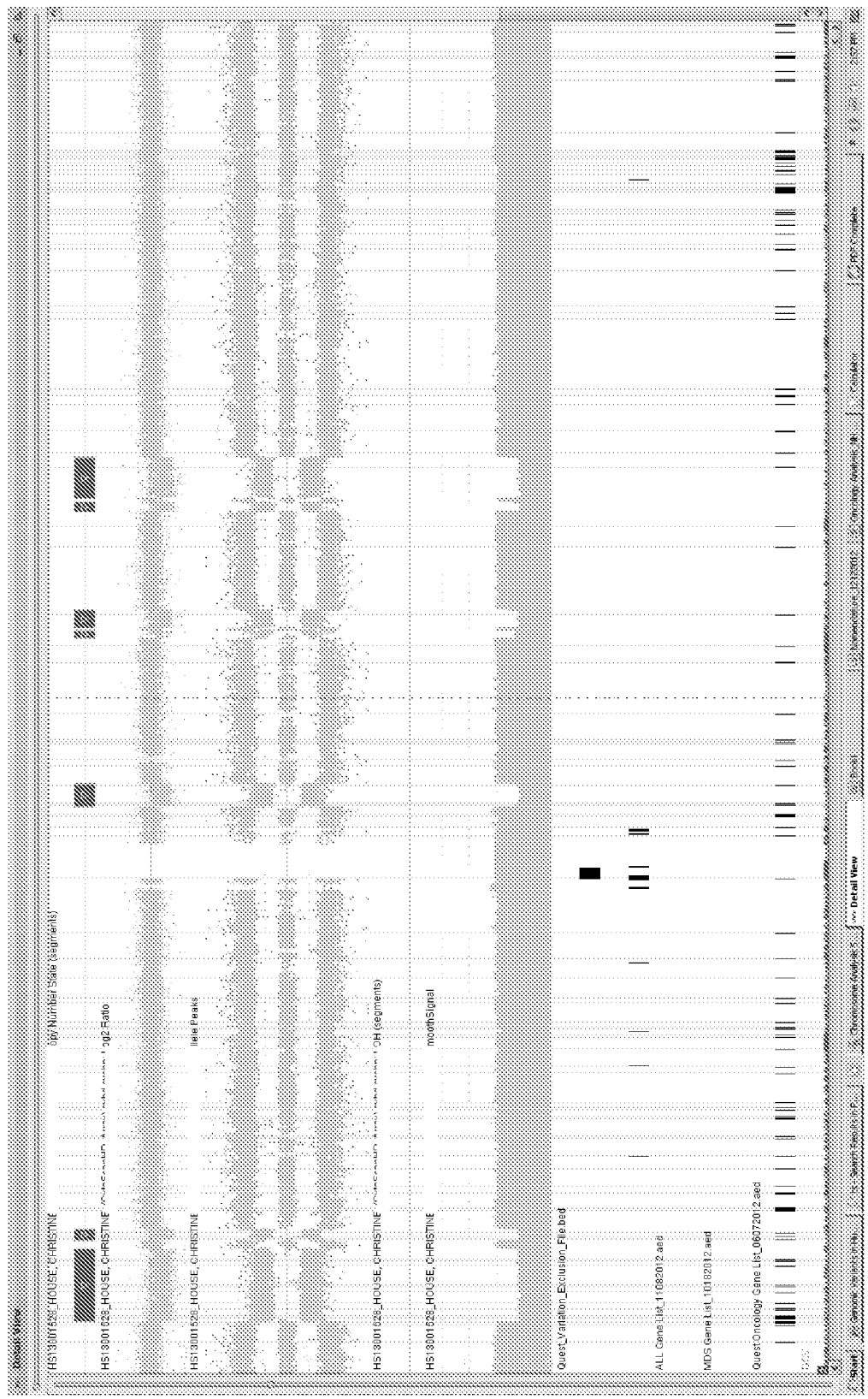
FIGS. 6A-6B. Microarray Results. Bone marrow cellular DNA was amplified and hybridized to a clinical microarray designed for investigation of chromosome abnormalities (Affymetrix Cytoscan HD array). Analysis of the copy number state and single nucleotide polymorphism variation using the Chromosome Analysis suite software revealed 7 distinct areas of chromosome 2 that were deleted (red boxes in screenshot (A)). A closer inspection of the 4th and 5th deleted regions reveals that CXCR4 is in the 5th deleted region (B).
Figure 6B:
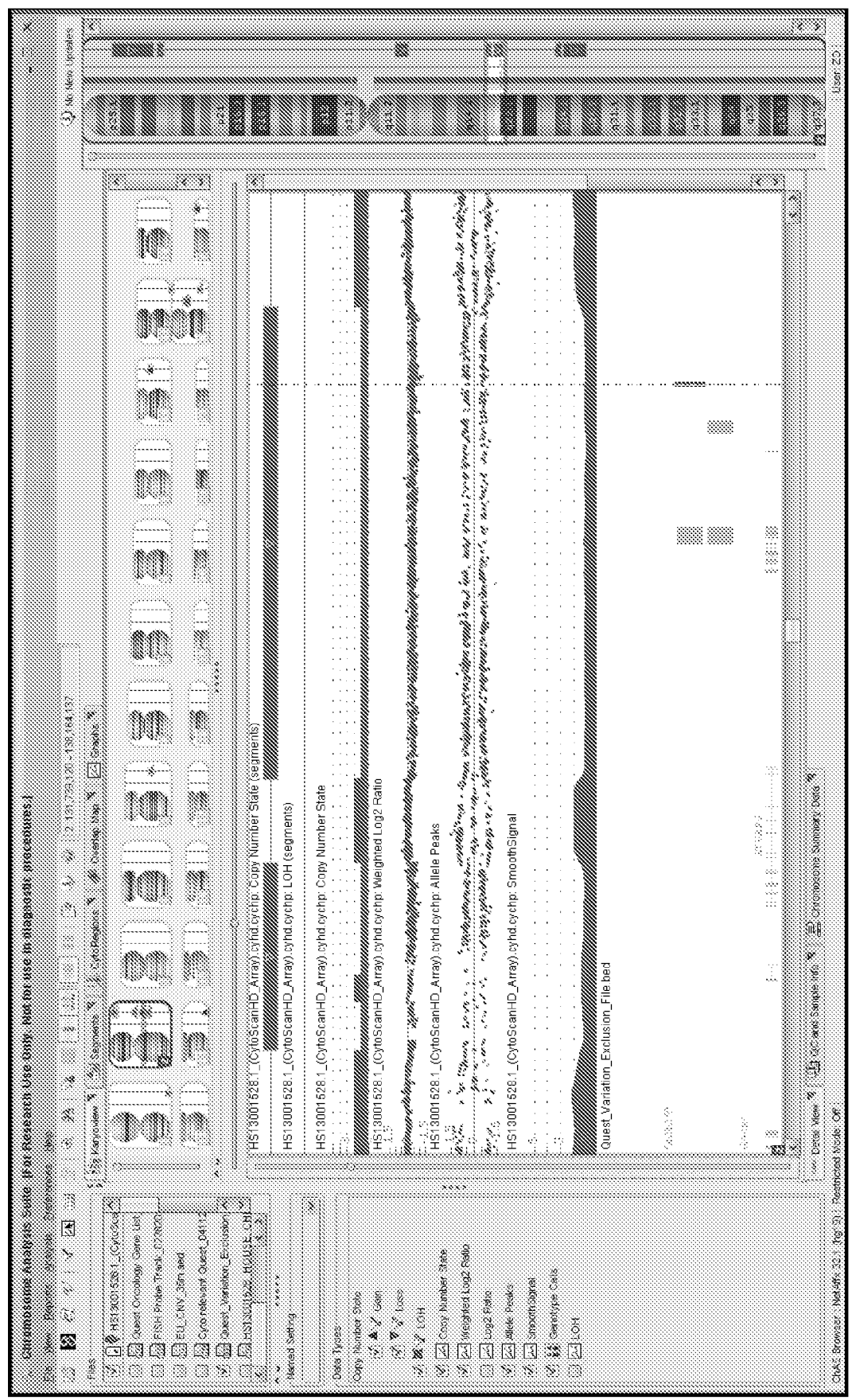

A clinical microarray was performed on the bone marrow cell DNA and compared with cultured fibroblast DNA. This revealed that the shortened chromosome 2 copy was due to 7 large deletions (FIG. 6A). This was demonstrated by the loss of heterozygosity in these regions and by an abrupt change in the relative copy number from 2 to 1. One of these deletions involved the MYCN gene and the normal position of ALK, confirming the FISH results. In addition, one of the deletions included the position of the CXCR4 gene (FIG. 6B). This had made the patient hemizygous for CXCR4 in cells from the myeloid lineage with loss of the $CXCR4^{R334X}$ mutation as well as loss of one copy of multiple other genes (Table 3).

TABLE 3

List of the orientation of the 18 pieces of the derivative chromosome of patient WHIM-09 and their nucleotide site of connections derived from whole genome sequencing of neutrophil DNA. Numbers are based on the chromosome 2 reference sequence of the hg19 version of the human genome project. Note underlined numbers are uncertain because of repetitive sequences in the region of the connection that make assigning a specific nucleotide ambiguous.

| Piece 1 | Piece 2 | Orientation | 5' End (Head) | 3' End (Tail) |
|---|---|---|---|---|
| 1 | 5 | Head to Head | 9650469 | 92323543 |
| 5 | 6 | Tail to Tail | 26227289 | 102167978 |
| 6 | 17 | Head to Tail | 102168450 | 156704625 |
| 17 | 12 | Head to Head | 157479872 | 134383040 |
| 12 | 3 | Tail to Tail | 134379440 | 18013669 |
| 3 | 15 | Head to Head | 18014058 | 137413687 |
| 15 | 16 | Tail to Head | 137402471 | 155186295 |

TABLE 3-continued

List of the orientation of the 18 pieces of the derivative chromosome of patient WHIM-09 and their nucleotide site of connections derived from whole genome sequencing of neutrophil DNA. Numbers are based on the chromosome 2 reference sequence of the hg19 version of the human genome project. Note underlined numbers are uncertain because of repetitive sequences in the region of the connection that make assigning a specific nucleotide ambiguous.

| Piece 1 | Piece 2 | Orientation | 5' End (Head) | 3' End (Tail) |
|---|---|---|---|---|
| 16 | 13 | Tail to Tail | 137413696 | 134383068 |
| 13 | 10 | Head to Head | <u>134384129</u> | 134208472 |
| 10 | 8 | Tail to Head | 133712996 | 132361705 |
| 8 | 4 | Tail to Head | 106220579 | 24238501 |
| 4 | 14 | Tail to Tail | 22647206 | <u>137344145</u> |
| 14 | 7 | Head to Tail | 137350425 | 92314297 |
| 7 | 2 | Head to Head | 102176282 | 13364053 |
| 2 | 9 | Tail to Tail | 13332820 | 133689046 |
| 9 | 11 | Head to Head | 133712975 | 134248797 |
| 11 | 18 | Tail to Tail | 134208529 | 164835205 |

This hemizygosity at CXCR4 with only the wild-type copy remaining thus provided an explanation for why the CXCR4$^{R334X}$ mutation in myeloid cell DNA was not detected by either DNA sequencing or PCR-RFLP. Thus, the genetic reversion had apparently been caused by multiple large deletions of the copy of chromosome 2 that bore the WHIM immunodeficiency causing mutation.

Example 6

Whole Genome Sequencing Revealed Evidence for Chromothripsis

Microarray has limitations in resolution of chromosomal rearrangement boundaries caused by the variable spacing of the polymorphic markers on the array. In addition, the microarray technique does not easily reveal translocated DNA if it has been moved but not mutated or deleted; however, it was known that such existed by the abnormal cytogenetic banding pattern and FISH results described above. Whole genome sequencing (WGS) was performed on the patient's blood neutrophil DNA to identify these chromosomal rearrangement boundaries using as a comparison the patient's fibroblast DNA and the standard human genome sequence (version hg19). An average of 40× coverage of both samples was obtained, and an analysis was performed to locate the stretches of DNA reads that had homology with multiple distinct areas of chromosome 2. This technique allowed precise basepair level identification of the translocations and deletions that had occurred on one copy of chromosome 2 (Table 4).

TABLE 4

Alphabetical List of Genes deleted in the derivative chromosome of patient WHIM-09 by whole genome sequencing

| Gene symbol | Entrez gene id | Map location | Type of gene | Full name |
|---|---|---|---|---|
| ACMSD | 130013 | 2q21.3 | protein-coding | aminocarboxymuconate semialdehyde decarboxylase |
| ACVR1 | 90 | 2q23-q24 | protein-coding | activin A receptor, type I |
| ACVR1C | 130399 | 2q24.1 | protein-coding | activin A receptor, type IC |
| ADAM17 | 6868 | 2p25 | protein-coding | ADAM metallopeptidase domain 17 |
| ADCY3 | 109 | 2p23.3 | protein-coding | adenylate cyclase 3 |
| ANKRD30BL | 554226 | 2q21.2 | pseudo | ankyrin repeat domain 30B-like |
| APOB | 338 | 2p24-p23 | protein-coding | apolipoprotein B (including Ag(x) antigen) |
| ASXL2 | 55252 | 2p24.1 | protein-coding | additional sex combs like 2 (Drosophila) |
| ATP6V1C2 | 245973 | — | protein-coding | ATPase, H+ transporting, lysosomal 42 kDa, V1 subunit C2 |
| BAZ2B | 29994 | 2q24.2 | protein-coding | bromodomain adjacent to zinc finger domain, 2B |
| C2orf27A | 29798 | 2q21.2 | protein-coding | chromosome 2 open reading frame 27A |
| C2orf27B | 408029 | 2q21 | protein-coding | chromosome 2 open reading frame 27B |
| C2orf43 | 60526 | 2p24.1 | protein-coding | chromosome 2 open reading frame 43 |
| C2orf44 | 80304 | 2p23.3 | protein-coding | chromosome 2 open reading frame 44 |
| C2orf48 | 348738 | 2p25.1 | protein-coding | chromosome 2 open reading frame 48 |
| C2orf49 | 79074 | 2q12.1 | protein-coding | chromosome 2 open reading frame 49 |
| C2orf50 | 130813 | 2p25.1 | protein-coding | chromosome 2 open reading frame 50 |
| C2orf84 | 653140 | 2p23.3 | protein-coding | chromosome 2 open reading frame 84 |
| CCDC148 | 130940 | 2q24.1 | protein-coding | coiled-coil domain containing 148 |
| CCNT2 | 905 | 2q21.3 | protein-coding | cyclin T2 |
| CD302 | 9936 | 2q24.2 | protein-coding | CD302 molecule |
| CENPO | 79172 | 2p23.3 | protein-coding | centromere protein O |
| CXCR4 | 7852 | 2q21 | protein-coding | chemokine (C-X-C motif) receptor 4 |
| CYS1 | 192668 | 2p25.1 | protein-coding | cystin 1 |
| CYTIP | 9595 | 2q11.2 | protein-coding | cytohesin 1 interacting protein |
| DAPL1 | 92196 | 2q24.1 | protein-coding | death associated protein-like 1 |
| DARS | 1615 | 2q21.3 | protein-coding | aspartyl-tRNA synthetase |

TABLE 4-continued

Alphabetical List of Genes deleted in the derivative chromosome
of patient WHIM-09 by whole genome sequencing

| Gene symbol | Entrez gene id | Map location | Type of gene | Full name |
| --- | --- | --- | --- | --- |
| DDX1 | 1653 | 2p24 | protein-coding | DEAD (Asp-Glu-Ala-Asp) box polypeptide 1 |
| DNAJC27 | 51277 | 2p23.3 | protein-coding | DnaJ (Hsp40) homolog, subfamily C, member 27 |
| DNAJC27-AS1 | 729723 | 2p23.3 | miscRNA | DNAJC27 antisense RNA 1 (non-protein coding) |
| DNMT3A | 1788 | 2p23 | protein-coding | DNA (cytosine-5-)-methyltransferase 3 alpha |
| DPP4 | 1803 | 2q24.3 | protein-coding | dipeptidyl-peptidase 4 |
| DTNB | 1838 | 2p24 | protein-coding | dystrobrevin, beta |
| E2F6 | 1876 | 2p25.1 | protein-coding | E2F transcription factor 6 |
| EFR3B | 22979 | 2p23.3 | protein-coding | EFR3 homolog B (*S. cerevisiae*) |
| ERMN | 57471 | 2q24.1 | protein-coding | ermin, ERM-like protein |
| FAM49A | 81553 | 2p24.2 | protein-coding | family with sequence similarity 49, member A |
| FAM84A | 151354 | 2p24.3 | protein-coding | family with sequence similarity 84, member A |
| FAP | 2191 | 2q23 | protein-coding | fibroblast activation protein, alpha |
| FHL2 | 2274 | 2q12.2 | protein-coding | four and a half LIM domains 2 |
| FIGN | 55137 | 2q24.3 | protein-coding | fidgetin |
| FKBP1B | 2281 | 2p23.3 | protein-coding | FK506 binding protein 1B, 12.6 kDa |
| FLJ12334 | 400946 | 2p24.1 | miscRNA | — |
| FLJ33534 | 285150 | 2p25.1 | miscRNA | — |
| GALNT13 | 114805 | 2q24.1 | protein-coding | UDP-N-acetyl-alpha-D-galactosamine: polypeptide N-acetylgalactosaminyltransferase 13 (GalNAc-T13) |
| GALNT5 | 11227 | 2q24.1 | protein-coding | UDP-N-acetyl-alpha-D-galactosamine: polypeptide N-acetylgalactosaminyltransferase 5(GalNAc-T5) |
| GCA | 25801 | 2q24.2 | protein-coding | grancalcin, EF-hand calcium binding protein |
| GCG | 2641 | 2q36-q37 | protein-coding | glucagon |
| GDF7 | 151449 | 2p24.1 | protein-coding | growth differentiation factor 7 |
| GEN1 | 348654 | 2p24.2 | protein-coding | Gen endonuclease homolog 1 (*Drosophila*) |
| GPR39 | 2863 | 2q21-q22 | protein-coding | G protein-coupled receptor 39 |
| GPR45 | 11250 | 2q11.1-q12 | protein-coding | G protein-coupled receptor 45 |
| GREB1 | 9687 | 2p25.1 | protein-coding | growth regulation by estrogen in breast cancer 1 |
| GRHL1 | 29841 | 2p25.1 | protein-coding | grainyhead-like 1 (*Drosophila*) |
| HPCAL1 | 3241 | 2p25.1 | protein-coding | hippocalcin-like 1 |
| HS1BP3 | 64342 | 2p24.1 | protein-coding | HCLS1 binding protein 3 |
| IFIH1 | 64135 | 2q24 | protein-coding | interferon induced with helicase C domain 1 |
| IL18R1 | 8809 | 2q12 | protein-coding | interleukin 18 receptor 1 |
| IL18RAP | 8807 | 2q12 | protein-coding | interleukin 18 receptor accessory protein |
| IL1R1 | 3554 | 2q12 | protein-coding | interleukin 1 receptor, type I |
| IL1R2 | 7850 | 2q12 | protein-coding | interleukin 1 receptor, type II |
| IL1RL1 | 9173 | 2q12 | protein-coding | interleukin 1 receptor-like 1 |
| IL1RL2 | 8808 | 2q12 | protein-coding | interleukin 1 receptor-like 2 |
| ITGB6 | 3694 | 2q24.2 | protein-coding | integrin, beta 6 |
| ITSN2 | 50618 | 2pter-p25.1 | protein-coding | intersectin 2 |
| KCNF1 | 3754 | 2p25 | protein-coding | potassium voltage-gated channel, subfamily F, member 1 |
| KCNH7 | 90134 | 2q24.2 | protein-coding | potassium voltage-gated channel, subfamily H (eag-related), member 7 |
| KCNJ3 | 3760 | 2q24.1 | protein-coding | potassium inwardly-rectifying channel, subfamily J, member 3 |
| KCNS3 | 3790 | 2p24 | protein-coding | potassium voltage-gated channel, delayed-rectifier, subfamily S, member 3 |
| KIF3C | 3797 | 2p23 | protein-coding | kinesin family member 3C |
| KLF11 | 8462 | 2p25 | protein-coding | Kruppel-like factor 11 |
| LAPTM4A | 9741 | 2p24.1 | protein-coding | lysosomal protein transmembrane 4 alpha |
| LCT | 3938 | 2q21 | protein-coding | lactase |
| LOC100129961 | 100129961 | 2q21.3 | miscRNA | — |
| LOC100144595 | 100144595 | — | protein-coding | — |
| LOC100287010 | 100287010 | 2q12.1 | miscRNA | — |

TABLE 4-continued

Alphabetical List of Genes deleted in the derivative chromosome
of patient WHIM-09 by whole genome sequencing

| Gene symbol | Entrez gene id | Map location | Type of gene | Full name |
|---|---|---|---|---|
| LOC100506421 | 100506421 | 2q12 | miscRNA | — |
| LOC100506474 | 100506474 | 2p24 | miscRNA | — |
| LOC100507600 | 100507600 | — | miscRNA | — |
| LOC150568 | 150568 | 2q12.1 | miscRNA | — |
| LOC284998 | 284998 | 2q12.1 | miscRNA | — |
| LOC285000 | 285000 | 2q12.2 | miscRNA | — |
| LOC375190 | 375190 | 2p23.3 | protein-coding | — |
| LOC554201 | 554201 | 2q24.1 | miscRNA | — |
| LOC645949 | 645949 | 2q24.1 | miscRNA | — |
| LPIN1 | 23175 | 2p25.1 | protein-coding | lipin 1 |
| LY75 | 4065 | 2q24 | protein-coding | lymphocyte antigen 75 |
| LY75-CD302 | 100526664 | 2q | protein-coding | LY75-CD302 readthrough |
| LYPD1 | 116372 | 2q21.2 | protein-coding | LY6/PLAUR domain containing 1 |
| MAP4K4 | 9448 | 2q11.2-q12 | protein-coding | mitogen-activated protein kinase 4 |
| MARCH7 | 64844 | 2q24.2 | protein-coding | membrane-associated ring finger (C3HC4) 7 |
| MATN3 | 4148 | 2p24-p23 | protein-coding | matrilin 3 |
| MCM6 | 4175 | 2q21 | protein-coding | minichromosome maintenance complex component 6 |
| MFSD2B | 388931 | 2p23.3 | protein-coding | major facilitator superfamily domain containing 2B |
| MFSD9 | 84804 | 2q12.1 | protein-coding | major facilitator superfamily domain containing 9 |
| MGAT5 | 4249 | 2q21.3 | protein-coding | mannosyl (alpha-1,6-)-glycoprotein beta-1,6-N-acetyl-glucosaminyltransferase |
| MIR128-1 | 406915 | 2q21.3 | miscRNA | microRNA 128-1 |
| MIR1301 | 100302246 | — | miscRNA | microRNA 1301 |
| MIR3125 | 100422986 | — | miscRNA | microRNA 3125 |
| MIR3679 | 100500878 | — | miscRNA | microRNA 3679 |
| MIR4261 | 100422929 | — | miscRNA | microRNA 4261 |
| MIR4262 | 100422996 | — | miscRNA | microRNA 4262 |
| MIR4429 | 100616469 | — | miscRNA | microRNA 4429 |
| MIR4757 | 100616307 | — | miscRNA | microRNA 4757 |
| MIR4772 | 100616157 | — | miscRNA | microRNA 4772 |
| MIR4785 | 100616364 | — | miscRNA | microRNA 4785 |
| MIR663B | 100313824 | — | miscRNA | microRNA 663b |
| MRPS9 | 64965 | 2q12.1 | protein-coding | mitochondrial ribosomal protein S9 |
| MSGN1 | 343930 | 2p24.2 | protein-coding | mesogenin 1 |
| MYCN | 4613 | 2p24.3 | protein-coding | v-myc myelocytomatosis viral related oncogene, neuroblastoma derived (avian) |
| MYCNOS | 10408 | 2p24.1 | miscRNA | MYCN opposite strand/antisense RNA (non-protein coding) |
| NBAS | 51594 | 2p24 | protein-coding | neuroblastoma amplified sequence |
| NCKAP5 | 344148 | 2q21.2 | protein-coding | NCK-associated protein 5 |
| NCOA1 | 8648 | 2p23 | protein-coding | nuclear receptor coactivator 1 |
| NOL10 | 79954 | 2p25.1 | protein-coding | nucleolar protein 10 |
| NT5C1B | 93034 | 2p24.2 | protein-coding | 5'-nucleotidase, cytosolic IB |
| NT5C1B-RDH14 | 100526794 | 2p | protein-coding | NT5C1B-RDH14 readthrough |
| NTSR2 | 23620 | 2p25.1 | protein-coding | neurotensin receptor 2 |
| ODC1 | 4953 | 2p25 | protein-coding | ornithine decarboxylase 1 |
| OSR1 | 130497 | 2p24.1 | protein-coding | odd-skipped related 1 (*Drosophila*) |
| PDIA6 | 10130 | 2p25.1 | protein-coding | protein disulfide isomerase family A, member 6 |
| PFN4 | 375189 | 2p23.3 | protein-coding | profilin family, member 4 |
| PKP4 | 8502 | 2q24.1 | protein-coding | plakophilin 4 |
| PLA2R1 | 22925 | 2q23-q24 | protein-coding | phospholipase A2 receptor 1, 180 kDa |
| POMC | 5443 | 2p23.3 | protein-coding | proopiomelanocortin |
| POTEKP | 440915 | 2q21.1 | pseudo | POTE ankyrin domain family, member K, pseudogene |
| POU3F3 | 5455 | 2q12.1 | protein-coding | POU class 3 homeobox 3 |
| PQLC3 | 130814 | 2p25.1 | protein-coding | PQ loop repeat containing 3 |
| PSMD14 | 10213 | 2q24.2 | protein-coding | proteasome (prosome, macropain) 26S subunit, non-ATPase, 14 |
| PTRHD1 | 391356 | 2p23.3 | protein-coding | peptidyl-tRNA hydrolase domain containing 1 |

TABLE 4-continued

Alphabetical List of Genes deleted in the derivative chromosome of patient WHIM-09 by whole genome sequencing

| Gene symbol | Entrez gene id | Map location | Type of gene | Full name |
|---|---|---|---|---|
| PUM2 | 23369 | 2p22-p21 | protein-coding | pumilio homolog 2 (*Drosophila*) |
| R3HDM1 | 23518 | 2q21.3 | protein-coding | R3H domain containing 1 |
| RAB3GAP1 | 22930 | 2q21.3 | protein-coding | RAB3 GTPase activating protein subunit 1 (catalytic) |
| RAD51AP2 | 729475 | 2p24.2 | protein-coding | RAD51 associated protein 2 |
| RBMS1 | 5937 | 2q24.2 | protein-coding | RNA binding motif, single stranded interacting protein 1 |
| RDH14 | 57665 | 2p24.2 | protein-coding | retinol dehydrogenase 14 (all-trans/9-cis/11-cis) |
| RHOB | 388 | 2p24 | protein-coding | ras homolog gene family, member B |
| ROCK2 | 9475 | 2p24 | protein-coding | Rho-associated, coiled-coil containing protein kinase 2 |
| RRM2 | 6241 | 2p25-p24 | protein-coding | ribonucleotide reductase M2 |
| SDC1 | 6382 | 2p24.1 | protein-coding | syndecan 1 |
| SF3B14 | 51639 | 2pter-p25.1 | protein-coding | — |
| SLC4A10 | 57282 | 2q23-q24 | protein-coding | solute carrier family 4, sodium bicarbonate transporter, member 10 |
| SLC9A2 | 6549 | 2q11.2 | protein-coding | solute carrier family 9 (sodium/hydrogen exchanger), member 2 |
| SLC9A4 | 389015 | 2q12.1 | protein-coding | solute carrier family 9 (sodium/hydrogen exchanger), member 4 |
| SMC6 | 79677 | 2p24.2 | protein-coding | structural maintenance of chromosomes 6 |
| SNORA80B | 100302743 | 2p25.1 | snoRNA | small nucleolar RNA, H/ACA box 80B |
| TAF1B | 9014 | 2p25 | protein-coding | TATA box binding protein (TBP)-associated factor, RNA polymerase I, B, 63 kDa |
| TANC1 | 85461 | 2q24.2 | protein-coding | tetratricopeptide repeat, ankyrin repeat and coiled-coil containing 1 |
| TANK | 10010 | 2q24-q31 | protein-coding | TRAF family member-associated NFKB activator |
| TBR1 | 10716 | 2q24 | protein-coding | T-box, brain, 1 |
| TGFBRAP1 | 9392 | 2q12.1 | protein-coding | transforming growth factor, beta receptor associated protein 1 |
| TMEM163 | 81615 | 2q21.3 | protein-coding | transmembrane protein 163 |
| TMEM182 | 130827 | 2q12.1 | protein-coding | transmembrane protein 182 |
| TP53I3 | 9540 | 2p23.3 | protein-coding | tumor protein p53 inducible protein 3 |
| TRIB2 | 28951 | 2p24.3 | protein-coding | tribbles homolog 2 (*Drosophila*) |
| TTC32 | 130502 | 2p24.1 | protein-coding | tetratricopeptide repeat domain 32 |
| UBXN4 | 23190 | 2q21.3 | protein-coding | UBX domain protein 4 |
| UPP2 | 151531 | 2q24.1 | protein-coding | uridine phosphorylase 2 |
| VSNL1 | 7447 | 2p24.3 | protein-coding | visinin-like 1 |
| WDR35 | 57539 | 2p24.1 | protein-coding | WD repeat domain 35 |
| WDSUB1 | 151525 | 2q24.2 | protein-coding | WD repeat, sterile alpha motif and U-box domain containing 1 |
| YSK4 | 80122 | 2q21.3 | protein-coding | YSK4 Sps1/Ste20-related kinase homolog (*S. cerevisiae*) |
| YWHAQ | 10971 | 2p25.1 | protein-coding | tyrosine 3-monooxygenase/tryptophan 5-monooxygenase activation protein, theta polypeptide |
| ZRANB3 | 84083 | 2q21.3 | protein-coding | zinc finger, RAN-binding domain containing 3 |

Figure 7A:
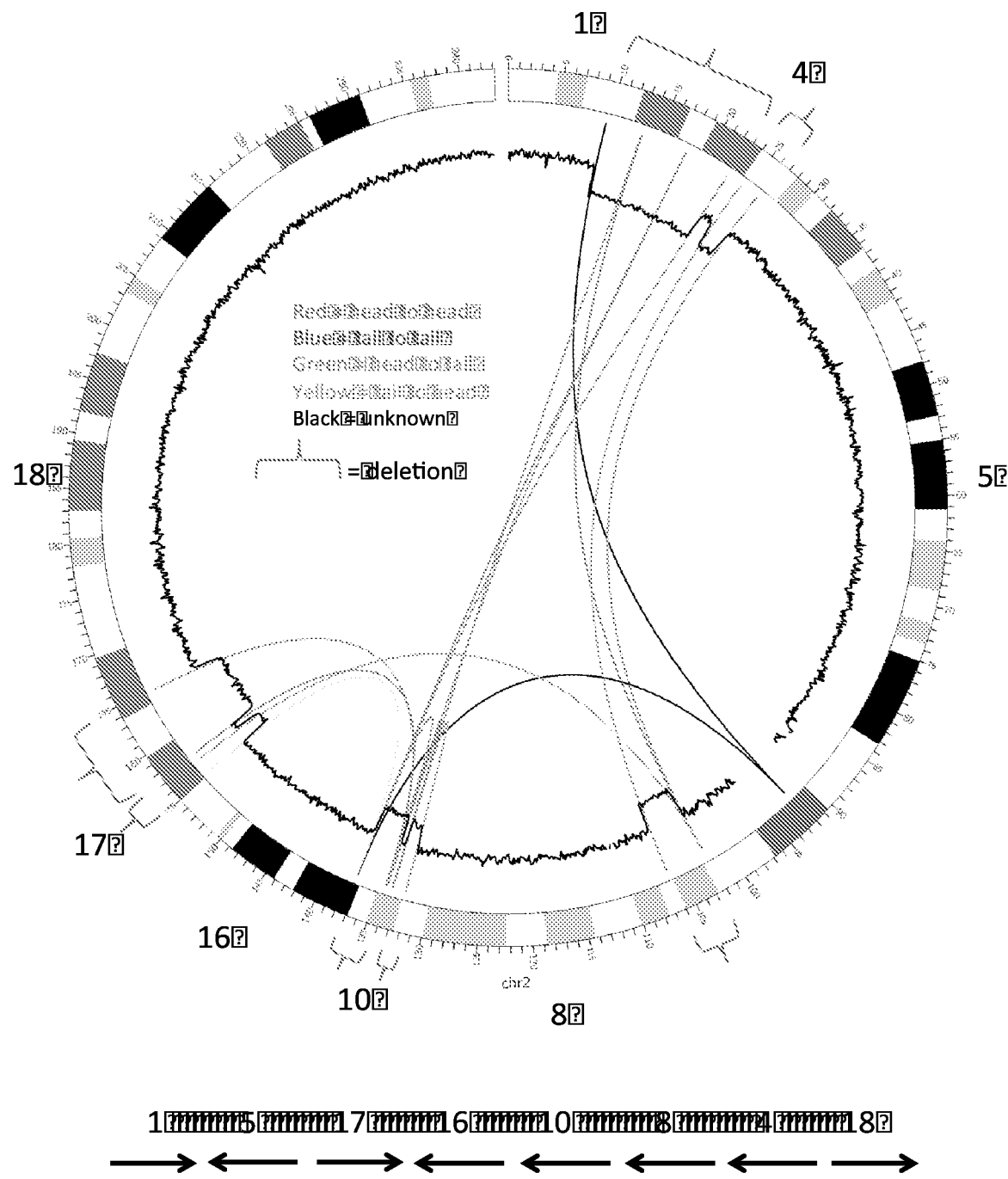
FIGS. 7A-7B. Whole Genome Sequencing of the Index Patient. Purified neutrophil DNA was isolated and subjected to whole genome sequencing with paired end analysis. Depicted in (A) is a circular plot from the program Circos of chromosome 2 and its Giemsa cytogenetic banding pattern labeled from the p arm telomere (0) to the q arm telomere (~240) in megabases. Large pieces of chromosome 2 were missing (deletions marked by brackets) and 18 remaining pieces were arranged in random order. Connections between these pieces and their orientation are depicted by the colored lines. Note that 2 connections were poorly defined because of the involvement of repetitive centromeric sequence. The inner circular trace is the copy number variation data derived from the microarray. Note that the sites of connections derived from the paired end sequencing analysis closely matches the sites where copy number variation abruptly falls from 2 to 1. 8 larger piece locations are labeled in bold around the outside of the circle. The arrangement of these 8 larger pieces is given in cartoon form below the plot. (B, left side) shows a cartoon of the Giemsa cytogenetic banding pattern and the order and orientation of the 18 pieces with the deletions called by microarray shaded in yellow. The resultant remaining chromosome 2 banding pattern predicted by whole genome sequencing closely matches that seen by cytogenetic analysis (see FIG. 5).
Figure 7B:
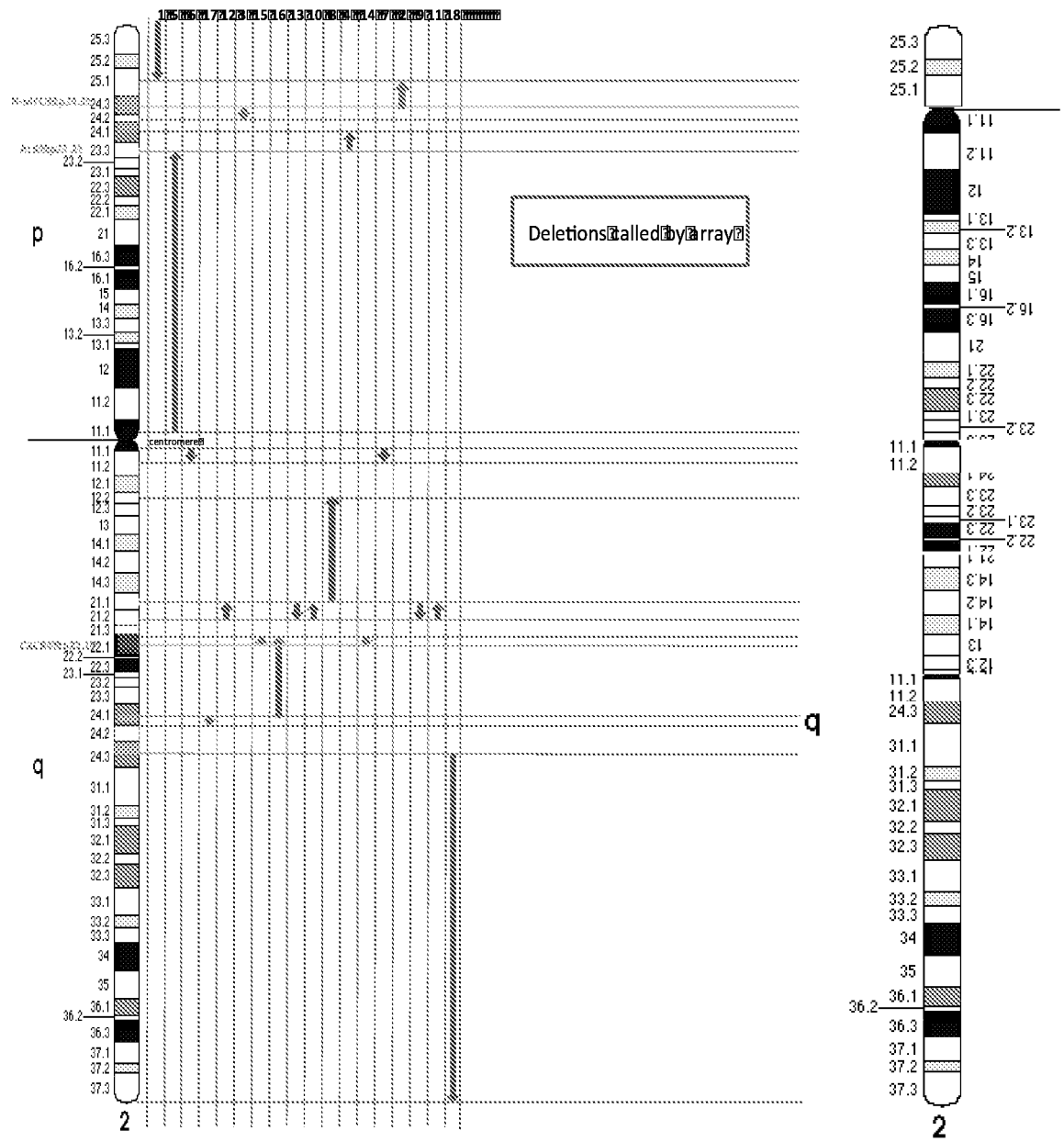

The changes seen in the microarray were confirmed but were actually more complex than had been initially revealed. The derivative chromosome was composed of 18 remaining pieces arranged in random orientation. These remaining stretches of the normal chromosome 2 had been ligated back together in a random fashion characteristic of the newly described genetic phenomenon called chromothripsis. A circular plot of the connections revealed by paired end whole genome sequencing of the neutrophil DNA is shown (FIG. 7A). The abnormal derivative chromosome was modeled using the breakpoints and connections discovered (FIG. 7B) and revealed a predicted structural banding pattern that was identical to what was observed using cytogenetics.

The microarray derived gene deletions were confirmed and the rearrangement breakpoints analyzed for the creation of novel fusion genes and two potential possibilities were identified (FIG. 15A); however, these genes are unlikely to be expressed or functional because they each lack a promoter and transcription initiation site, and major regions of the potentially fused genes are deleted. Thus, a novel driver mutation was not identified that would have given these cells a growth advantage other than loss of one copy (haploinsufficiency) of 164 genes on the shortened derivative chromosome that resulted when chromothripsis occurred.

Example 7

Purification and In Vitro Culture of HSC and Hematopoietic Progenitors

Chromothripsis results when a chromosome or chromosomes are shattered into multiple pieces in a single event which is then repaired by the cellular DNA damage repair machinery. Thus it became apparent that the multiple genetic changes observed had occurred in a single HSC as an isolated event.

Figure 8A:
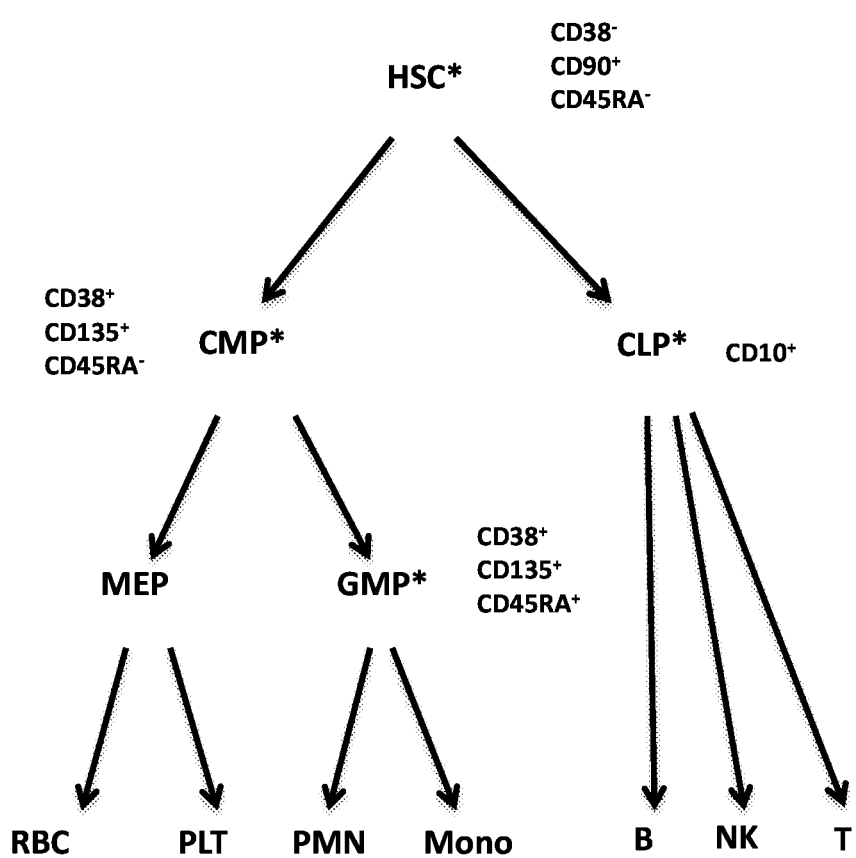
FIGS. 8A-8B. Hematopoietic Differentiation Precursor Markers and Chromothripsis Analysis in Precursors. (A) shows a cartoon of the differentiation proceeding from the hematopoietic stem cell (HSC) to final blood elements through the multipotent precursor (MPP) to the common myeloid precursor (CMP) to the megakaryocyte-erythroid precursor (MEP) and granulocyte-monocyte precursor (GMP). The MPP can also differentiate into the common lymphoid precursor (CLP). Cell surface markers used in flow cytometric sorting of these precursors is also shown. Red + symbol indicates precursors and final elements found to have evidence of chromothripsis and green − symbol indicates those that retain the $CXCR4^{R334X}$ allele. CD, cluster of differentiation. (B) shows the results of DNA from the purified bone marrow precursors after PCR-RFLP to detect the $CXCR4^{R334x}$ mutation (left side gel) and amplification using primers specific for one of the 18 chromothripsis rearrangements (right side gel). Note CLP demonstrate continued presence of the $CXCR4^{R334x}$ heterozygous mutation and lack amplification for the derivative chromosome that resulted from chromothripsis. BM CD16+ indicate purified CD16+ neutrophils given as a positive control, HD PBMC indicates healthy donor peripheral blood mononuclear cell DNA as a negative control. PCR− indicates amplification in the absence of input DNA as a negative control.
Figure 8B:
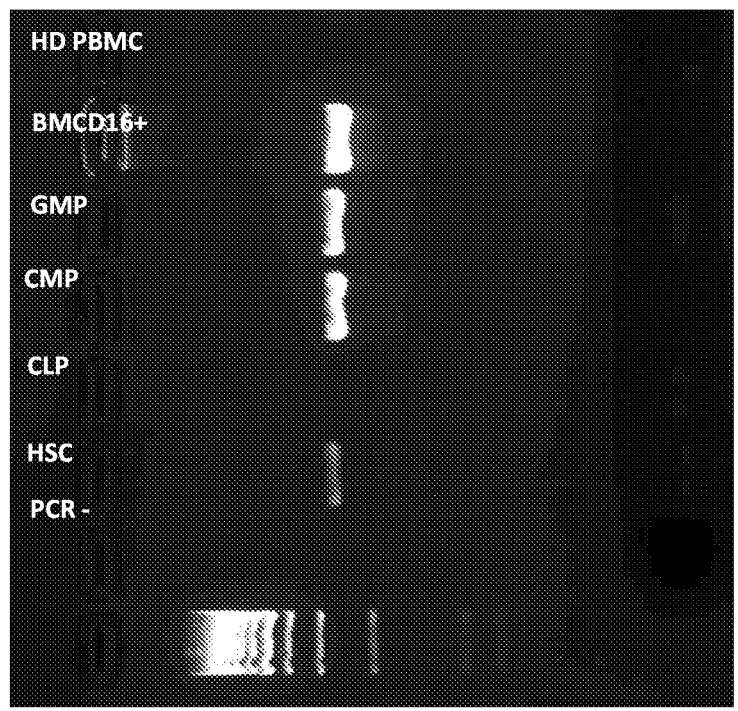
Figure 8B:
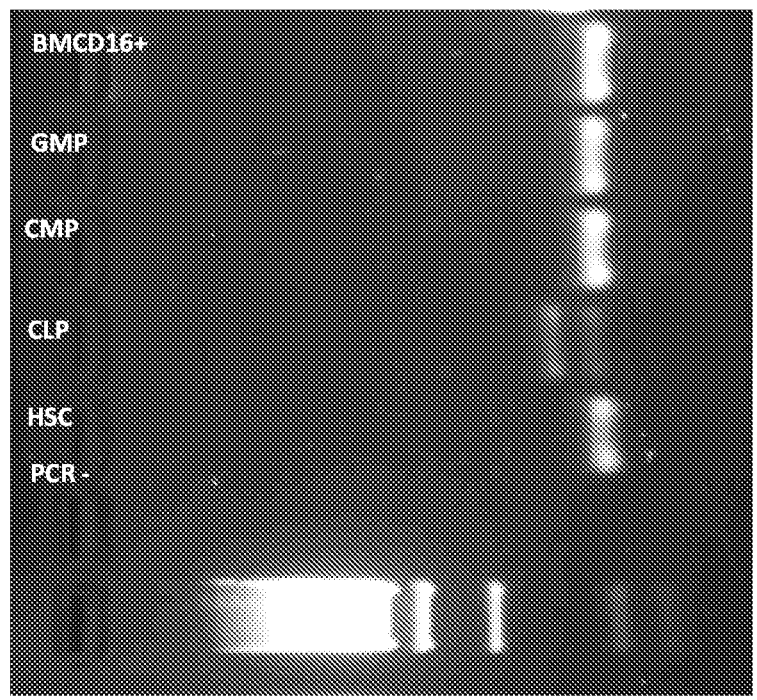
Figure 15A:
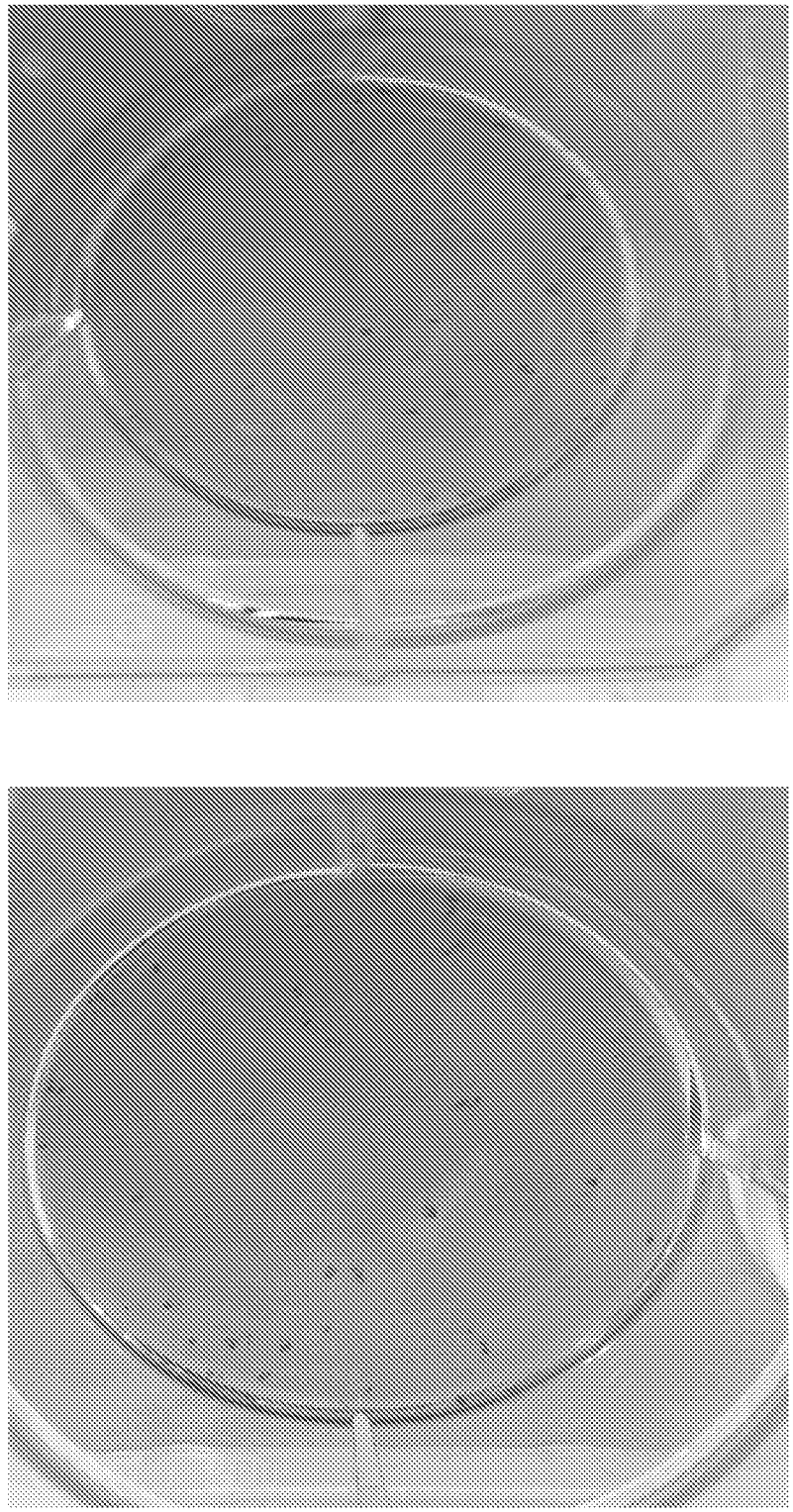
FIGS. 15A and 15B. Bone Marrow Progenitor In vitro Culture Assay and PCR. (A) Representative example of the in vitro culture and differentiation of a healthy blood donor (HD) and WHIM-09's (W9) CD34+ HSC cultured to create burst forming unit-erythroid (BFU-E) colonies. DNA isolated from these colonies was then used in the PCR-RFLP assay for the CXCR4$^{R334X}$ allele. (B) Demonstrates that BFU-E colonies lack the WHIM allele.
Figure 15B:
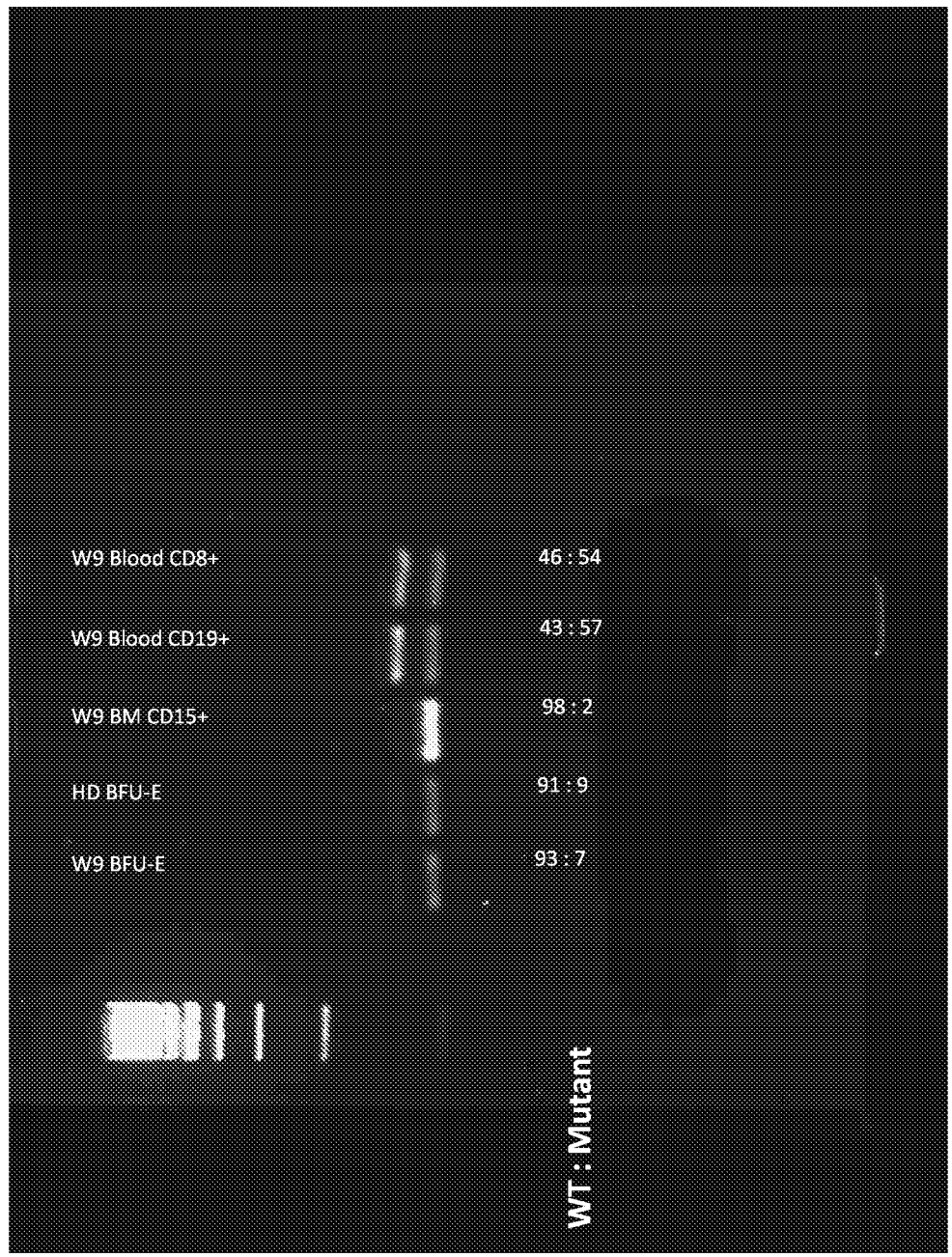

A scheme of hematopoietic differentiation is given in FIG. 8A. Knowledge of the exact breakpoints and orientations of the rearranged pieces allowed for the creation of four specific PCR amplification assays that confirmed the chromosomal rearrangement breakpoints predicted by the computer analysis of the WGS data and could detect DNA that had undergone chromothripsis. One of these PCR assays was used to investigate the hematopoietic system mosaicism further. Bone marrow aspirate was stained with fluorescent monoclonal antibodies and then underwent flow cytometric sorting to separate HSC, common lymphoid progenitors (CLP), common myeloid progenitors (CMP), and granulocyte macrophage progenitors (GMP). DNA isolated from these cell groups and subjected to the chromosomal rearrangement PCR described above revealed that three of the four hematopoietic progenitor types had evidence of chromothripsis (FIG. 8B). CLP was the only progenitor type that did not show chromothripsis consistent with the patient's $CD19^+$ B and $CD3^+$ T cells lacking evidence of chromothripsis and retaining the $CXCR4^{R334X}$ mutation. In vitro cultures of purified $CD34^+$ progenitor cells were performed under conditions that allowed development of progenitor colonies and PCR of DNA from these revealed a similar dichotomy (FIGS. 15A and 15B).

Example 8

Cytokine Abnormalities

Figure 9:
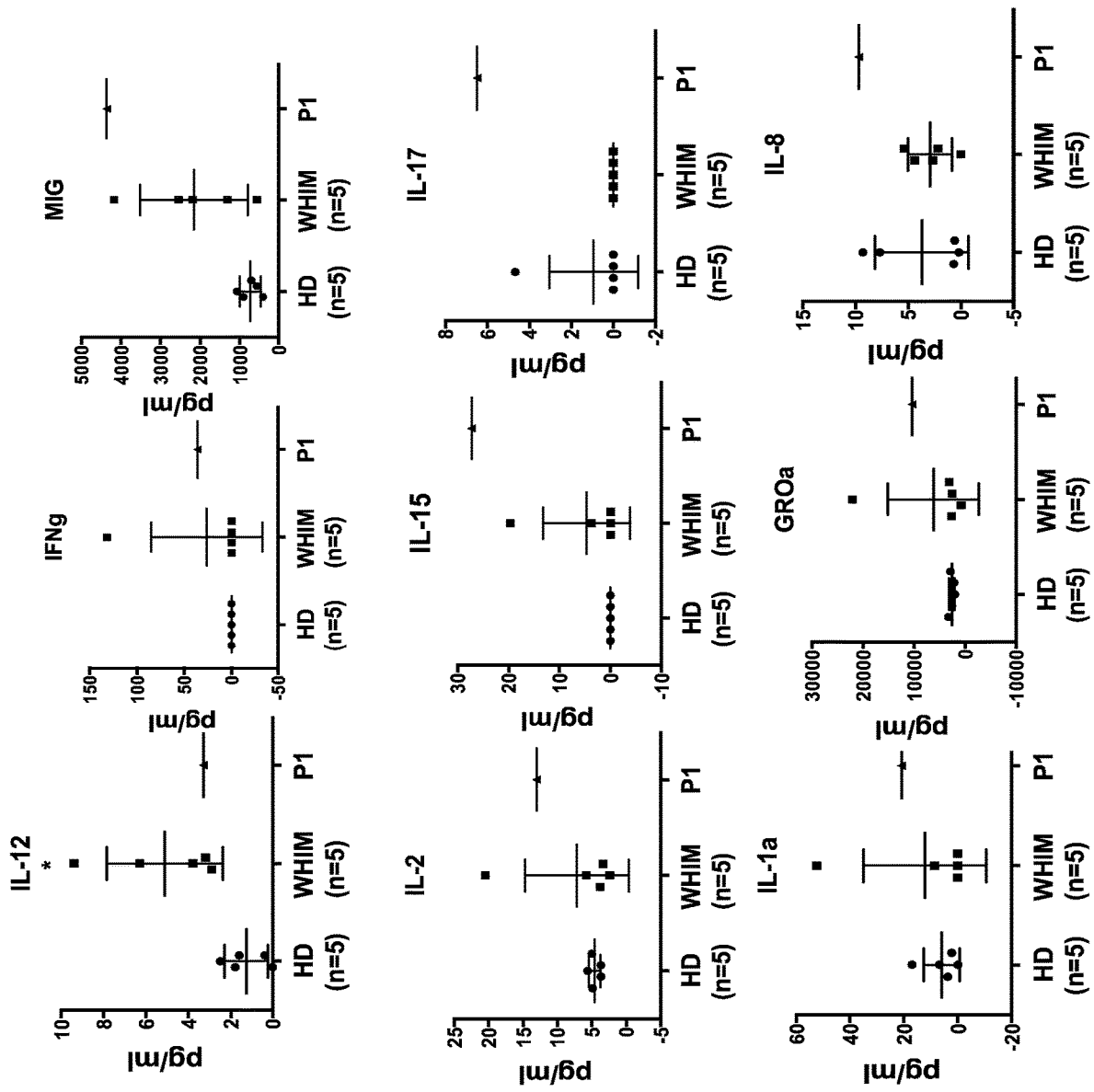
FIG. 9. Serum Cytokines. Frozen serum from the index patient, 5 healthy donors and 5 WHIM patients was sent for measurement of 26 cytokines. Shown are selected results in picograms/milliliter (pg/ml) where each value for an individual is a dot with circles representing healthy donors (HD), squares representing WHIM patients, and W9 representing the index patient (WHIM-09). The lines represent the mean±the standard error of the mean. See Table 3 for a complete list.

To further understand why the index patient had neutrophilia, monocytosis and increased effector memory T cells, cytokine, interleukin, and chemokine levels in her blood were analyzed. Frozen serum samples from the index patient, 5 healthy blood donors, and 5 WHIM patients were used for determination of a variety of cytokine, interleukin, and chemokine levels (FIG. 9, Table 5). This revealed that the patient had increased levels of a variety of molecules known to stimulate neutrophils, monocytes and T cells. In particular, CXCL8 (aka Interleukin-8), CXCL1 (aka Growth-regulated protein alpha) and Interleukin-17 (IL-17) are known to stimulate and attract neutrophils; while Interleukins (IL) such as IL-2, IL-12, and IL-15 act to stimulate memory T cells. Interferon gamma (IFN-γ) and CXCL9 (aka monokine induced by gamma interferon or MIG) and IL-1 have broad effects on the immune system and stimulate all three cell types.

TABLE 5

Serum cytokine concentrations of the index patient compared to 5 other WHIM patients and 5 Healthy Donors

| Cytokines (pg/ml) | HDs (n = 5) Mean ± SEM | WHIM (n = 5) Mean ± SEM | WHIM-09 |
|---|---|---|---|
| G-CSF | 0.0 ± 0.0 | 1.8 ± 1.0 | 0.0 |
| GM-CSF | 0.0 ± 0.0 | 0.3 ± 0.3 | 0.0 |
| M-CSF | 5.2 ± 1.2 | 13.4 ± 6.3 | 6 |
| IFNγ | 0.0 ± 0.0 | 26.4 ± 26.4 | 35.8 |
| IL-1α | 6 ± 3 | 12.2 ± 10.2 | 20.9 |
| IL-1β | 5.7 ± 0.4 | 17.4 ± 9.8 | 6.7 |
| IL-2 | 4.6 ± 0.4 | 7.2 ± 3.4 | 13 |
| IL-4 | 1.4 ± 0.1 | 2.5 ± 1.5 | 1.3 |
| IL-6 | 3.9 ± 1.7 | 5.8 ± 2.5 | 0.0 |
| IL-7 | 30.1 ± 4.6 | 35.6 ± 13.5 | 17.2 |
| IL-8 | 3.7 ± 2 | 2.9 ± 0.9 | 9.8 |
| IL-12 | 1.3 ± 0.5 | 5.1 ± 1.2 | 3.3 |
| IL-13 | 0.0 ± 0.0 | 0.6 ± 0.4 | 0.0 |
| IL-15 | 0.0 ± 0.0 | 4.7 ± 3.8 | 27.3 |
| IL-17 | 0.9 ± 0.9 | 0.0 ± 0.0 | 6.5 |
| CXCL1 | 2616 ± 232 | 6256 ± 3977 | 10369.4 |
| CXCL9 | 732.2 ± 118.1 | 2161 ± 609.9 | 4361.3 |
| CXCL10 | 136.1 ± 20 | 168.3 ± 54.9 | 103.8 |
| CXCL11 | 41.6 ± 11.8 | 27.1 ± 8.1 | 32.1 |
| CXCL12 | 661.1 ± 265.9 | 2904 ± 2143 | 347.7 |
| CCL2 | 366.1 ± 76.4 | 440.5 ± 53.2 | 385.2 |
| CCL3 | 132.1 ± 19.5 | 81.3 ± 25.4 | 135.6 |
| CCL5 | 4014 ± 389.3 | 3871 ± 520 | 4212.1 |
| CCL15 | 1718 ± 450.5 | 1353 ± 727.3 | 3723 |
| TGF-β1 | 1071 ± 55.5 | 1059 ± 125.8 | 1109.7 |
| TNF-α | 30.1 ± 2.4 | 53.3 ± 24 | 37.1 |

G-CSF, Granulocyte Colony-Stimulating Factor;
GM-CSF, Granulocyte-Macrophage Colony-Stimulating Factor;
M-CSF, Macrophage Colony-Stimulating Factor;
IFN, Interferon;
IL, Interleukin;
CXCL, CXC Chemokine Ligand;
CCL, CC Chemokine Ligand,
TGF, Transforming Growth Factor;
TNF, Tumor Necrosis Factor;
HD, Healthy Donor;
WHIM, Warts, Hypogammaglobulinemia, Infections, Myelokathexis Syndrome Patient;
WHIM-09, index patient of this report Example 9

Loss of One Copy of CXCR4 Causes a Transplantation Advantage for $CD34^+$ HSC

To model the effects of loss of CXCR4 haploinsufficiency on HSC engraftment in transplantation, wild-type Cxcr4 ($Cxcr4^{+/+}$), hemizygous Cxcr4 ($Cxcr4^{+/-}$), and WHIM syndrome ($Cxcr4^{+/S338X}$) mice were used to perform competitive repopulation experiments. Leukocytes from these strains were specifically marked with either CD45.1 or CD45.2 or both, allowing tracking of transplanted donor cell fate in vivo by FACS.

Cxcr4 floxed mice (Strain 008767, B6.129P2-$Cxcr4^{tm2Yzo}$/J) and EIIa promoter driven Cre recombinase transgenic mice (Strain 003724, B6.FVB-Tg(EIIa-cre)C5379Lmgd/J) were obtained from The Jackson Laboratory (Bar Harbor, Me.) and bred together to generate $Cxcr4^{+/-}$ mice on a homozygous CD45.2 background. $Cxcr4^{+/+}$ mice were obtained from Jackson Laboratory on the homozygous CD45.1 and homozygous CD45.2 backgrounds. Creation of WHIM knockin mice bearing a heterozygous $Cxcr4^{+/S338X}$ mutation has been previously described (Balabanian et al., 2012) and sperm from these mice were used for in vitro fertilization to impregnate female C57BL/6 mice from Taconic Farms (Hudson, N.Y.) to produce $Cxcr4^{+/S338X}$ on a homozygous CD45.2 background. Both $Cxcr4^{+/-}$ and Cxcr4$^{+/S338X}$ mice on the homozygous CD45.2 background were bred to Cxcr4$^{+/+}$ mice on a homozygous CD45.1 background to produce Cxcr4$^{+/-}$ and Cxcr4$^{+/S338X}$ mice on a heterozygous CD45.1/CD45.2 background. In this way, differentially marked donor bone marrow cells could be tracked in vivo during competitive transplantation experiments. Five million bone marrow cells, or 2000 HSCs, (~50% from each donor) were transferred via tail vein injection into recipient mice that had undergone lethal irradiation (900 rads) 8 hours prior to transplant. The mice were fed with neomycin water for four weeks post irradiation. All animal experiments were performed using an NIAID Animal Care and Use Committee (ACUC) approved protocol in approved and certified facilities. In some experiments, ten million bone marrow cells were injected into non-irradiated mice. To isolate mouse hematopoietic stem cells (HSCs), the mixed bone marrow cells were lineage-depleted by negative selection with Lineage Cell Depletion Kit (Miltenyi Biotech Inc., San Diego, Calif.) and then HSCs (lineage$^-$Sca1$^+$ c-Ki$^+$CD48$^-$CD34$^-$CD150$^+$) were sorted using a sorting cytometer (FACS Aria II, BD Biosciences, San Jose, Calif.).

To study the proliferation of HSCs, bone marrow cells from donors with a Cxcr4$^{+/-}$ genotype on a homozygous CD45.2 background were mixed (47%:53%) with bone marrow cells from donors with a Cxcr4$^{+/+}$ genotype on a heterozygous CD45.1/CD45.2 background and then 5 million bone marrow cells were injected intravenously into each CD45.1 recipient mouse that had been lethally irradiated 8 hours prior. Six days after bone marrow transplantation, each mouse was given 1.25 mg of BrdU ip. Twenty hours later, the mice were euthanized for HSC proliferation analysis with FITC BrdU Flow Kit (BD Biosciences, San Jose, Calif.).

Figure 10A:
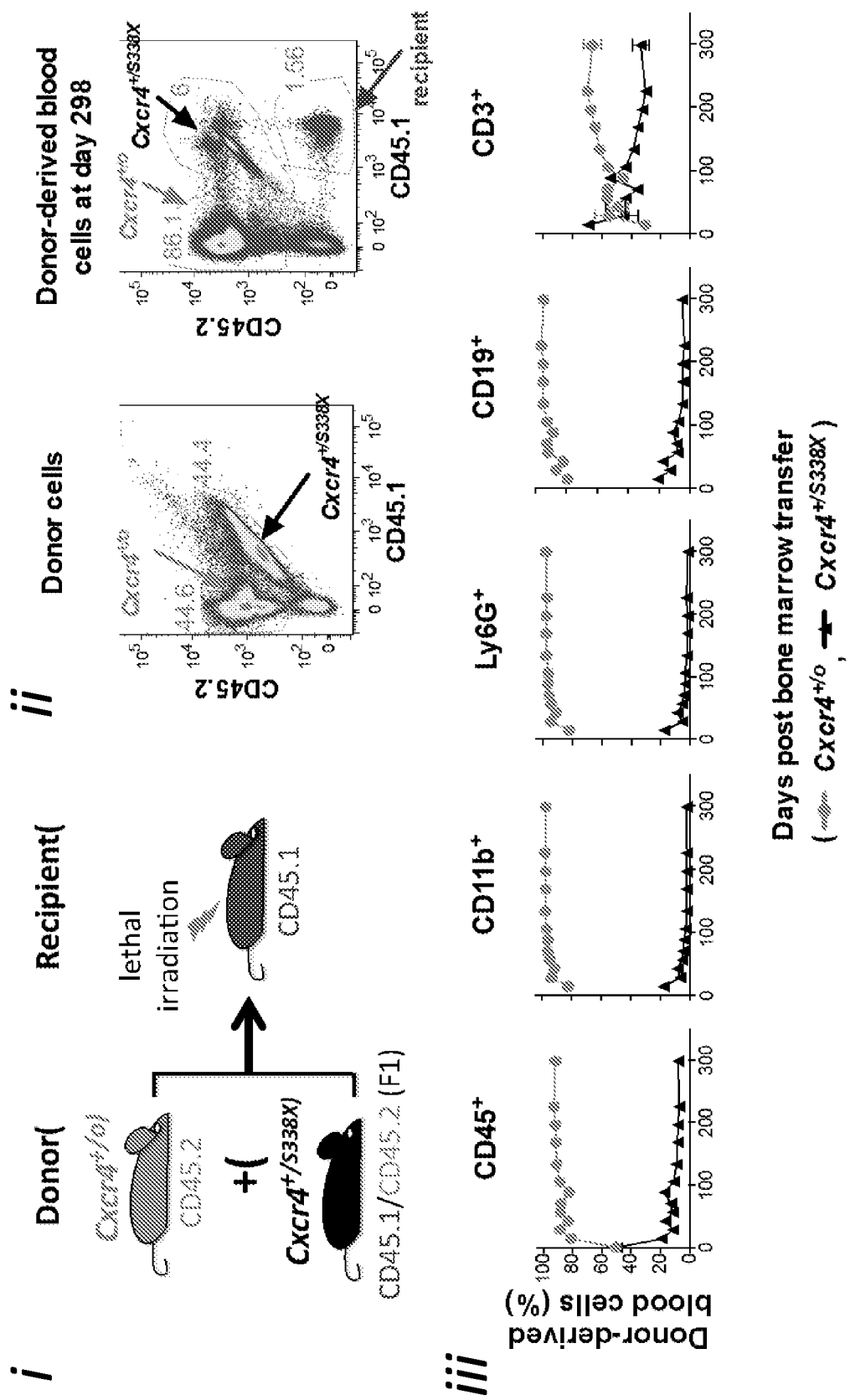
FIGS. 10A-10B. Cxcr4 Haploinsufficiency Enhances Bone Marrow Engraftment in WHIM Syndrome Mouse Model. (A) Competitive bone marrow transplantation experiment in irradiated recipients: $Cxcr4^{+/-}$ versus $Cxcr4^{+/S338X}$ (mouse model of WHIM syndrome). (i) Experimental design: Bone marrow cells from donors with a $Cxcr4^{+/-}$ genotype on a CD45.2 homozygous and $Cxcr4^{+/S338X}$ on a CD45.1/45.2 heterozygous background were mixed equally and then 5 million bone marrow cells were injected intravenously into each CD45.1 recipient mouse that had been lethally irradiated 8 hours prior. Serial blood draws every 2 weeks for flow cytometry were then performed to determine which mouse bone marrow could engraft more readily. (ii) Representative flow cytometry plots demonstrating the relative contributions of CD45 congenic markers in mixed donor bone marrow prior to transplantation (left panel) and in blood 298 days after bone marrow transplantation (right panel) in a single mouse. (iii) Cell frequency data for the leukocyte subsets indicated at the top of each panel ($CD45^+$ hematopoietic cells, $CD11b^+$ monocytes, $Ly6G^+$ neutrophils, $CD19^+$ B cells, and $CD3^+$ T cells), presented as the mean±SEM percentage (%) of total donor-derived cells for each subset (n=10 mice per data point). SEM was <5% of the mean in all cases and therefore is not visible for most data points (red circles=blood cells from $Cxcr4^{+/-}$ donors and black triangles=blood cells from $Cxcr4^{+/S338X}$ donors). Results were verified in two additional independent experiments. (B) Competitive bone marrow transplantation experiments in non-irradiated $Cxcr4^{+/S338X}$ recipients: (i) $Cxcr4^{+/+}$ versus $Cxcr4^{+/S338X}$ and (ii) $Cxcr4^{+/-}$ versus $Cxcr4^{+/+}$. Left panels: Experimental design. Bone marrow cells from donors with a $Cxcr4^{+/S338X}$ genotype (i) or a $Cxcr4^{+/-}$ genotype (ii) on a CD45.2 background were mixed equally with bone marrow cells from $Cxcr4^{+/+}$ on a CD45.1 background and then 10 million bone marrow cells were injected intravenously into each non-irradiated $Cxcr4^{+/S338X}$ recipient mouse on a CD45.1/45.2 heterozygous background. Serial blood draws every 2 weeks for flow cytometry were then performed to determine which mouse bone marrow could engraft more readily. Right panels: Donor-derived blood cell frequency data for the leukocyte subsets indicated at the top of each panel, presented as the mean±SEM percentage (%) of total cells for each subset (n=5 mice per data point). Red circles=blood cells from $Cxcr4^{+/-}$ donors, blue triangles=blood cells from $Cxcr4^{+/S338X}$ donors, and black triangles=blood cells from $Cxcr4^{+/+}$ donors. Results were verified in one additional independent experiment.
Figure 10B:
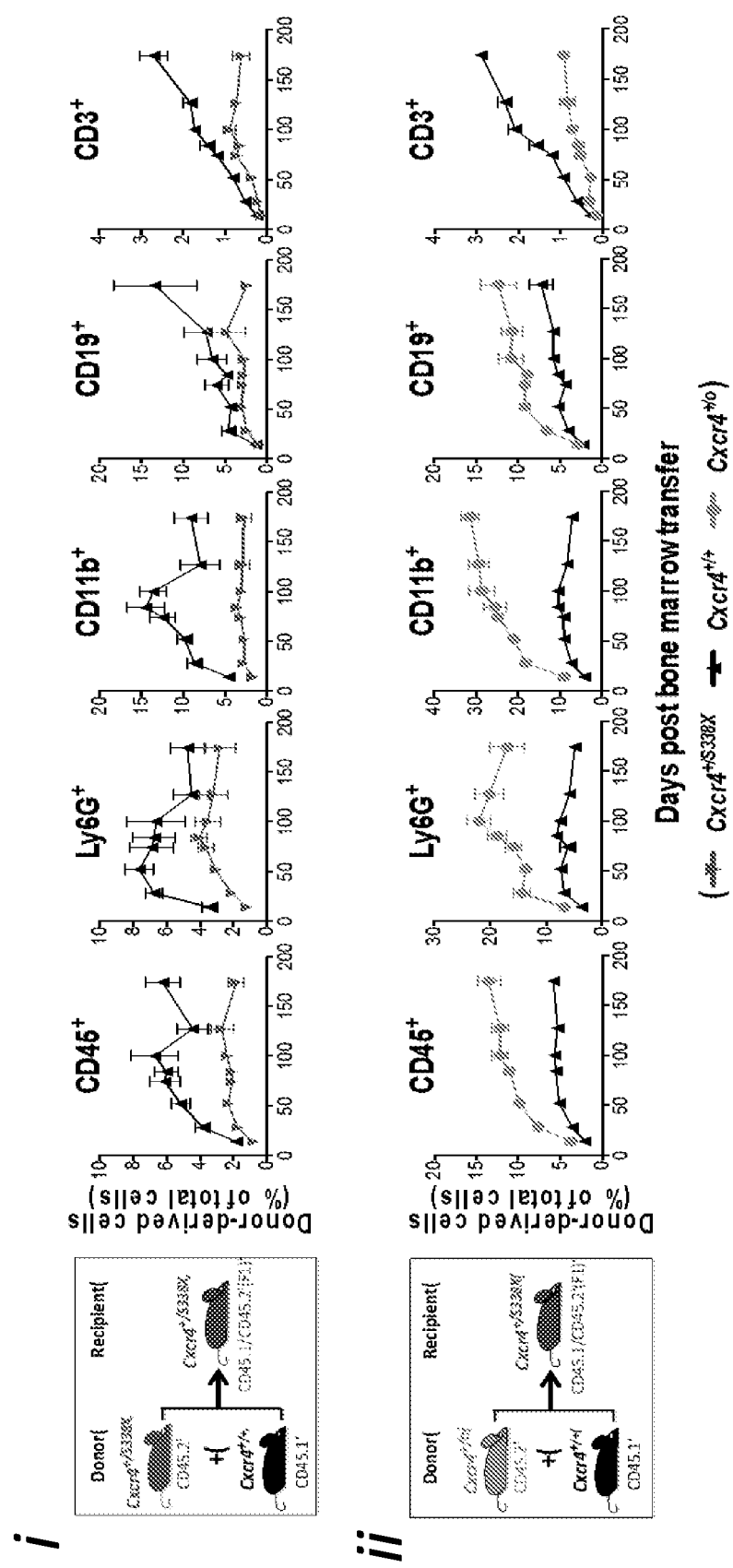
Figure 11A:
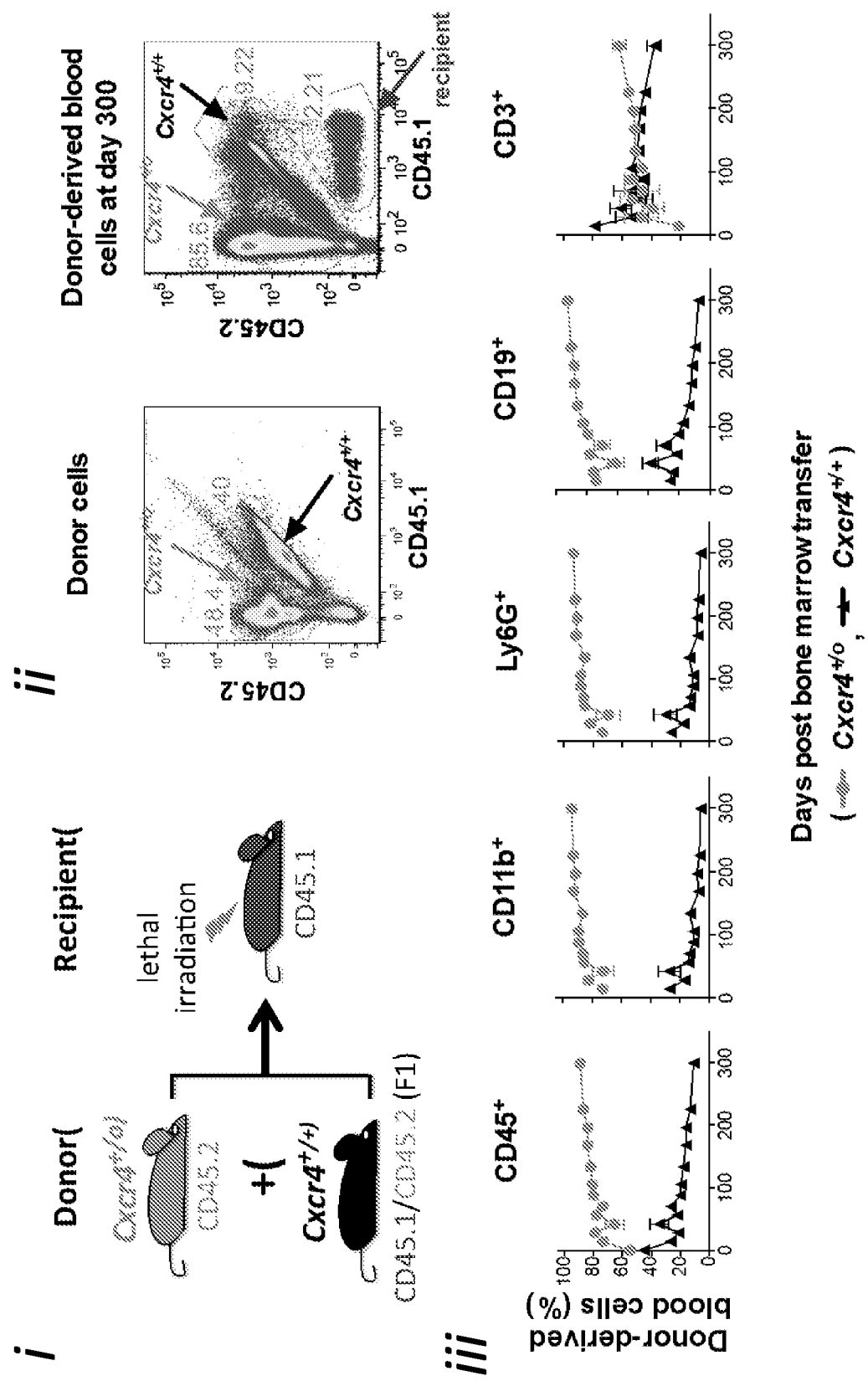
FIGS. 11A-11B. Cxcr4 Haploinsufficiency Enhances Bone Marrow Engraftment. (A) Competitive bone marrow transplantation experiment in irradiated recipients: $Cxcr4^{+/-}$ versus $Cxcr4^{+/+}$. (i) Experimental design: Bone marrow cells from donors with a $Cxcr4^{+/-}$ genotype on a CD45.2 homozygous and a $Cxcr4^{+/+}$ genotype on a CD45.1/45.2 heterozygous background were mixed equally and then 5 million mixed bone marrow cells were injected intravenously into each CD45.1 recipient mouse that had been lethally irradiated 8 hours prior. Serial blood draws every 2 weeks for flow cytometry were then performed to determine which mouse bone marrow could engraft more readily. (ii) Representative flow cytometry plots demonstrating the relative contributions of CD45 congenic markers in mixed donor bone marrow prior to transplantation (left panel) and in blood 300 days after bone marrow transplantation (right panel) in a single mouse. (iii) Cell frequency data for the leukocyte subsets indicated at the top of each panel (CD45$^+$ hematopoietic cells, CD11b$^+$ monocytes, Ly6G$^+$ neutrophils, CD19$^+$ B cells, and CD3$^+$ T cells), presented as the mean±SEM percentage (%) of total donor-derived cells for each subset (n=10 mice per data point). SEM was <5% of the mean in all cases and therefore is not visible for most data points (red circles=blood cells from Cxcr4$^{+/-}$ donors and black triangles=blood cells from Cxcr4$^{+/+}$ donors). Results were verified in two additional independent experiments. (B) Competitive bone marrow transplantation experiments in non-irradiated Cxcr4$^{+/+}$ recipients: Cxcr4$^{+/-}$ versus Cxcr4$^{+/+}$. Left panel: Experimental design. Bone marrow cells from donors with a Cxcr4$^{+/-}$ genotype on a CD45.2 background were mixed equally with bone marrow cells from donors with a Cxcr4$^{+/+}$ genotype on a CD45.1 background, and then 10 million mixed bone marrow cells were injected intravenously into each non-irradiated Cxcr4$^{+/+}$ recipient mouse on a CD45.1/45.2 heterozygous background. Serial blood draws every 2 weeks for flow cytometry were then performed to determine which mouse bone marrow could engraft more readily. Right panels: Donor-derived blood cell frequency data for the leukocyte subsets indicated at the top of each panel, presented as the mean±SEM percentage (%) of total cells for each subset (n=5 mice per data point). Red circles=blood cells from Cxcr4$^{+/-}$ donors and black triangles=blood cells from Cxcr4$^{+/+}$ donors. Results were verified in one additional independent experiment.
Figure 11B:
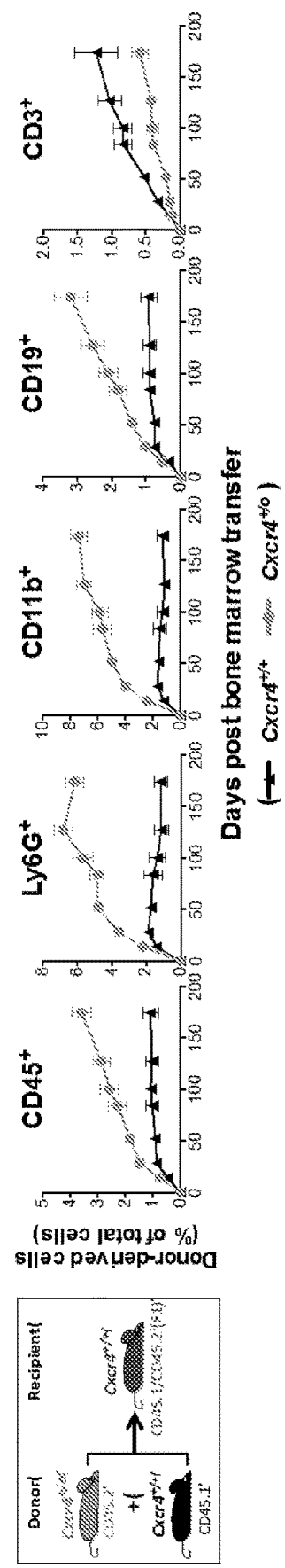
Figure 12A:
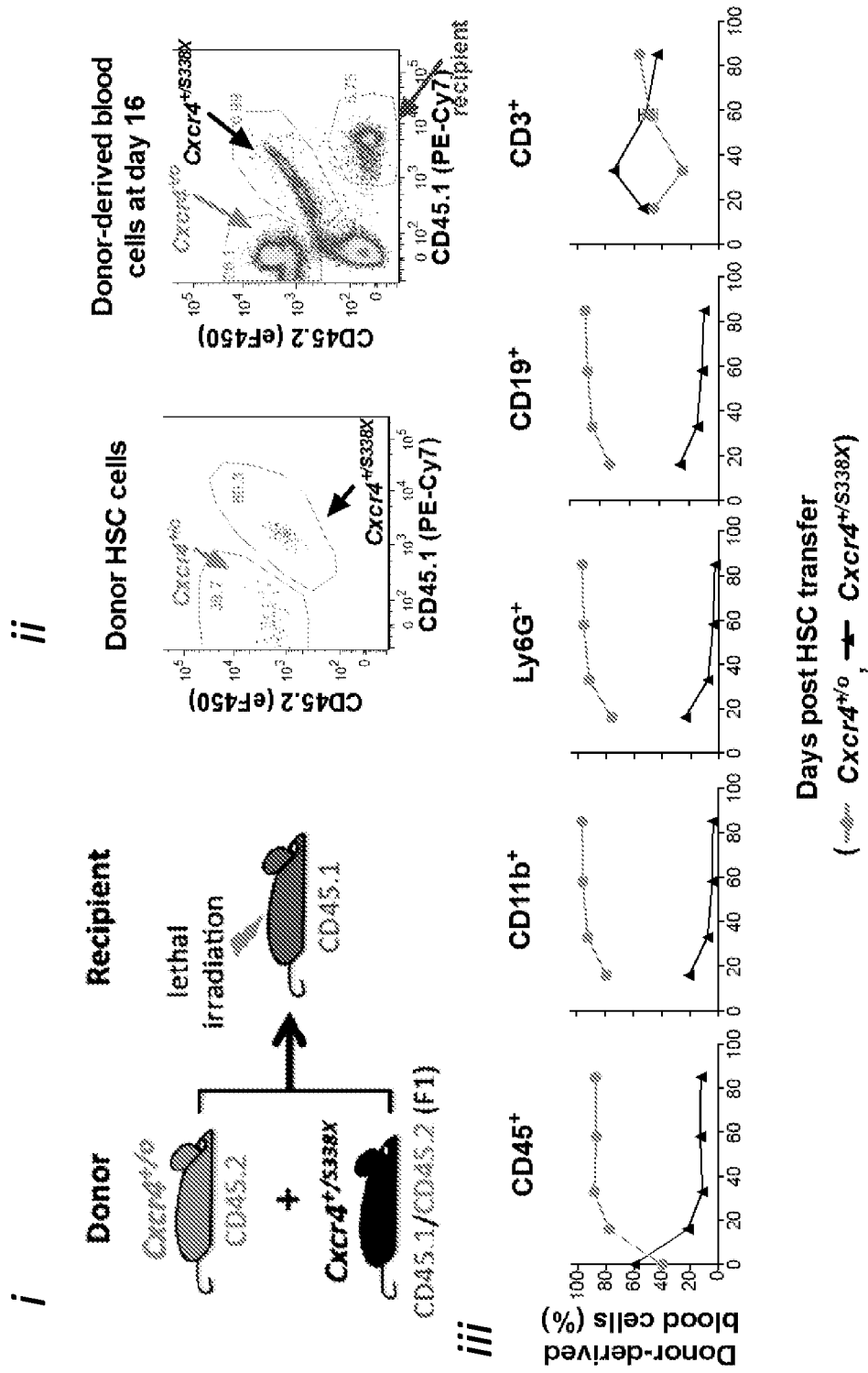
FIGS. 12A-12B. Cxcr4 Haploinsufficiency Enhances Bone Marrow Engraftment in mice in a Hematopoietic Stem Cell (HSC) Intrinsic Manner. (A) Competitive HSC transplantation experiment in irradiated recipients: Cxcr4$^{+/-}$ versus Cxcr4$^{+/S338X}$. (i) Experimental design: Bone marrow cells from donors with a Cxcr4$^{+/-}$ genotype on a CD45.2 homozygous and from donors with a Cxcr4$^{+/S338X}$ genotype on a CD45.1/45.2 heterozygous background were mixed equally. The mixed BM cells were lineage-depleted by negative selection with Lineage Cell Depletion Kit (Miltenyi Biotech Inc) and then HSC cells (lineage$^-$Scal$^+$c-Kit$^+$CD48$^-$CD34$^-$CD150$^+$) were sorted with a flow cytometer. 2000 isolated HSC cells were injected intravenously into each CD45.1 recipient mouse that had been lethally irradiated 8 hours prior. Serial blood draws every 2 weeks for flow cytometry were then performed to determine which mouse bone marrow could engraft more readily. (ii) Representative flow cytometry plots demonstrating the relative contributions of CD45 congenic markers in mixed donor HSCs prior to transplantation (left panel) and in blood 16 days after HSC transplantation (right panel) in a single mouse. (iii) Cell frequency data for the leukocyte subsets indicated at the top of each panel, presented as the mean±SEM percentage (%) of total donor-derived cells for each subset (n=5 mice per data point). SEM was <5% of the mean in all cases and therefore is not visible for most data points. (B) Competitive HSC transplantation experiment in irradiated recipients: Cxcr4$^{+/-}$ versus Cxcr4$^{+/+}$. (i) Experimental design: Bone marrow cells from donors with a Cxcr4$^{+/-}$ genotype on a CD45.2 homozygous and from donors with a Cxcr4$^{+/+}$ genotype on a CD45.1/45.2 heterozygous background were mixed equally. The mixed BM cells were lineage-depleted by negative selection with Lineage Cell Depletion Kit (Miltenyi Biotech Inc) and then HSC cells (lineage$^-$Scal$^+$c-Kit$^+$CD48$^-$CD34$^-$CD150+) were sorted with flow cytometer. 2000 isolated HSCs were injected intravenously into each CD45.1 recipient mouse that had been lethally irradiated 8 hours prior. Serial blood draws every 2 weeks for flow cytometry were then performed to determine which mouse bone marrow could engraft more readily. (ii) Representative flow cytometry plots demonstrating the relative contributions of CD45 congenic markers in mixed donor HSCs prior to transplantation (left panel) and in blood 16 days after HSC transplantation (right panel) in a single mouse. (iii) Cell frequency data for the leukocyte subsets indicated at the top of each panel, presented as the mean±SEM percentage (%) of total donor-derived cells for each subset (n=5 mice per data point). SEM was <5% of the mean in all cases and therefore is not visible for most data points.
Figure 12B:
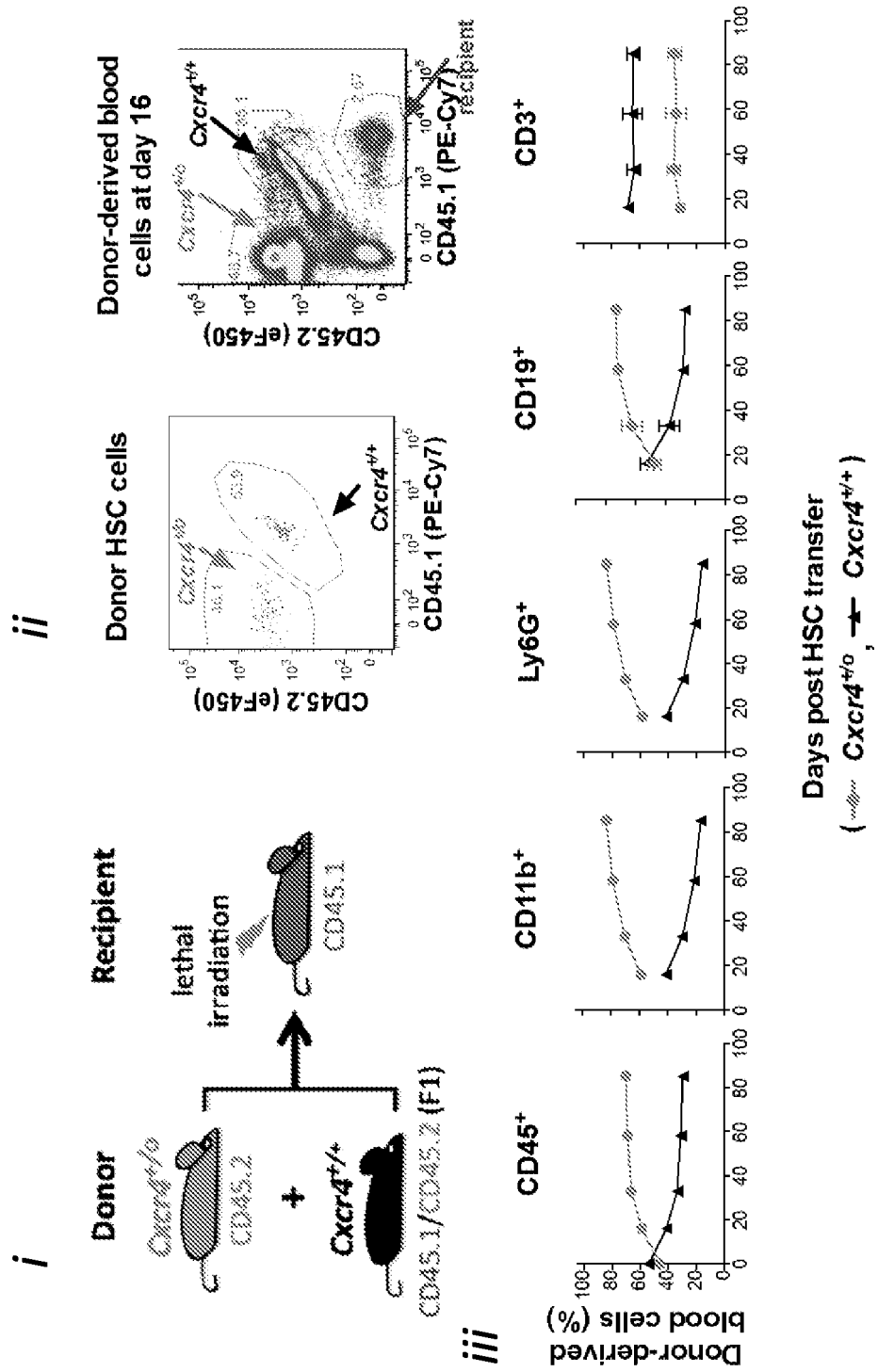

When donor bone marrow cells from two different Cxcr4 genotype mice were mixed together in equal proportions (~50%:50%) and transplanted into lethally irradiated or non-irradiated Cxcr4$^{+/+}$ recipients, the results showed that in both irradiated and non-irradiated recipient mice there was much more rapid and complete engraftment of the donor bone marrow from the Cxcr4$^{+/-}$ mice than from either the Cxcr4$^{+/S338X}$ mice (FIGS. 10A and 10B) or the Cxcr4$^{+/+}$ mice (FIGS. 11A and 11B). The same effect was observed with HSC transplantation (FIGS. 12A and 12B), indicating that the enhanced engraftment attributable to Cxcr4 haplo-insufficiency is HSC intrinsic.

Figure 13A:
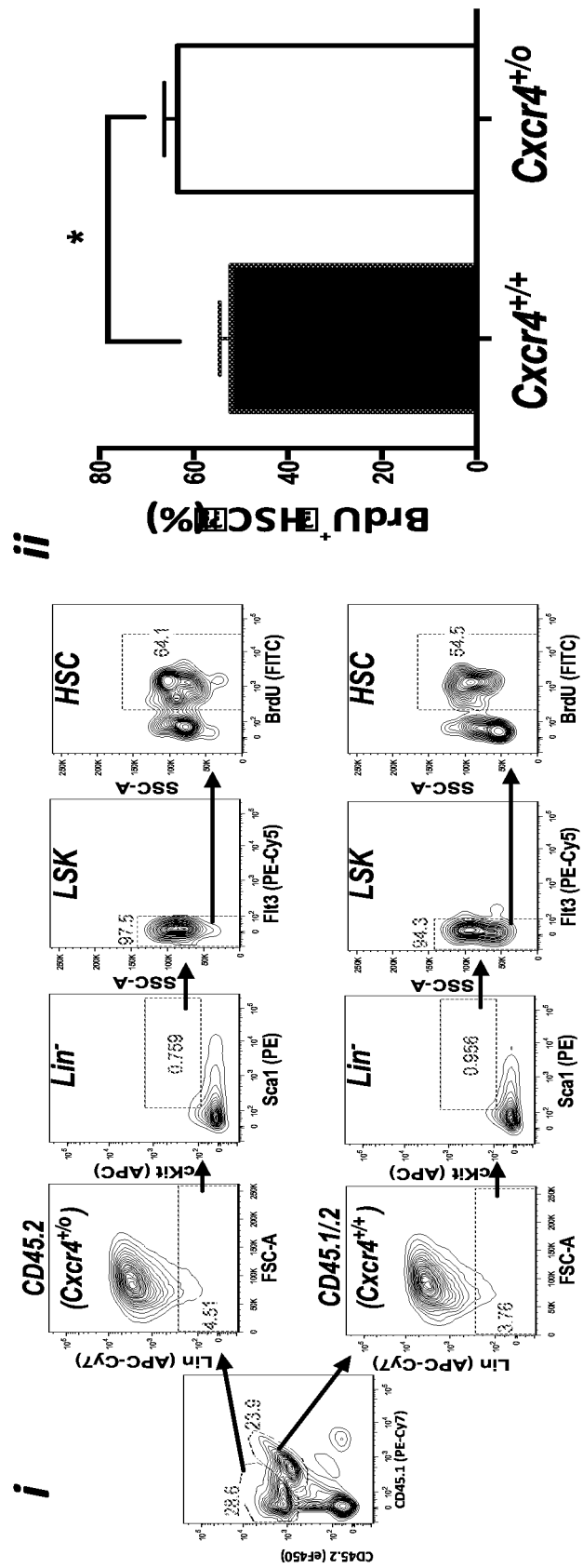
FIGS. 13A-13B. Cxcr4 haploinsufficiency enhances HSC engraftment in a mouse bone marrow transplantation model. (A) Haploinsufficiency of Cxcr4 promotes enhanced proliferation of HSCs. Bone marrow cells from donors with a Cxcr4$^{+/-}$ genotype on a CD45.2 homozygous and from donors with a Cxcr4$^{+/+}$ genotype on a CD45.1/45.2 heterozygous background were mixed (47:53) and then 5 million mixed bone marrow cells were injected intravenously into each CD45.1 recipient mouse that had been lethally irradiated 8 hours prior. 6 days after bone marrow transplantation, each mouse was given 1.25 mg of BrdU$^+$ ip. 20 hours later, the mice were euthanized for HSC proliferation analysis. (i) Gating scheme for BrdU$^+$ HSCs. Bone marrow cells were first gated with CD45.2 (Cxcr4$^{+/-}$) and CD45.1/2 (Cxcr4$^{+/+}$), then HSCs were gated as Flt3$^-$Lin$^-$Scal$^+$ c-Kit$^+$ (Flt3$^-$LSK) which includes long-term and short-term HSCs. The HSCs that proliferated in the last 20 hours were further gated as BrdU$^+$. (ii) Percentage of BrdU$^+$ HSCs in each donor. Data are expressed as mean±SEM from four mice, and the experiment was repeated once with similar results. (B) Selective advantage of Cxcr4$^{+/-}$ over Cxcr4$^{+/+}$ donor hematopoietic progenitor cells for durable engraftment of normally differentiating cells. Bone marrow cells from donors with a Cxcr4$^{+/-}$ genotype on a CD45.2 background and from donors with a Cxcr4$^{+/+}$ genotype on a CD45.1 background were mixed (42:58), and then 5 million mixed bone marrow cells were injected intravenously into each recipient mouse that had been lethally irradiated 8 hours prior. The mice were euthanized for hematopoietic progenitor population analysis 303 days after bone marrow transplantation. One experiment was performed with five CD45.1 and five CD45.2 male recipient mice and the results were combined in the figure because they were identical. (i) Gating scheme for the long term HSC (LT-HSC: CD34$^+$ Flt3$^-$Lin$^-$Scal$^+$ c-Kit$^+$), short term HSC (ST-HSC: CD34$^+$ Flt3$^-$Lin$^-$Scal$^+$c-Kit$^+$), multipotent progenitors (MPP: CD34$^+$Flt3$^+$Lin$^-$Scal$^+$ c-Kit$^+$), and common lymphoid progenitors (CLP: IL7ra$^+$ Lin$^-$ Scal$^{low}$ c-Kit$^{low}$). (ii) The high proportion of Cxcr4$^{+/-}$ as compared to Cxcr4$^{+/+}$ donor derived hematopoietic progenitor populations in bone marrow indicates a selective advantage of Cxcr4$^{+/-}$ cells for long term engraftment. (iii) The similar frequency of Cxcr4$^{+/-}$ and Cxcr4$^{+/+}$ derived hematopoietic progenitor cells in corresponding CD45$^+$ cell populations indicates that differentiation was not affected by Cxcr4 haploinsufficiency.
Figure 13B:
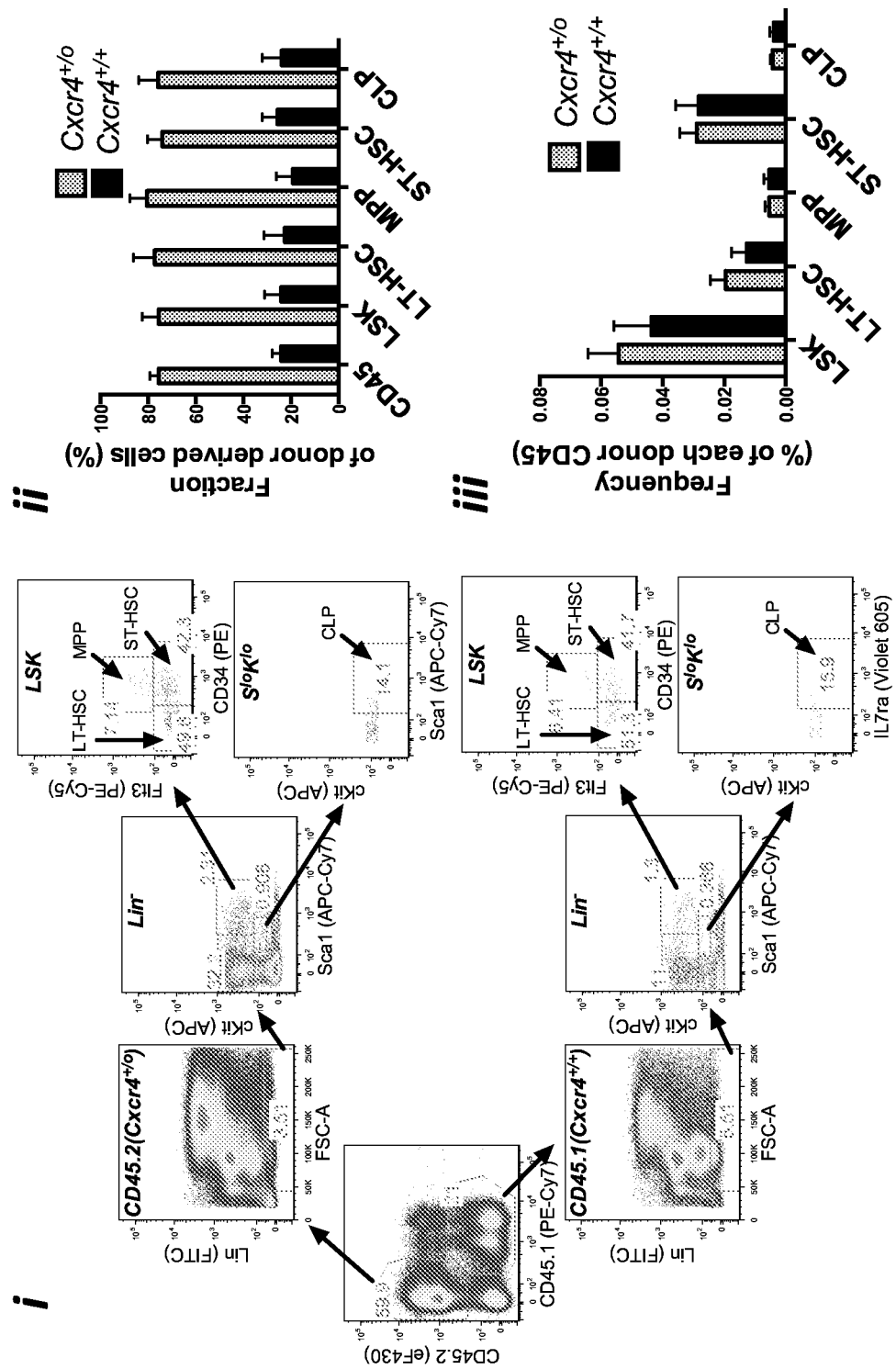

To investigate the mechanism for the apparent competitive advantage of Cxcr4$^{+/-}$ over Cxcr4$^{+/+}$ bone marrow cells for reconstituting the blood, the proliferative status of the corresponding HSCs in vivo by BrdU incorporation early after transplantation (day 7) was measured (FIG. 13A). The results indicated ~20% greater frequency of BrdU$^+$ Cxcr4$^{+/-}$ HSCs as compared to Cxcr4$^{+/+}$ HSCs, indicating a proliferative advantage of Cxcr4$^{+/-}$ HSCs in the bone marrow. To test whether differential retention of leukocytes in the bone marrow might also contribute to the skewed distribution of mature leukocytes in the blood, mice were sacrificed at day 298 after competitive transplantation with Cxcr4$^{+/-}$ and Cxcr4$^{+/+}$ bone marrow cells (the same combination of donor bone marrow cells as were analyzed in the proliferation experiments). The results showed that Cxcr4$^{+/-}$ HSCs, HPCs (hematopoietic progenitor cells) and total CD45$^+$ cells (mostly mature leukocytes) predominated in the bone marrow by the same 4:1 ratio over the corresponding Cxcr4$^{+/+}$ cells as was found for mature leukocytes in the blood. Thus, the predominance of mature Cxcr4$^{+/-}$ over Cxcr4$^{+/+}$ leukocytes in the blood of competitively transplanted mice cannot be simply explained by low retention of mature Cxcr4$^{+/-}$ leukocytes relative to the retention of mature Cxcr4$^{+/+}$ leukocytes in the bone marrow. Moreover, the results at this very late time point clarify that enhanced Cxcr4$^{+/-}$ HSC proliferation does not result in long term depletion of HSCs. The frequency distribution of stem and progenitor subtypes was the same for each genotype, indicating no block to progenitor cell differentiation (FIG. 13B).

Example 10

Discussion

Figure 2A:
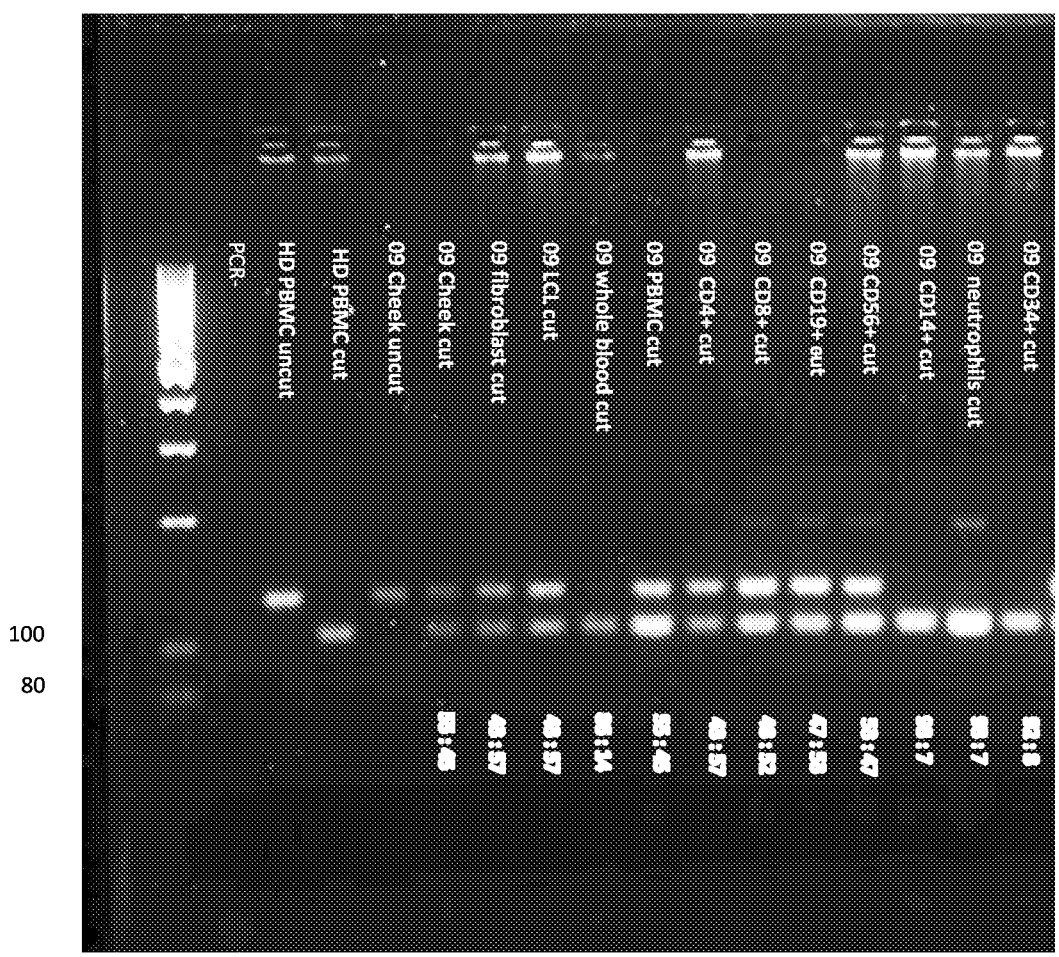
FIGS. 2A-2B. Loss of the WHIM allele in myeloid derived cells from the index patient. (A) blood, (B) bone marrow. Shown are representative results from a polymerase chain reaction-restriction fragment length polymorphism (PCR-RFLP) designed to detect the $CXCR4^{R334X}$ mutation performed on DNA from a variety of cell types purified from blood (using magnetic bead purification) or bone marrow aspirate (using flow cytometric sorting). PCR–, amplification in the absence of target DNA serving as a negative control; HD, healthy donor; PBMC, peripheral blood mononuclear cells; uncut, not subjected to restriction enzyme digestion; cut, cut with BstUI restriction enzyme; LCL, lymphoblastoid cell line derived from PBMC; CD4$^+$, purified CD4$^+$ T cells; CD8$^+$, purified CD8$^+$ T cells; CD19$^+$, purified CD19$^+$ B cells; CD56$^+$, purified CD56$^+$ natural killer cells; CD14$^+$, purified CD14$^+$ monocytes; CD34$^+$, purified CD34$^+$ hematopoietic stem cells; CD3$^+$, purified CD3$^+$ T cells; CD15$^+$, purified CD15$^+$ neutrophils; cultured CD34$^+$, purified CD34$^+$ hematopoietic stem cells grown ex vivo.
Figure 2B:
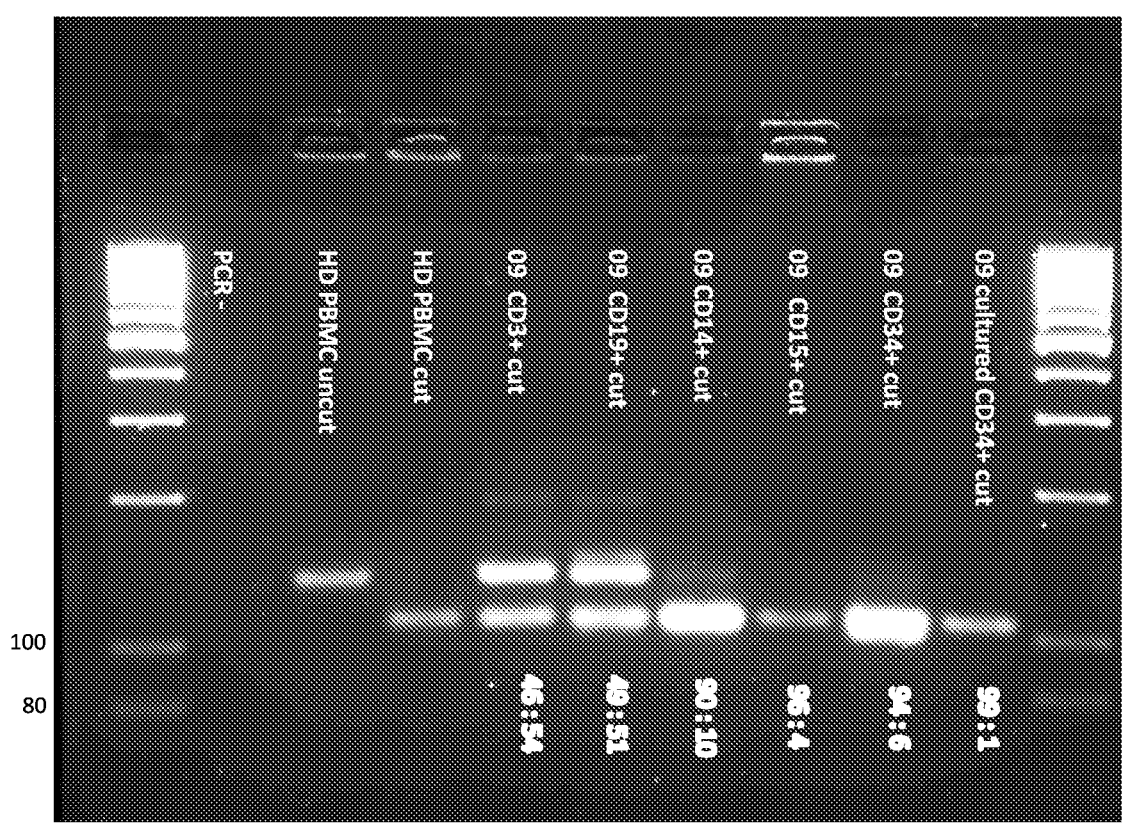

This patient represents the first example of a genetic reversion of the rare immunodeficiency WHIM syndrome. The data demonstrate that she is a somatic mosaic within the hematopoietic system (FIGS. 1C, 2A, and 2B). Her erythroid and myeloid lineages exhibited loss of the CXCR4$^{WHIM}$ allele and presence of a derivative chromosome while lymphoid lineages exhibit retention of the CXCR4$^{WHIM}$ allele and lack of the derivative chromosome (FIG. 2). Multiple lines of evidence point to this genetic reversion occurring in a single primitive hematopoietic stem cell in early adulthood which then resulted in reversal of neutropenia, monocytopenia, bacterial infections and severe cutaneous HPV disease (FIGS. 3 and 4). Unexpectedly this reversion is the consequence of a complex chromosomal rearrangement of only the chromosomal copy where the mutant CXCR4$^{WHIM}$ allele was located (FIGS. 5 and 6). Whole genome sequencing and microarray demonstrated that this rearrangement bears all the hallmarks of the recently defined chromothripsis phenomenon (FIG. 7) (Korbel and Campbell, 2013). Chromothripsis has been identified to date as a source of complex chromosomal rearrangements present in various cancers (Jones and Jallepalli, 2012). Thus, this is the first example of chromothripsis resulting in a positive outcome and fully understanding this patient will have important implications to understanding the biology of the immune response to human papillomavirus (HPV) infection, hematopoietic stem cells (HSC) and bone marrow transplantation (BMT) and gene therapy of HSC.

Implications for HPV disease

HPV is a chronic problem in WHIM patients once they become infected with this virus (Beaussant Cohen et al., 2012; Kawai and Malech, 2009; Tassone et al., 2009; Wetzler et al., 1990). Cutaneous and anogenital disease is typically recurrent despite surgical removal and other destructive methods being utilized, immunostimulants like imiquimod are ineffective, and chronic disease has led to lethal cancers in WHIM patients. HPV has evolved multiple ways to evade the immune system and can become a chronic infection even in normal individuals; however, patients with a wide variety of different immunodeficiencies are at increased risk of chronic HPV infection that progresses to cancer (Leiding and Holland, 2012). WHIM-09's reversal of HPV hand warts without treatment is unprecedented in WHIM syndrome and strongly indicates that the myeloid arm (monocytes and/or granulocytes) of the immune system plays an important and previously unsuspected role in successful viral clearance because the derivative chromosome was not found in the lymphoid arm (B, T, and NK cells) of the patient's immune system (FIG. 2). In addition since the derivative chromosome was not found in the skin keratinocytes or fibroblasts, her case also indicates that mutation of CXCR4 in these cells is not the primary driver of HPV persistence (FIG. 2). These findings reinforce the importance of the immune response in clearing the virus once infection develops and provide further hope that correcting the immune system defects either through drug therapy with CXCR4 antagonists like plerixafor, directed gene therapy to remove the mutant CXCR4 allele, or BMT with allogeneic HSC could ameliorate this problem.

Implications for HSC Biology

HSC are the only cells in the bone marrow that are both pluripotent and long lived (Seita and Weissman, 2010). These rare cells can be identified by a combination of characteristic cell surface markers and undergo a tightly controlled, hierarchical differentiation process into the mature elements of the blood (FIG. 8A). The data herein demonstrate that the HSC and myeloid compartments of the immune system were nearly completely or completely replaced by cells that bore the derivative chromosome (FIG. 8B). This indicates that this genetic change created some type of survival or proliferative advantage for these mutated HSC versus the WHIM HSC that the patient was born with. This advantage was capable of repopulating the HSC compartment without the application of any standard methods used to clear the stem cell niche in BMT such as radiation therapy or chemotherapy. Therefore, it is likely that the chromothripsis induced genetic change enhanced the ability of the HSC to populate, proliferate or survive in the niche. This idea is consistent with prior knowledge that CXCL12 abundant reticular (CAR) cells that contact HSC in the bone marrow niche enhance their quiescence by stimulating CXCR4 signaling (Sugiyama et al., 2006). However, in previously published mouse models using HSC transfected with $CXCR4^{+/+}$ or $CXCR4^{WHIM}$, it was demonstrated that constructs containing the WHIM mutation can enhance trafficking of infused HSC to the bone marrow (Kawai et al., 2007). Therefore prior to understanding more about this patient, it would have been believed that increased rather than reduced CXCR4 signaling would be beneficial to engraftment.

Implications for BMT and HSC Gene Therapy

BMT using HSC is an increasingly common medical therapy for severe hematologic cancers and primary hematologic immunodeficiencies (Copelan, 2006). However, for significant engraftment to occur there must usually be pre-transplant conditioning with either irradiation or chemotherapy or both. The purpose of this conditioning is to kill the rapidly growing cancer cells and clear bone marrow niches for the infused HSC in the case of hematologic malignancy. However, reduced intensity conditioning is needed for BMT even in the case of most immunodeficiencies to create marrow space for the infused HSC. This pre-transplant conditioning causes cellular and immune system damage that is directly or indirectly responsible for most of the morbidity and mortality associated with BMT.

The patient described herein however was able to replace her HSC clonally without the need for either pre-transplant conditioning regimen (FIG. 8B). This indicates that her chromothripsis induced derivative chromosome had a genetic change that created a marked proliferative or survival advantage for the resultant mutated HSC. Since no evidence was found for creation of a novel fusion gene in the derivative chromosome, the data supported that the loss of one copy of a gene (haploinsufficiency) on chromosome 2 had created the advantage. Inspection of the list of genes (Table 4) that she was haploinsufficient for indicates that CXCR4 is a logical candidate gene as previous studies had indicated that CXCR4 signaling resulting from CXCL12 secretion by CAR cells in the bone marrow niche played a role in HSC quiescence (Sugiyama et al., 2006).

The CXCL12/CXCR4 system is highly conserved in the mouse and functions quite similarly to the human system (Bachelerie et al., 2014). A WHIM mouse model ($Cxcr4^{+/S338X}$) was previously generated by creating a truncation mutation in a single copy of the mouse gene with a human disease causing mutation (5338X) (Balabanian et al., 2012). This enabled the use of a competitive bone marrow repopulation assay in a mouse model of bone marrow transplantation to confirm that loss of one copy of CXCR4 was creating an engraftment advantage. When the recipient mouse was lethally irradiated prior to the infusion of donor marrow (FIG. 10A), the bone marrow cells lacking one copy of CXCR4 ($Cxcr4^{+/0}$) were rapidly able to take over the bone marrow production of granulocytes ($Ly6G^+$), monocytes ($CD11b^+$) and B cells ($CD19^+$) and nearly completely effaced the $Cxcr4^{+/WHIM}$ bone marrow within the first 30 days of BMT. These results were stable for up to 10 months when the experiment was terminated. Results with T cells ($CD3^+$) were less impressive but this is probably inherent in this model because adult mice were transplanted who likely lacked a functional thymus necessary for full T cell development. In addition memory T cells are radioresistant (allowing continued presence of these cells in the recipient (CD45.1 mice) and capable of self-proliferation in the periphery. When experiments were performed without irradiating the recipient mice (FIG. 10B), markedly enhanced engraftment of the $Cxcr4^{+/-}$ derived bone marrow was observed as compared to $Cxcr4^{+/WHIM}$ derived bone marrow. This latter model is most comparable to the patient's likely mechanism of bone marrow repopulation and provides significant support of the conclusion that CXCR4 is the major factor producing her outcome. The selective advantage in $Cxcr4^{+/-}$ derived bone marrow was also evident in competition experiments with $Cxcr4^{+/+}$ derived bone marrow in both irradiated and non-irradiated recipient mice (FIGS. 11A and 11B).

Example 11

Methods to Knock-Out One Allele of CXCR4

This example describes methods used to knock-out one allele of CXCR4 using gene editing tools.

Materials and Methods

Guides: Wild-type CRISPR-Cas9, Cas9-D10A nickase, guides and CXCR4-copGFP-CXCR4 donor were purchased from GeneCopoeia (Rockville, Md.). TALEN vectors were generated using the FastTALE system from Sidansai Biotechnology (Shanghai, China) according to manufacturer's instruction.

Cell culture: HeLa cells were grown in EMEM media (Quality Biological, Gaithersburg, Md.) supplemented with 10% fetal bovine serum (Quality Biological, Gaithersburg, Md.), minimum non-essential amino acids (Corning, Corning, N.Y.), sodium pyruvate (Corning, Corning, N.Y.) and penicillin-streptomycin antibiotics (Life Technologies, Carlsbad, Calif.). Cells were maintained at 37° C. with 5% $CO_2$.

Transfection: 1 million HeLa cells were transfected with 2 µg of maxGFP (Lonza, Walkersville, Md.), 2 µg CXCR4-copGFP-CXCR4 donor, 6 µg CXCR4-copGFP-CXCR4 donor and 6 µg TALEN L1, 6 µg CXCR4-copGFP-CXCR4 donor along with 3 µg TALEN L1 and 3 µg TALEN R2, 1 µg of wild-type Cas9 and 1 µg of each guide or 1 µg of Cas9-nickase and 0.5 µg of each guide using 4D-Nucleofector (Lonza) according to manufacturer's instructions with the following additions. Prior to plating, 0.5 mls of media was added to cells in nucleocuvettes and the cells were incubated at 37° C. in for 30 minutes.

FACS analysis: Unless otherwise noted, cells were harvested 6 days after nucleofection and stained with CXCR4-PE (BD Pharmingen, San Jose, Calif.) or isotype control antibodies according to the manufacturer's instructions. Cells were sorted using the FACS Ariall system.

Indel analysis from bulk populations of cells: Edited cells were harvested and indel analysis was carried out using the Clontech Indel Identification kit (Mountain View, Calif.) according to the manufacturer's instructions. Briefly, lysate was made from harvested cells after which PCR amplification of genomic DNA was carried out using the primers:

```
CXCR4-indel forward;
                                      (SEQ ID NO: 7)
5'-CGGTACCCGGGGATCTTGTGCCCTTAGCCCACTAC-3'

CXCR4-indel reverse;
                                      (SEQ ID NO: 8)
5' -CGACTCTAGAGGATCCCACCTTTTCAGCCAACAGC-3'
```

The PCR products were sub-cloned into vectors followed by transformation into bacteria. CXCR4 sequences were PCR amplified from bacteria and sequenced.

Single cell clonal analysis: Cells were serially diluted to produce single cells in 96 well plates. Single cell cultures were grown for 4 weeks and genomic DNA was extracted using Wizard Genomic DNA extraction kit (Promega, Madison, Wis.) according to the manufacturer's instructions with the modification that the DNA was resuspended into a volume of 25 µl. 5 µl DNA was CXCR4 amplified in 25 µl volumes using PCR master mix (Life Technologies) according to the manufacturer's instructions and using the following primers and cycling conditions:

```
                                      (SEQ ID NO: 9)
CXCR4 forward;    5'-AGCGTCTCAGTGCCCTTTTG-3'

(SEQ ID NO: 10)
CXCR4 reverse;    5'-ATCTGCCTCACTGACGTTGG-3'
```

Cycling conditions: 95° C., 3 minutes; 95° C., 40 seconds; 55° C., 40 seconds; 72° C., 40 seconds; 72° C., 7 minutes for a total of 40 cycles.

The PCR products were TA cloned into vectors using the TOPO-TA cloning kit (Life Technologies, Grand Island, N.Y.) according to the manufacturer's instructions. PCR products in TA vectors were sequenced.

Surveyor assay: Genomic DNA was extracted using Wizard Genomic DNA extraction kit (Promega, Madison, Wis.) according to the manufacturer's instructions with the modification that the DNA was resuspended into a volume of 25 µl. CXCR4 DNA was PCR amplified as above, mixed with nuclease free water and NEB buffer 2 in a final volume of 18 µl, after which the PCR products were denatured and re-annealed using the cycling conditions: 95° C., 10 minutes for denaturation; decrease at 0.1°/sec to 85° C.; hold at 85° C. for 2 minutes; decrease at 0.1°/sec to 75° C.; hold at 75° C. for 3 minutes; decrease at 0.1°/sec to 65° C.; hold at 65° C. for 3 minutes; decrease at 0.1°/sec to 65° C.; hold at 65° C. for 3 minutes; decrease at 0.1°/sec to 55° C.; hold at 55° C. for 3 minutes; decrease at 0.1°/sec to 45° C.; hold at 45° C. for 3 minutes; decrease at 0.1°/sec to 45° C.; hold at 45° C. for 3 minutes; decrease at 0.1°/sec to 35° C.; hold at 35° C. for 3 minutes; decrease at 0.1°/sec to 25° C.; hold at 25° C. for 3 minutes; then hold at 4° C. Each reaction was split into two, 0.5 µl per reaction of Surveyor enzyme (Transgenomics (Omaha, Nebr.) was added to one set of reactions along with nuclease free water and NEB Buffer 2 in final volumes of 20 µl volumes while the other set of reactions only received nuclease-free water and NEB Buffer 2. The samples were incubated at 37° C. for 40 minutes. 45 mM EDTA was used to stop the reaction after which the samples were mixed with DNA loading dye and run on 2% ethidium bromide stained gels.

Results

Single Allele Editing of CXCR4

Figure 16B:
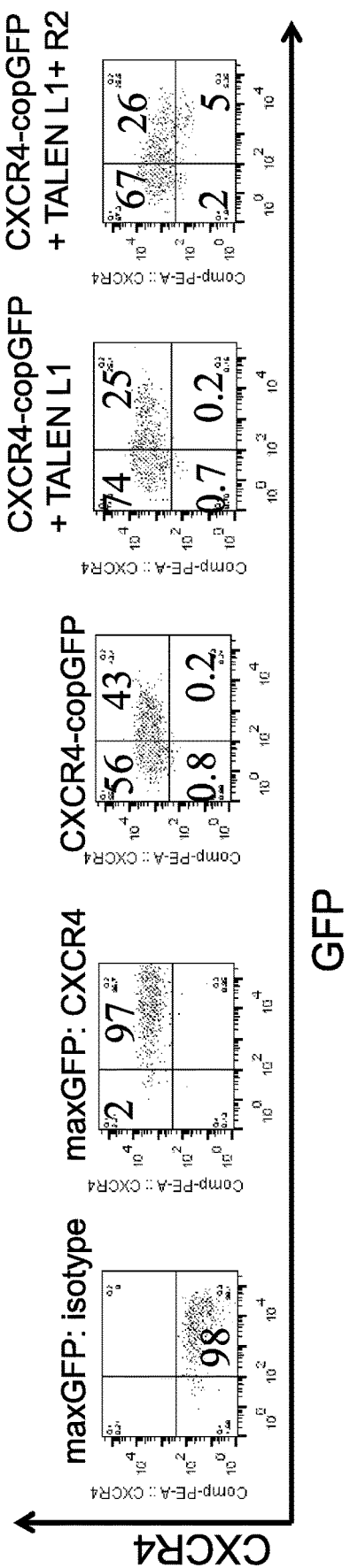
Figure 16C:
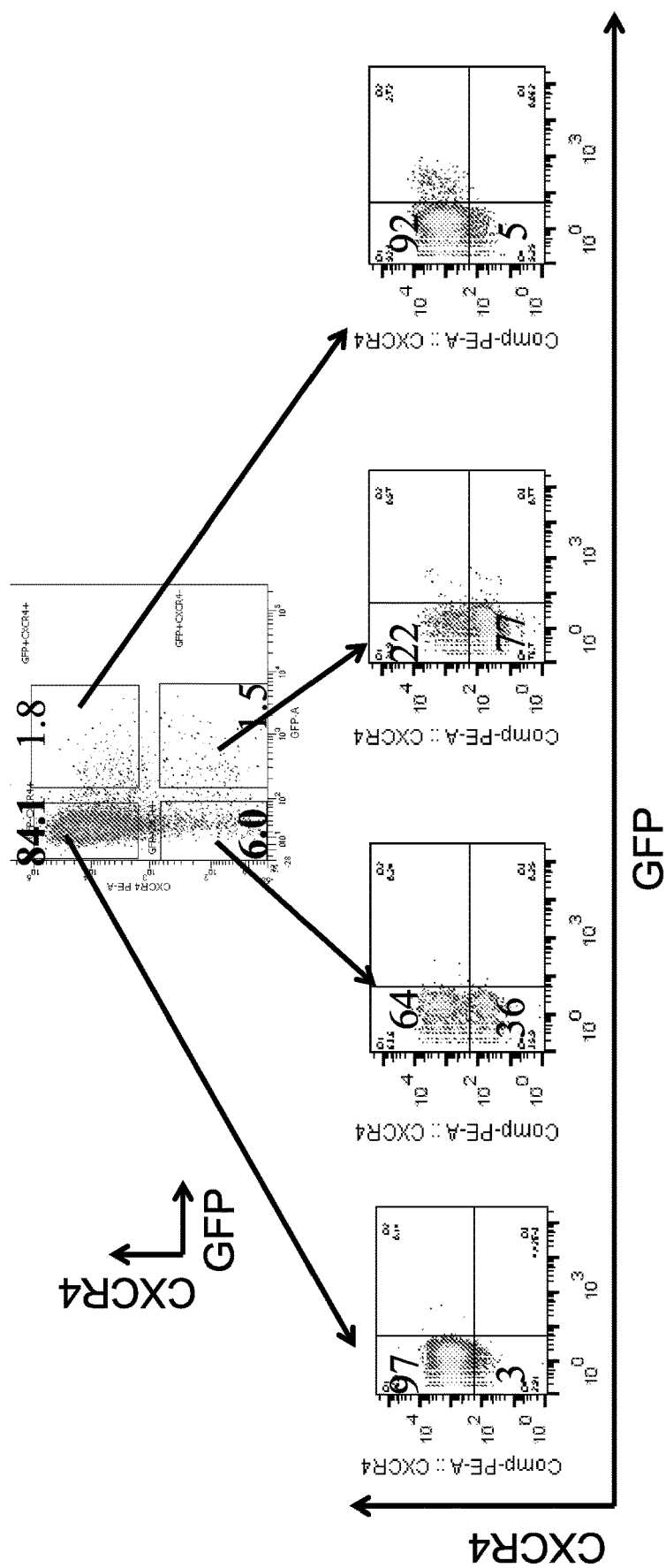
Figure 16D:
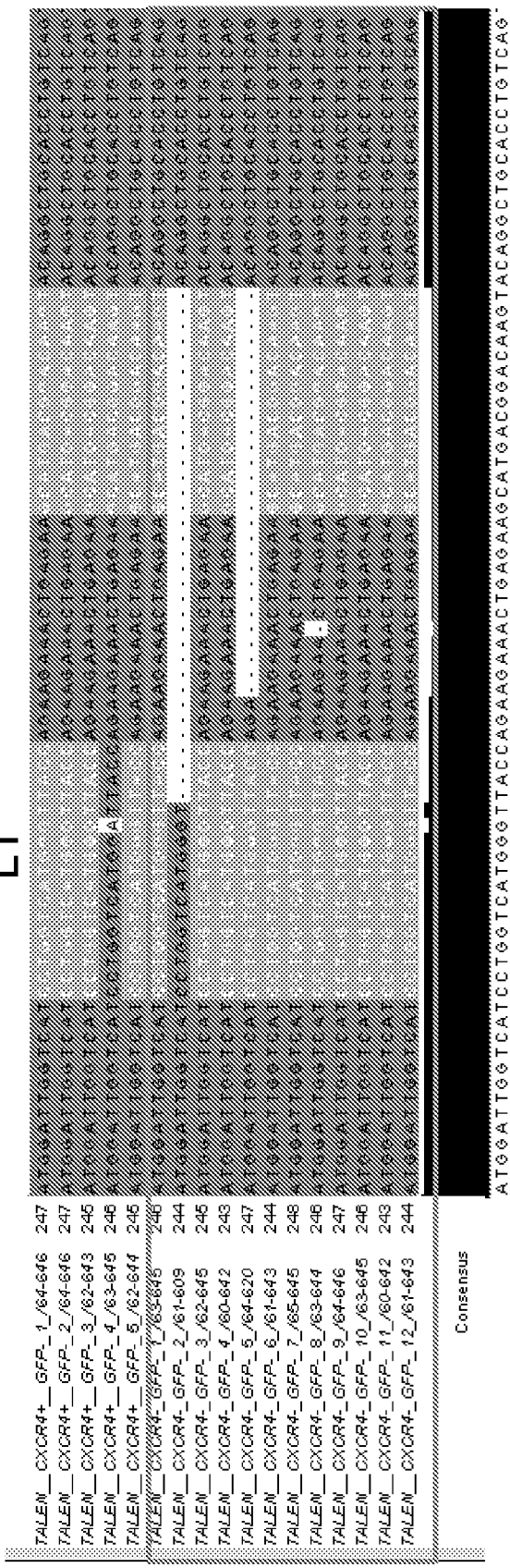

Transfection of the complete TALEN system (L1+R2) into HeLa cells generated mutations in CXCR4 as demonstrated by a reduction in CXCR4 protein expression by FACS analysis (FIGS. 16B and 16C) and by sequence analysis (FIG. 16D). 25% of the TALEN sequences sorted from the CXCR4 low cells (CXCR4 lo) carried deletions varying from one (SEQ ID NO: 17) to several nucleotides (FIG. 16D, and SEQ ID NOS: 15 and 16). On the contrary, transfection of the incomplete system did not affect CXCR4 expression (FIG. 16B) or sequence (FIG. 16D) indicating that the effect is specific to TALEN-mediated gene editing. Interestingly, cells that were sorted initially as CXCR4 Lo expressed significant amounts of the protein when cultured (FIGS. 16C, 17C).

Figure 17A:
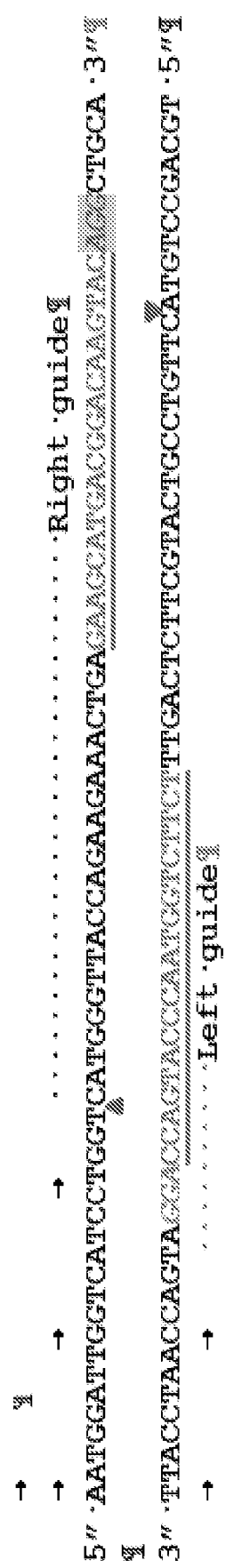
Figure 17B:
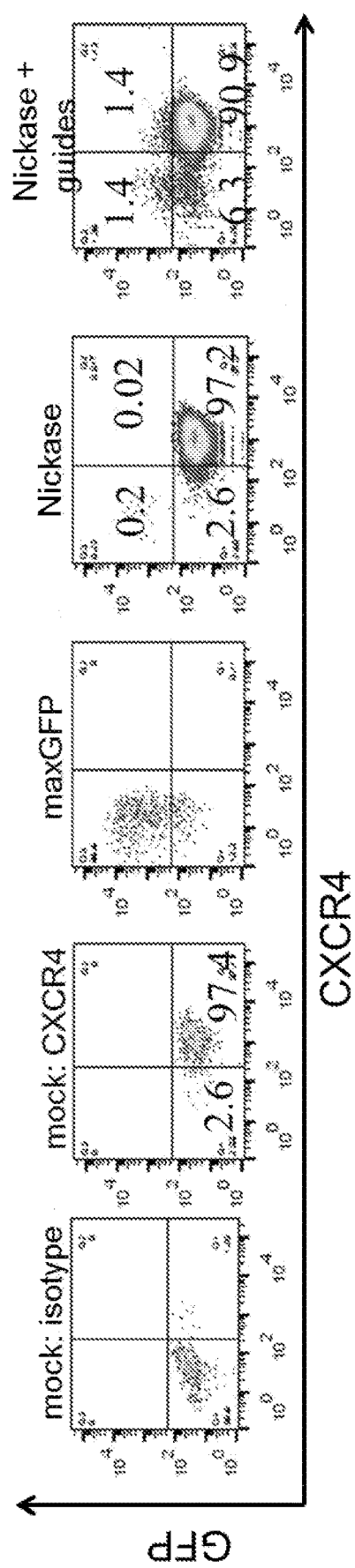
Figure 17C:
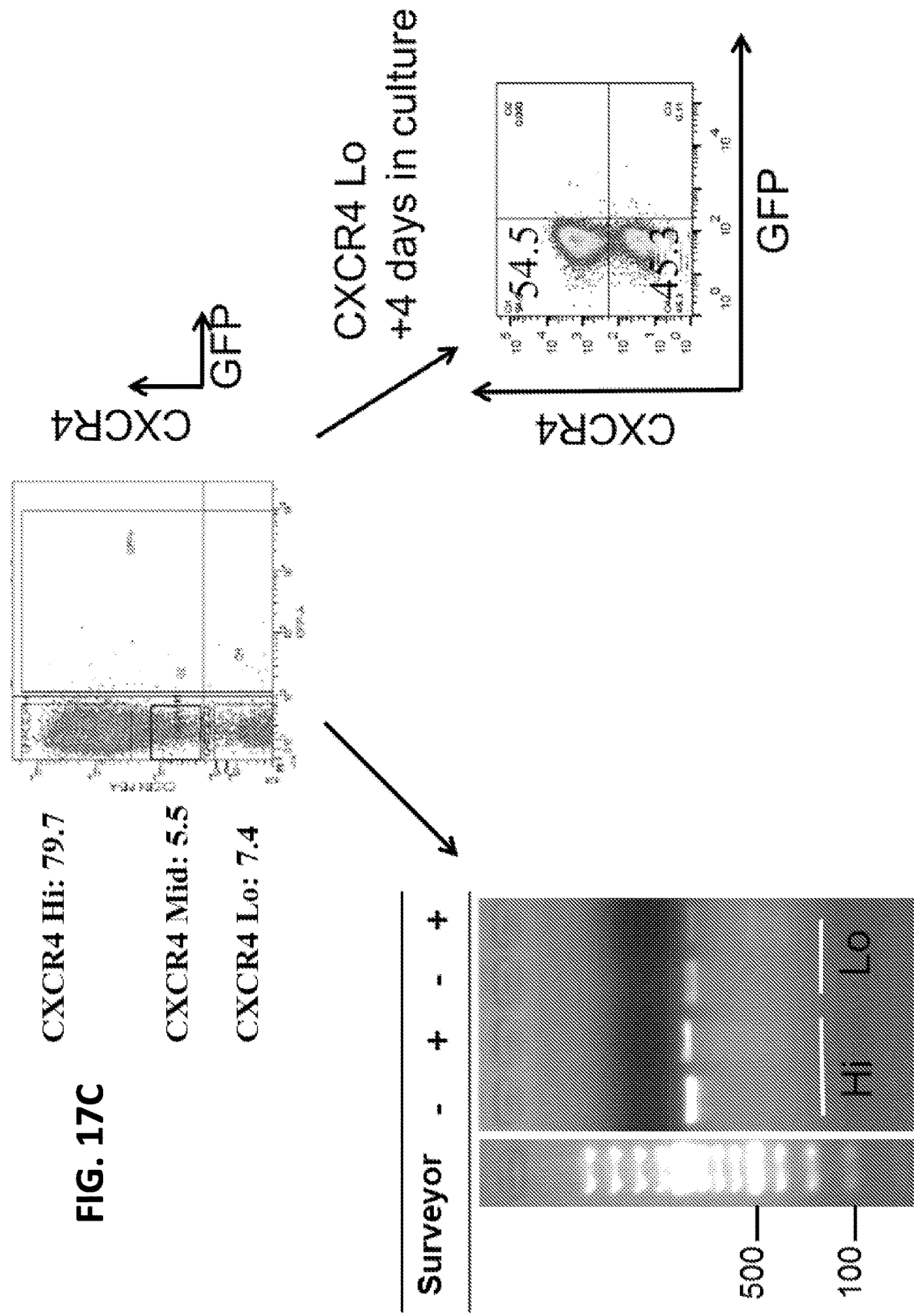
Figure 17D:
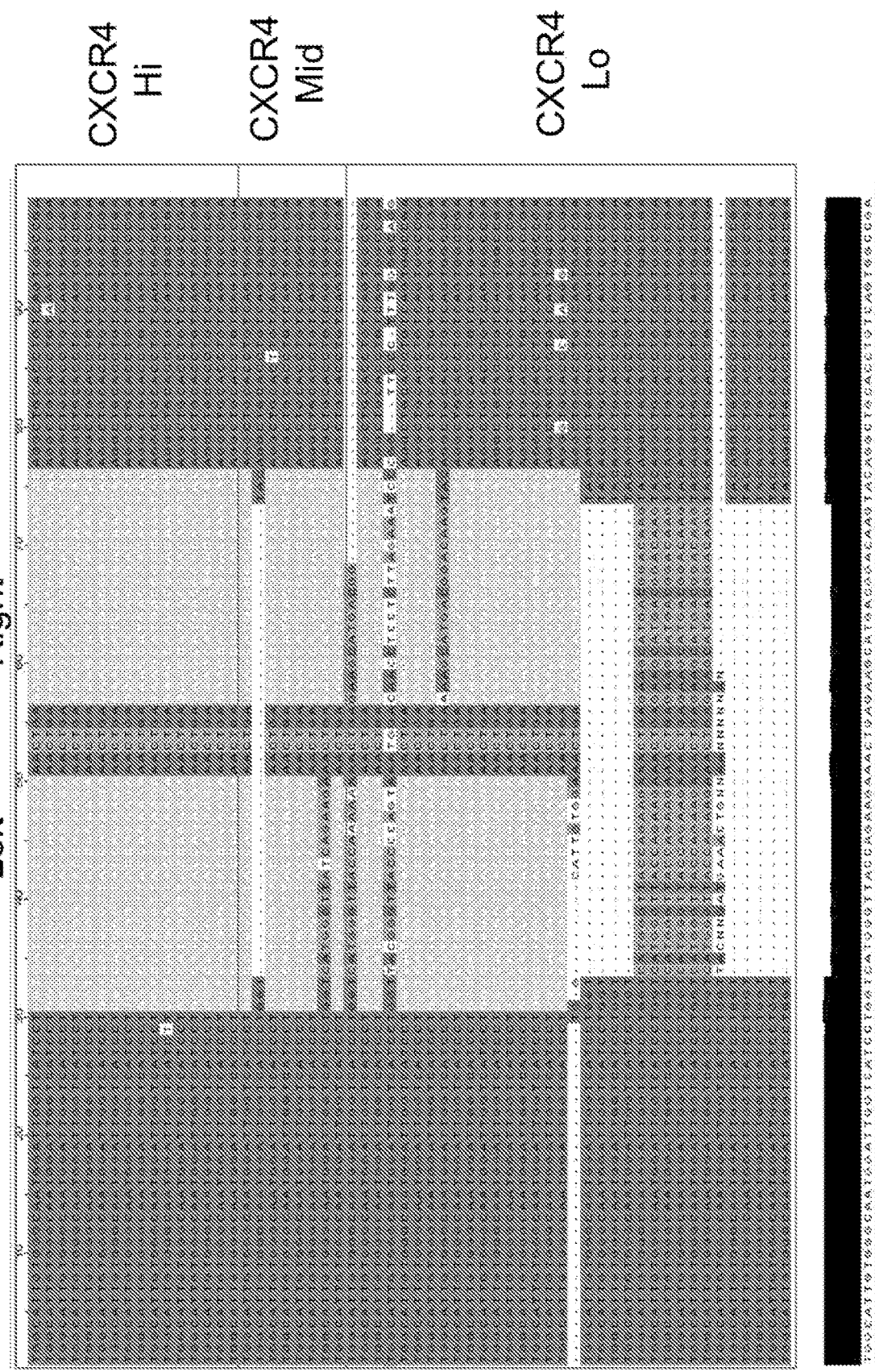
Figure 17E:
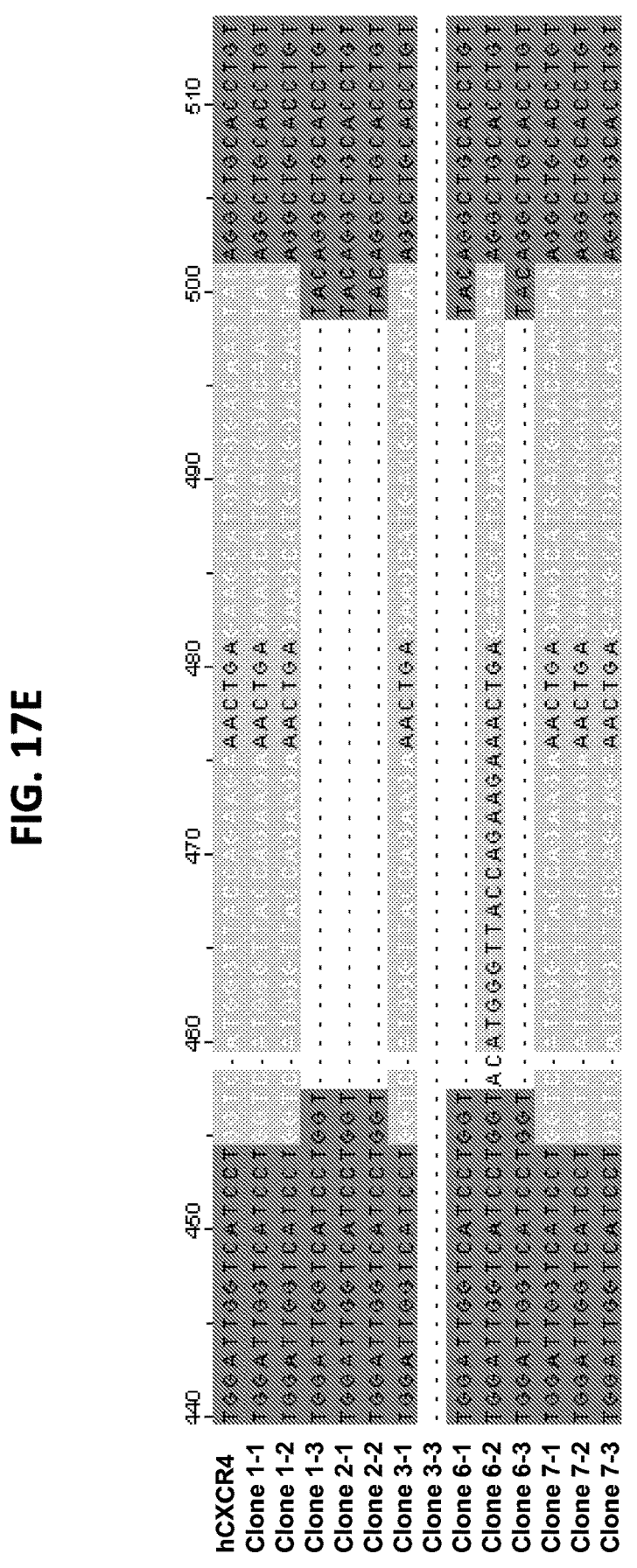

The CRISPR-Cas9 system was also used to create deletions in human CXCR4 (FIG. 17A). Transfection of only Cas9-D10A nickase into HeLa cells did not affect the expression of CXCR4 whereas the combination of nickase and guides down-regulated CXCR4 expression indicating that the effect was specific (FIG. 17B). Surveyor assay confirmed the presence of mutations in the population of cells that expressed little or no CXCR4 (CXCR4 Lo) (as indicated by the presence of 2 additional bands upon Surveyor treatment, (FIG. 17C) whereas no mutations were detected by Surveyor for the population of cells that expressed high levels of CXCR4 (CXCR4 Hi) (FIG. 17C). The presence of a remaining band of the original 800 base pair size after Surveyor treatment indicated the presence of wild-type CXCR4 in the cells and suggested that the cells are hemizygous, containing one wild-type and one null allele of CXCR4. Sequencing confirmed the presence of mutations in the populations of cells that expressed medium (CXCR4 Mid) and low (CXCR4 Lo) levels of CXCR4 (FIG. 17C). Interestingly, approximately 60% of the mutations obtained were an identical 40 base pair deletion (FIG. 17D). When examined at the single cell clone level, sequencing analysis confirmed that only one copy of CXCR4 had been mutated in 60% of the clones (FIG. 17E).

Example 12

Treatment of Sickle Cell Anemia in Mice

Commercially available humanized sickle cell mice (Jackson Laboratories strain #013071) can be used. These mice develop infarcted organs, enlarged spleens, anemia, and sickled red cells as they age because the mouse hemoglobin genes have been replaced by human versions and the hemoglobin B gene (HBB) has the exact same mutation as is found in human sickle cell patients.

HSCs obtained from CXCR4+/− mice as described above will be introduced into the sickle cell mice as described above. It will then be determined if these donor HSCs will engraft and cure the disease symptoms in these mice without a requirement for bone marrow conditioning.

In some examples, donor HSCs from $Cxcr4^{+/+}$ congenic as well as from sickle cell mice will be manipulated ex vivo to downregulate CXCR4 and correct the mutated HBB using CRISPR-Cas9 to cure the sickle cell disease. The Crispr/Cas system will be used to target CXCR4 for disruption by NHEJ. A second plasmid will encode a single guide RNA to create a DSB or 2 SSB near the HBB mutation that will then be repaired by homologous recombination using a donor sequence on either a third plasmid carrying wt HBB or a specifically designed oligonucleotide sequence designed to repair the mutation. This will be done in sickle cell mice obtained commercially from The Jackson Laboratory (Bar Harbor, Me.). Similar experiments can be done using the TALEN system. Exemplary sequences that can be used are shown in Table 6.

TABLE 6

Exemplary Crisper and TALEN sequences to knock-down CXCR4

| Sample | Sequence (SEQ ID NO:) | Targeted Gene Region |
|---|---|---|
| sgRNA1 | 5'-*G*TGATGAAGTAGATGGTGGGC-3' (36) | 5'-WT mCXCR4 Exon 2 |
| sgRNA2 | 5'-*G*TTGACTGGCATAGTCGGCAA-3' (37) | 5'-WT mCXCR4 Exon 2 |
| sgRNA3 | 5'-GTTCCTTTGGAAAGGATCTTG-3' (38) | 3'-WT mCXCR4 Exon 2 |
| sgRNA4 | 5'-GTGGACACT*CTT*CCGTCTCCA-3' (39) | 3'-WT mCXCR4 Exon 2 |
| sgRNA5 | 5'-GTGGACACTGATCCGTCTCCA-3' (40) CXCR4-5338X mutant specific | 3'-M mCXCR4 Exon 2 |
| TALEN L1 | 5'-CCTGGTCATGGGTTACC-3' (41) | 5'-WT mCXCR4 Exon 2 |
| TALEN L2 | 5'-GGTCATGGGTTA-3' (42) | 5'-WT mCXCR4 Exon 2 |
| TALEN L3 | 5'-CCTGGTCATGGGT-3' (43) | 5'-WT mCXCR4 Exon 2 |
| TALEN R1 | 5'-ACTTGTCCGTCATGC-3' (44) | 5'-WT mCXCR4 Exon 2 |
| TALEN R2 | 5'-ACTTGTCCGTCATG-3' (45) | 5'-WT mCXCR4 Exon 2 |
| sgRNA6 | 5'-TCTTCTGGTAACCATGACC-3' (46) | 5'-WT hCXCR4 Exon 2 |
| sgRNA7 | 5'-GAAGCATGACGGACAAGTAC-3' (47) | 5'-WT hCXCR4 Exon 2 |
| sgRNA8 | 5'-GCTGGACCCTCTGCTCACAG-3' (48) | 3'-WT hCXCR4 Exon 2 |
| sgRNA9 | 5'-CTCTCCAAAGGAAAG*C*GAGG-3' (49) | 3'-WT hCXCR4 Exon 2 |
| sgRNA10 | 5'-CTCTCCAAAGGAAAG*T*GAGG-3' CXCR4-R334X mutant specific (50) | 3'-M hCXCR4 Exon 2 |

WT = wild type, M = mutant, bold/italic letters indicate deliberate mismatch to WT sequence

REFERENCES

Bachelerie, F., Ben-Baruch, A., Burkhardt, A. M., Combadiere, C., Farber, J. M., Graham, G. J., Horuk, R., Sparre-Ulrich, A. H., Locati, M., Luster, A. D., et al. (2014). International Union of Pharmacology. LXXXIX. Update on the extended family of chemokine receptors and introducing a new nomenclature for atypical chemokine receptors. Pharmacological reviews 66, 1-79.

Balabanian et al., Blood 119, 5722-5730, 2012.

Beaussant et al., Orphanet journal of rare diseases 7, 71, 2012.

Berger et al., (1999). Chemokine receptors as HIV-1 coreceptors: roles in viral entry, tropism, and disease. Annual review of immunology 17, 657-700.

Bleul et al., (1996). J. Exp. Med. 184, 1101-1109.

Broxmeyer et al., (2003a). J Immunol 170, 421-429.

Broxmeyer et al., (2003b). Journal of leukocyte biology 73, 630-638.

Broxmeyer et al. (2005). J. Exp. Med. 201, 1307-1318.

Copelan, E. A. (2006). The New England J. Med. 354, 1813-1826.

Dale et al., (2011). The CXCR4 antagonist plerixafor is a potential therapy for myelokathexis, WHIM syndrome. Blood. 118:4963-6.

Dotta et al., (2011). Current molecular medicine 11, 317-325.

Feng et al., (1996). Science 272, 872-877.

Haribabu et al., (1997). The J. Biol. Chem. 272, 28726-28731.

Hernandez et al., (2003). Nat Genet 34, 70-74.

Jones, M. J., and Jallepalli, P. V. (2012). Developmental cell 23, 908-917.

Kawai et al., (2007). Blood 109, 78-84.

Kawai, T., and Malech, H. L. (2009). Curr Opin Hematol 16, 20-26.

Kim et al., (2013). Genome biology 14, R36.

Kloosterman et al. (2011). Human molecular genetics 20, 1916-1924.

Korbel, J. O., and Campbell, P. J. (2013). Criteria for inference of chromothripsis in cancer genomes. Cell 52, 1226-1236.

Krill et al., (1964). The New England journal of medicine 270, 973-979.

Krzywinski et al., (2009). Genome research 19, 1639-1645.

Lawnicki et al., (2003). JMD 5, 82-87.

Leiding, J. W., and Holland, S. M. (2012). The Journal of allergy and clinical immunology 130, 1030-1048.

McDermott et al. (2011). Blood. 118:4957-62.

McDermott et al. (2014). Blood 123, 2308-2316.

Nie et al., (2008). J. Exp. Med. 205, 777-783.

Ramasamy et al., (1992). Journal of clinical pathology 45, 770-775.

Rausch et al. (2012). Cell 148, 59-71.

Robinson et al., (2011). Nature biotechnology 29, 24-26.

Seita, J., and Weissman, I. L. (2010). Hematopoietic stem cell: self-renewal versus differentiation. Wiley interdisciplinary reviews Systems biology and medicine 2, 640-653.

Signoret et al., (1998). J Cell Sci 111 (Pt 18), 2819-2830.

Stephens et al. (2011). Cell 144, 27-40.

Sugiyama et al., (2006). Immunity 25, 977-988.

Tassone et al., (2009). The Journal of allergy and clinical immunology 123, 1170-1173, 1173 e1171-1173.

van Dongen, et al. (2003). Leukemia 17, 2257-2317.

Venkatesan et al., (2003). Mol. Biol. Cell 14, 3305-3324.

Wetzler et al., (1990). Am J Med 89, 663-672.

Zuelzer, W. W. (1964). New England J. Med 270, 699-704.

In view of the many possible embodiments to which the principles of the disclosure may be applied, it should be recognized that the illustrated embodiments are only examples of the invention and should not be taken as limiting the scope of the invention. Rather, the scope of the disclosure is defined by the following claims. We therefore claim as our invention all that comes within the scope and spirit of these claims.

We claim:

1. A method of increasing hematopoietic stem cell (HSC) engraftment in a recipient subject having warts, hypogammaglobulinemia, infections, and myelokathexis (WHIM) syndrome, comprising:
   (i) transfecting ex vivo a donor $CD34^+$ HSC that is autologous or allogeneic to the recipient with (a) a Cas9 protein or a nucleic acid encoding a Cas9 protein, and (b) a nucleic acid molecule encoding a guide RNA (gRNA) specific for a CXCR4 allele to delete one CXC chemokine receptor 4 (CXCR4) allele, thereby generating a CXCR4 knockdown HSC with reduced expression of CXCR4; and
   (ii) intravenously administering a therapeutically effective amount of the CXCR4 knockdown HSC to the recipient subject having WHIM syndrome, thereby increasing HSC engraftment and hematopoietic reconstitution in blood at least 3-fold in the recipient subject having WHIM syndrome compared to engraftment of the donor HSC prior to deleting one CXCR4 allele.

2. The method of claim 1, wherein expression of CXCR4 is reduced by at least 50% in the CXCR4 knockdown HSC as compared to expression of CXCR4 in the donor HSC prior to deleting one CXCR4 allele.

3. The method of claim 1, wherein the donor HSCs are obtained from the recipient subject.

4. The method of claim 1, wherein the donor HSCs are obtained from a subject different from the recipient subject.

5. The method of claim 1, wherein the recipient subject has not received chemotherapy and/or total body irradiation prior to administering the CXCR4 knockdown HSCs to the recipient subject.

6. The method of claim 1, wherein the recipient subject is a human subject.

7. The method of claim 1, wherein the gRNA comprises the nucleotide sequence as set forth in SEQ ID NO: 36.

8. The method of claim 1, wherein the therapeutically effective amount of the CXCR4 knockdown HSC comprises at least $1 \times 10^6$ CXCR4 knockdown HSCs.

9. The method of claim 1, wherein the recipient subject has received chemotherapy and/or total body irradiation prior to administering the CXCR4 knockdown HSCs to the recipient subject.

* * * * *

SEQUENCE LISTING

```
<160> NUMBER OF SEQ ID NOS: 50

<210> SEQ ID NO 1
<211> LENGTH: 24
<212> TYPE: DNA
<213> ORGANISM: Artificial Sequence
<220> FEATURE:
<223> OTHER INFORMATION: primer

<400> SEQUENCE: 1
atcctctatg ctttccttgg agcc                                          24

<210> SEQ ID NO 2
<211> LENGTH: 25
<212> TYPE: DNA
<213> ORGANISM: Artificial Sequence
<220> FEATURE:
<223> OTHER INFORMATION: primer

<400> SEQUENCE: 2
gtggaaacag atgaatgtcc accgc                                         25

<210> SEQ ID NO 3
<211> LENGTH: 24
<212> TYPE: DNA
<213> ORGANISM: Artificial Sequence
<220> FEATURE:
<223> OTHER INFORMATION: primer

<400> SEQUENCE: 3
ggaatctcac atccagaatc atgc                                          24

<210> SEQ ID NO 4
<211> LENGTH: 23
<212> TYPE: DNA
<213> ORGANISM: Artificial Sequence
<220> FEATURE:
<223> OTHER INFORMATION: primer

<400> SEQUENCE: 4
ttgttctcac ctttggccag tgg                                           23

<210> SEQ ID NO 5
<211> LENGTH: 8747
```

```
<212> TYPE: DNA
<213> ORGANISM: Homo sapiens
<220> FEATURE:
<221> NAME/KEY: CDS
<222> LOCATION: (2721)..(2735)
<220> FEATURE:
<221> NAME/KEY: CDS
<222> LOCATION: (4844)..(5908)

<400> SEQUENCE: 5
```

| | | | | | |
|---|---|---|---|---|---|
| caattctgaa | tcctgccttt | tgcacttaat | gtttcataag | tatttcccca | tgtcactaaa | 60 |
| aattcttcca | aataacattc | acgatgtcca | tatggaattt | cagatgtgga | tgaaccaaaa | 120 |
| tcttgtcaac | tattccacta | acagtggtta | tttaggatg | ttcagacatt | tcactattta | 180 |
| aaaaaaaatg | tttccacaaa | tacctttgtg | gcataagttt | ttatgagtgg | agttactgtt | 240 |
| ctgaagttcc | tgctgaatag | aaaatgcttt | ccagtgaggc | tgtcccaagc | cacattccca | 300 |
| tcagtgacaa | gcgagagaca | gctggtcttt | tcaaatccgg | agaccaaata | ttatctttga | 360 |
| aaaaaaatgg | atttttgcct | aatttggtag | tcaccaaata | gcatctcatt | gttcttttaa | 420 |
| ttatctgctt | ccttttagta | gagatcccta | aaaagatctg | aaaggagtct | tcagataaag | 480 |
| gaaggagctt | tcttttgtct | gtctacaatc | aacaaatatt | tattatgcaa | accattttgc | 540 |
| tccgagtttt | ctcctctttc | ccttttggga | cagatttggg | agatctcacc | tttcaggttt | 600 |
| tagacatcgt | gcagggagga | gttttgaggt | agggtgcagc | ttacggtcca | ggataaaaca | 660 |
| tactgattct | gccactacca | ggctttgtga | aaagcaagtc | atgaaaacgc | tctgaaattc | 720 |
| tagaccttca | gtagatagga | tctaccgtgt | ctataaaaat | atgaagatcc | ttaagtttta | 780 |
| ttaaagattc | gaaaaaagta | aaagtgtttt | tacggtttta | ttttcatttt | tatttcttac | 840 |
| cgttatcgtt | tattataaag | gatattataa | aggatacaga | tgaagagata | cgtaatgcaa | 900 |
| ggcctgtgag | aaggggcgtg | gagcttccga | aacctcttcc | agccaccacc | ctccaagaac | 960 |
| ctggagtttc | tttttttttt | tttaattcta | caaatgtaat | attagaattg | attttatctg | 1020 |
| gccattagtg | tgtgtcctaa | ctcgttcgtt | tctgagagtc | ccatctcccg | gcccgggata | 1080 |
| tcatctttcc | tgtgtcagtg | aaagtgcaga | gtagatgaga | acctttaacc | accaacatta | 1140 |
| gggagggtc | ccagacaaag | ggggtaagtc | atgctctgta | gagaaaaggt | tccctgcctc | 1200 |
| cgaactacct | ctggaacact | ccagtaaatg | tttcctcttt | tgatatagaa | agagggatc | 1260 |
| gtgtgtagag | tgcagtctgg | gcaatccctc | tcctcgggac | catttcgggg | taggggcctc | 1320 |
| tggggtccgt | gtcgcgacgc | acgcgcctcg | gtcccagcta | tctccgcagc | gggccacccc | 1380 |
| gcctgcggac | gcagtttctc | ggccccgccc | cacactcgct | cccccgcccc | acccagtctc | 1440 |
| cgcgccggag | ggaagtggcg | cgaggggaa | agcactgtct | gcgcgcccac | tgcaaacctc | 1500 |
| agccagtctg | agatcgcttt | aaacgtctga | ccccccaccccc | cactccgccc | cgcccagttc | 1560 |
| ttcaacctaa | tttctgattc | gtgccaaagc | ttgtcctctg | ctcaaaatcg | tggaagacgc | 1620 |
| cgagtatggg | gaccgaagac | ctgggttcaa | gccggcttg | gaatccctgc | ccatccctgg | 1680 |
| catttcatct | ctccgggctt | atttgctggt | ttctccgaat | gcgggccttg | tctggttcac | 1740 |
| gctggatccc | caacgcctag | aacagtgcgt | ggcacgcagt | tcgtccttct | ataaatatcg | 1800 |
| gactaaatgc | atctctgtga | tggtaatacc | cacacggtgt | tgtgagaatg | aatgagtgat | 1860 |
| tctgtgcaag | ttcctagtga | tctgttacaa | aaagtactgg | tcgctaaatt | actcttataa | 1920 |
| taaagcatac | ttttaggata | ataaagcact | attcgcgaat | tggttaccgc | tattatgaaa | 1980 |
| ttactgagca | atacatatct | acatctgatc | agtctccaga | attatgccaa | atcctacctt | 2040 |

-continued

```
cttctgaaag tatctcctaa ttatctgcac ctgaccctag tgatgctgtg aatgtgcaag    2100
tatagctaca tcctccgaag gaaaggatct ttactccttt tacctcctga atgggctgcg    2160
tctgctgaaa gcgcggggga atgggcggtt ggaagcttgg ccctacttcc agcattgccg    2220
cctactggtt gggttactcc agcaagtcac tccccttccc tgggcctcag tgtctctact    2280
gtagcattcc caggtctgga attccatcca ctttagcaag gatggacgcg ccacagagag    2340
acgcgttcct agcccgcgct tcccacctgt cttcaggcgc atcccgcttc cctcaaactt    2400
aggaaatgcc tctgggaggt cctgtccggc tccggactca ctaccgacca cccgcaaaca    2460
gcagggtccc ctgggcttcc caagccgcgc acctctccgc cccgcccctg cgccctcctt    2520
cctcgcgtct gcccctctcc cccacccgc cttctccctc ccgccccag cggcgcatgc      2580
gccgcgctcg gagcgtgttt ttataaaagt ccggccgcgg ccagaaactt cagtttgttg    2640
gctgcggcag caggtagcaa agtgacgccg agggcctgag tgctccagta gccaccgcat    2700
ctggagaacc agcggttacc atg gag ggg atc agt gtaagtccag tttcaacctg     2755
                      Met Glu Gly Ile Ser
                        1               5
ctttgtcata aatgtacaaa cgtttgaact tagagcgcag cccctctccg agcgggcaga    2815
agcggccagg acattggagg tacccgtact ccaaaaaagg gtcaccgaaa ggagttttct    2875
tgaccatgcc tatatagtgc gggtgggtgg gggggagca ggattggaat cttttttctct    2935
gtgagtcgag gagaaacgac tggaaagagc gttccagtgg ctgcatgtgt ctcccccttg    2995
agtcccgccg cgcgcggcgg cttgcacgct gtttgcaaac gtaagaacat tctgtgcaca    3055
agtgcagaga aggcgtgcgc gctgcctcgg gactcagacc accggtctct tccttgggga    3115
agcggggatg tcttggagcg agttacattg tctgaattta gaggcggagg gcggcgtgcc    3175
tgggctgagt tccaggagg agattgcgcc cgctttaact tcggggttaa gcgcctggtg     3235
actgttcttg acactgggtg cgtgtttgtt aaactctgtg cggccgacgg agctgtgcca    3295
gtctcccagc acagtaggca gagggcggga gaggcgggtg gacccaccgc gccgatcctc    3355
tgaggggatc gagtggtggc agcagctagg agttgatccg cccgcgcgct ttgggtttga    3415
gggggaaacc ttcccgccgt ccgaagcgcg cctcttcccc acggccgcga gtgggtcctg    3475
cagttcgaga gtttggggtc gtgcagaggt cagcggagtg gtttgacctc cccttttgaca   3535
ccgcgcagct gccagccctg agatttgcgc tccggggata ggagcgggta cggggtgagg   3595
ggcgggggcg gttaagaccg cacctgggct gccaggtcgc cgccgcgaag actggcaggt    3655
gcaagtgggg aaaccgtttg gctctctccg agtccagttg tgatgtttaa ccgtcggtgg    3715
tttccagaaa cctttttgaaa ccctcttgct agggagtttt tggtttcctg cagcggcgcg   3775
caattcaaag acgctcgcgg cggagccgcc cagtcgctcc ccagcaccct gtgggacaga    3835
gcctggcgtg tcgcccagcg gagcccctgc agcgctgctt gcggcggtt ggcgtggtg      3895
tagtgggcag ccgcggcggc ccggggctgg acgaccccggc ccccgcgtg cccaccgcct    3955
ggaggcttcc agctgcccac ctccggccgg gttaactgga tcagtggcgg ggtaatggga    4015
aaccacccgg gagagtgagg aaatgaaact tggggcgagg accacgggtg cagacccccgt   4075
taccttctcc acccaggaaa atgccccgct ccctaacgtc ccaaacgcgc caagtgataa    4135
acacgaggat ggcaagagac ccacacaccg gaggagcgcc cgcttggggg aggaggtgcc    4195
gtttgttcat tttctgacac tcccgcccaa tataccccaa gcaccgaagg gccttcgttt    4255
taagaccgca ttctcttttac ccactacaag ttgcttgaag cccagaatgg tttgtattta    4315
ggcaggcgtg ggaaaattaa gttttttgcgc cttaggagaa tgagtctttg caacgccccc    4375
```

-continued

```
gccctccccc cgtgatcctc ccttctcccc tcttccctcc ctgggcgaaa aacttcttac    4435
aaaaagttaa tcactgcccc tcctagcagc acccacccca cccccacgc cgcctgggag     4495 tggcctcttt gtgtgtattt ttttttttcct cctaaggaag gttttttttc ttccctctag   4555
tgggcggggc agaggagtta gccaagatgt gactttgaaa ccctcagcgt ctcagtgccc    4615
ttttgttcta acaaagaat tttgtaattg gttctaccaa agaaggatat aatgaagtca     4675
ctatgggaaa agatggggag agagttgta ggattctaca ttaattctct tgtgcccttta    4735 gcccactact tcagaatttc ctgaagaaag caagcctgaa ttggtttttt aaattgcttt    4795
aaaaaatttt tttaactggg ttaatgcttg ctgaattgga agtgaatg tcc att cct     4852
                                                      Ser Ile Pro
```

| | | | | | | | | | | | | | | | | |
|---|---|---|---|---|---|---|---|---|---|---|---|---|---|---|---|---|
| ttg | cct | ctt | ttg | cag | ata | tac | act | tca | gat | aac | tac | acc | gag | gaa | atg | 4900 |
| Leu | Pro | Leu | Leu | Gln | Ile | Tyr | Thr | Ser | Asp | Asn | Tyr | Thr | Glu | Glu | Met | |
| | 10 | | | | 15 | | | | | 20 | | | | | | |
| ggc | tca | ggg | gac | tat | gac | tcc | atg | aag | gaa | ccc | tgt | ttc | cgt | gaa | gaa | 4948 |
| Gly | Ser | Gly | Asp | Tyr | Asp | Ser | Met | Lys | Glu | Pro | Cys | Phe | Arg | Glu | Glu | |
| 25 | | | | 30 | | | | | 35 | | | | | 40 | | |
| aat | gct | aat | ttc | aat | aaa | atc | ttc | ctg | ccc | acc | atc | tac | tcc | atc | atc | 4996 |
| Asn | Ala | Asn | Phe | Asn | Lys | Ile | Phe | Leu | Pro | Thr | Ile | Tyr | Ser | Ile | Ile | |
| | | | | 45 | | | | | 50 | | | | | 55 | | |
| ttc | tta | act | ggc | att | gtg | ggc | aat | gga | ttg | gtc | atc | ctg | gtc | atg | ggt | 5044 |
| Phe | Leu | Thr | Gly | Ile | Val | Gly | Asn | Gly | Leu | Val | Ile | Leu | Val | Met | Gly | |
| | | | 60 | | | | | 65 | | | | | 70 | | | |
| tac | cag | aag | aaa | ctg | aga | agc | atg | acg | gac | aag | tac | agg | ctg | cac | ctg | 5092 |
| Tyr | Gln | Lys | Lys | Leu | Arg | Ser | Met | Thr | Asp | Lys | Tyr | Arg | Leu | His | Leu | |
| | | 75 | | | | | 80 | | | | | 85 | | | | |
| tca | gtg | gcc | gac | ctc | ctc | ttt | gtc | atc | acg | ctt | ccc | ttc | tgg | gca | gtt | 5140 |
| Ser | Val | Ala | Asp | Leu | Leu | Phe | Val | Ile | Thr | Leu | Pro | Phe | Trp | Ala | Val | |
| | 90 | | | | | 95 | | | | | 100 | | | | | |
| gat | gcc | gtg | gca | aac | tgg | tac | ttt | ggg | aac | ttc | cta | tgc | aag | gca | gtc | 5188 |
| Asp | Ala | Val | Ala | Asn | Trp | Tyr | Phe | Gly | Asn | Phe | Leu | Cys | Lys | Ala | Val | |
| 105 | | | | 110 | | | | | 115 | | | | | 120 | | |
| cat | gtc | att | tac | aca | gtc | aac | ctc | tac | agc | agt | gtc | ctc | atc | ctg | gcc | 5236 |
| His | Val | Ile | Tyr | Thr | Val | Asn | Leu | Tyr | Ser | Ser | Val | Leu | Ile | Leu | Ala | |
| | | | | 125 | | | | | 130 | | | | | 135 | | |
| ttc | atc | agt | ctg | gac | cgc | tac | ctg | gcc | atc | gtc | cac | gcc | acc | aac | agt | 5284 |
| Phe | Ile | Ser | Leu | Asp | Arg | Tyr | Leu | Ala | Ile | Val | His | Ala | Thr | Asn | Ser | |
| | | | 140 | | | | | 145 | | | | | 150 | | | |
| cag | agg | cca | agg | aag | ctg | ttg | gct | gaa | aag | gtg | gtc | tat | gtt | ggc | gtc | 5332 |
| Gln | Arg | Pro | Arg | Lys | Leu | Leu | Ala | Glu | Lys | Val | Val | Tyr | Val | Gly | Val | |
| | | 155 | | | | | 160 | | | | | 165 | | | | |
| tgg | atc | cct | gcc | ctc | ctg | ctg | act | att | ccc | gac | ttc | atc | ttt | gcc | aac | 5380 |
| Trp | Ile | Pro | Ala | Leu | Leu | Leu | Thr | Ile | Pro | Asp | Phe | Ile | Phe | Ala | Asn | |
| | 170 | | | | | 175 | | | | | 180 | | | | | |
| gtc | agt | gag | gca | gat | gac | aga | tat | atc | tgt | gac | cgc | ttc | tac | ccc | aat | 5428 |
| Val | Ser | Glu | Ala | Asp | Asp | Arg | Tyr | Ile | Cys | Asp | Arg | Phe | Tyr | Pro | Asn | |
| 185 | | | | 190 | | | | | 195 | | | | | 200 | | |
| gac | ttg | tgg | gtg | gtt | gtg | ttc | cag | ttt | cag | cac | atc | atg | gtt | ggc | ctt | 5476 |
| Asp | Leu | Trp | Val | Val | Val | Phe | Gln | Phe | Gln | His | Ile | Met | Val | Gly | Leu | |
| | | | | 205 | | | | | 210 | | | | | 215 | | |
| atc | ctg | cct | ggt | att | gtc | atc | ctg | tcc | tgc | tat | tgc | att | atc | atc | tcc | 5524 |
| Ile | Leu | Pro | Gly | Ile | Val | Ile | Leu | Ser | Cys | Tyr | Cys | Ile | Ile | Ile | Ser | |
| | | | 220 | | | | | 225 | | | | | 230 | | | |
| aag | ctg | tca | cac | tcc | aag | ggc | cac | cag | aag | cgc | aag | gcc | ctc | aag | acc | 5572 |
| Lys | Leu | Ser | His | Ser | Lys | Gly | His | Gln | Lys | Arg | Lys | Ala | Leu | Lys | Thr | |
| | | 235 | | | | | 240 | | | | | 245 | | | | |
| aca | gtc | atc | ctc | atc | ctg | gct | ttc | ttc | gcc | tgt | tgg | ctg | cct | tac | tac | 5620 |

```
Thr Val Ile Leu Ile Leu Ala Phe Phe Ala Cys Trp Leu Pro Tyr Tyr
    250                 255                 260 att ggg atc agc atc gac tcc ttc atc ctc ctg gaa atc atc aag caa      5668
Ile Gly Ile Ser Ile Asp Ser Phe Ile Leu Leu Glu Ile Ile Lys Gln
265                 270                 275                 280 ggg tgt gag ttt gag aac act gtg cac aag tgg att tcc atc acc gag      5716
Gly Cys Glu Phe Glu Asn Thr Val His Lys Trp Ile Ser Ile Thr Glu
                285                 290                 295 gcc cta gct ttc ttc cac tgt tgt ctg aac ccc atc ctc tat gct ttc      5764
Ala Leu Ala Phe Phe His Cys Cys Leu Asn Pro Ile Leu Tyr Ala Phe
                    300                 305                 310 ctt gga gcc aaa ttt aaa acc tct gcc cag cac gca ctc acc tct gtg      5812
Leu Gly Ala Lys Phe Lys Thr Ser Ala Gln His Ala Leu Thr Ser Val
                315                 320                 325 agc aga ggg tcc agc ctc aag atc ctc tcc aaa gga aag cga ggt gga      5860
Ser Arg Gly Ser Ser Leu Lys Ile Leu Ser Lys Gly Lys Arg Gly Gly
                330                 335                 340 cat tca tct gtt tcc act gag tct gag tct tca agt ttt cac tcc agc      5908
His Ser Ser Val Ser Thr Glu Ser Glu Ser Ser Ser Phe His Ser Ser
345                 350                 355                 360 taacacagat gtaaaagact ttttttttata cgataaataa cttttttttta agttacacat   5968 ttttcagata taaaagactg accaatattg tacagttttt attgcttgtt ggattttttgt   6028 cttgtgtttc tttagttttt gtgaagttta attgacttat ttatataaat tttttttgtt    6088
tcatattgat gtgtgtctag gcaggacctg tggccaagtt cttagttgct gtatgtctcg    6148
tggtaggact gtagaaaagg gaactgaaca ttccagagcg tgtagtgaat cacgtaaagc    6208
tagaaatgat ccccagctgt ttatgcatag ataatctctc cattcccgtg gaacgttttt    6268
cctgttctta agacgtgatt ttgctgtaga agatggcact tataaccaaa gcccaaagtg    6328
gtatagaaat gctggttttt cagttttcag gagtgggttg atttcagcac ctacagtgta    6388
cagtcttgta ttaagttgtt aataaaagta catgttaaac ttacttagtg ttatgttctg    6448
atttctgttg acattctttt ggctagtaga agacaaaagt aatacattta tggtatgcaa    6508
agcactatcc taggtatttc attgtaatat tttacttacc ccttatcaca actctgatag    6568
attctgcttc tgttactaat tacatttttat agaagaggaa acggaggcac agaaagccta    6628
agtaacttgg ttaaaggcat gtagtaagta tcaaatcctg tatttttaaac caggtaacat    6688 gacttaacga atctgaagcc ttcaccactt taaattcaaa tggaagttta gaaatggcca    6748
gccagcacct atttgtatga aaggtcatct ttcagaggat aagcatgtat aaagaagaaa    6808
aggtatgcag tcgtgtttgg attttactcc accatccact tgtgaaaccc aggtctgtgc    6868
aatgccagac ggtgtgtgct ttcctcatcc agtatcctca gtgtagataa ccatcactcc    6928
cttttcacag acaagagaac tgagattcag agactttcca tacattgcac tttcaagggg    6988
gcaaagccaa gaactaattc tgtttattgt tccagctctt gctcttaact cttacctact    7048
attgcccttc agaacacctg gcataagtc aactgaactg ctaataaaga aagccaaaag     7108
tgaatgtttt cttcataaaa ttaaccatga ccaaaatact cctcttgtaa tatcttctat    7168
gcaaatctca acactttat tcttaaacta tcgcaacacc tagcacctcc tcaaggactc     7228
agccaagcag ctacaagtta atactgatat ttgttagagt cagaaggaag gtccactgaa    7288
gcaagctccc tgttgctcac attttgcaca agatttttgga gacttatgta accacccgtt   7348
gctattaaca cgaccattgt gcaagcccca ggctcttgag taaatttcag ctttggtttc    7408
tatttaaaga taatttctaa actctagcca tacctacctc acattggaac acaaacaggg    7468
```

```
tacactccag gcatgcactc agataataag taggatataa ttacgacaat atttggtcta    7528 ctttagtaa ttgtttctgg cacagaaaat ccatttggaa ggaaaaattg caatgcctta    7588
tctttctgag gcaaatcaca tttgttcaag gcaaattata gatcctgtga agggaaataa    7648
cttaattact taaaatagaa tccaatttgg ctgtacattt ttgctgccgt ctatggatct    7708
ggggtaattc aaagtggtat tcatattcta cttgaggaca caattagatt tcagatagga    7768
aattatcttg aggtttcttg gttttccctg agaagcctaa ttggatcacc cttcatttaa    7828
gcatagtttt acatgcactc tctcaaaggc ttagtcttaa agccacaacc attgagacag    7888
acttcacttg aaccctctct ataaatattt attctccggg agacaataga agaaatcctt    7948
ggaaggcatg ctttttcttt ctcatcttgg cttgaaacct ccttacccca gattcctctc    8008
ctttaccgtg gagtcacaac aaaaggaact gagccaaaac aaaattccca gtgtcaccag    8068
tcttaatgga tatttcattc tcccttggaa caaagatgga atagcttttt ttccaaaaga    8128
aaaacaagcc ttggctctct ccctgcccca aaagggtgcc ccccaccccc atcattctct    8188
gtcccaaccc tgccatgtta gagcgtctcc aaagccttcc ctgtgtcgtg gtttgtctga    8248
caatgtgggg aaacccagtc tgctggccag cccttgcatg aagtagctga ttgttccctc    8308
tcctcatccc ttatgaatgg ggcccttgaa gttcagtcat gtagattcag ttgtataatg    8368
aaagctaaaa tatttaaatt gtatgcatgc tgccaataac agcatacatc tgacatctaa    8428
cttattaata acattaagcc tgcaactagg ggggaaagtg gatgttttt cttgcaaagc    8488 ctttgttttc ctaaaatgac acttgaaaat ttatctcccc ctactgcagg cttcccagcc    8548
cccttttata attatgctta aattaaaata atgattctgg gatactcttt tggggagata    8608
ccctacaggc tttatttaa taattgaact aagtgtttgt gactttctcc tagatattgt    8668
caaatattaa ataaaggctc cataaacaat tgagctgtct tattcccaga taatacccat    8728
ttaggagggg caaggatcc                                                 8747
```

<210> SEQ ID NO 6
<211> LENGTH: 360
<212> TYPE: PRT
<213> ORGANISM: Homo sapiens

<400> SEQUENCE: 6

```
Met Glu Gly Ile Ser Ser Ile Pro Leu Pro Leu Leu Gln Ile Tyr Thr
1               5                   10                  15

Ser Asp Asn Tyr Thr Glu Glu Met Gly Ser Gly Asp Tyr Asp Ser Met
            20                  25                  30

Lys Glu Pro Cys Phe Arg Glu Asn Ala Asn Phe Asn Lys Ile Phe
        35                  40                  45

Leu Pro Thr Ile Tyr Ser Ile Ile Phe Leu Thr Gly Ile Val Gly Asn
    50                  55                  60

Gly Leu Val Ile Leu Val Met Gly Tyr Gln Lys Lys Leu Arg Ser Met
65                  70                  75                  80

Thr Asp Lys Tyr Arg Leu His Leu Ser Val Ala Asp Leu Leu Phe Val
                85                  90                  95

Ile Thr Leu Pro Phe Trp Ala Val Asp Ala Val Ala Asn Trp Tyr Phe
            100                 105                 110

Gly Asn Phe Leu Cys Lys Ala Val His Val Ile Tyr Thr Val Asn Leu
        115                 120                 125

Tyr Ser Ser Val Leu Ile Leu Ala Phe Ile Ser Leu Asp Arg Tyr Leu
    130                 135                 140
```

```
Ala Ile Val His Ala Thr Asn Ser Gln Arg Pro Arg Lys Leu Leu Ala
145                 150                 155                 160

Glu Lys Val Val Tyr Val Gly Val Trp Ile Pro Ala Leu Leu Leu Thr
                165                 170                 175

Ile Pro Asp Phe Ile Phe Ala Asn Val Ser Glu Ala Asp Asp Arg Tyr
            180                 185                 190

Ile Cys Asp Arg Phe Tyr Pro Asn Asp Leu Trp Val Val Phe Gln
        195                 200                 205

Phe Gln His Ile Met Val Gly Leu Ile Leu Pro Gly Ile Val Ile Leu
        210                 215                 220

Ser Cys Tyr Cys Ile Ile Ile Ser Lys Leu Ser His Ser Lys Gly His
225                 230                 235                 240

Gln Lys Arg Lys Ala Leu Lys Thr Thr Val Ile Leu Ile Leu Ala Phe
                245                 250                 255

Phe Ala Cys Trp Leu Pro Tyr Tyr Ile Gly Ile Ser Ile Asp Ser Phe
            260                 265                 270

Ile Leu Leu Glu Ile Ile Lys Gln Gly Cys Glu Phe Glu Asn Thr Val
        275                 280                 285

His Lys Trp Ile Ser Ile Thr Glu Ala Leu Ala Phe Phe His Cys Cys
290                 295                 300

Leu Asn Pro Ile Leu Tyr Ala Phe Leu Gly Ala Lys Phe Lys Thr Ser
305                 310                 315                 320

Ala Gln His Ala Leu Thr Ser Val Ser Arg Gly Ser Ser Leu Lys Ile
                325                 330                 335

Leu Ser Lys Gly Lys Arg Gly Gly His Ser Ser Val Ser Thr Glu Ser
                340                 345                 350

Glu Ser Ser Ser Phe His Ser Ser
            355                 360
```

<210> SEQ ID NO 7
<211> LENGTH: 35
<212> TYPE: DNA
<213> ORGANISM: Artificial Sequence
<220> FEATURE:
<223> OTHER INFORMATION: primer

<400> SEQUENCE: 7
cggtacccgg ggatcttgtg cccttagccc actac                         35

<210> SEQ ID NO 8
<211> LENGTH: 35
<212> TYPE: DNA
<213> ORGANISM: Artificial Sequence
<220> FEATURE:
<223> OTHER INFORMATION: primer

<400> SEQUENCE: 8
cgactctaga ggatcccacc ttttcagcca acagc                         35

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
agcgtctcag tgcccttttg                                          20

```
<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
atctgcctca ctgacgttgg                                                   20

<210> SEQ ID NO 11
<211> LENGTH: 70
<212> TYPE: DNA
<213> ORGANISM: Artificial Sequence
<220> FEATURE:
<223> OTHER INFORMATION: human CXCR4 with TALEN sequences

<400> SEQUENCE: 11
aatggattgg tcatcctggt catgggttac cagaagaaac tgagaagcat gacggacaag       60
tacaggctgc                                                              70

<210> SEQ ID NO 12
<211> LENGTH: 71
<212> TYPE: DNA
<213> ORGANISM: Artificial Sequence
<220> FEATURE:
<223> OTHER INFORMATION: human CXCR4 seuqence containing TALEN sequences

<400> SEQUENCE: 12
ttacctaacc agtaggacca gtacccaatg gtcttctttg actcttcgta ctgcctgttc       60
atgtccgacg t                                                            71

<210> SEQ ID NO 13
<211> LENGTH: 78
<212> TYPE: DNA
<213> ORGANISM: Artificial Sequence
<220> FEATURE:
<223> OTHER INFORMATION: sequence identified using TALEN system

<400> SEQUENCE: 13
atggattggt catcctggtc atgggttacc agaagaaact gagaagcatg acggacaagt       60
acaggctgca cctgtcag                                                     78

<210> SEQ ID NO 14
<211> LENGTH: 78
<212> TYPE: DNA
<213> ORGANISM: Artificial Sequence
<220> FEATURE:
<223> OTHER INFORMATION: sequence identified with TALEN system

<400> SEQUENCE: 14
atggattggt catcctggtc atggattacc agaagaaact gagaagcatg acggacaagt       60
acaggctgca cctgtcag                                                     78

<210> SEQ ID NO 15
<211> LENGTH: 44
<212> TYPE: DNA
<213> ORGANISM: Artificial Sequence
<220> FEATURE:
<223> OTHER INFORMATION: sequence identified with TALEN system

<400> SEQUENCE: 15
atggattggt catcctggtc atgggtacag gctgcacctg tcag                        44
```

<210> SEQ ID NO 16
<211> LENGTH: 51
<212> TYPE: DNA
<213> ORGANISM: Artificial Sequence
<220> FEATURE:
<223> OTHER INFORMATION: sequence identified with TALEN system

<400> SEQUENCE: 16
atggattggt catcctggtc atgggttacc agaacaggct gcacctgtca g    51

<210> SEQ ID NO 17
<211> LENGTH: 77
<212> TYPE: DNA
<213> ORGANISM: Artificial Sequence
<220> FEATURE:
<223> OTHER INFORMATION: sequence identified with TALEN system

<400> SEQUENCE: 17
atggattggt catcctggtc atgggttacc agaagaactg agaagcatga cggacaagta    60
caggctgcac ctgtcag    77

<210> SEQ ID NO 18
<211> LENGTH: 71
<212> TYPE: DNA
<213> ORGANISM: Artificial Sequence
<220> FEATURE:
<223> OTHER INFORMATION: CXCR4 containing CRISPR sequences

<400> SEQUENCE: 18
aatggattgg tcatcctggt catgggttac cagaagaaac tgagaagcat gacggacaag    60
tacaggctgc a    71

<210> SEQ ID NO 19
<211> LENGTH: 71
<212> TYPE: DNA
<213> ORGANISM: Artificial Sequence
<220> FEATURE:
<223> OTHER INFORMATION: CXCR4 containing CRISPR sequences

<400> SEQUENCE: 19
ttacctaacc agtaggacca gtacccaatg gtcttctttg actcttcgta ctgcctgttc    60
atgtccgacg t    71

<210> SEQ ID NO 20
<211> LENGTH: 99
<212> TYPE: DNA
<213> ORGANISM: Artificial Sequence
<220> FEATURE:
<223> OTHER INFORMATION: sequence identified using CRISPR

<400> SEQUENCE: 20
tggcattgtg ggcaatggat tggtcatcct ggtcatgggt taccagaaga aactgagaag    60
catgacggac aagtacaggc tgcacctgtc agtggccga    99

<210> SEQ ID NO 21
<211> LENGTH: 99
<212> TYPE: DNA
<213> ORGANISM: Artificial Sequence
<220> FEATURE:
<223> OTHER INFORMATION: sequence identified with CRISPR

<400> SEQUENCE: 21
tggcattgtg ggcaatggat tggtcatcct ggtcatgggt taccagaaga aactgagaag    60

-continued

```
catgacggac aagtacaggc tgcacctgta agtggccga                                99
```

<210> SEQ ID NO 22
<211> LENGTH: 99
<212> TYPE: DNA
<213> ORGANISM: Artificial Sequence
<220> FEATURE:
<223> OTHER INFORMATION: sequence identified with CRISPR

<400> SEQUENCE: 22

```
tggcattgtg ggcaatggat tggtcatctt ggtcatgggt taccagaaga aactgagaag       60
catgacggac aagtacaggc tgcacctgtc agtggccga                                99
```

<210> SEQ ID NO 23
<211> LENGTH: 59
<212> TYPE: DNA
<213> ORGANISM: Artificial Sequence
<220> FEATURE:
<223> OTHER INFORMATION: sequence idenified with CRISPR

<400> SEQUENCE: 23

```
tggcattgtg ggcaatggat tggtcatcct ggttacaggc tgcacctgtc agtggccga        59
```

<210> SEQ ID NO 24
<211> LENGTH: 99
<212> TYPE: DNA
<213> ORGANISM: Artificial Sequence
<220> FEATURE:
<223> OTHER INFORMATION: sequence identified with CRISPR

<400> SEQUENCE: 24

```
tggcattgtg ggcaatggat tggtcatcct ggtcatgggt taccagaaga aactgagaag       60
catgacggac aagtacaggc tgcacttgtc agtggccga                                99
```

<210> SEQ ID NO 25
<211> LENGTH: 99
<212> TYPE: DNA
<213> ORGANISM: Artificial Sequence
<220> FEATURE:
<223> OTHER INFORMATION: sequence identified with CRISPR

<400> SEQUENCE: 25

```
tggcattgtg ggcaatggat tggtcatcct ggtcatgggt tatcagaaga aactgagaag       60
catgacggac aagtacaggc tgcacctgtc agtggccga                                99
```

<210> SEQ ID NO 26
<211> LENGTH: 68
<212> TYPE: DNA
<213> ORGANISM: Artificial Sequence
<220> FEATURE:
<223> OTHER INFORMATION: sequence identified using CRISPR

<400> SEQUENCE: 26

```
tggcattgtg ggcaatggat tggtcatcct ggtcatgggt taccaaaaaa aactgagaag       60
catgacgg                                                                 68
```

<210> SEQ ID NO 27
<211> LENGTH: 94
<212> TYPE: DNA
<213> ORGANISM: Artificial Sequence
<220> FEATURE:
<223> OTHER INFORMATION: sequence identified using CRISPR

<400> SEQUENCE: 27
tggcattgtg ggcaatggat tggtcatcct ggttacgggt taccccgtaa atggacaacc    60
tcctcttacg aaatccggtt ccctttgggg cagg                                94

<210> SEQ ID NO 28
<211> LENGTH: 99
<212> TYPE: DNA
<213> ORGANISM: Artificial Sequence
<220> FEATURE:
<223> OTHER INFORMATION: sequence identified using CRISPR

<400> SEQUENCE: 28
tggcattgtg ggcaatggat tggtcatcct ggtcatgggt taccagaaga aactgaaaag    60
catgacggac aagtacaggc tgcacctgtc agtggccga                           99

<210> SEQ ID NO 29
<211> LENGTH: 99
<212> TYPE: DNA
<213> ORGANISM: Artificial Sequence
<220> FEATURE:
<223> OTHER INFORMATION: sequence identified with CRISPR

<400> SEQUENCE: 29
tggcattgtg ggcaatggat tggtcatcct ggtcatgggt taccagaaga aactgagaag    60
catgacggac aagtacaggg tgcaccgta aggggccga                            99

<210> SEQ ID NO 30
<211> LENGTH: 60
<212> TYPE: DNA
<213> ORGANISM: Artificial Sequence
<220> FEATURE:
<223> OTHER INFORMATION: sequence identified with CRISPR

<400> SEQUENCE: 30
tggcattgtg aaactgagaa gcatgacgga caagtacagg ctgcacctgt cagtggccga    60

<210> SEQ ID NO 31
<211> LENGTH: 59
<212> TYPE: DNA
<213> ORGANISM: Artificial Sequence
<220> FEATURE:
<223> OTHER INFORMATION: sequence identified with CRISPR

<400> SEQUENCE: 31
tggcattgtg ggcaatggat tggtcatcct ggttacaggc tgcacctgtc agtggccga    59

<210> SEQ ID NO 32
<211> LENGTH: 59
<212> TYPE: DNA
<213> ORGANISM: Artificial Sequence
<220> FEATURE:
<223> OTHER INFORMATION: sequence identified with CRISPR
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (53)..(57)
<223> OTHER INFORMATION: n is a, c, g, or t
<220> FEATURE:
<221> NAME/KEY: misc_feature

```
<222> LOCATION: (59)..(59)
<223> OTHER INFORMATION: n is a, c, g, or t

<400> SEQUENCE: 32
tggcattgtg ggcaatggat tggtcatcct ggttacnnga tgaaactgnn aannnnnan    59

<210> SEQ ID NO 33
<211> LENGTH: 74
<212> TYPE: DNA
<213> ORGANISM: Artificial Sequence
<220> FEATURE:
<223> OTHER INFORMATION: human CXCR4 with CRISPR sequence

<400> SEQUENCE: 33
tggattggtc atcctggtca tgggttacca gaagaaactg agaagcatga cggacaagta    60
caggctgcac ctgt                                                      74

<210> SEQ ID NO 34
<211> LENGTH: 34
<212> TYPE: DNA
<213> ORGANISM: Artificial Sequence
<220> FEATURE:
<223> OTHER INFORMATION: sequence identified using CRISPR

<400> SEQUENCE: 34
tggattggtc atcctggtta caggctgcac ctgt                                34

<210> SEQ ID NO 35
<211> LENGTH: 75
<212> TYPE: DNA
<213> ORGANISM: Artificial Sequence
<220> FEATURE:
<223> OTHER INFORMATION: sequence identified with CRISPR

<400> SEQUENCE: 35
tggattggtc atcctggtac atgggttacc agaagaaact gagaagcatg acggacaagt    60
acaggctgca cctgt                                                     75

<210> SEQ ID NO 36
<211> LENGTH: 21
<212> TYPE: DNA
<213> ORGANISM: Artificial Sequence
<220> FEATURE:
<223> OTHER INFORMATION: sequence that targets wild type mCXCR4 exon 2

<400> SEQUENCE: 36
gtgatgaagt agatggtggg c                                              21

<210> SEQ ID NO 37
<211> LENGTH: 21
<212> TYPE: DNA
<213> ORGANISM: Artificial Sequence
<220> FEATURE:
<223> OTHER INFORMATION: sequence that targets wild type mCXCR4 exon 2

<400> SEQUENCE: 37
gttgactggc atagtcggca a                                              21

<210> SEQ ID NO 38
<211> LENGTH: 21
<212> TYPE: DNA
<213> ORGANISM: Artificial Sequence
<220> FEATURE:
<223> OTHER INFORMATION: sequence that targets wild type mCXCR4 exon 2
```

<400> SEQUENCE: 38
gttcctttgg aaaggatctt g                                             21

<210> SEQ ID NO 39
<211> LENGTH: 21
<212> TYPE: DNA
<213> ORGANISM: Artificial Sequence
<220> FEATURE:
<223> OTHER INFORMATION: sequence that targets wild type mCXCR4 exon 2

<400> SEQUENCE: 39
gtggacactc ttccgtctcc a                                             21

<210> SEQ ID NO 40
<211> LENGTH: 21
<212> TYPE: DNA
<213> ORGANISM: Artificial Sequence
<220> FEATURE:
<223> OTHER INFORMATION: sequence that targets mutant mCXCR4 exon 2

<400> SEQUENCE: 40
gtggacactg atccgtctcc a                                             21

<210> SEQ ID NO 41
<211> LENGTH: 17
<212> TYPE: DNA
<213> ORGANISM: Artificial Sequence
<220> FEATURE:
<223> OTHER INFORMATION: TALEN sequence that targets wild type mCXCR4
      exon 2

<400> SEQUENCE: 41
cctggtcatg ggttacc                                                  17

<210> SEQ ID NO 42
<211> LENGTH: 12
<212> TYPE: DNA
<213> ORGANISM: Artificial Sequence
<220> FEATURE:
<223> OTHER INFORMATION: TALEN sequence that targets wild type mCXCR4
      exon 2

<400> SEQUENCE: 42
ggtcatgggt ta                                                       12

<210> SEQ ID NO 43
<211> LENGTH: 15
<212> TYPE: DNA
<213> ORGANISM: Artificial Sequence
<220> FEATURE:
<223> OTHER INFORMATION: TALEN sequence that targets wild type mCXCR4
      exon 2

<400> SEQUENCE: 43
cctggtcatg ggtta                                                    15

<210> SEQ ID NO 44
<211> LENGTH: 15
<212> TYPE: DNA
<213> ORGANISM: Artificial Sequence
<220> FEATURE:
<223> OTHER INFORMATION: TALEN sequence that targets wild type mCXCR4
      exon 2

<400> SEQUENCE: 44
acttgtccgt catgc                                                    15

```
<210> SEQ ID NO 45
<211> LENGTH: 14
<212> TYPE: DNA
<213> ORGANISM: Artificial Sequence
<220> FEATURE:
<223> OTHER INFORMATION: TALEN sequence that targets mutant mCXCR4
      exon 2

<400> SEQUENCE: 45
acttgtccgt catg                                                        14

<210> SEQ ID NO 46
<211> LENGTH: 20
<212> TYPE: DNA
<213> ORGANISM: Artificial Sequence
<220> FEATURE:
<223> OTHER INFORMATION: sequence that targets wild type hCXCR4 exon 2

<400> SEQUENCE: 46
tcttctggta acccatgacc                                                  20

<210> SEQ ID NO 47
<211> LENGTH: 20
<212> TYPE: DNA
<213> ORGANISM: Artificial Sequence
<220> FEATURE:
<223> OTHER INFORMATION: sequence that targets wild type hCXCR4 exon 2

<400> SEQUENCE: 47
gaagcatgac ggacaagtac                                                  20

<210> SEQ ID NO 48
<211> LENGTH: 20
<212> TYPE: DNA
<213> ORGANISM: Artificial Sequence
<220> FEATURE:
<223> OTHER INFORMATION: sequence that targets wild type hCXCR4 exon 2

<400> SEQUENCE: 48
gctggaccct ctgctcacag                                                  20

<210> SEQ ID NO 49
<211> LENGTH: 20
<212> TYPE: DNA
<213> ORGANISM: Artificial Sequence
<220> FEATURE:
<223> OTHER INFORMATION: sequence that targets wild type hCXCR4 exon 2

<400> SEQUENCE: 49
ctctccaaag gaaagcgagg                                                  20

<210> SEQ ID NO 50
<211> LENGTH: 20
<212> TYPE: DNA
<213> ORGANISM: Artificial Sequence
<220> FEATURE:
<223> OTHER INFORMATION: sequence that targets mutant  hCXCR4 exon 2

<400> SEQUENCE: 50
ctctccaaag gaaagtgagg                                                  20
```